(12) United States Patent
Xu et al.

(10) Patent No.: US 12,383,222 B2
(45) Date of Patent: Aug. 12, 2025

(54) STRETCHABLE ULTRASONIC TRANSDUCER DEVICES

(71) Applicant: THE REGENTS OF THE UNIVERSITY OF CALIFORNIA, Oakland, CA (US)

(72) Inventors: Sheng Xu, La Jolla, CA (US); Lin Zhang, La Jolla, CA (US); Chonghe Wang, La Jolla, CA (US); Hongjie Hu, La Jolla, CA (US); Xiaoshi Li, La Jolla, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 478 days.

(21) Appl. No.: 16/477,060

(22) PCT Filed: Jan. 10, 2018

(86) PCT No.: PCT/US2018/013116
§ 371 (c)(1),
(2) Date: Jul. 10, 2019

(87) PCT Pub. No.: WO2018/132443
PCT Pub. Date: Jul. 19, 2018

(65) Prior Publication Data
US 2019/0328354 A1    Oct. 31, 2019

Related U.S. Application Data

(60) Provisional application No. 62/586,645, filed on Nov. 15, 2017, provisional application No. 62/444,524, filed on Jan. 10, 2017.

(51) Int. Cl.
*A61B 8/04* (2006.01)
*A61B 8/00* (2006.01)
(Continued)

(52) U.S. Cl.
CPC .............. *A61B 8/04* (2013.01); *A61B 8/0891* (2013.01); *A61B 8/14* (2013.01); *A61B 8/4455* (2013.01);
(Continued)

(58) Field of Classification Search
CPC .......... A61B 8/04; A61B 8/0891; A61B 8/14; A61B 8/4455; A61B 8/4488;
(Continued)

(56) References Cited

U.S. PATENT DOCUMENTS

| 5,655,276 A | 8/1997 | Pattanayak |
| 5,982,708 A | 11/1999 | Pearce |

(Continued)

FOREIGN PATENT DOCUMENTS

| EP | 1066119 A2 | 1/2001 |
| EP | 2345066 A1 | 7/2011 |
| WO | 2016/008690 A1 | 1/2016 |

OTHER PUBLICATIONS

Smith, Wallace A. "The application of 1-3 piezocomposites in acoustic transducers." [Proceedings] 1990 IEEE 7th International Symposium on Applications of Ferroelectrics. IEEE, 1990. pp. 145-152 (Year: 1990).*

(Continued)

*Primary Examiner* — Sean D Mattson
*Assistant Examiner* — Michael Yiming Fang
(74) *Attorney, Agent, or Firm* — Stuart H. Mayer; Kaplan Breyer Schwarz LLP

(57) ABSTRACT

A conformable piezoelectric transducer array for performing ultrasound or the like includes a silicone elastomer substrate and a silicone elastomer superstrate. A plurality of piezoelectric transducer elements are disposed between the substrate and superstrate. A first electrical interconnect layer electrically interconnects a first surface of the transducer (Continued)

elements adjacent to the substrate and a second electrical interconnect layer electrically interconnecting a second surface of the transducer elements adjacent to the superstrate.

8 Claims, 134 Drawing Sheets

(51) Int. Cl.
*A61B 8/08* (2006.01)
*A61B 8/14* (2006.01)
*B06B 1/06* (2006.01)
*H10N 30/073* (2023.01)
*H10N 30/85* (2023.01)
*H10N 30/87* (2023.01)

(52) U.S. Cl.
CPC .......... *A61B 8/4488* (2013.01); *A61B 8/4494* (2013.01); *A61B 8/5207* (2013.01); *B06B 1/0622* (2013.01); *B06B 1/0685* (2013.01); *H10N 30/073* (2023.02); *H10N 30/852* (2023.02); *H10N 30/875* (2023.02); *B06B 2201/76* (2013.01)

(58) Field of Classification Search
CPC ... A61B 8/4494; A61B 8/5207; B06B 1/0622; B06B 1/0685; B06B 2201/76; H01L 41/0475; H01L 41/183; H01L 41/313; H10N 30/073; H10N 30/852; H10N 30/875
See application file for complete search history.

(56) References Cited

U.S. PATENT DOCUMENTS

| | | | |
|---|---|---|---|
| 6,315,933 B1 * | 11/2001 | Mamayek | H04R 17/00 264/102 |
| 8,421,311 B2 | 4/2013 | Chuang | |
| 2002/0036446 A1 | 3/2002 | Toda et al. | |
| 2007/0038111 A1 * | 2/2007 | Rehrig | A61B 8/06 600/459 |
| 2009/0108710 A1 * | 4/2009 | Brown | H01L 41/08 310/367 |
| 2009/0115290 A1 | 5/2009 | Alexander | |
| 2011/0050039 A1 * | 3/2011 | Toda | H01L 41/09 310/327 |
| 2012/0172721 A1 * | 7/2012 | Curra | A61B 8/4494 600/447 |
| 2015/0078136 A1 | 3/2015 | Sun et al. | |
| 2015/0373831 A1 * | 12/2015 | Rogers | H01M 10/02 429/121 |
| 2018/0106689 A1 * | 4/2018 | Tian | H01L 41/0475 |
| 2019/0150884 A1 * | 5/2019 | Maharbiz | B06B 1/06 |
| 2019/0310231 A1 * | 10/2019 | Mihajlovic | G01N 29/2406 |
| 2023/0165154 A1 * | 5/2023 | Ohashi | B06B 1/0622 600/459 |

OTHER PUBLICATIONS

Yihui Zhang et al: "Buckling in serpentine microstructures and applications in elastomer-supported ultra-stretchable electronics with high areal coverage", Soft Matter, vol. 9, No. 33, Jan. 1, 2013 (Jan. 1, 2013), p. 8062.
Hu et al., "Stretchable ultrasonic transducer arrays for three-dimensional imaging on complex surfaces"; Science Advances, vol. 4, Issue 4 (Mar. 2018), p. 1-11.

* cited by examiner

BRIDGE INTERCONNECTION  ISLAND

1ST LAYER

2ND LAYER

3RD LAYER

4TH LAYER

1ST LAYER CIRCUIT

APPLYING MASK

3RD LAYER

INTEGRATED CIRCUIT

Power: 0.228 mJ
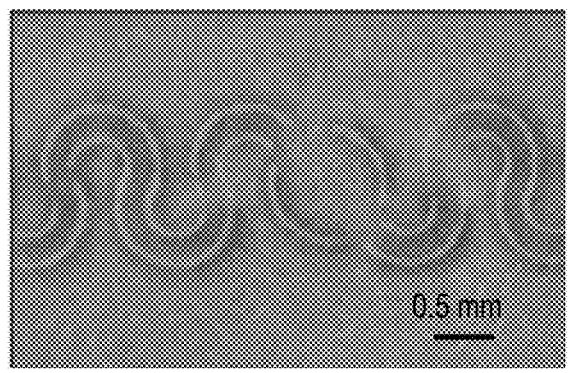
Partial ablation
FIG. 15A
Power: 0.342 mJ
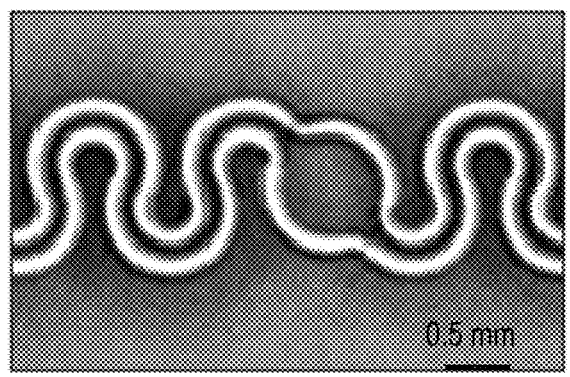
Complete ablation
FIG. 15B
| POWER (%) | POWER (MJ) | FREQUENCY (KHZ) | SPEED (MM/S) | PULSE WIDTH (µS) |
|---|---|---|---|---|
| 60 | 0.342 | 35 | 300 | 1 |
| 40 | 0.228 | 35 | 300 | 1 |
FIG. 15C

Wire widrh: 150 μm

Wire widrh: 120 μm

Wire widrh: 90 μm

Wire widrh: 60 μm

Wire widrh: 50 μm

Wire widrh: 40 μm

→ Breaking points

Wire widrh: 30 μm

Normal polarization at 52.38 kV/cm

Breakdown above 52.38 kV/cm

STRETCHABLE ULTRASONIC TRANSDUCER DEVICES

CROSS-REFERENCE TO RELATED APPLICATION

This application is a 371 National Phase of PCT/US18/13116, filed Jan. 10, 2019, which claims priority to U.S. Provisional Application No. 62/444,524, filed Jan. 10, 2017 and 62/586,645, filed Nov. 15, 2017, the contents of which are incorporated herein by reference.

BACKGROUND

Ultrasound imaging technologies have been widely used to visualize internal discontinuities in objects for non-destructive evaluation, structural health monitoring, and medical diagnosis due to their non-invasiveness, high accuracy, great sensitivity, and strong penetration capabilities. Ultrasound probes with flat bases have been created to successfully accommodate different components of planar surfaces. However, these rigid probes cannot achieve a solid interfacial contact and therefore good coupling with irregular nonplanar surfaces, which are ubiquitous in real objects. Air gaps at these interfaces lead to large acoustic energy reflections and wave distortions, thereby creating unreliable testing results (FIG. 6). Ultrasonic couplants, such as water and gel, are typically used to remove the air gaps. However, an abundant use of the couplants will lead to high-pass filter effect of the ultrasonic signals, causing huge canceling of small response echoes. Furthermore, extensively using of the couplants will bring about ~80% incident energy transmission loss at the interface between the couplant and the subject due to the significant mismatch of their acoustic impedances. In addition, these rigid and bulky probes cannot be applied to hard-to-reach locations such as small cavities and slits. Thus, components at such locations normally have to be disassembled for a reliable diagnosis. At the same time, the stress concentrations present at the geometrical discontinuities of load-bearing objects make these regions particularly prone to defects. Although many methods have been reported to solve this interfacial coupling problem, a number of disadvantages of the existing approaches remain, such as limited specimen size, demanding probe offset, and bulky probe housing, all of which compromise the feasibility of in-situ detection, detection accuracy and sensitivity, and operation convenience of ultrasonic measurements.

Recent efforts have focused on developing flexible ultrasonic probes that can be mainly divided into three categories: using organic piezoelectric films as transducers, embedding piezoelectric ceramic into polymer substrates, and fabricating capacitive micromachined ultrasonic transducers (CMUTs). The organic piezoelectric films have good flexibility. However, the polymer piezoelectrets, typically polyvinylidene fluoride and its copolymer films, are not suitable for serving as transmitters due to their low electromechanical coupling coefficients (a parameter that characterizes the coupling between electrical energy and mechanical energy), low dielectric constants and high dielectric losses. Moreover, their low Curie points make them difficult to process, and high temperature applications result in phase transformations, which completely degrade piezoelectric properties. The piezoelectric ceramics produce superior electromechanical performance and ease of processing. However, they cannot conform to curved surfaces without external forces due to the large elastic moduli of substrates. The external force, usually applied manually, is often inconsistent. As a result, noise or even artifacts in the acquired pulse-echo signals can arise due to variations of the coupling conditions at the transducer-specimen interface. What's more, for some applications related to long-term structural condition monitoring, such as fatigue crack growth at hidden or hard-to-access places of aircrafts and steamboats, the mechanical robot cannot support the testing. The CMUTs are fabricated on disjoined silicon wafers and the polydimethylsiloxane (PDMS) refilling the trenches among the elements makes transducers flexible. This passive polymer filler compromises their conformability on curved surfaces. Besides, the silicon substrates are likely to be secondary resonators that generate longitudinal waves with unwanted frequencies and eventually result in artifacts in the images. Also, CMUTs generally have lower electromechanical efficiency than piezoelectric ceramics due to inhomogeneity and parasitic capacitances among the arrayed elements. In all cases, these flexible probes can only conform to developable surfaces (such as cylindrical surfaces), not to non-developable surfaces (such as spherical surfaces). In addition, the flexible conductive interconnections are subject to breaking or de-bonding when repeatedly used, because being flexible is insufficient to accommodate the sophisticated and time-dynamic motion of the electrodes and the device during the measurements. These drawbacks represent a bottleneck for the development of advanced probes that combine excellent ultrasonic performance with desirable mechanical properties that allow for application to general complex surfaces.

SUMMARY

Disclosed are materials, devices, systems and methods that pertain to stretchable ultrasound probes that can conform and detect on nonplanar complex surfaces. In some embodiments these probes rely on piezoelectric materials and advanced microfabrication of soft electronics. The devices can be seamlessly integrated with the human body for rapid and compact healthcare applications, e.g. wearable deep tissue imaging and therapy.

In an exemplary embodiment, a device is microfabricated by transfer printing thin layers of patterned metal electrodes, inorganic piezoelectric single crystal arrays, and polymer encapsulation materials on a biocompatible silicone membrane. By engineering the overall device structure, the mechanical properties of the device would match those of the biological tissues, and therefore minimize the mechanical loading of these devices.

In one embodiment, a stretchable ultrasound probe comprising a 10×10 array of high-performance 1-3 piezoelectric composite transducers exploiting an "island-bridge" layout with multi-layer electrodes, encapsulated by thin and compliant silicone elastomers, has exhibited excellent electromechanical coupling, minimal cross-talk, and over 50% stretchability. Its performance is demonstrated by reconstructing defects in 3D space with high spatial resolution through flat, concave, and convex surfaces.

The resulting device has excellent electromechanical coupling coefficient ($k_{eff}$~0.60), high signal-to-noise-ratio (SNR) (~20.28 dB), wide bandwidth (~47.11%), negligible cross-talk level between adjacent elements (~−70 dB), and high spatial resolution (~610 μm) at different depths. The "island-bridge" layout offers biaxial reversible stretchability of over 50% with minimal impact on transducer performance, which allows the device to work on nonplanar complex surfaces. With these unique properties, the device can obtain 3D images of complex defects under flat, concave, and convex surfaces.

In another embodiment, a skin-integrated conformal ultrasonic device with an ultrathin profile (240 μm in thickness), a high reversible stretchability (60%), and a comparable axial resolution (400 μm) with commercial transducers, has been demonstrated to launch ultrasonic waves penetrating into deep tissues non-invasively to acquire accurate central blood pressure (CBP) waveforms at deeply embedded arterial and venous sites to monitor cardiovascular events in a gel-free manner.

BRIEF DESCRIPTION OF THE DRAWINGS

FIGS. 15A-15C show optical images of the Cu serpentine interconnections under different laser parameters.

FIG. 69D provide statistics of the PWV in these measurements.

DETAILED DESCRIPTION

Stretchable Ultrasonic Array Overview

Figure 1A:
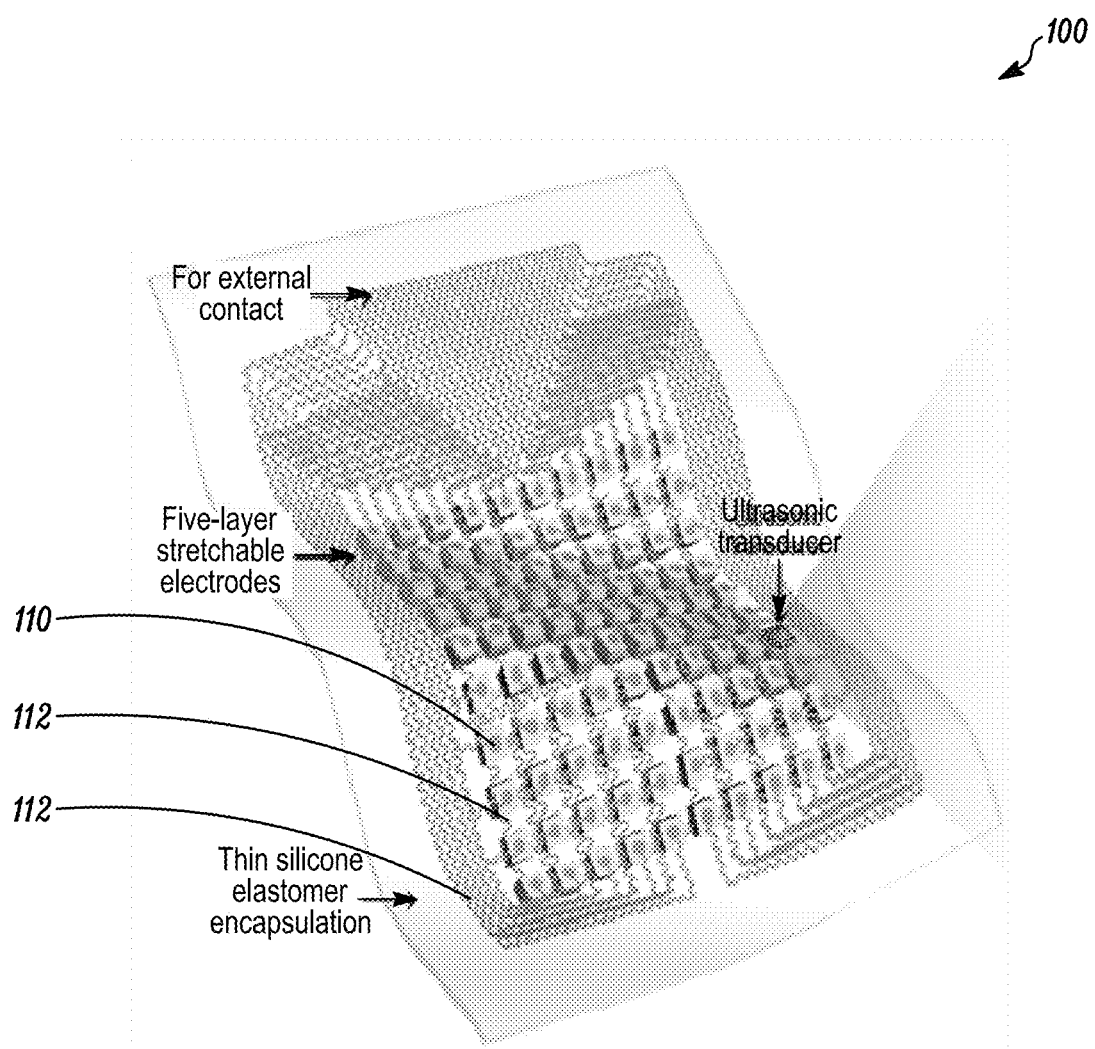
FIGS. 1A-1H schematically illustrate the design of one example of a stretchable ultrasonic transducer array.

One example of a stretchable ultrasonic transducer array 100 is shown in FIG. 1A. The piezoelectric transducers are arranged in a 10×10 array, connected by an "island-bridge" structured matrix. Each island hosts a rigid transducer element 110. The wavy bridges 112 can unfold to accommodate the externally applied strain, with limited strain on the components themselves. Therefore, the matrix is rigid locally but soft globally. Each transducer element in the array is individually addressable. The soft probe can consequently reconstruct the target morphology in multi-section images.

Figure 1B:
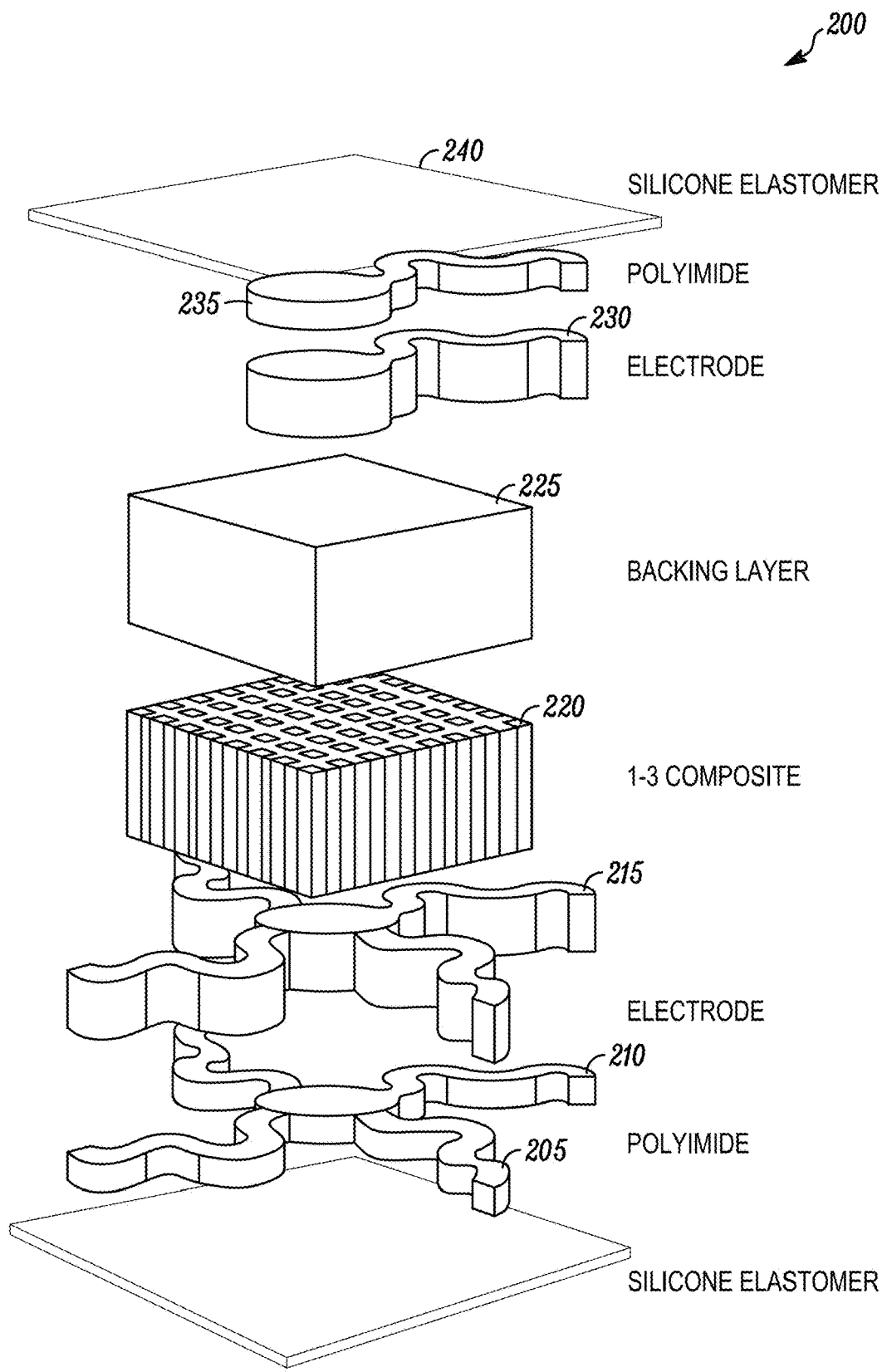
Figure 8:
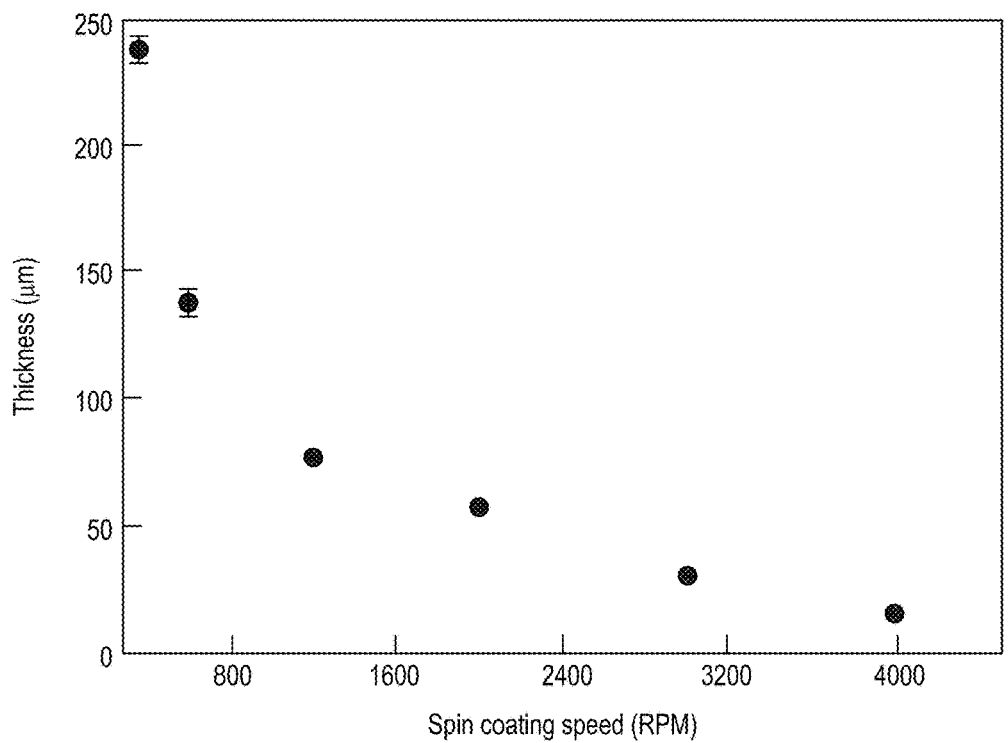
FIG. 8 shows the Ecoflex thickness as a function of spin coating speed on a glass slide.
Figure 9:
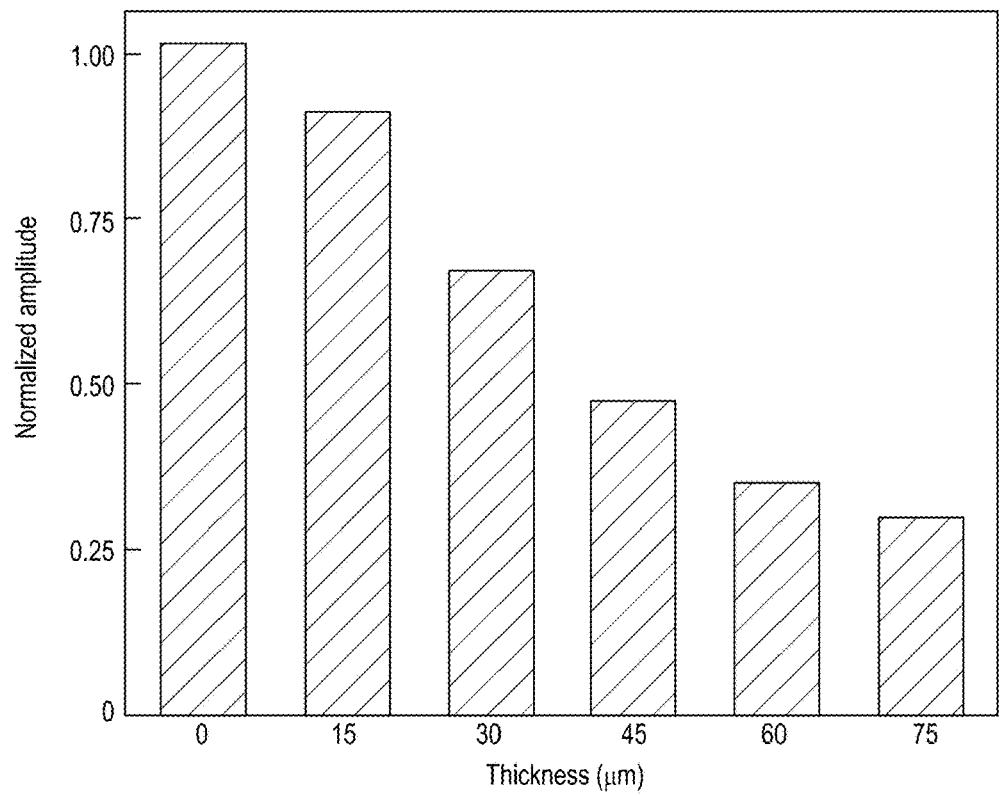
FIG. 9 illustrate the acoustic damping effects of silicone substrates.

FIG. 1B shows the exploded view of one transducer element 200. In this example both the substrate and superstrate are silicone elastomer thin films, whose low modulus (~70 kPa) and large stretchability (~900%) offer an extremely compliant platform to accommodate a diverse class of building blocks, such as piezoelectric elements, metal interconnects, backing layers, and solder paste. More specifically, in this example the transducer element 200 includes a substrate 205, a first patterned bilayer that includes a polymide layer 210 and an electrode 215, a piezoelectric electric 220, a backing layer 225, a second patterned bilayer that includes a polymide layer 235 and an electrode 230, and a superstrate 240. The elastomer substrate and superstrate thickness are 15 μm to provide both high acoustic performance and mechanical robustness of the device (FIGS. 8 and 9). As noted above, the islands and bridges are formed from patterned bilayers of Cu (20 μm)/polyimide (PI, 2 μm). The PI layer greatly enhances the bonding strength between the Cu and elastomer.

Figure 1C:
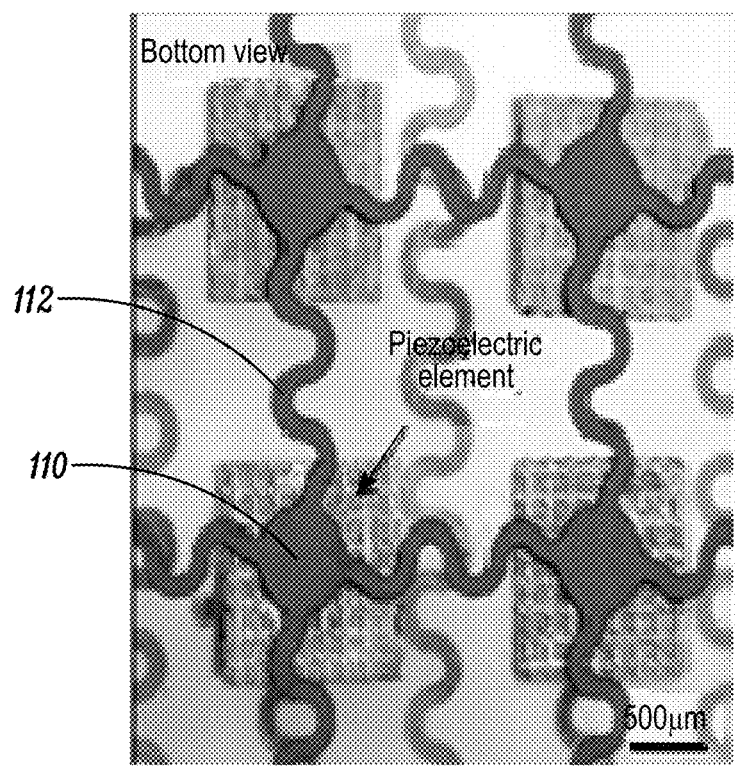
Figure 1D:
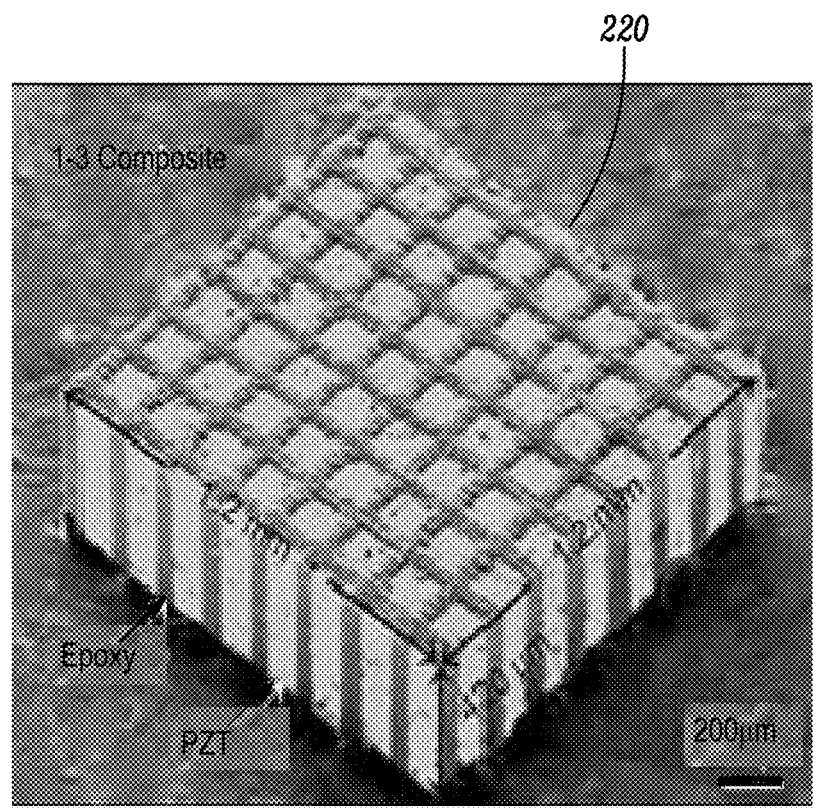
Figure 10A:
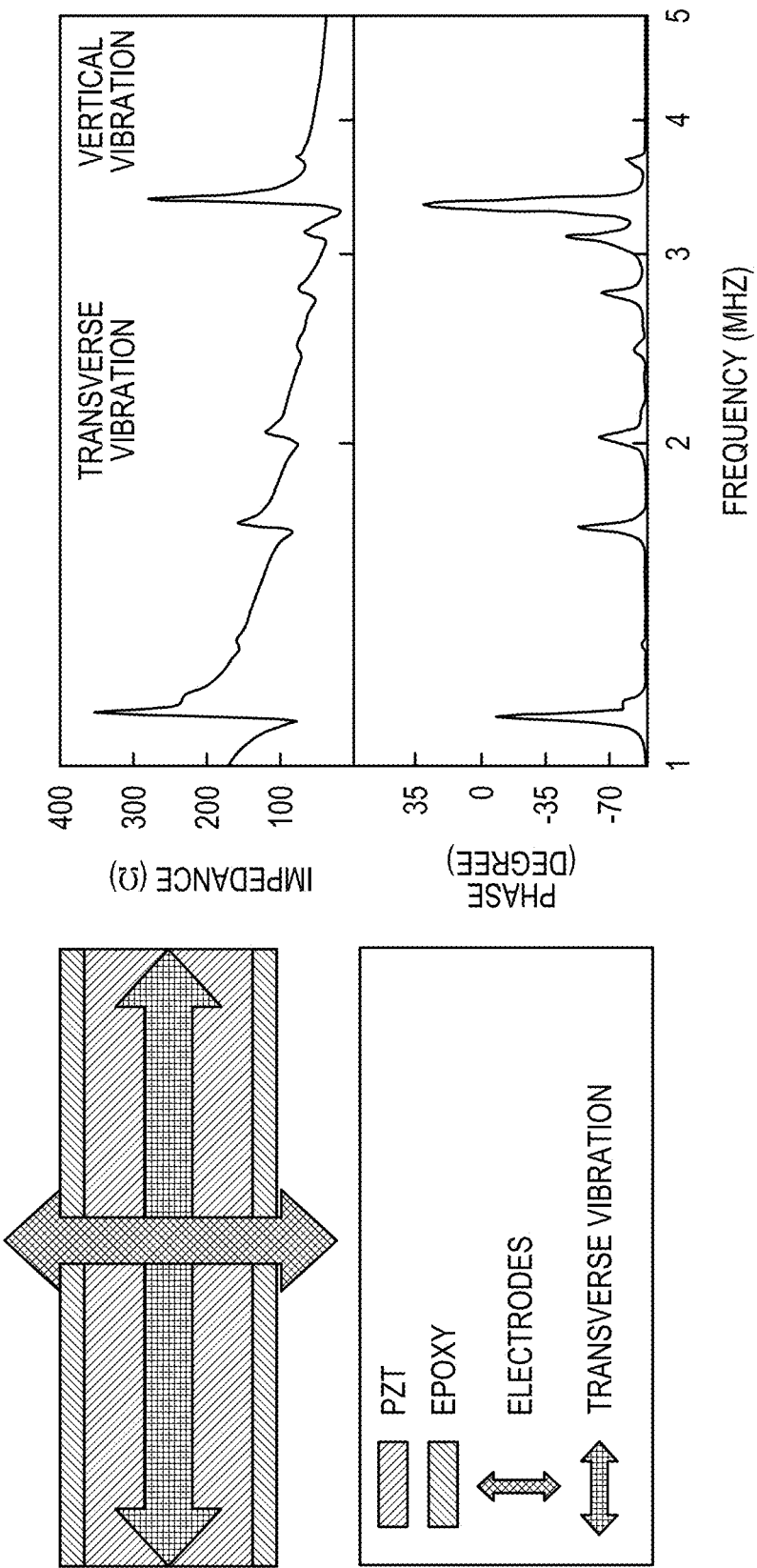
FIGS. 10A and 10B show a comparison of the vibrational modes of conventional PZT material and 1-3 composites, respectively.
Figure 10B:
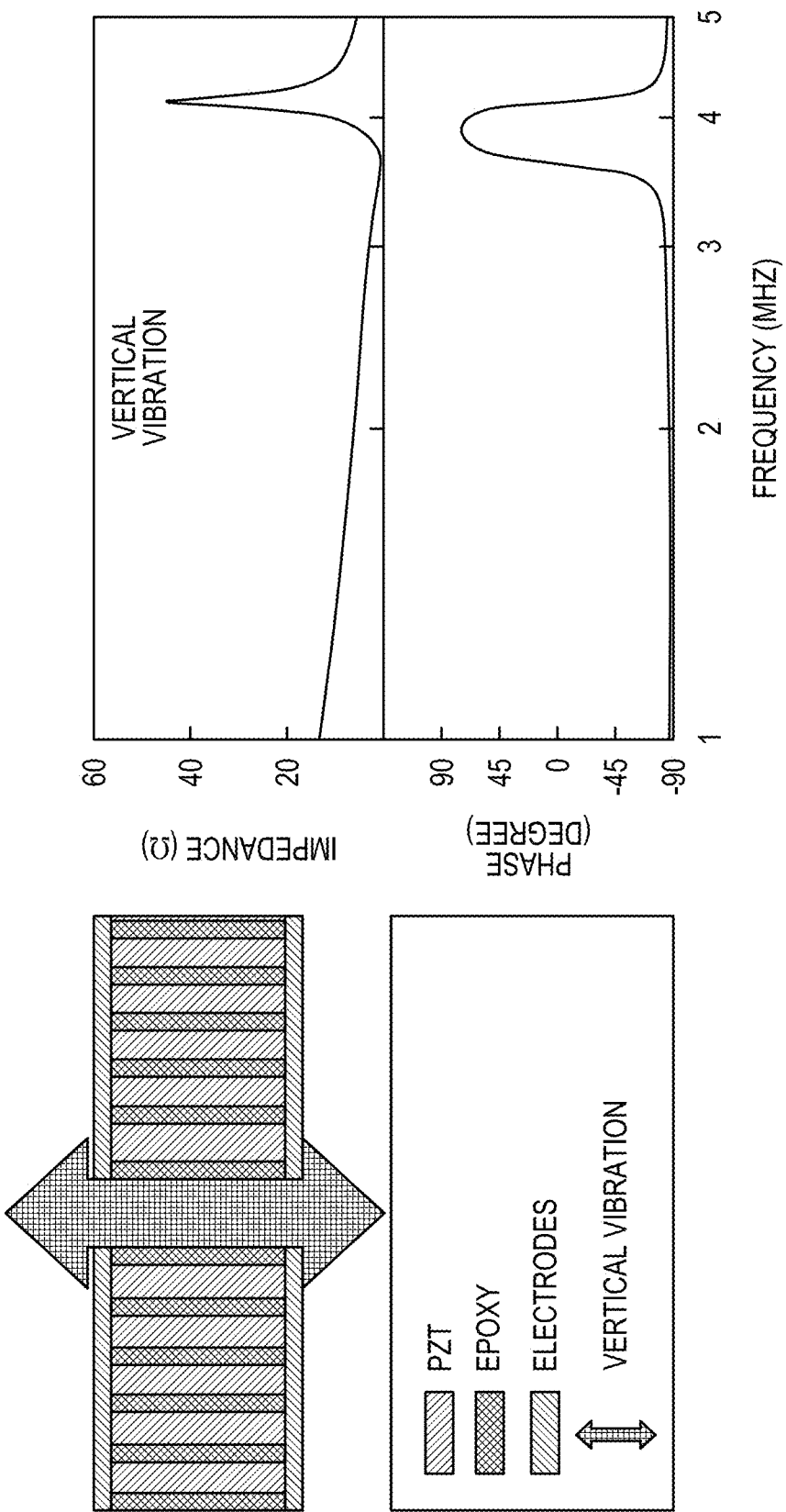
Figure 11A:
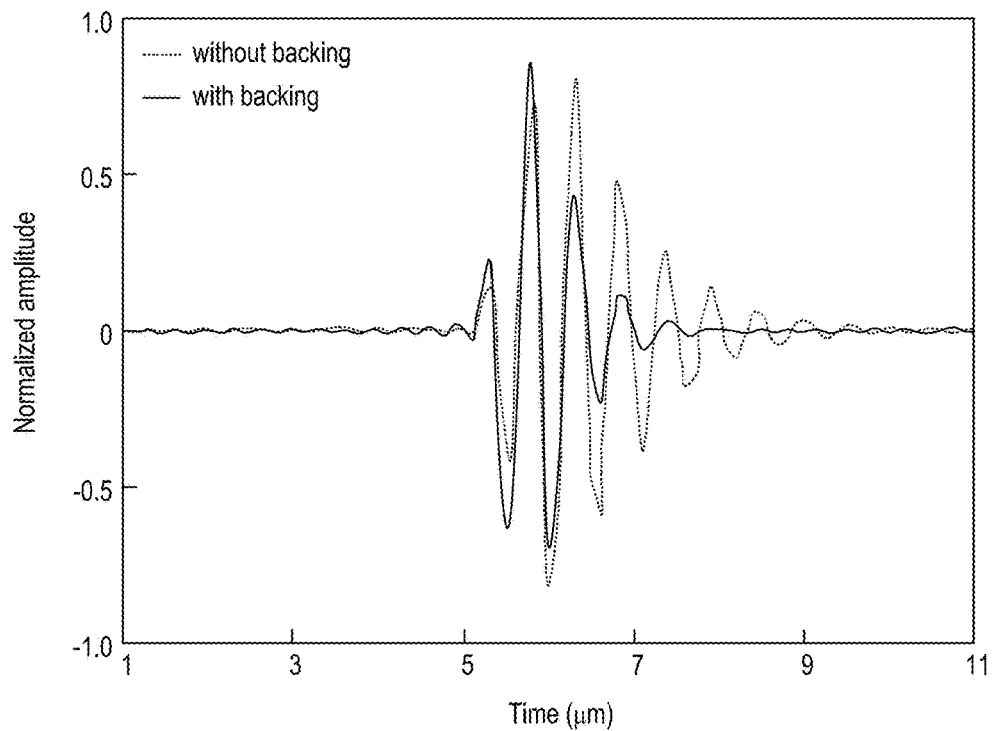
FIGS. 11A and 11B respectively show the pulse-echo response and bandwidth differences of transducers with and without the backing layer (KLM simulation).
Figure 11B:
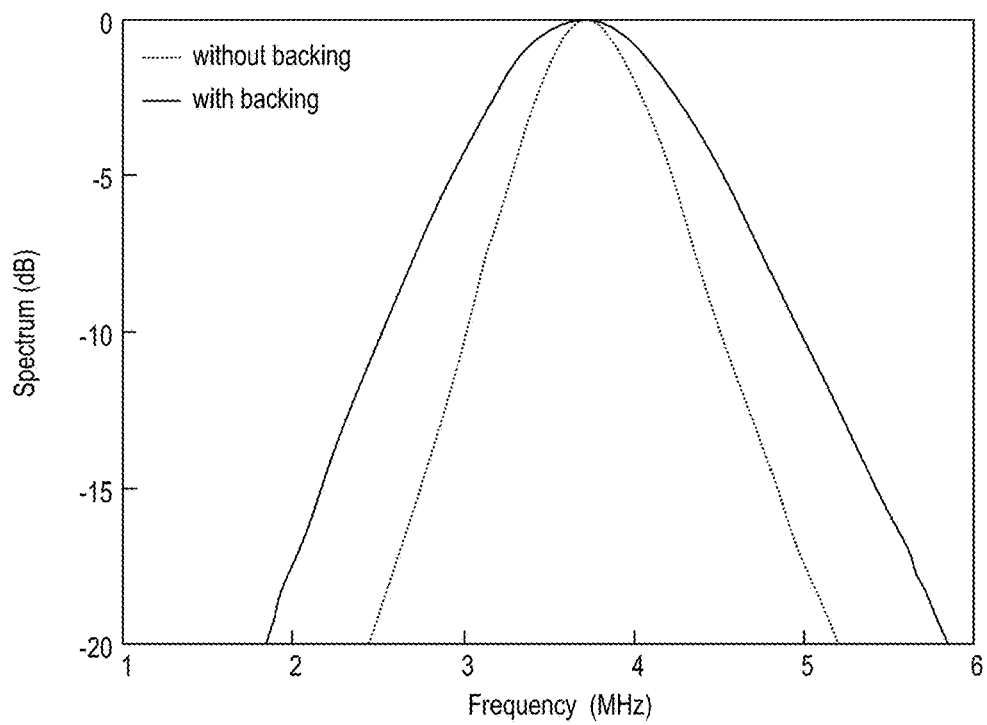

In one embodiment, piezoelectric 1-3 composites are chosen as the active material of the transducers. FIG. 1C shows an optical image of a bottom view four transducer elements 110 and FIG. 1D an SEM image of a piezoelectric 1-3 composite. Compared with an isotropic PZT, the anisotropic 1-3 composites have superior electromechanical coupling coefficients (thickness mode) that convert the majority of electric energy to vibration energy. In addition, the surrounding epoxy filler effectively suppresses transverse vibrations of PZT pillars (FIGS. 10A and 10B), leading to enhanced longitudinal waves that go into the targeted objects. As seen in the optical image of FIG. 1E, the backing layer 225 effectively dampens ringing effects (excessive vibrations) of the piezoelectrics, which shortens spatial pulse lengths, and broadens the bandwidth and thus improves the image axial resolution. This is illustrated in the KLM simulations of the pulse-echo response and bandwidth differences of transducers with and without the backing layer shown in FIGS. 11(A) and 11(B). Silver epoxy and solder paste are used to build robust and electrically conductive interfaces of 1-3 composite/backing layer and 1-3 composite/metal electrode, respectively. Because of the close acoustic impedances of 1-3 composite (~20 Mrayl) and the targets to be tested (Al, ~18 Mrayl), the matching layer is not necessary in this study.

On the one hand, the pitch between adjacent transducer elements should be small to reduce side lobe and grating lobe artifacts in the acquired images. On the other hand, sufficient space between elements should be allocated to the serpentine interconnects for sufficient stretchability. In one embodiment, a pitch of 2.0 mm (1.2 mm×1.2 mm element footprint with a spacing of 0.8 mm between each column) is employed, which can achieve over 30% reversible stretchability. The high spatial resolution (~610 μm), negligible cross-talk level between adjacent elements (~−70 dB), and artifact-free images validates this pitch design. Within such limited footprints, the "island-bridge" electrode layout design is critical considering the large number of electrical connections needed for wiring the 10×10 array. An active multiplexing matrix under the ultrasound transducers could be a potential solution. However, the structural support materials introduced by the multiplexing matrix will negatively impact the device stretchability. Multilayered electrodes have been demonstrated, but the electrode design, passive dielectrics, and the substrate make the devices only flexible but not stretchable. To individually address the 100 transducer elements, a minimum of 101 electrodes with a common ground electrode is needed. It is very challenging to place this large number of electrodes within limited footprints using conventional single layer designs.

Figure 12A:
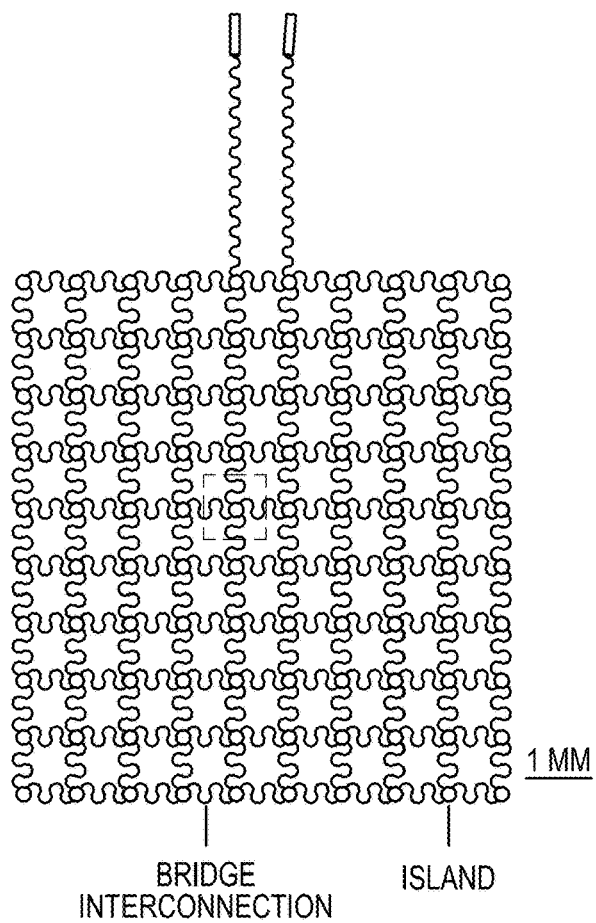
FIGS. 12A and 12B show an optical image of the bottom electrode design and one unit of the bottom electrode, respectively.
Figure 12B:
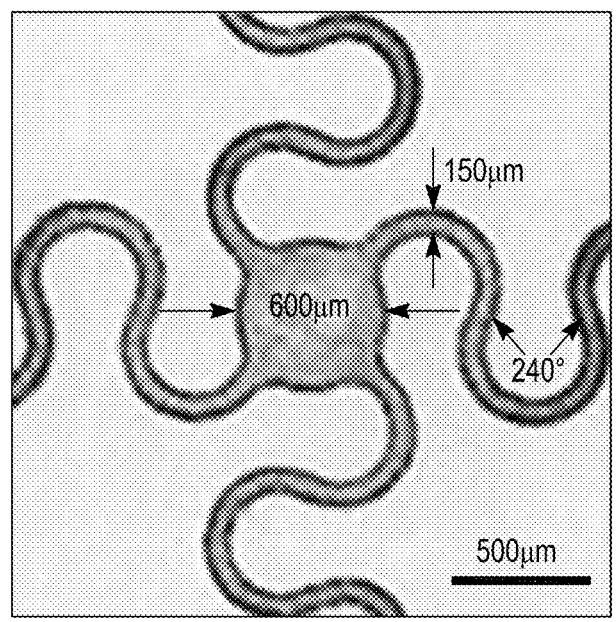
Figure 13A:
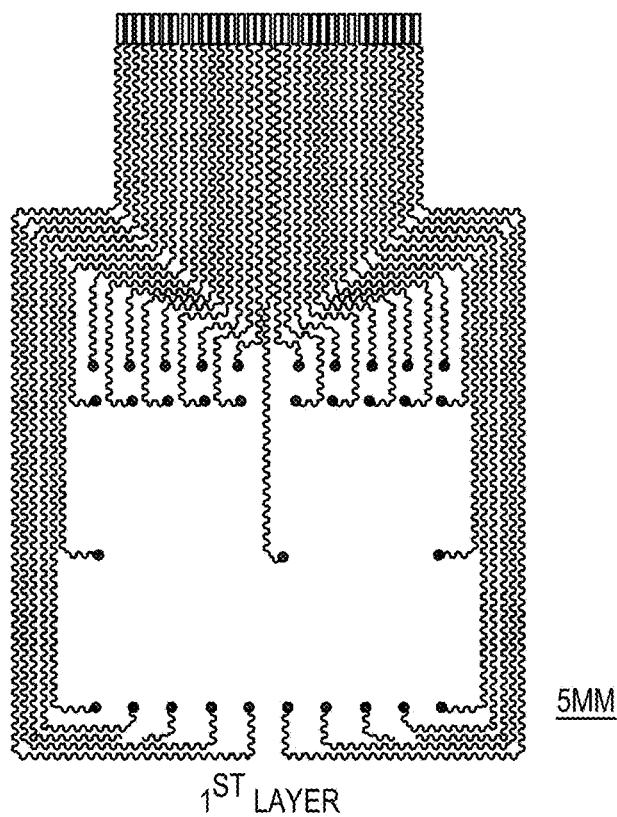
FIGS. 13A-13D show the $1^{st}$, $2^{nd}$, $3^{rd}$, and the $4^{th}$ layer electrodes, respectively.
Figure 13B:
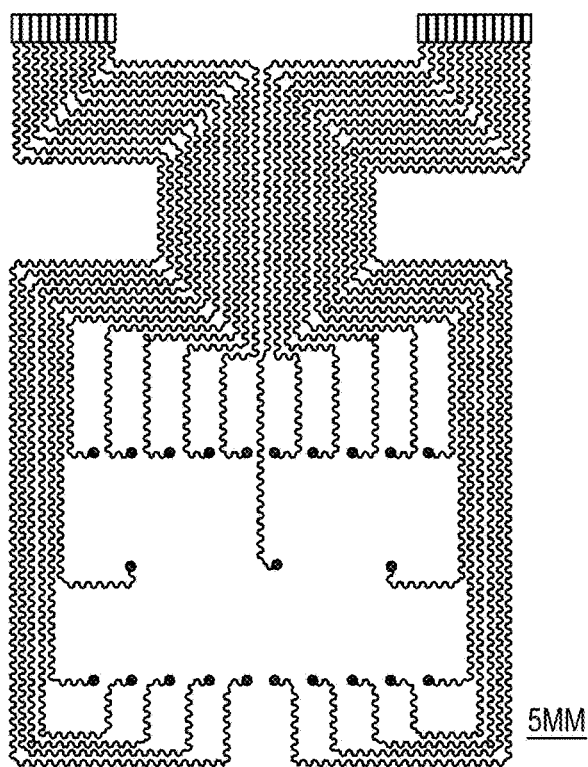
Figure 13C:
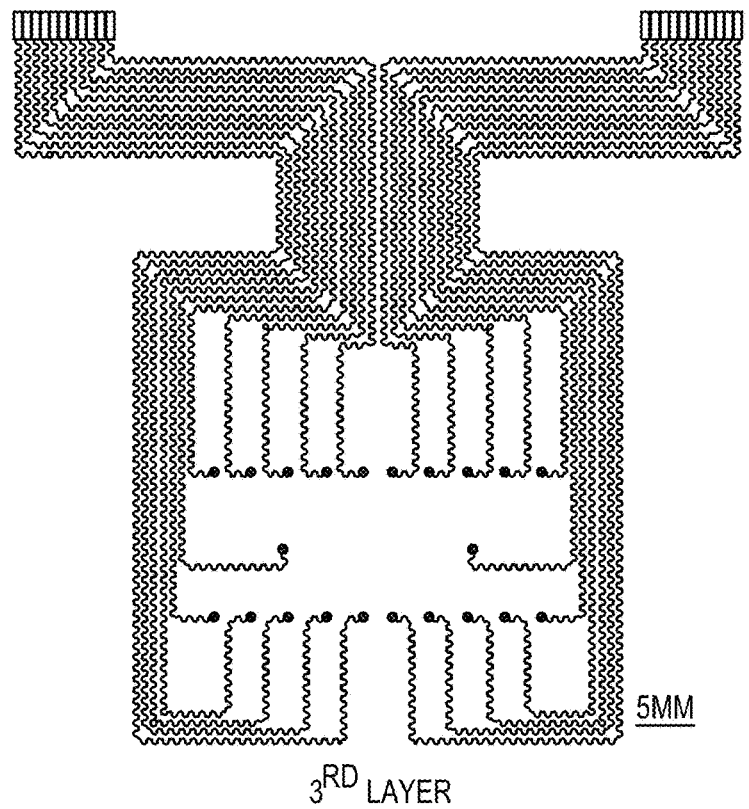
Figure 13D:
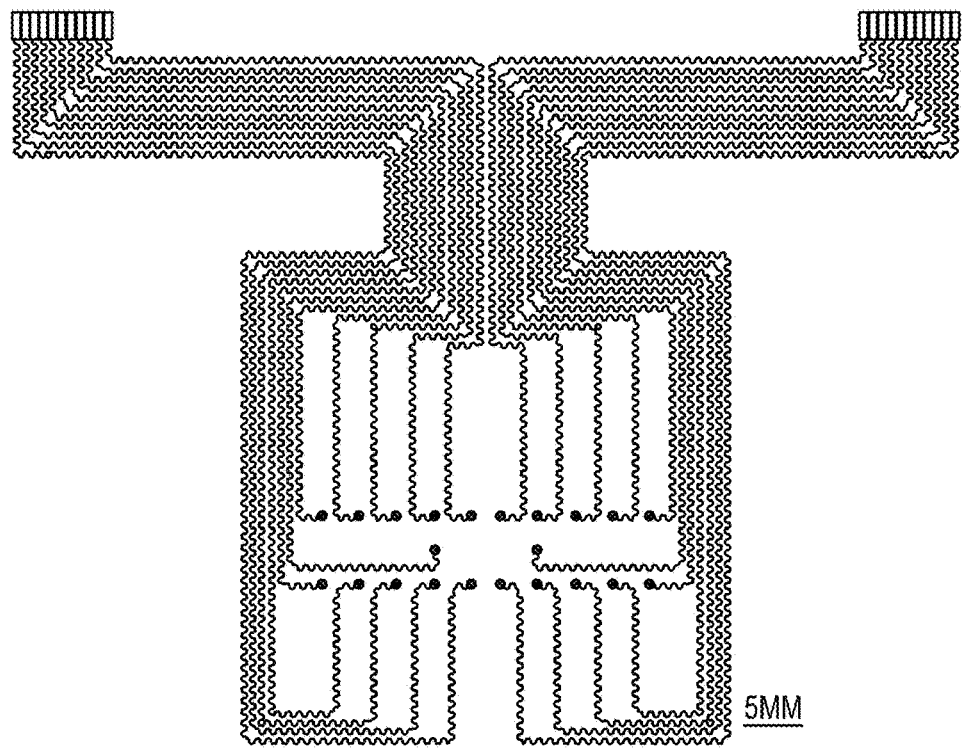
Figure 13E:
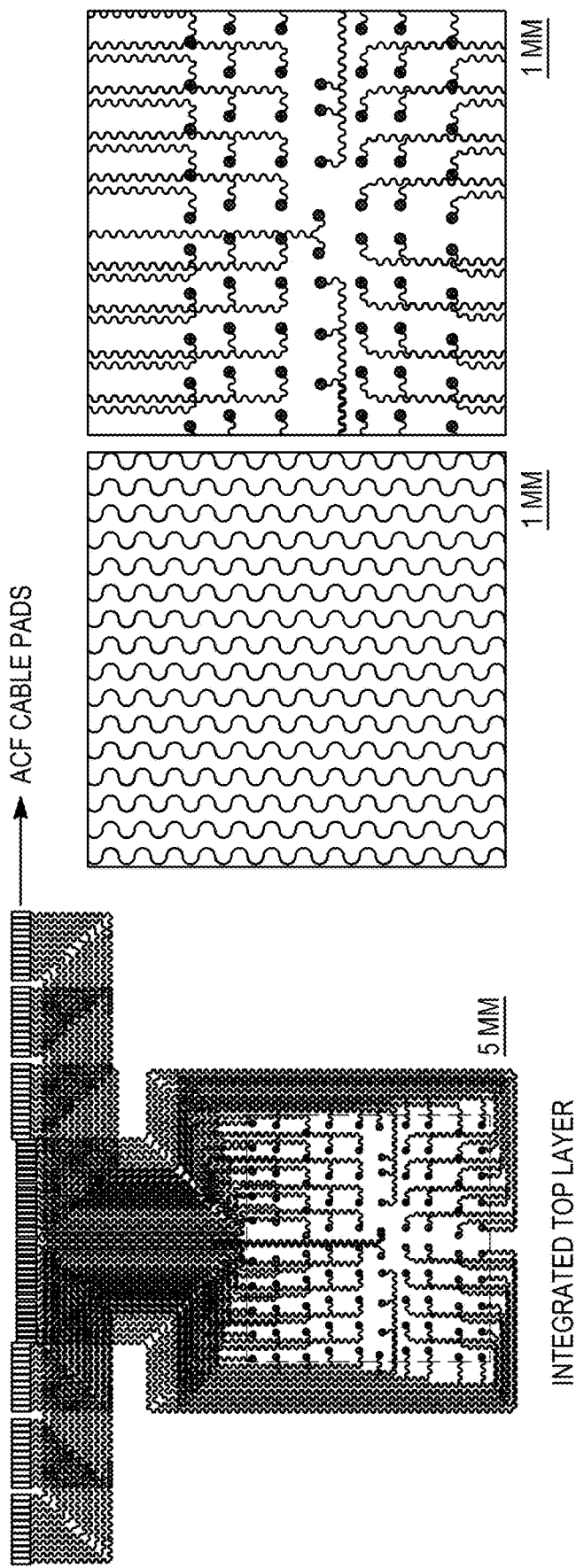
FIG. 13E shows the integrated top electrode, with zoomed-in images showing aligned multilayered serpentine electrodes and contact pads for the transducer elements.
Figure 14A:
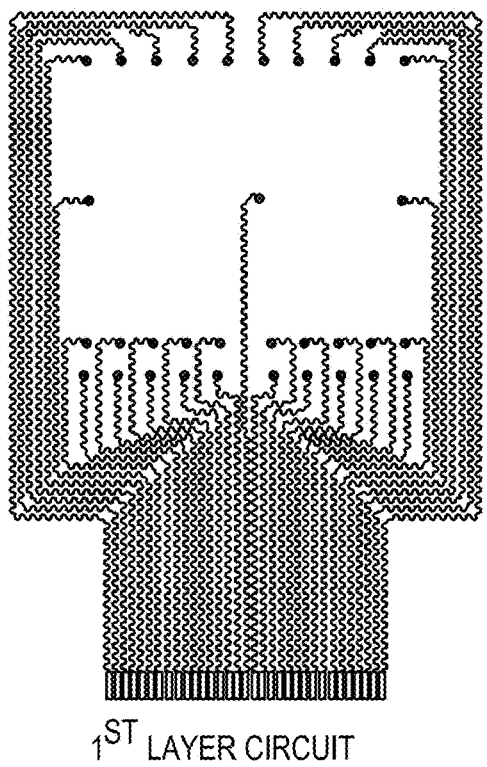
FIGS. 14A-14H show the four-layer top electrode fabrication processes.
Figure 14B:
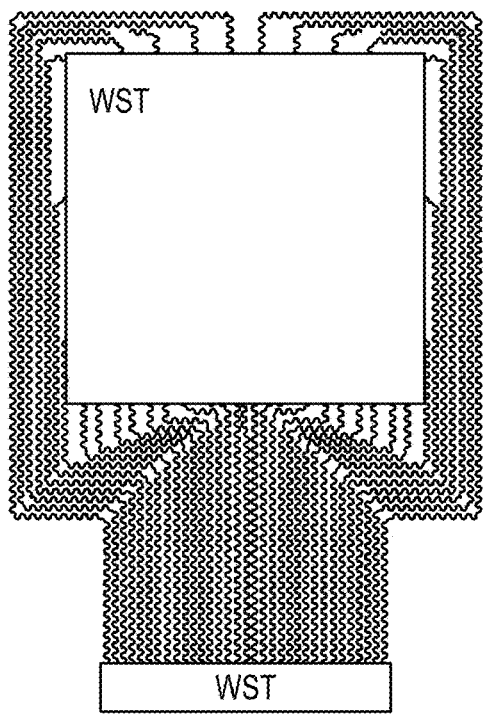
Figure 14C:
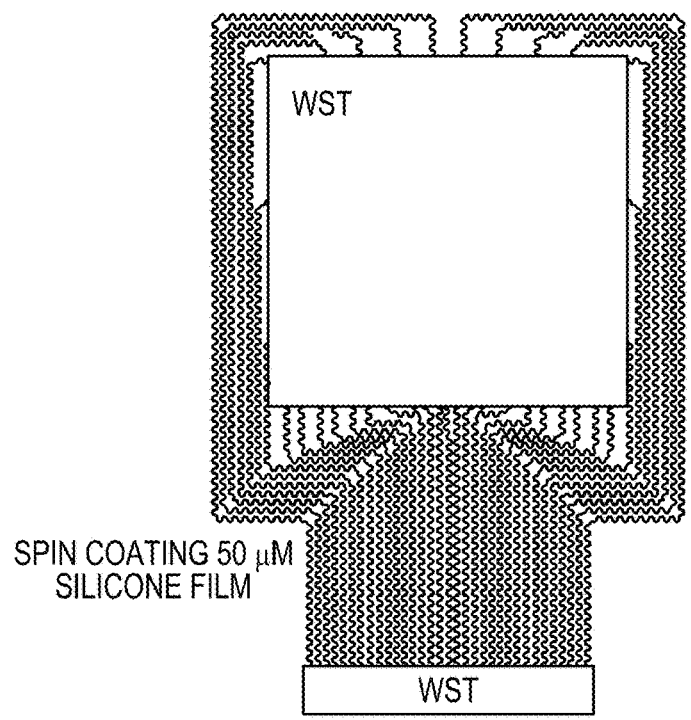
Figure 14D:
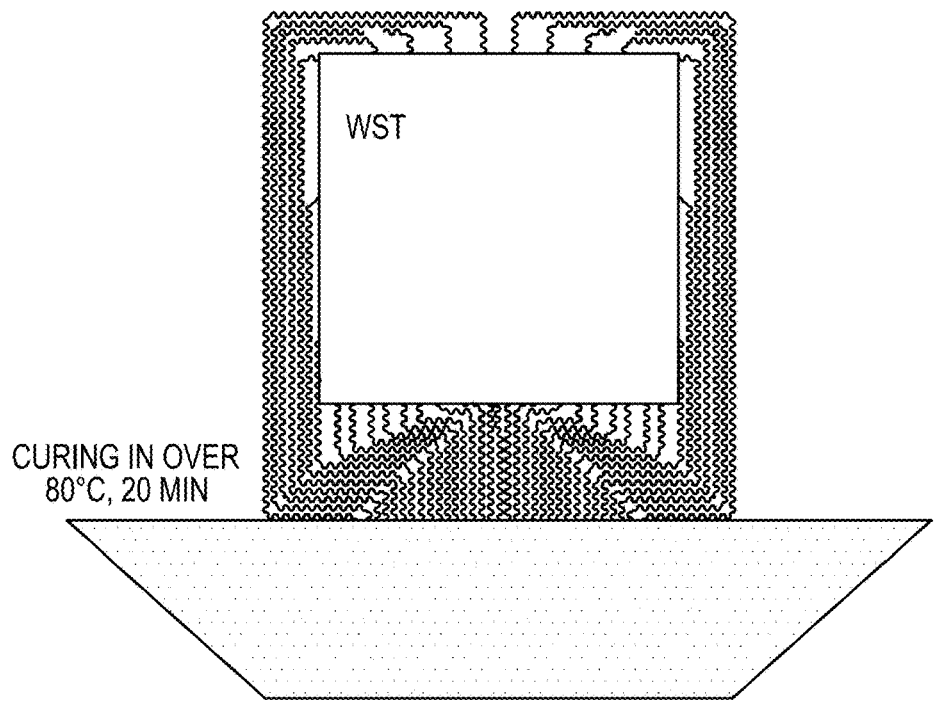
Figure 14E:
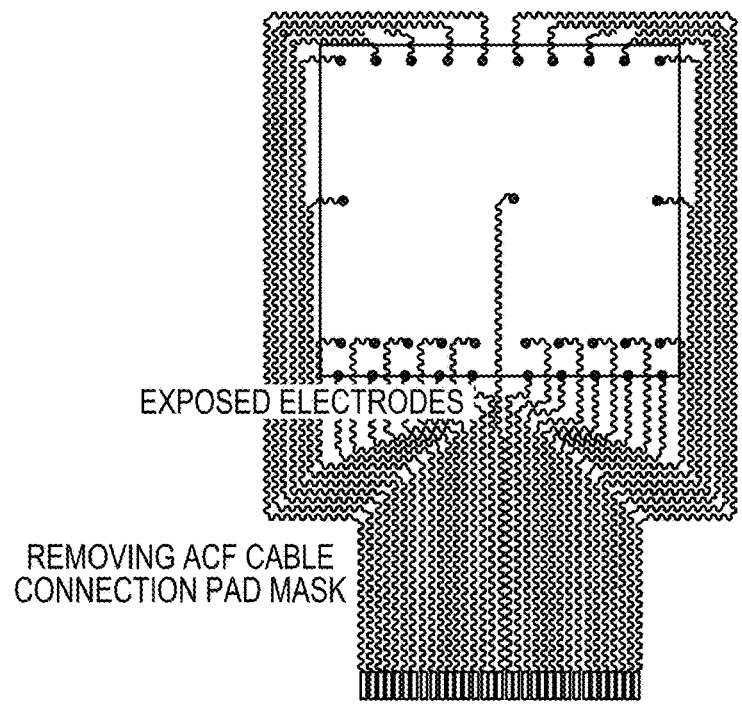
Figure 14F:
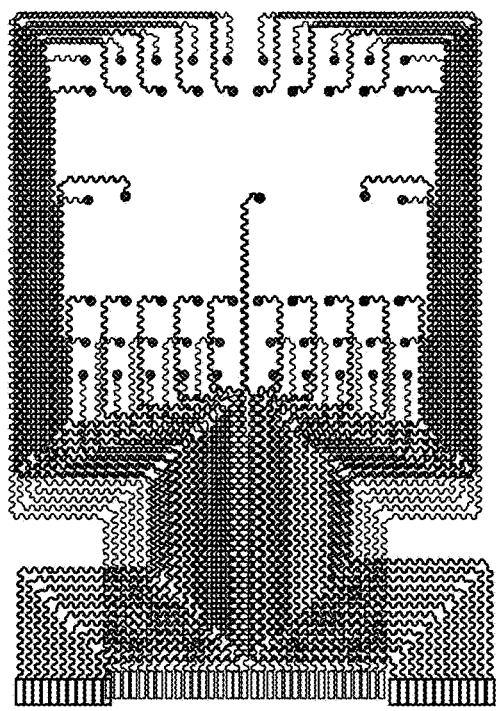
Figure 14G:
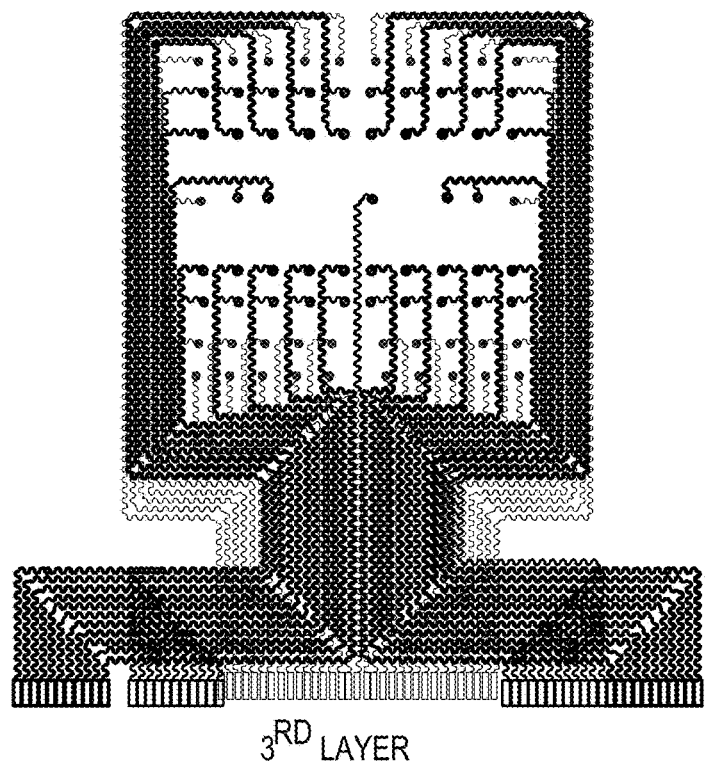
Figure 14H:
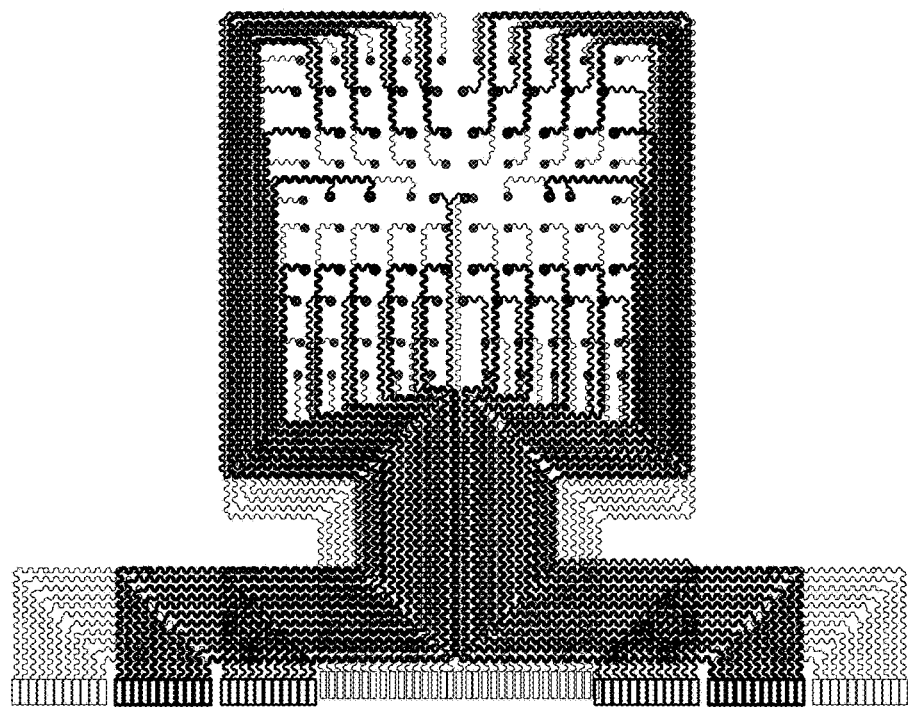
Figure 16A:
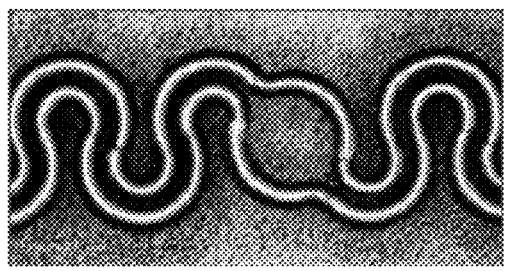
FIG. 16A-FIG. 16G show laser ablation resolution experiments in which Cu serpentine wires are designed from 150 μm to 30 μm.
Figure 16B:
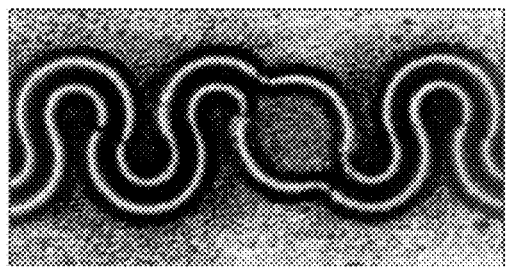
Figure 16C:
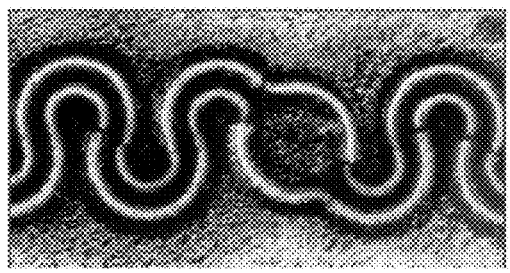
Figure 16D:
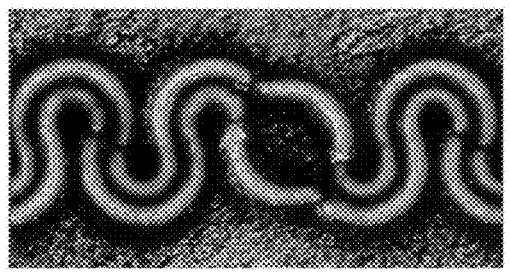
Figure 16E:
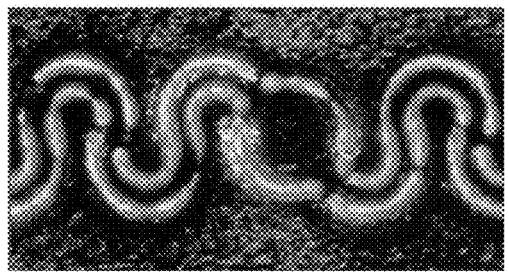
Figure 16F:
Figure 16G:

Thus, a multilayered electrode design has been developed based on the "transfer printing" method, which greatly enhanced the level of device integration compared to single layer designs. In one embodiment, this design includes five layers of "horse-shoe" configured serpentine electrodes. One electrode lies at the bottom of the transducers as a common ground layer. FIG. 12A shows the island-bridge structured interconnection of the bottom electrode and FIG. 12B shows one unit of the bottom electrode. The other 100 electrodes are well aligned and distributed into four layers on top of the transducers as stimulating electrodes. FIGS. 13A-D show the $1^{st}$, $2^{nd}$, $3^{rd}$, and the $4^{th}$ layer electrodes, respectively, and FIG. 13E shows the integrated top electrode, with zoomed-in images showing aligned multilayered serpentine electrodes and contact pads for the transducer elements.

Thin films of silicone elastomer (35 μm thick) provide insulation and adhesion between adjacent layers. The central area of each layer is selectively protected using customized masks during fabrication to allow the islands (bonding pads) to be exposed to the array elements. FIGS. 14A-14H illustrate the four-layer top electrode fabrication processes in which the electrodes and connection pads are selectively hidden using water soluble tape (WST) masks. Laser ablation is used to quickly pattern serpentine structures, which is shown in FIGS. 15A and 15B for both partial ablation and complete ablation. FIGS. 16A-16G shows laser ablation resolution experiments in which Cu serpentine wires are designed from 150 μm to 30 μm. Wires with widths of 150 μm to 40 μm remain intact and discontinuities start to arise when the wire width is 30 μm. This method has been mostly focused on rigid or flexible substrates but few studies on silicone substrates for stretchable electronics. The challenges for using on stretchable substrates are (1) controlling the laser power to fully ablate the pattern while avoiding the pattern delamination from the temporary PDMS substrate, and (2) tuning the surface tackiness of the temporary PDMS substrate to allow the subsequent transfer printing of the patterned electrodes. These challenges have been overcome and a fabrication protocol has been developed for stretchable electronics using the laser ablation, which will be discussed in more detail below.

Figure 1E:
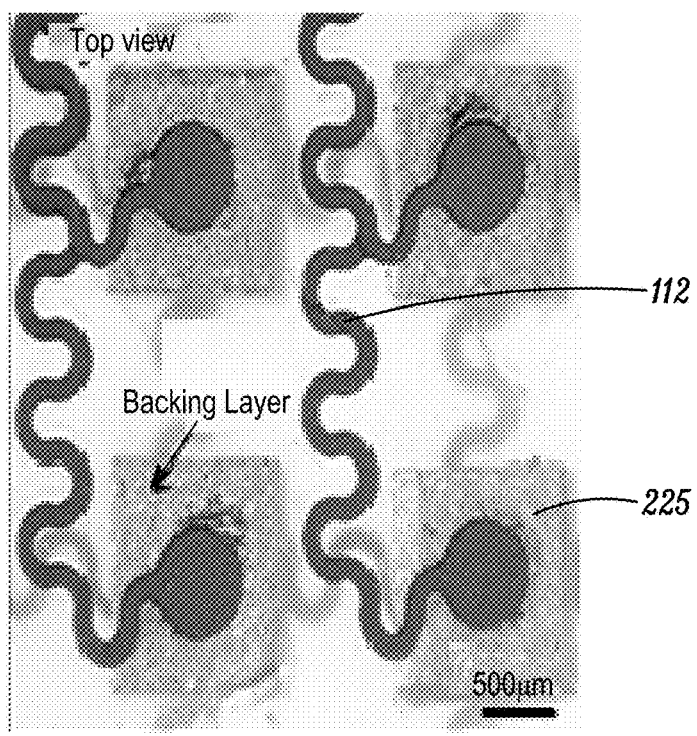
Figure 1F:
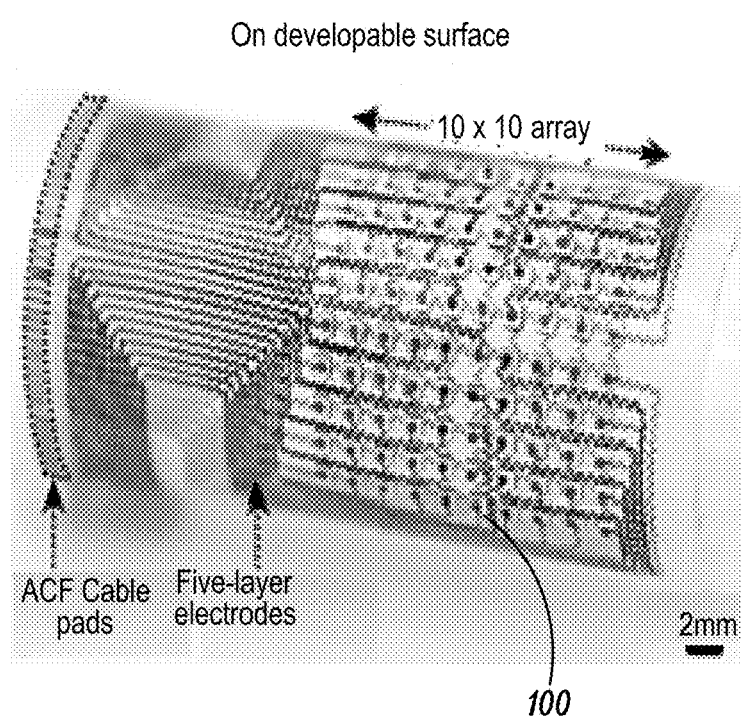
Figure 1G:
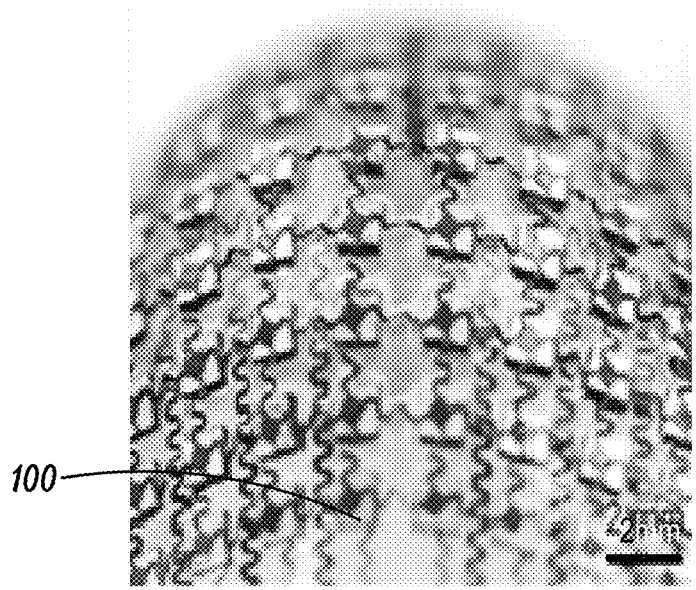
Figure 1H:
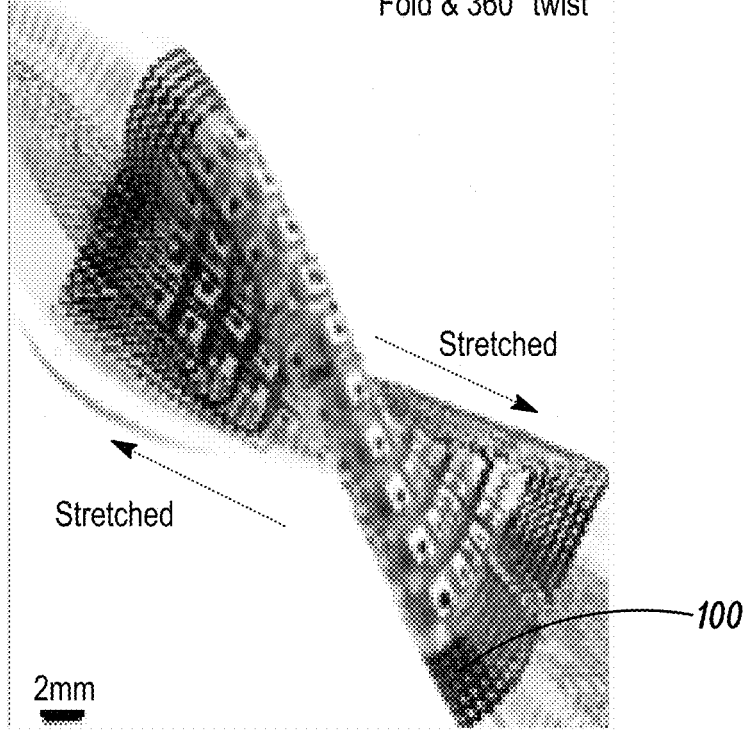

Compared with microfabrication methods by lithography and etching, which requires sophisticated fabrication processes, chemicals, shadow masks, and a cleanroom environment, laser ablation is time efficient, low cost, and offers high throughput. The as-fabricated final device is seen in FIGS. 1F to 1H, which highlight its excellent mechanical properties when conforming to developable (cylindrical) and non-developable (spherical) surfaces, and under mixed modes of folding, stretching and twisting. In particular, FIGS. 1F-1H respectively show optical images of the stretchable device when bent around a developable surface, wrapped on a non-developable surface, and in a mixed mode of folding, stretching, and twisting, showing its mechanical robustness.

Figure 17A:
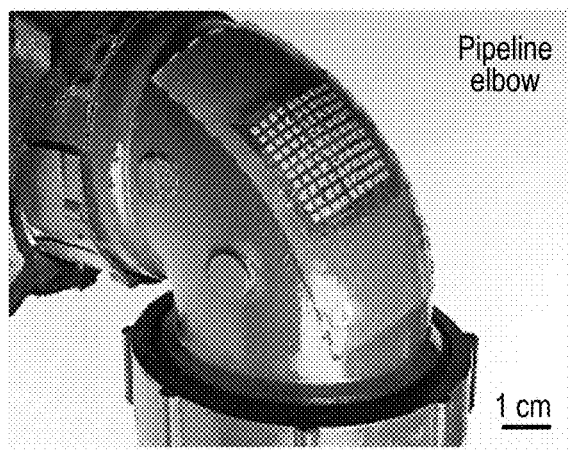
FIGS. 17A-17C show photographs of the transducer device seamlessly laminated on different curved surfaces.
Figure 17B:
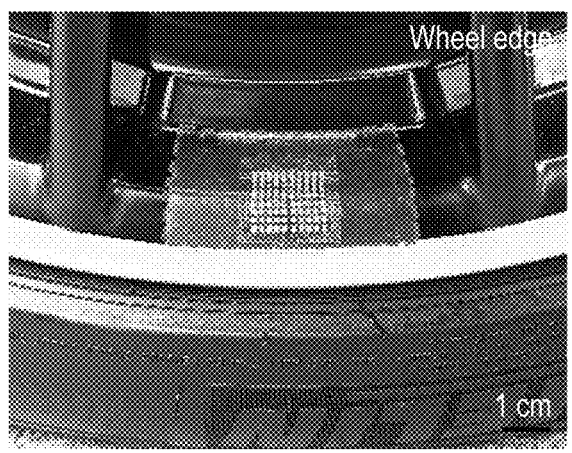
Figure 17C:
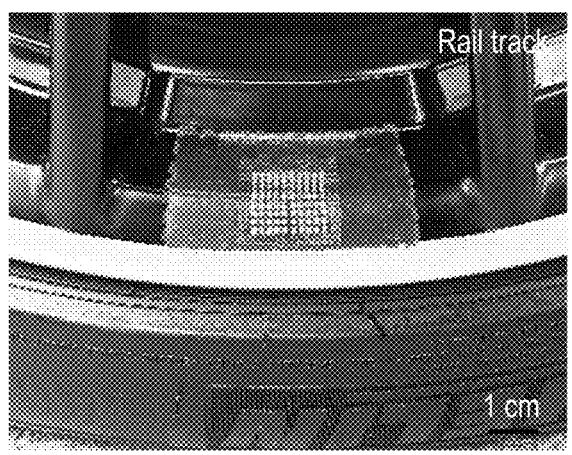
Figure 18:
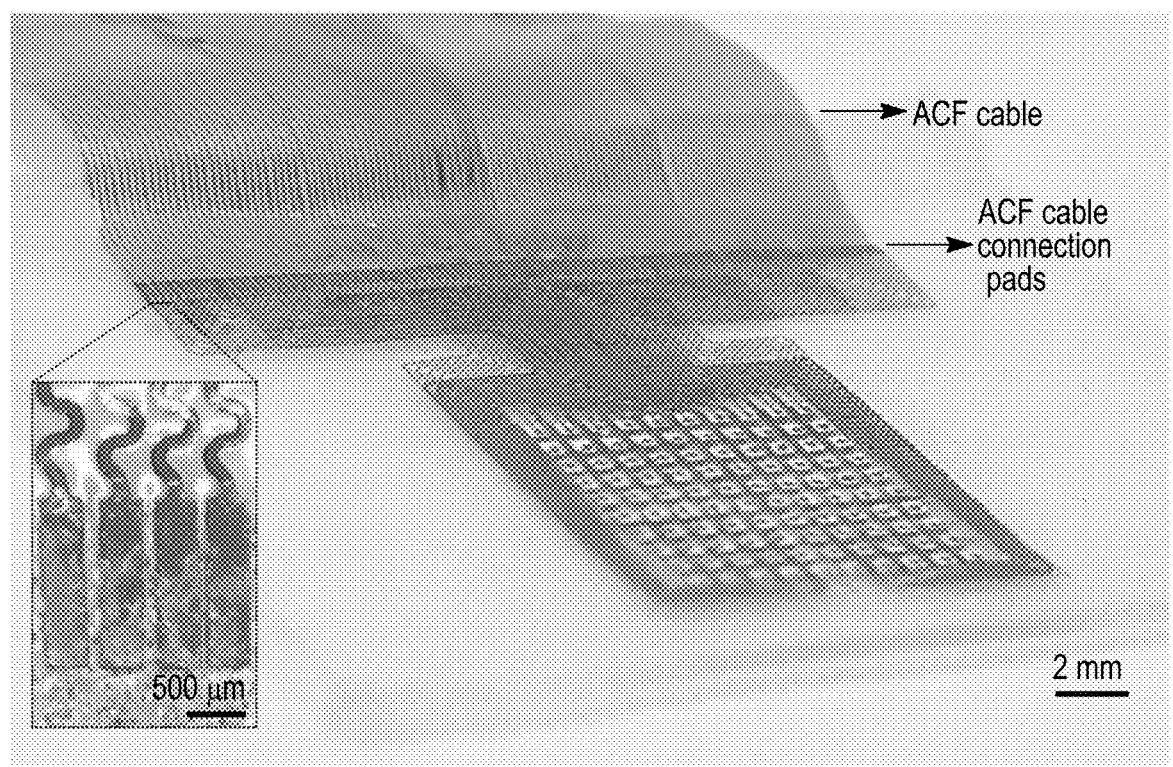
FIG. 18 shows the ACF cable bonding.

The device can easily achieve conformal contact to various nonplanar surfaces of real components, such as pipeline elbows, wheel edges, and rail tracks. This is illustrated in FIGS. 17A-17C, which shows that the device conforms on a pipeline elbow (FIG. 17A), a wheel edge (FIG. 17B) and a rail track (FIG. 17C). As shown in FIG. 18, an anisotropic conductive film (ACF) bonded to the Cu interconnects offers conductive access to external power supplies and data acquisition (FIG. 18).

Electromechanical Characterizations

Figure 2A:
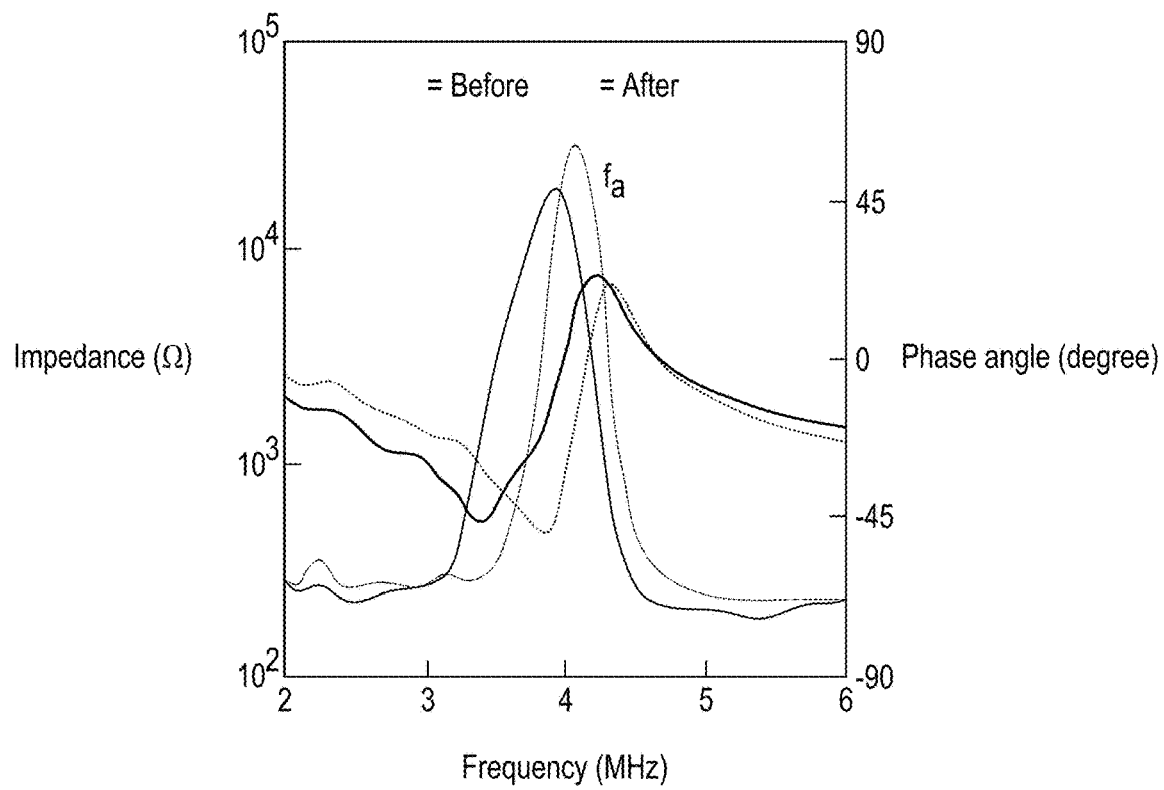
FIGS. 2A-2G show piezoelectric and mechanical properties of the stretchable ultrasonic transducer array.

Ultrasound emission and sensing rely on the reversible conversion of mechanical and electrical energy. The electromechanical coupling capability is thus a key metric to evaluate the ultrasound transducer performance. As illustrated in FIG. 2A, the electrical impedance and phase angle spectra of the 1-3 composite before and after fabrication are measured, from which we can obtain the electromechanical coupling coefficient k ($k_t$ and $k_{eff}$) and the degree of poling, respectively. The darker curves show two sets of well-defined peaks, corresponding to the resonance frequency $f_r$ and the anti-resonance frequency $f_a$. Accordingly, the $k_t$ and $k_{eff}$ of the 1-3 composite before and after the fabrication are calculated to be ~0.55 and ~0.60, respectively. The phase angle of the 1-3 composite at the central frequency slightly dropped from ~60° before fabrication to ~50° after fabrication, due to the heat-induced slight depolarization of the 1-3 composite. The final phase angle of ~50°, which significantly exceeds many previous reports in flexible or rigid ultrasound probes due to due to the intrinsic properties of the 1-3 composite material and optimized fabrication processes, demonstrates that most of the dipoles in the 1-3 composite align during poling, thereby indicating the outstanding electromechanical coupling properties of our device.

Figure 2B:
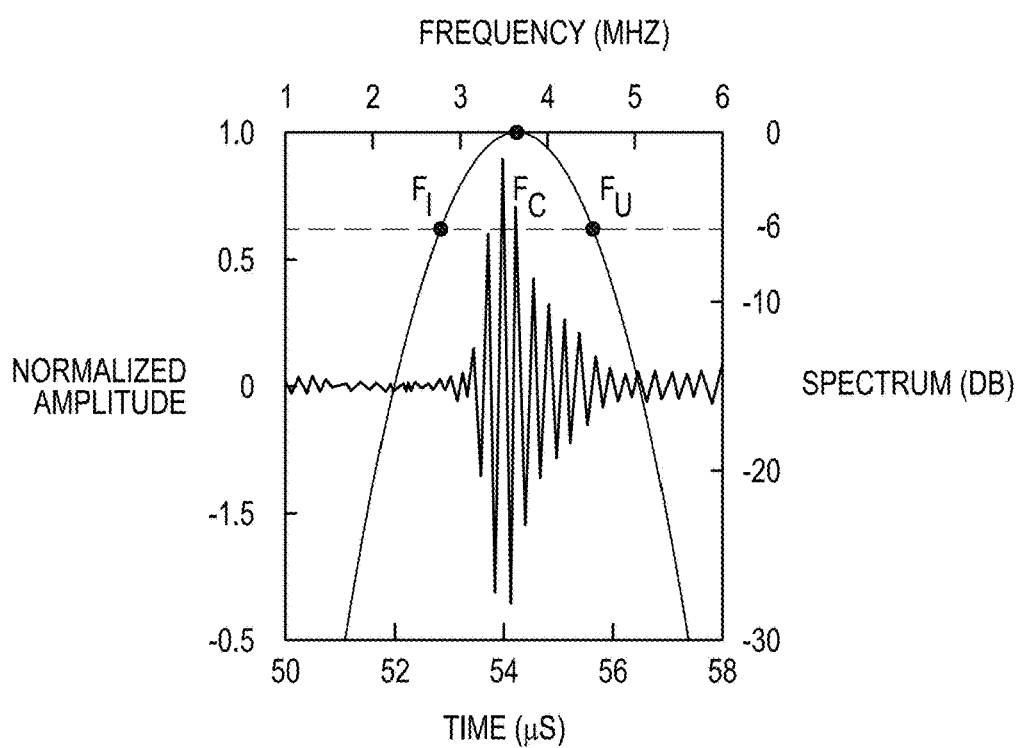
Figure 19:
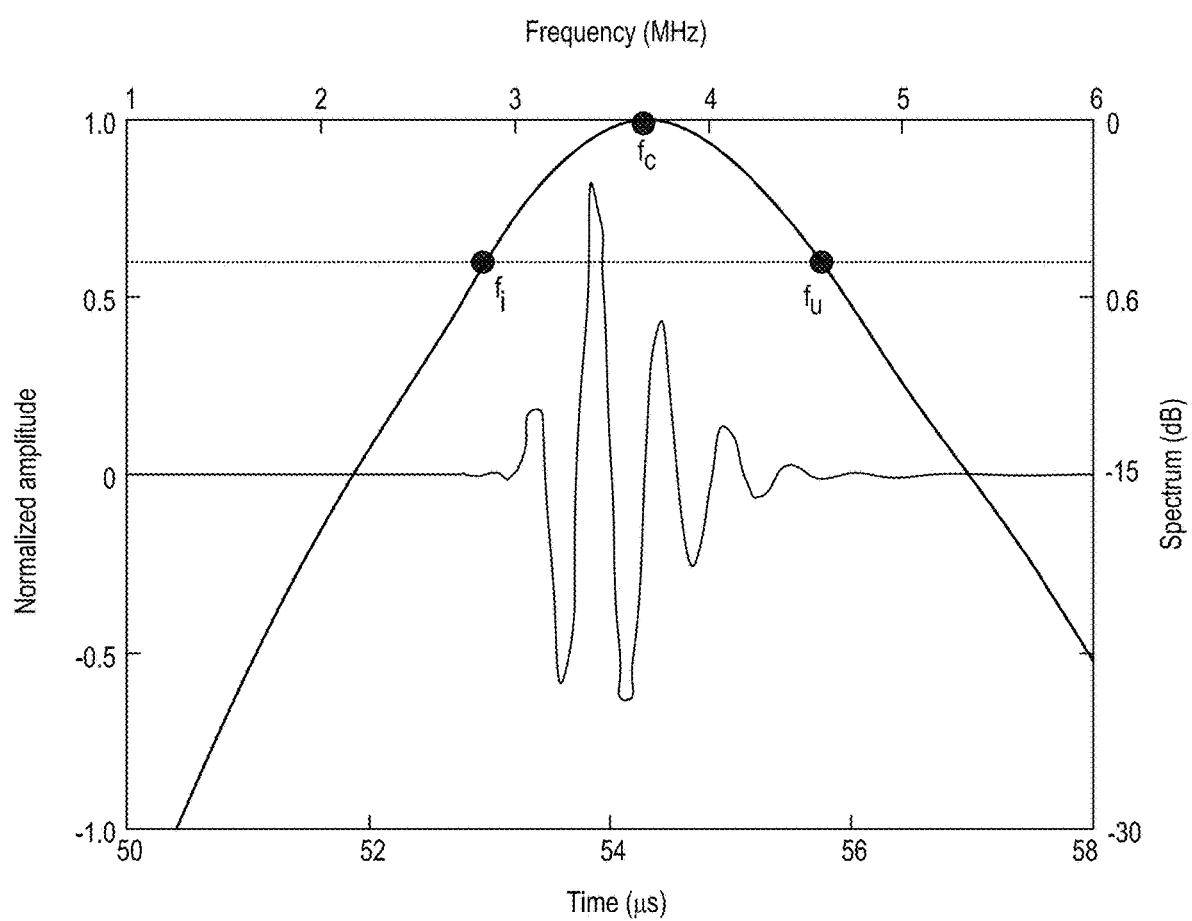
FIG. 19 show simulation results from the KLM model.
Figure 33:
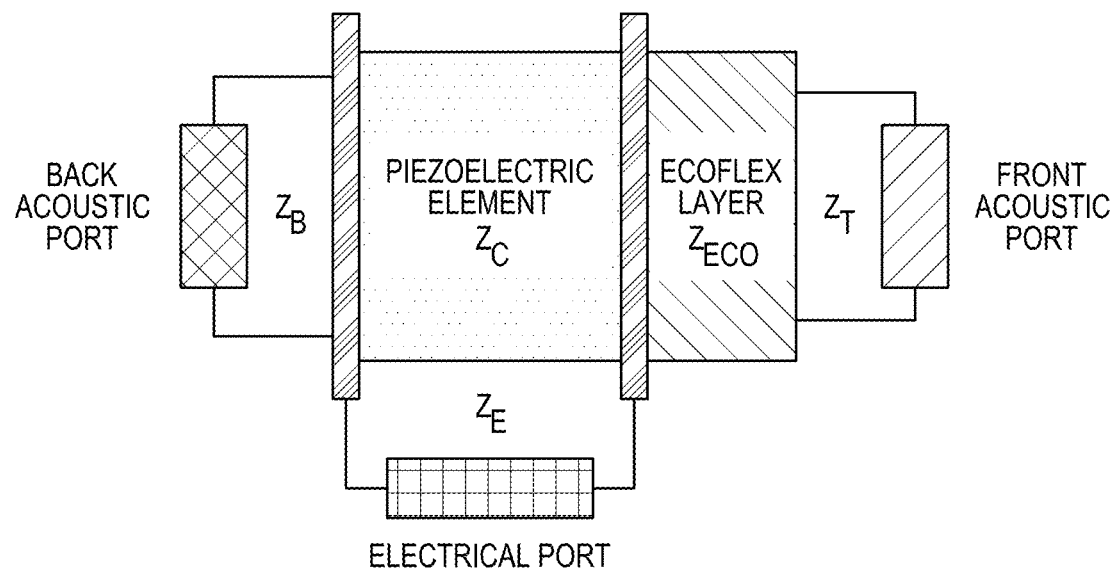
FIG. 33 shows a simplified schematic of a transducer element.
Figure 34:
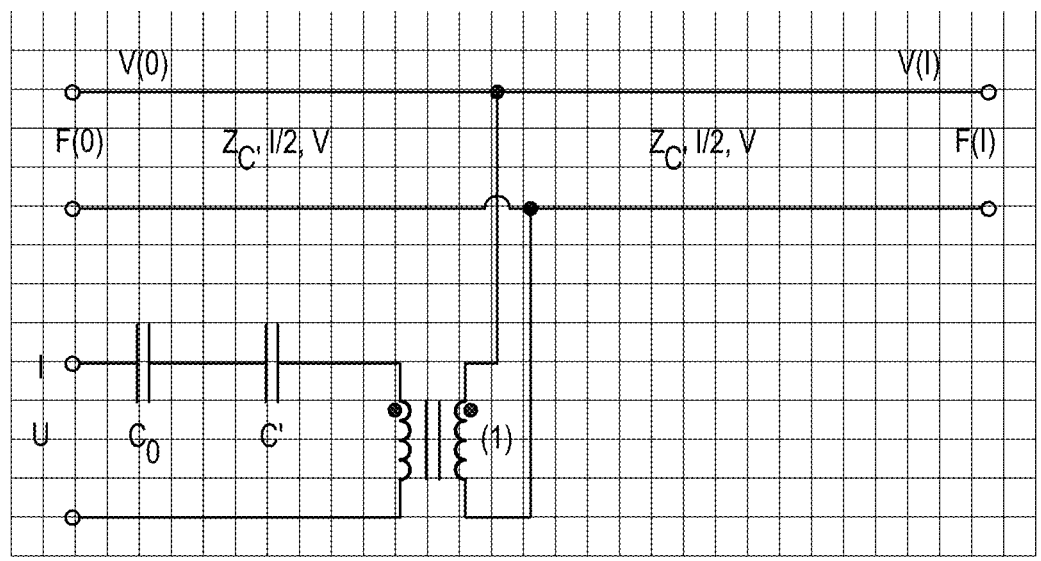
FIG. 34 shows an electrical model of a transducer element using the KLM model.
Figure 35:
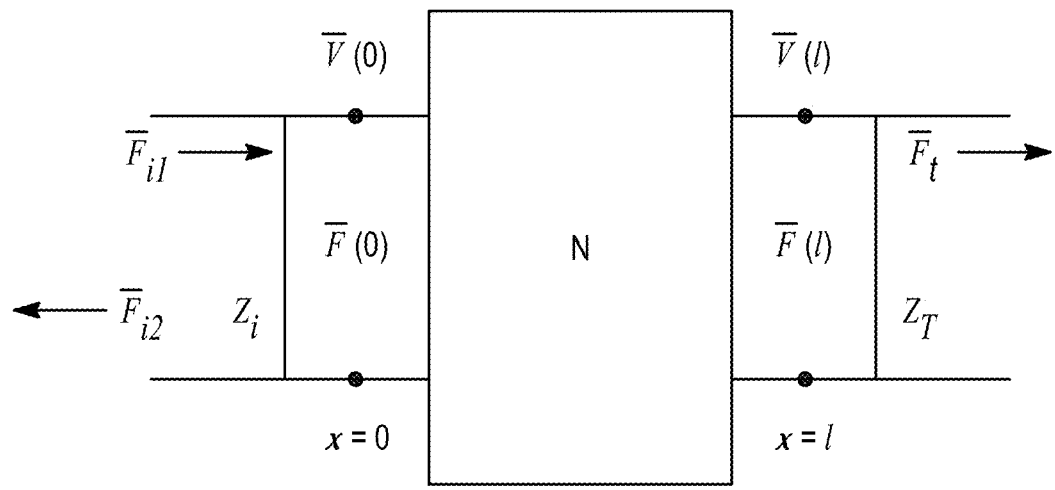
FIG. 35 shows a transmission line model of a two-port system.

The KLM model in MATLAB allows for prediction of the impulse response of the transducer (See FIGS. 33, 34 and 35), as a theoretical validation for our device design. The simulated results demonstrate the superb performance of the device in terms of spatial pulse length, bandwidth, and SNR. FIG. 19 shows the pulse-echo signal response (dark curve) and the ~6 dB bandwidth (light curve). FIG. 2B shows the experimental results of pulse-echo response and its frequency spectrum. The pulse-echo response, with narrow spatial pulse length (~1.94 µs), large frequency bandwidth (~47.11%) and high SNR (~20.24 dB), matches well with the simulation result (FIG. 19) and is on par with that of commercial flexible ultrasonic transducers. The outstanding transducer performance results from 1) the excellent electromechanical coupling of the transducer; 2) the optimized backing layer that reduces ringing effects.

Figure 2C:
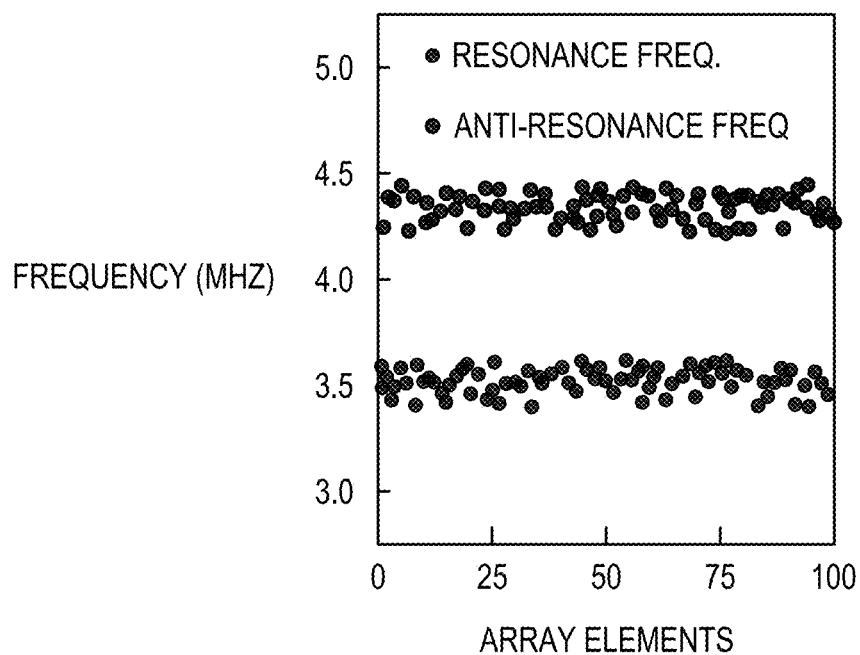
Figure 20A:
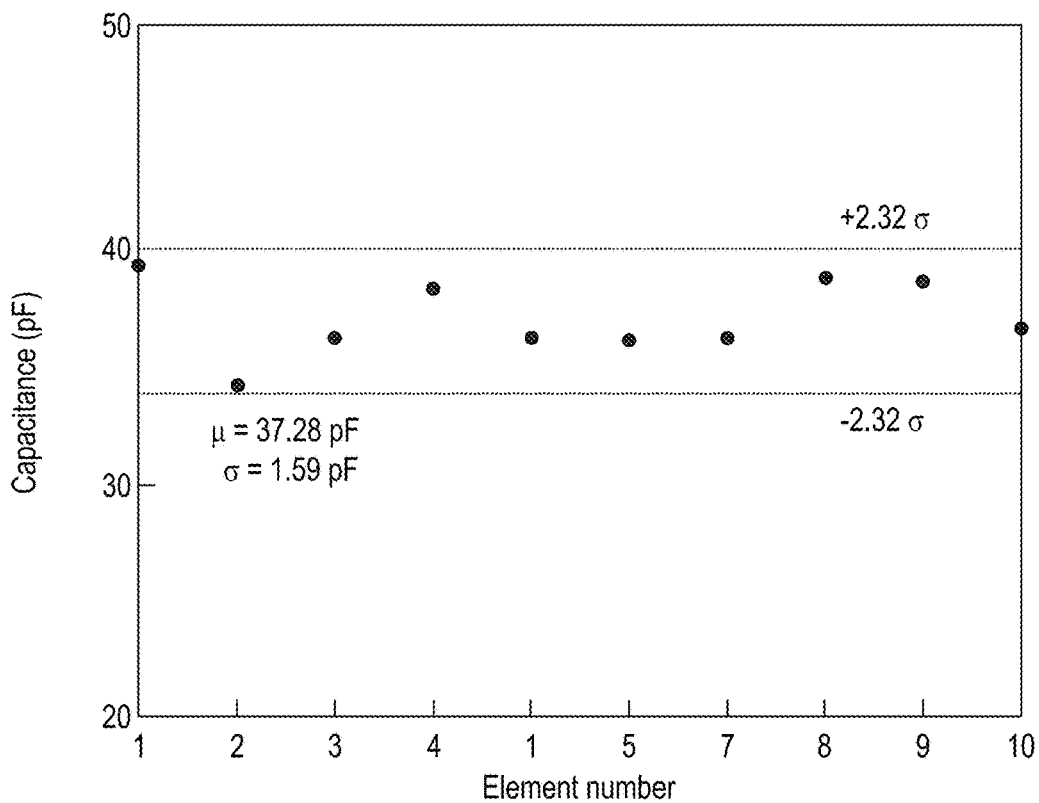
FIG. 20A shows the capacitance and FIG. 20B show the dielectric loss of a 1×10 linear array.
Figure 20B:
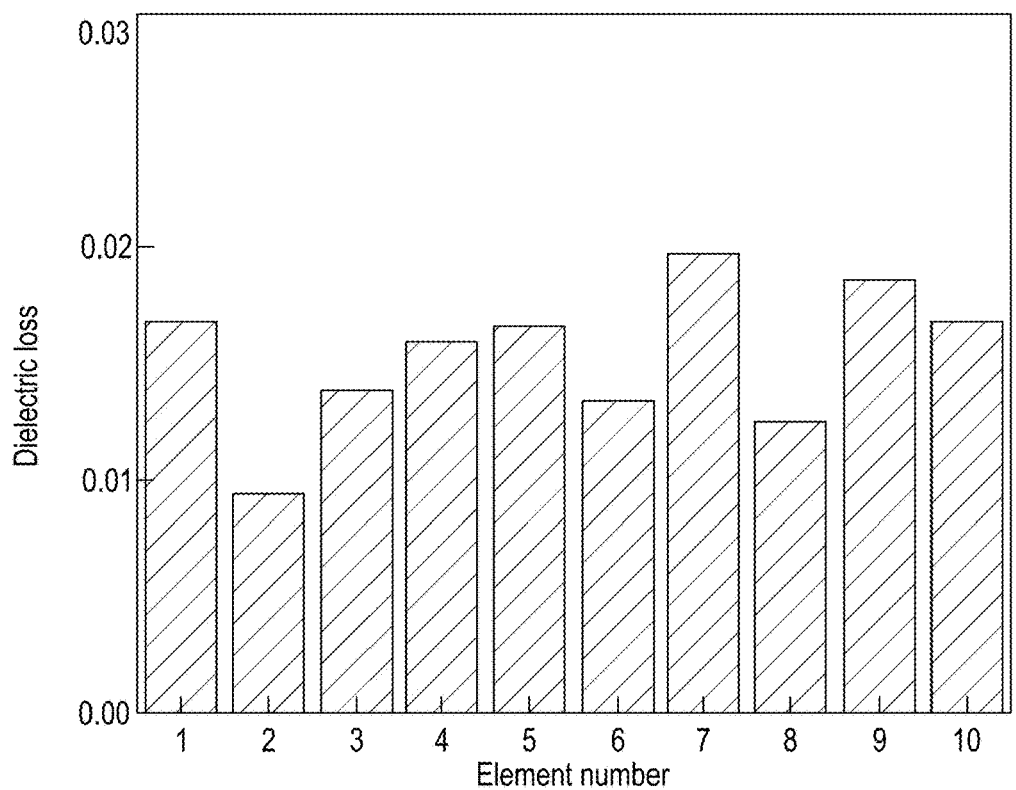
Figure 21A:
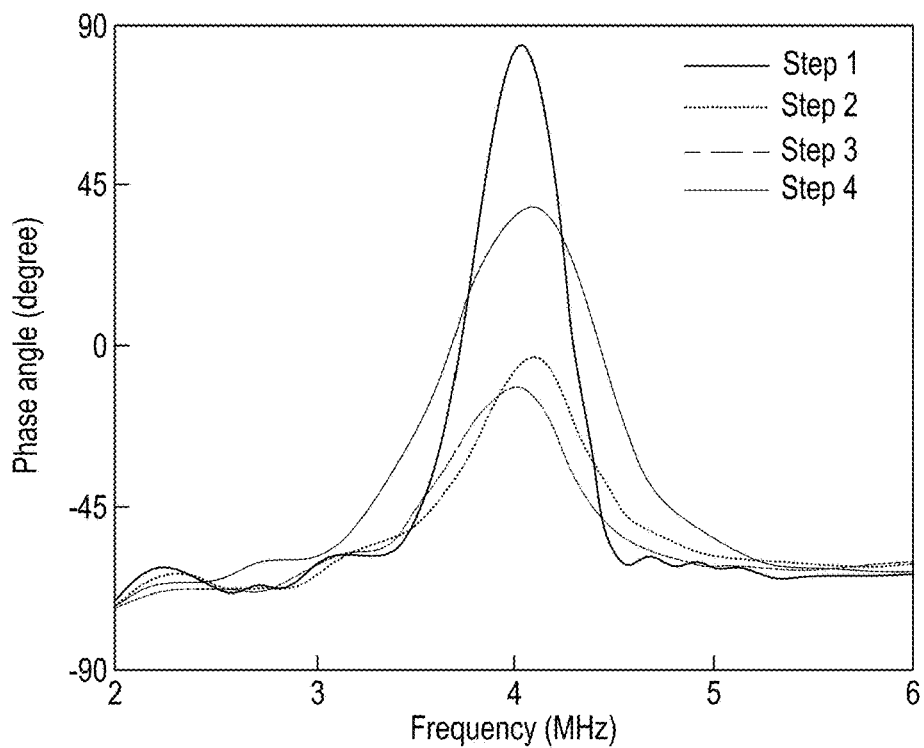
FIGS. 21A and 21B show the phase angle change during the fabrication process and after repetitive testing, respectively.
Figure 21B:
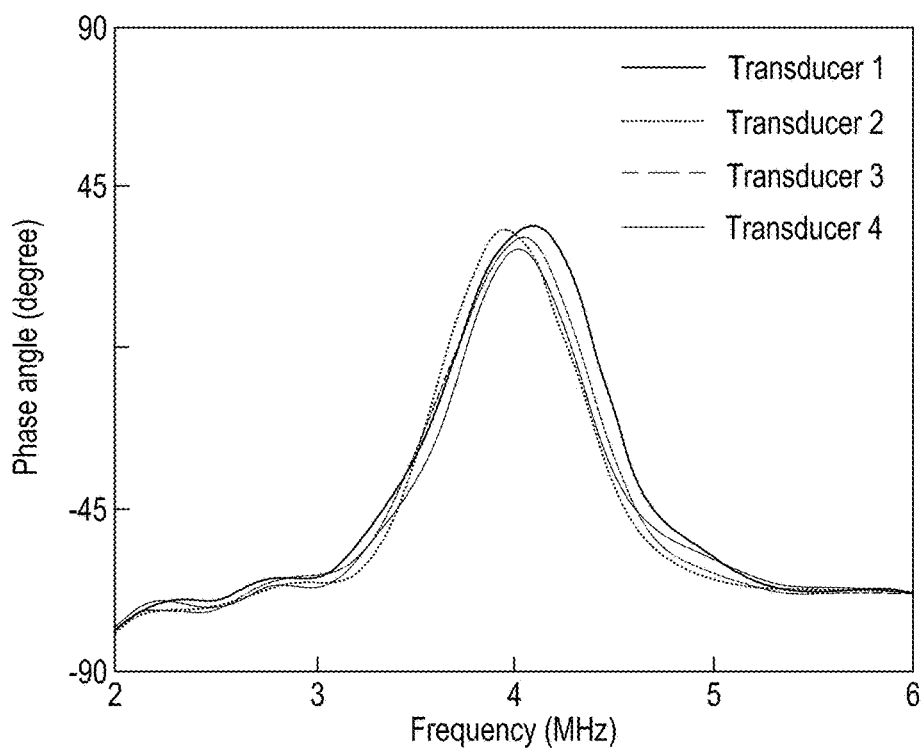
Figure 22A:
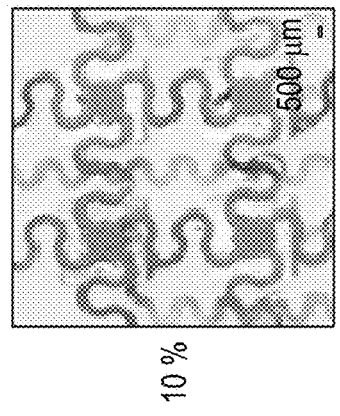
FIGS. 22A-22F show experimental and simulation results of a small array under biaxial tensile strain.
Figure 22B:
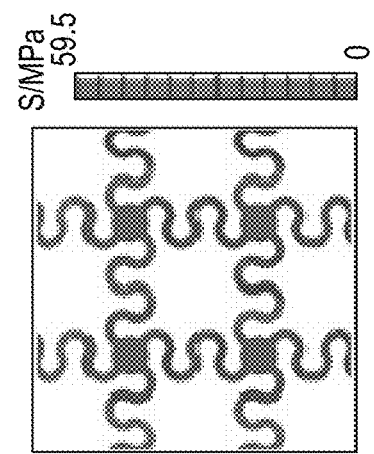
Figure 22B:
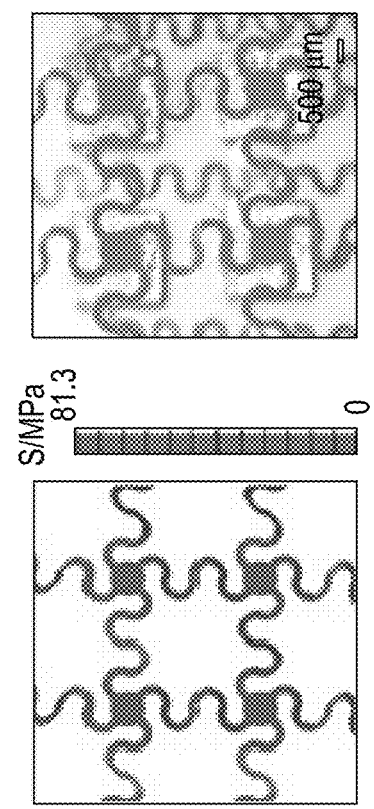
Figure 22B:
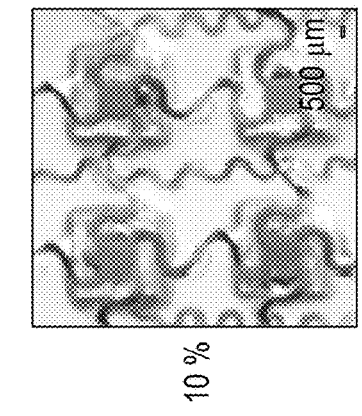
Figure 22C:
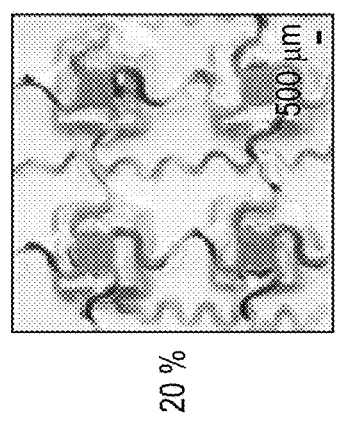
Figure 22C:
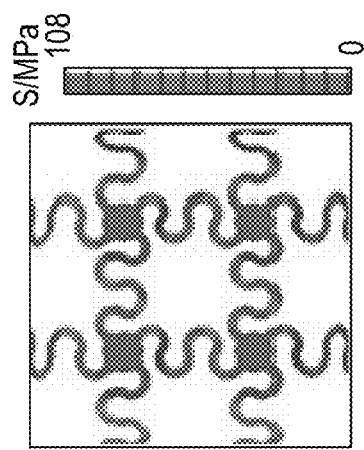
Figure 22C:
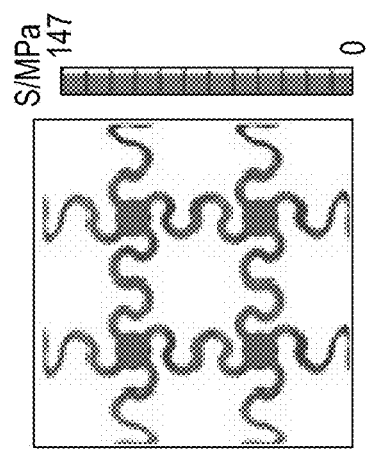
Figure 22D:
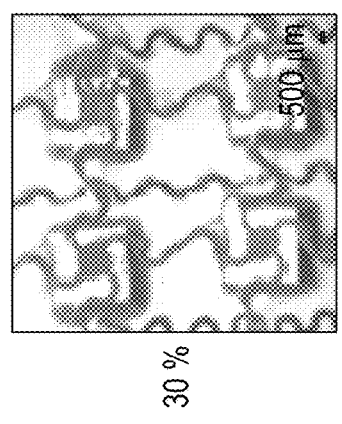
Figure 22D:
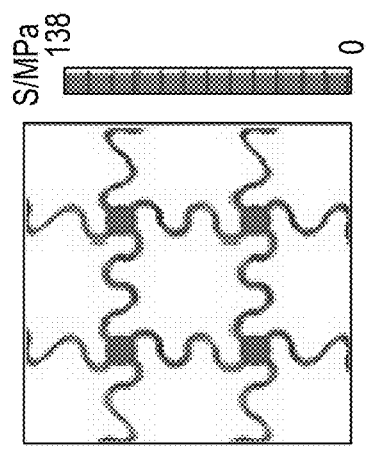
Figure 22D:
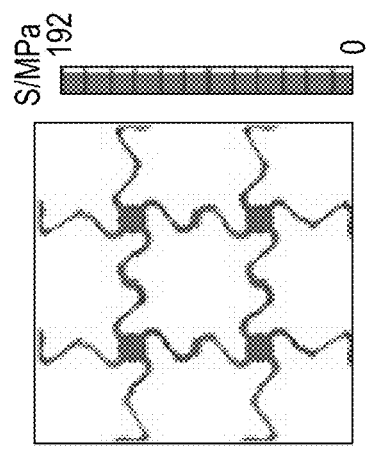
Figure 22E:
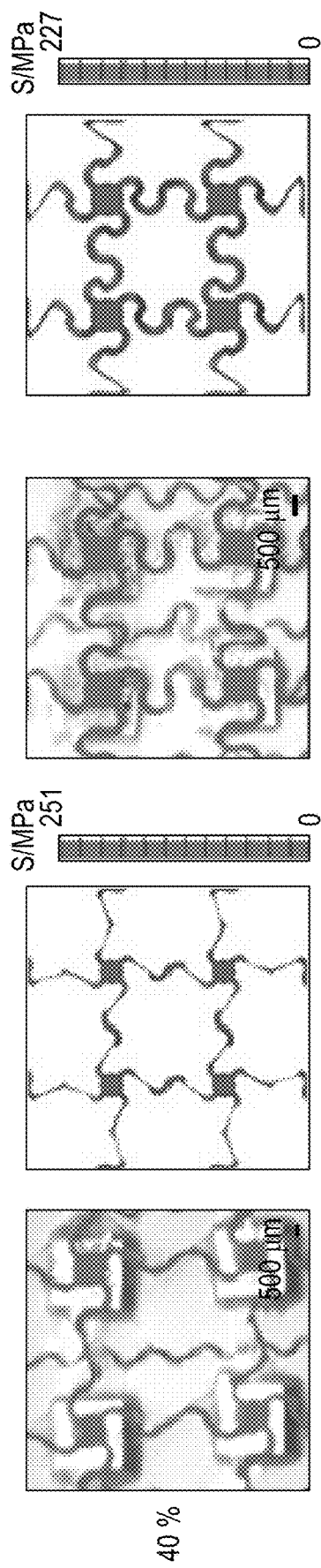
Figure 22F:
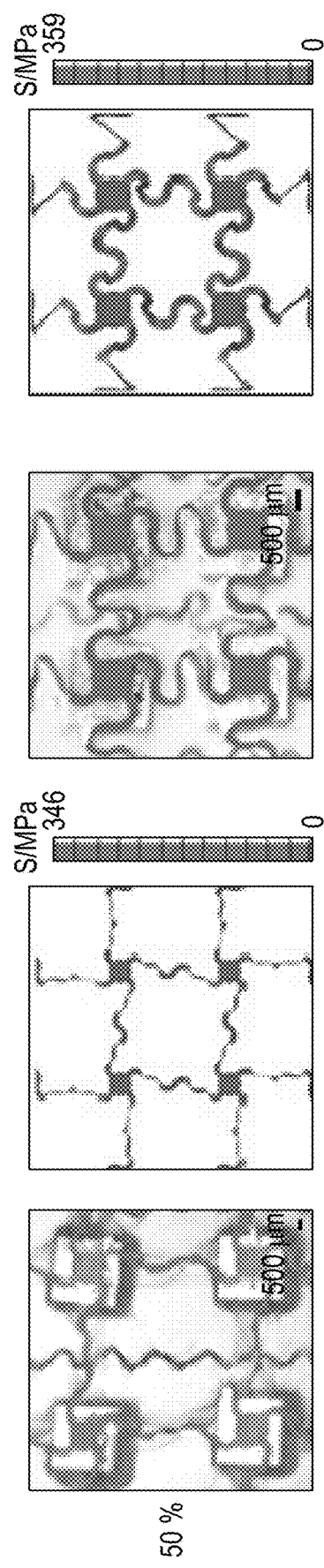

The impedance measurements enable extraction of the resonant and anti-resonant frequencies of each element in the 10×10 array. FIG. 2C shows the resonance and anti-resonance frequency variations of the 100 transducer elements. All 100 elements were functional. The mean values are 3.51 MHz (resonant) and 4.30 MHz (anti-resonant), with small standard deviations of 56.8 kHz and 59.1 kHz, respectively. The stable capacitance (~37.28 pF) and low dielectric loss (tan δ<0.02) of the array (shown in FIGS. 20A and 20B) further suggest a remarkable uniformity across the array and a reliable fabrication method. FIG. 21A shows the phase angle change during the fabrication process, where step 1 is to dice the 1-3 composite, step 2 is to bond the backing layer, step 3 is to bond the top and bottom Cu electrodes and step 4 is to encapsulate and pole the 1-3 composite under 52.38 kV/cm for 15 minutes. FIG. 21B shows that after processing, four transducer elements have similar phase angles, showing the reproducibility and robustness of the process.

Figure 2D:
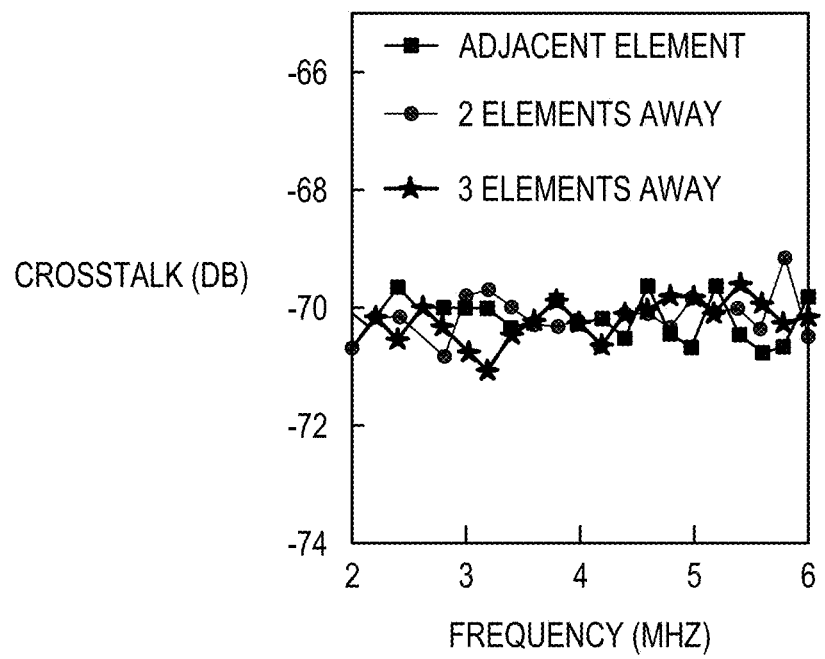
Figure 2E:
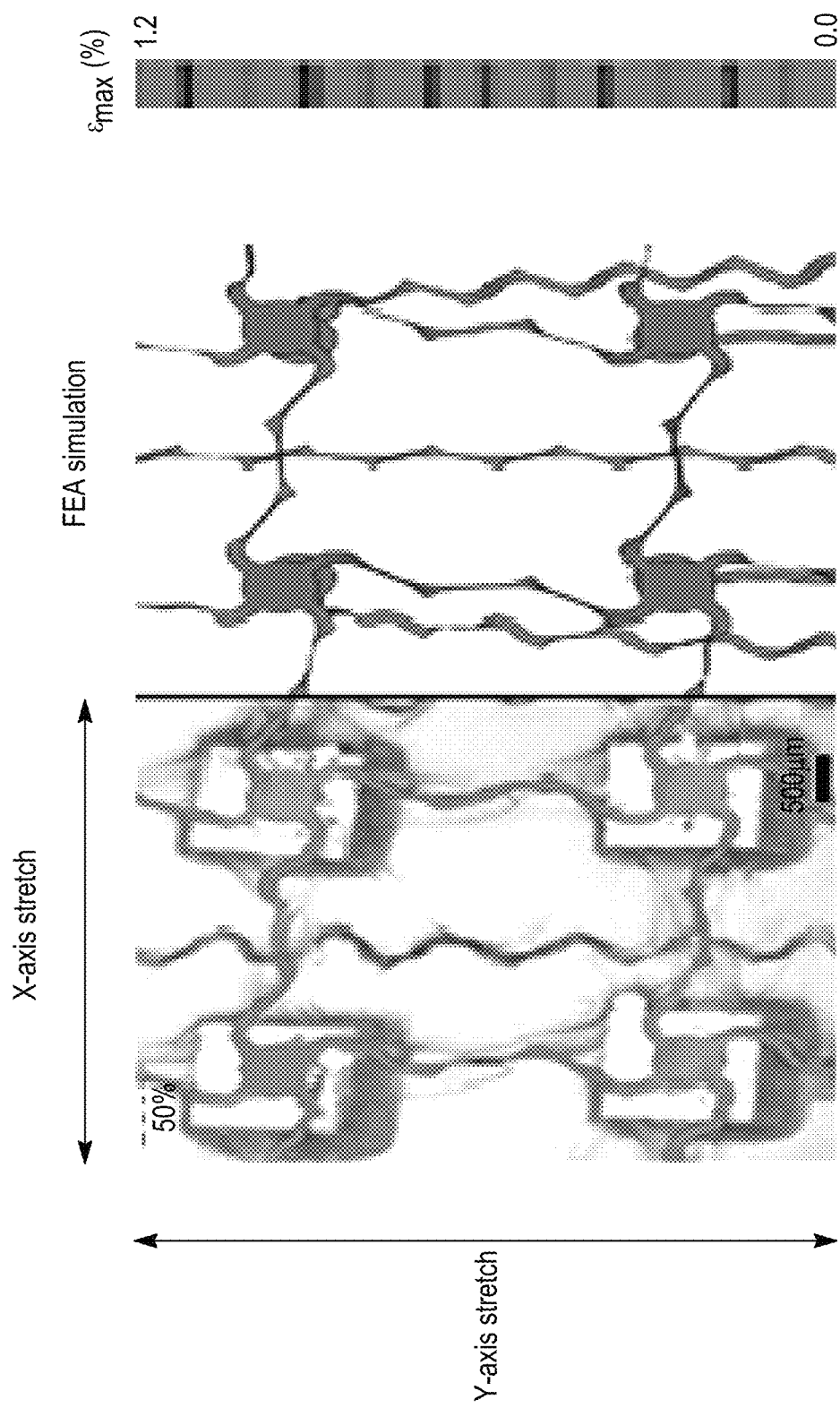

Another important metric that assesses the performance of the array is the cross-talk, which indicates the degree of interference between the elements. FIG. 2D shows the cross-talk between elements with different spacing. All cross-talk levels are around −70 dB, with slight fluctuations, which is significantly lower than the standard −30 dB in the field. The outstanding anti-interference properties arise from the 1-3 composites' effective suppression of spurious shear and from the silicone elastomer providing effective isolation among the elements. Overall, this combination of properties ensures low levels of noise in the ultrasonic imaging system.

Mechanical Characterization

Figure 2F:
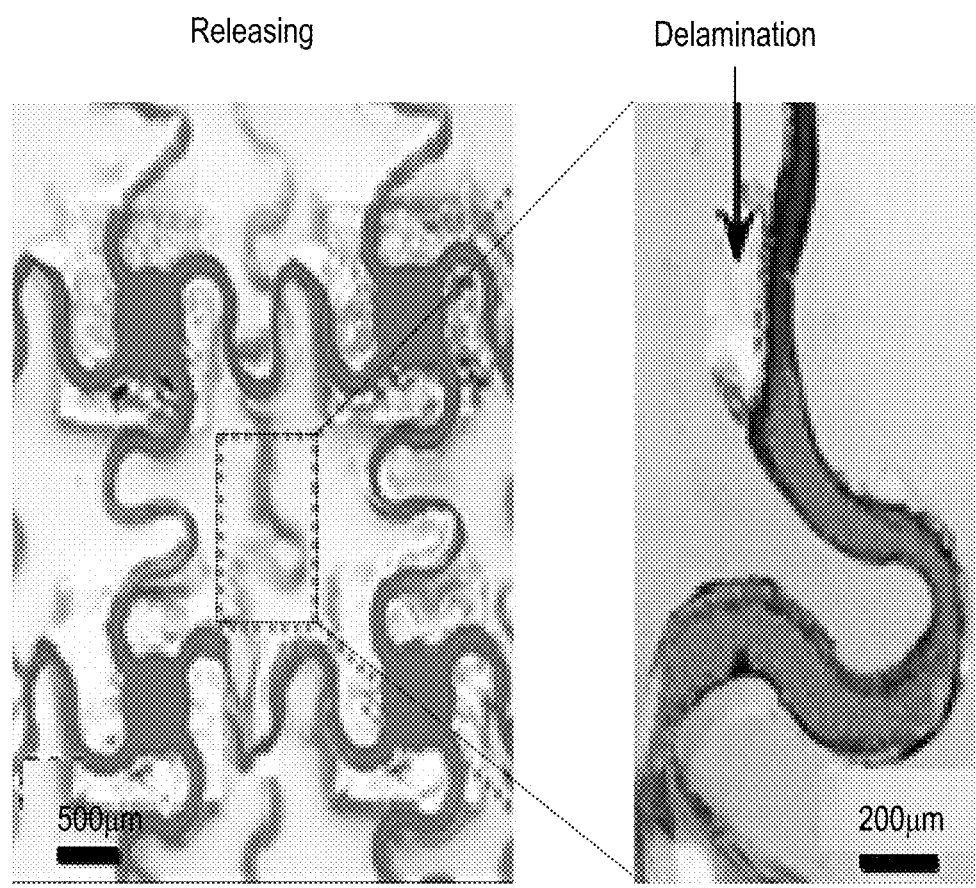
Figure 2G:
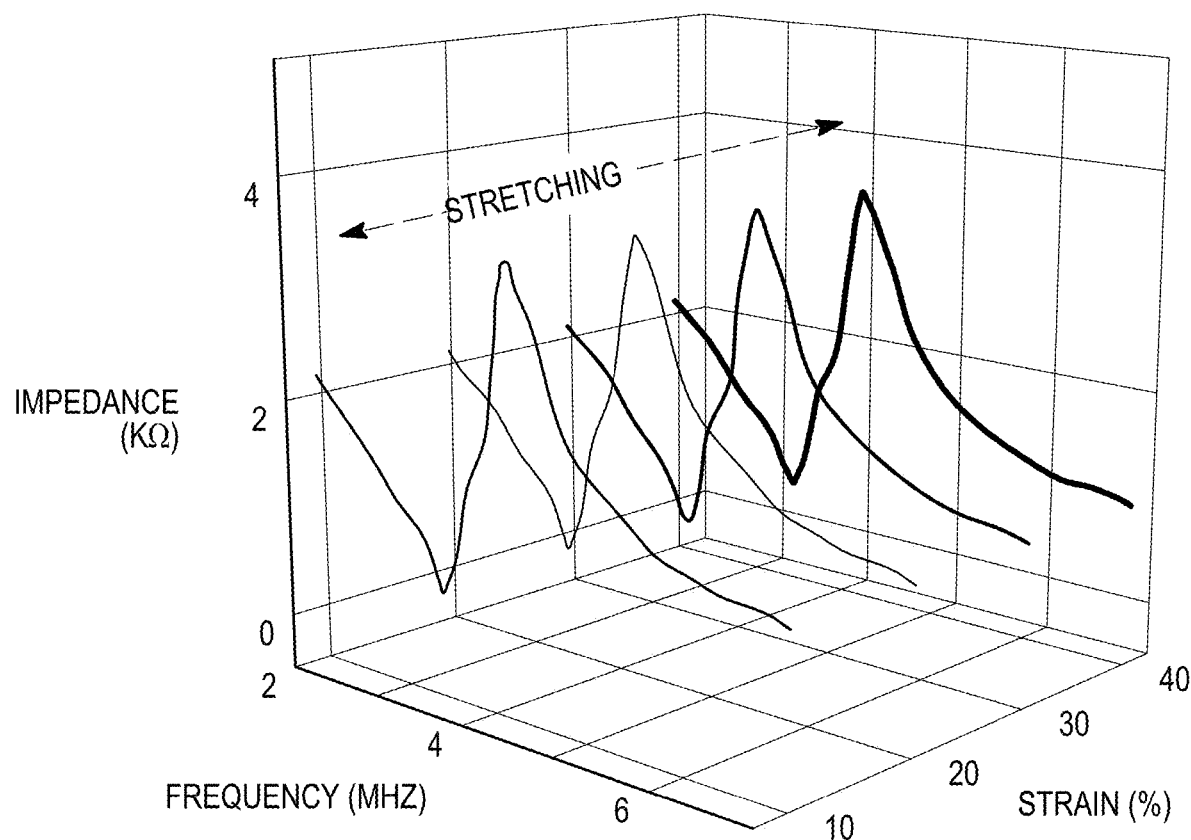
Figure 23:
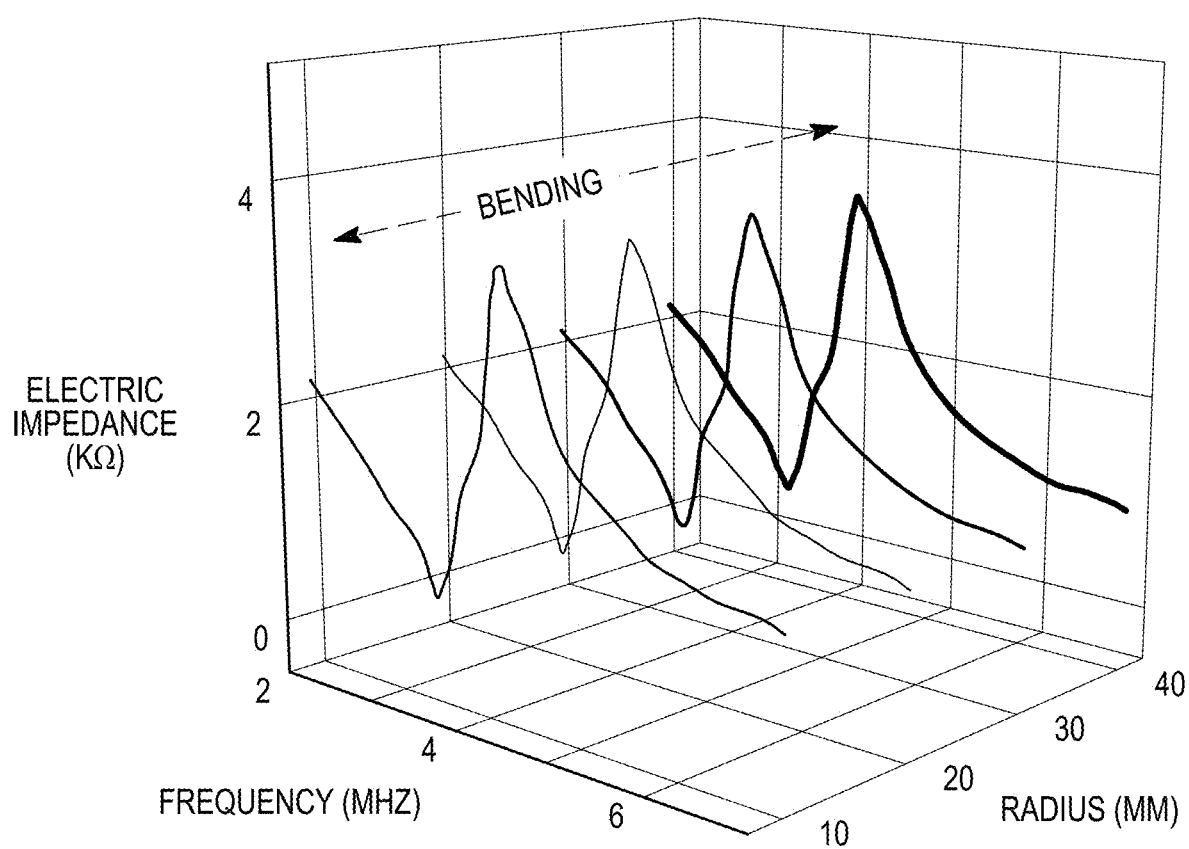
FIG. 23 show the electric impedances under different bending curvatures.
Figure 24A:
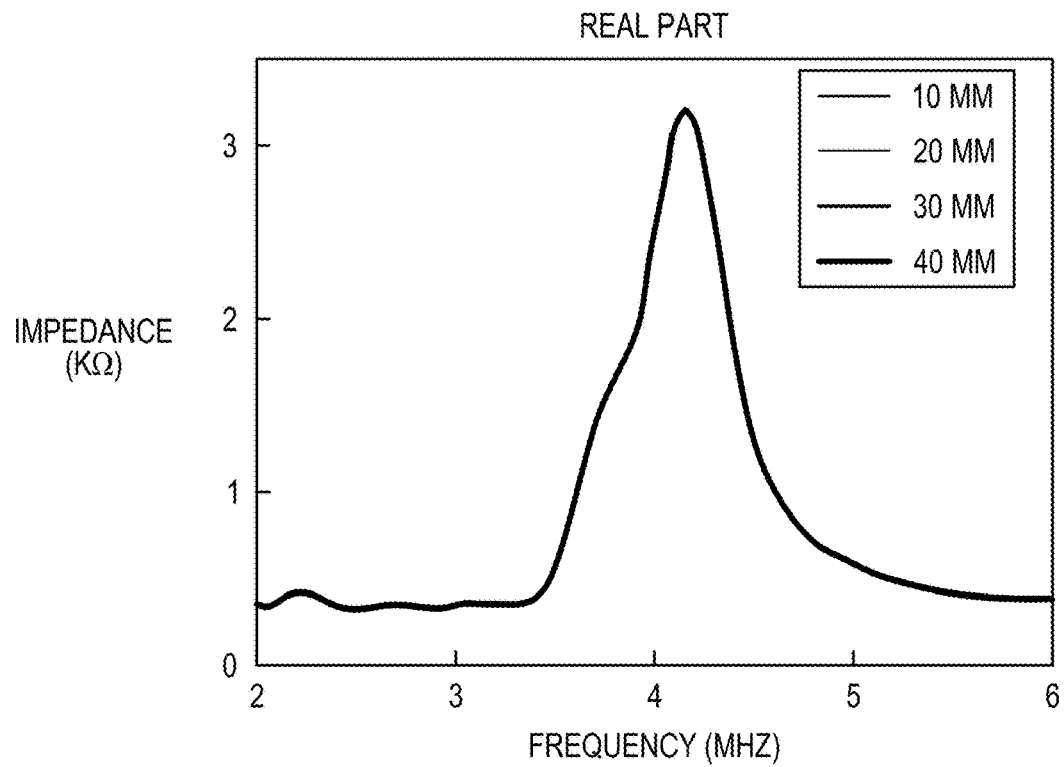
FIG. 24A-24D shows the real and imaginary parts of the electrical impedance under different levels of bending and stretching.
Figure 24B:
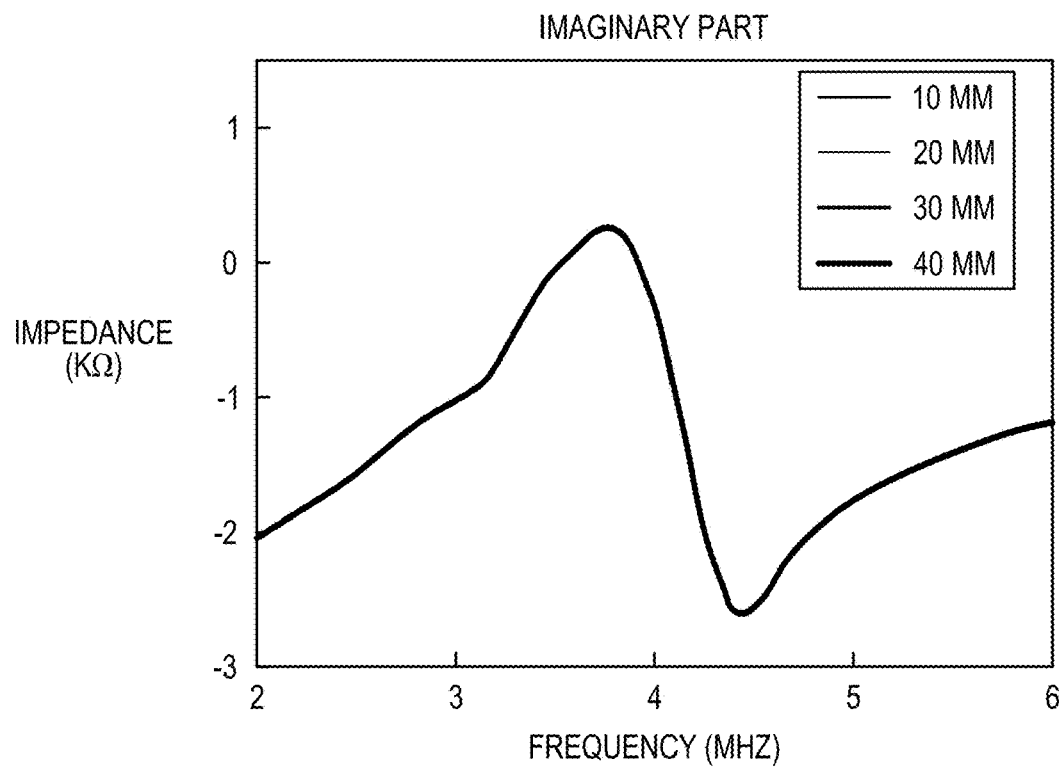
Figure 24C:
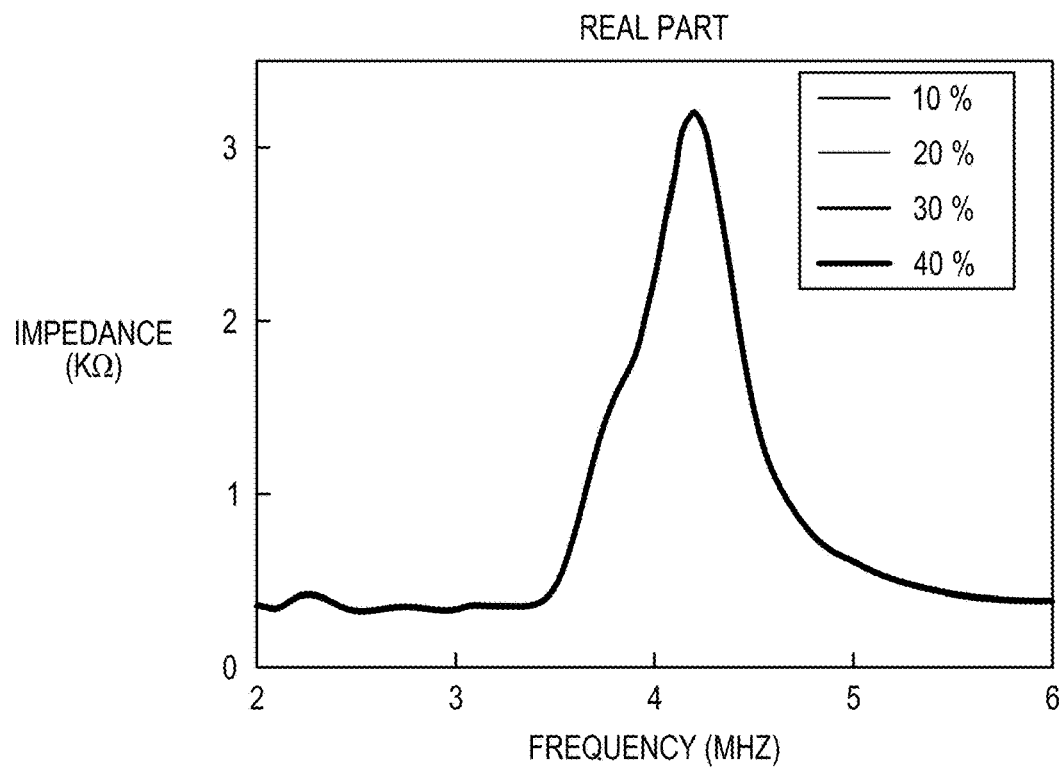
Figure 24D:
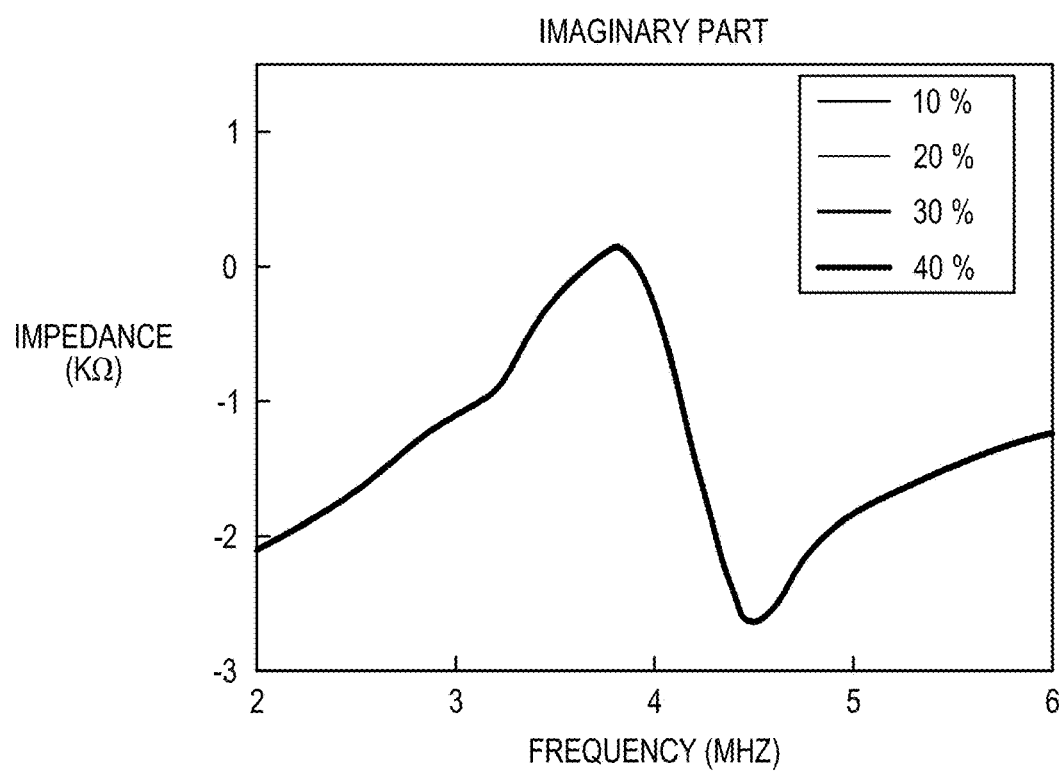

Mechanical properties of conductive interconnects are important for flexible and stretchable devices. Experimental results from biaxial stretching of the layered structures of serpentines between 0% to 50% and corresponding 3D Finite Element Analysis (FEA) are shown in FIG. 2E, and FIGS. 22A-22F, which show that there is good agreement between experiment and simulation. A 2×2 array of elements is selected for visualization of the key mechanics involved. Under tensile loading, the "horse-shoe" serpentines undergo an in-plane unraveling process as well as out-of-plane rotation and twisting, both of which mitigate the level of strain in the islands themselves. Specifically, in these ultrasound arrays, 50% biaxial stretching produces a maximum of only ~1.2% tensile strain in the Cu interconnects, as shown in the FEA image of FIG. 2E. After the serpentines have fully unraveled (i.e., finished rotating in-plane), the tensile strain in the Cu interconnects increases rapidly, thus defining the stretching limit of the serpentines, which is between ~50%-60% in this case. Going beyond this limit will lead to fracture of the serpentines. Additionally, for the reliability of these devices, they must be capable of sustaining mechanical integrity upon repetitive loading. In metals such as Cu, cycling into the plastic regime will cause permanent deformation of the interconnects, which may affect device performance or may eventually produce fatigue cracks. According to both the simulations and the experiments, ~30%-40% biaxial stretching produces irreversible deformation in the serpentines upon releasing (unloading) (as FIGS. 22A-22F indicate) and partial delamination between the serpentines and the silicone elastomer, as highlighted in FIG. 2F. However, below 30%-40% biaxial stretching, mechanical integrity is maintained. Moreover, mechanical deformations have minimal influence on device performance, which is reflected by the stable impedances of each element and resistance of the serpentines (FIG. 25) at various levels of tensile strains and bending curvatures. This is illustrated in FIG. 2G, which shows the electrical impedance of the transducer under different strain levels and FIG. 23, which shows the electrical impedances under different bending curvatures. FIGS. 24A-24D show the real and imaginary parts of the electrical impedance under different levels of bending to different radii of curvature and FIGS. 24C-24D show the real and imaginary parts of the electrical impedance under different tensile strains.

Spatial Resolution Characterization

Figure 3A:
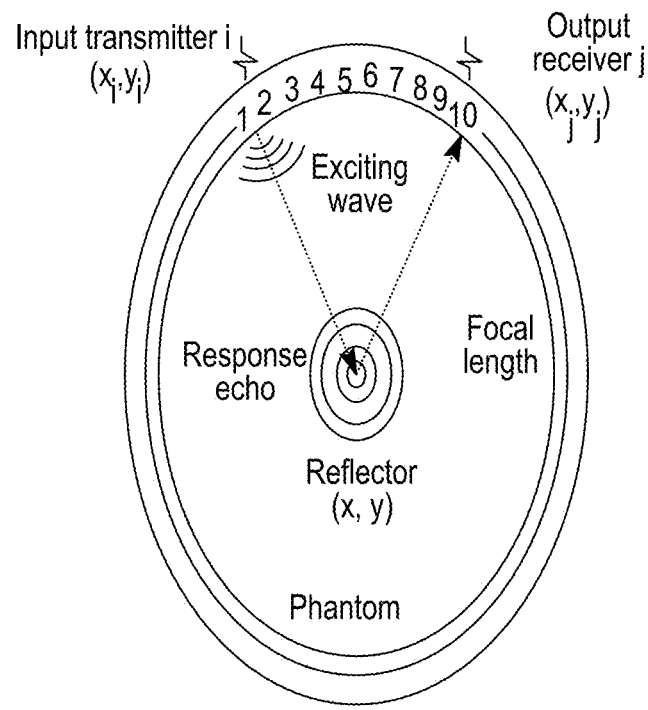
FIG. 3A-3F illustrates the spatial resolution of the stretchable ultrasonic transducer array.
Figure 3B:
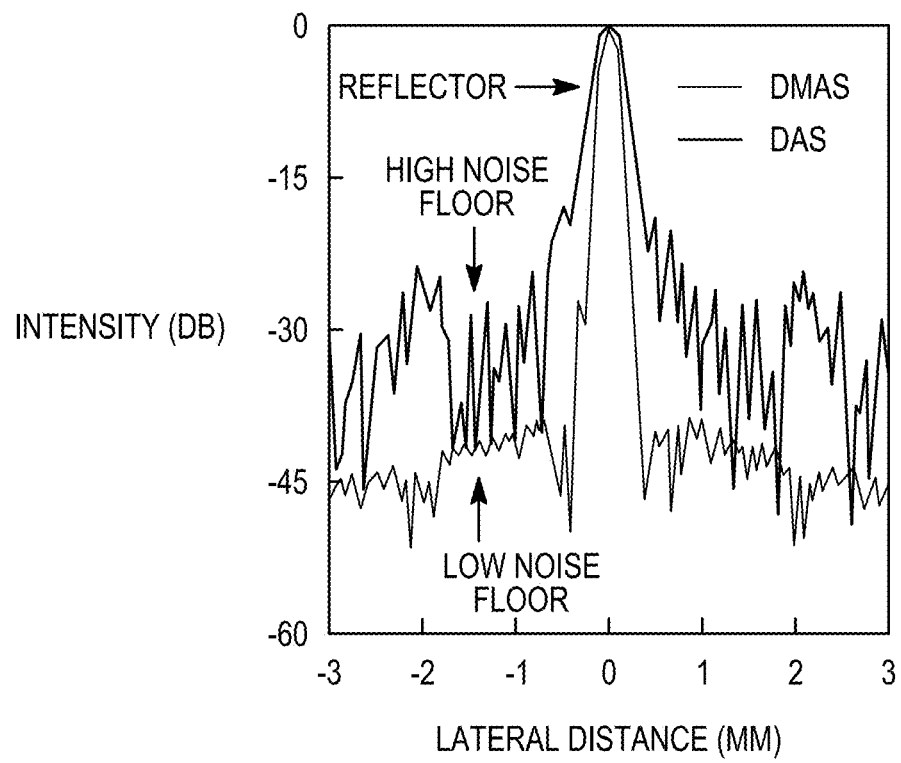
Figure 3C:
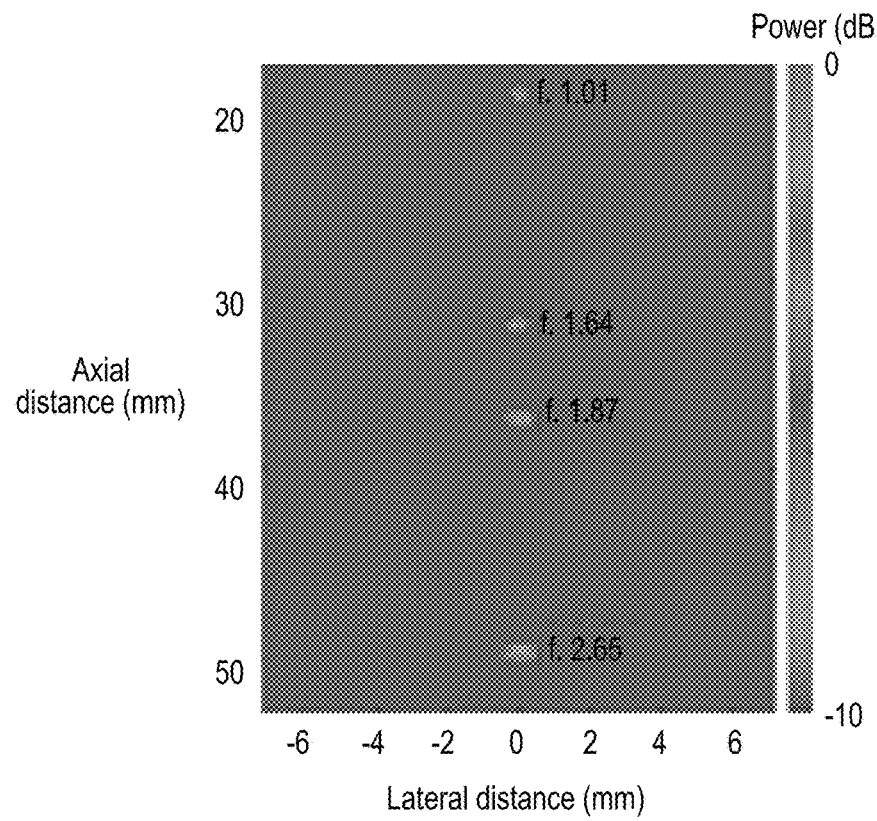

One of the important performance metrics of ultrasound imaging systems is the spatial resolution, in both axial and lateral directions. For the stretchable ultrasound probe, the axial resolution stays constant under different bending curvatures at a defined resonant frequency and bandwidth of the transducer. The lateral resolution is mainly dependent on device geometry which impacts the focal length and aperture size. The f-number is used to define the ratio between the focal length and the aperture size. To comprehensively explore the lateral resolution of the probe with various f-numbers, we performed a series of imaging experiments in which the ultrasonic probe is bent to different curvatures. As shown in FIG. 3A, the spatial resolution was evaluated by focusing the array at focal lengths of 20 mm, 32 mm, 37 mm, and 52 mm, respectively, to image a Cu wire (300 µm in diameter) located at a particular focal point in a phantom sample. The image is reconstructed using the Delay-Multiply-And-Sum (DMAS) algorithm, which more effectively suppresses the level of noise floor (~−40 dB, causing the energy ratio of noise to reflector to be only 0.01%) compared with a conventional algorithm such as Delay-And-Sum (DAS). FIG. 3B shows a comparison of noise floors reconstructed by DMAS and DAS algorithms, revealing the benefits of the DMAS algorithm. In light of this metric, the side lobes and grating lobes in images can be greatly reduced by using DMAS and the results from these four tests are combined in FIG. 3C, which shows images of wire phantom combining the four tests with different f-numbers, showing the capability of focusing at different depths and obtaining high-resolution images. A configuration of −10 dB dynamic range together with an image resolution of 20 pixels per mm is applied to highlight the imaging capabilities. The imaging principle of the DMAS algorithm and its detailed comparison with DAS will be further discussed below.

Figure 3D:
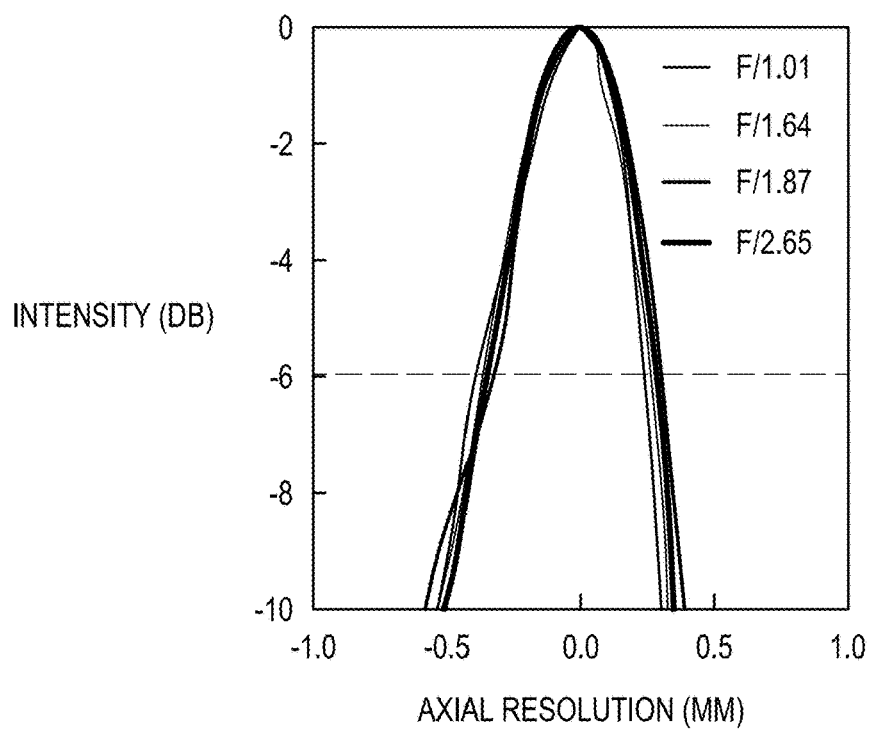
Figure 3E:
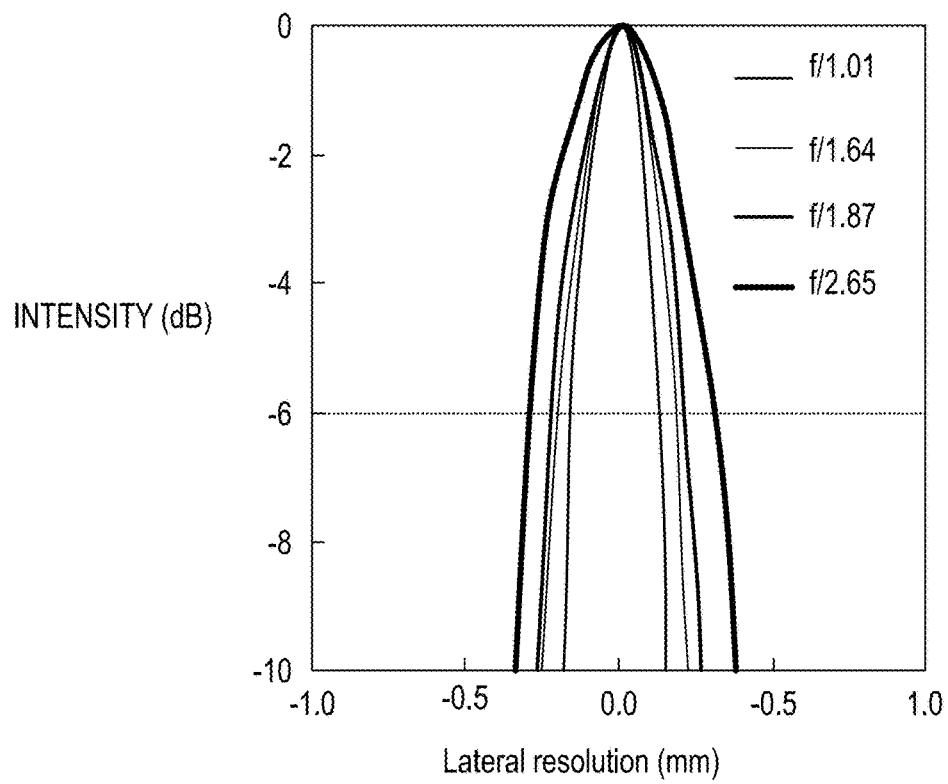
Figure 3F:
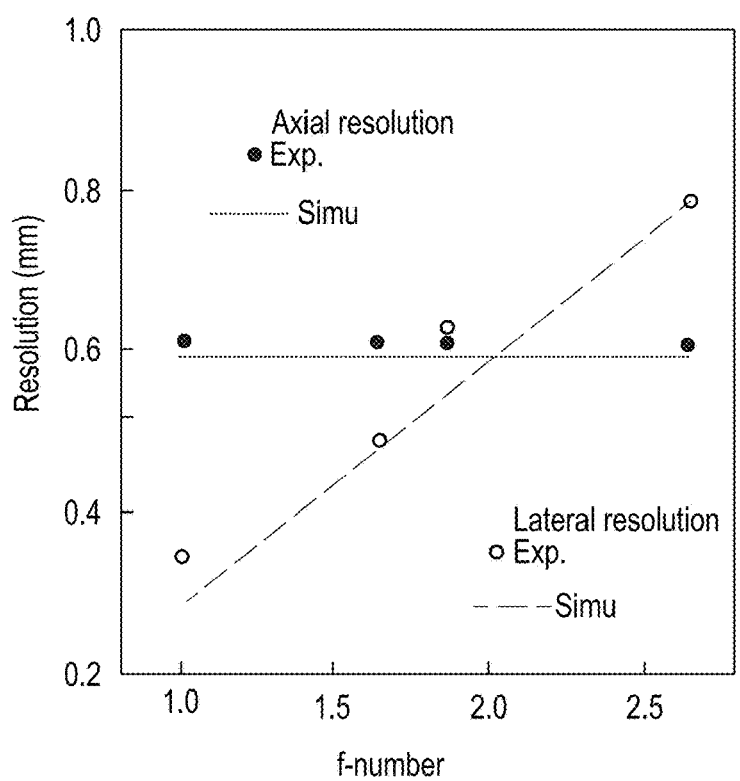

Plots of the axial and lateral line spread functions of the obtained images (FIG. 3B) are shown in FIGS. 3D and 3E. The measured full-width-at-half-maximum (FWHM) resolutions (−6 dB) were calculated for the axial (FIG. 3D) and lateral (FIG. 3E) directions, as indicated by the dashed lines. As the f-number decreases, the axial resolution stays relatively constant at around 610 and the lateral resolution improves approximately linearly from 789 μm to 344 These results are in line with the theoretical results (axial resolution of around 601 μm; lateral resolutions ranging from 787 μm to 284 μm) from the MATLAB k-wave toolbox simulations (FIG. 3F). The fine spatial resolution at the focal point, which is comparable to the 3.5 MHz commercial ultrasound probe resolution of 610 is due to the combined effects of the high-performance transducers, a strategic device structural design, and an advanced imaging algorithm.

Multi-View Imaging on Complex Surfaces

Figure 4A:
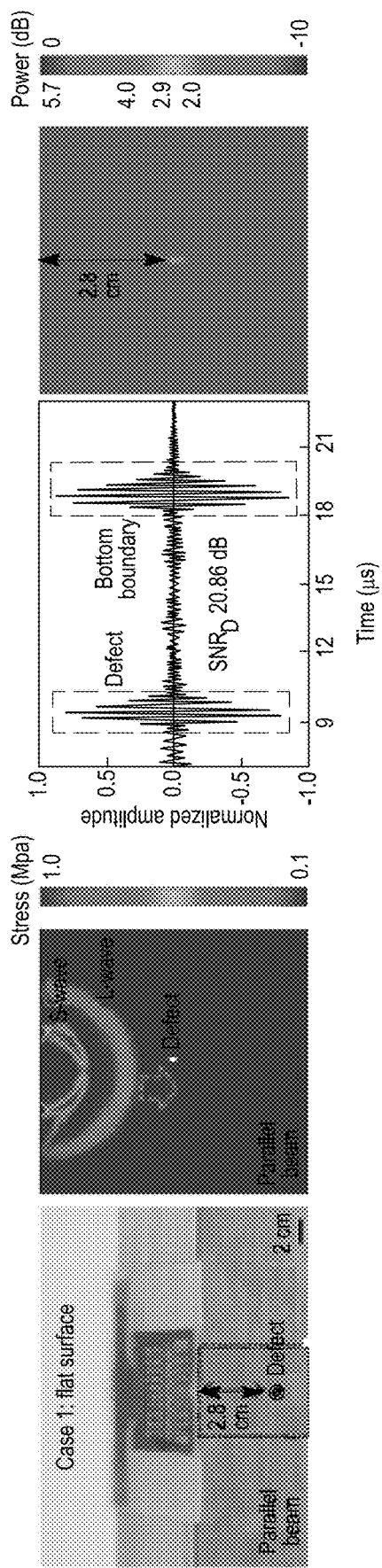
FIGS. 4A-4C show 2D images of a linear defect under complex surfaces illustrated in the first column, with simulation results showing the different wave fields and sensing modes shown in the second column, pulse-echo signals from the defects and boundaries with high SNR shown in the third column, and acquired 2D images using DMAS algorithms with accurate and artifact-free positions shown in the fourth column.
Figure 4B:
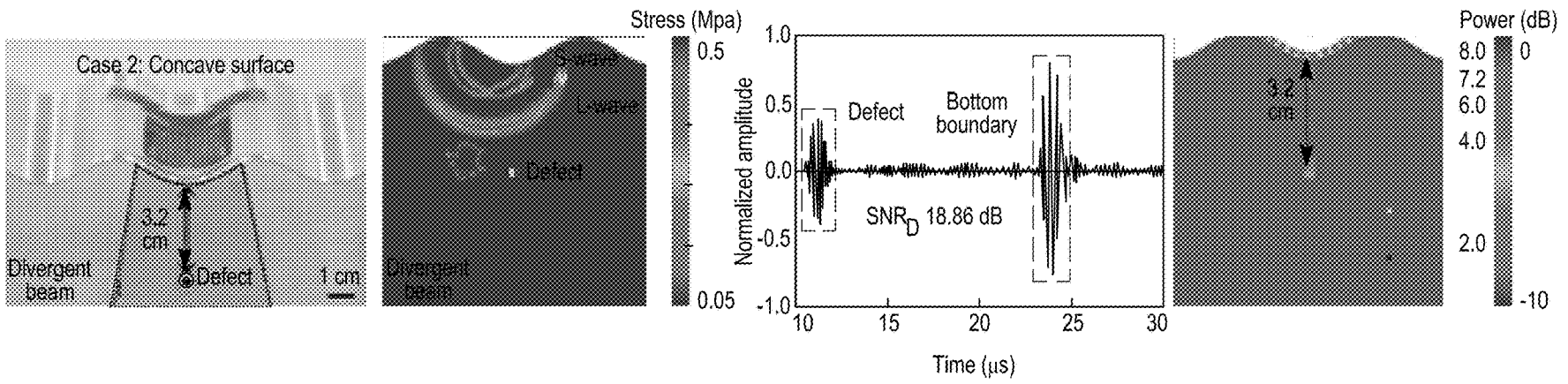
Figure 4C:
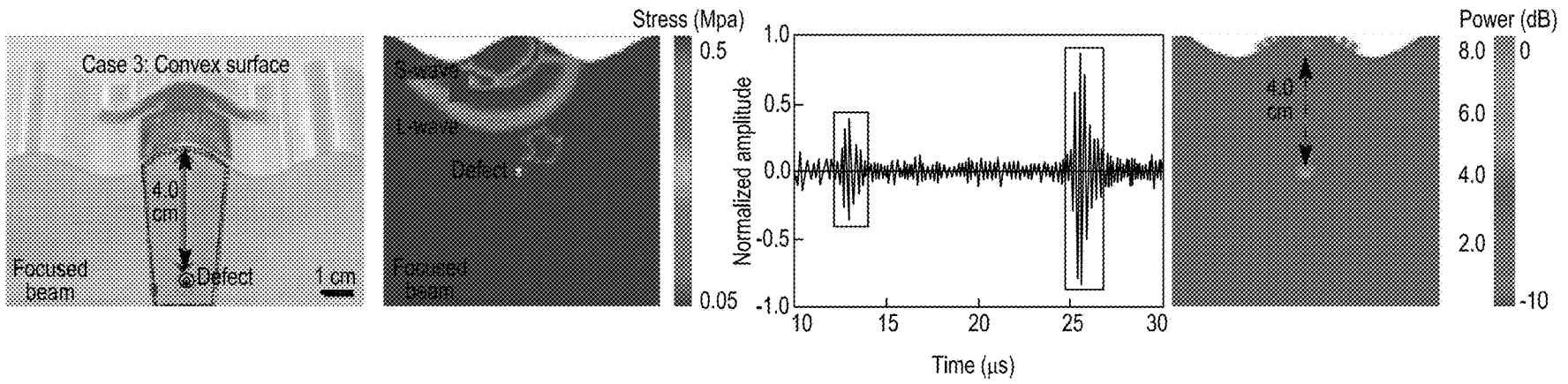

The stretchable ultrasonic device was used to image customized Al work pieces with embedded defects under planar, concave, and convex surfaces. The detailed experimental setup and method will be discussed below. In all cases, a straight defect (2 mm in diameter, orthogonal to the side surface) is created with different distances from the top surface (FIGS. 4A to 4C, first column). The device was laminated seamlessly on the test surfaces. The Synthetic Aperture Focus method was applied to reconstruct the corresponding images. The Synthetic Aperture Focus method will now be discussed.

Ultrasonic imaging is one of the most popular and successful methods to visualize internal discontinuities in structural or biomedical materials. One widely implemented method is the Phased-Array technique, where multiple transducer elements are excited simultaneously with designed time delays to focus and steer the ultrasonic beam. As an alternative option with simplified hardware requirements, Synthetic Aperture Focus (SAF) for ultrasonic imaging allows a more efficient means of operating the array with excitation of individual elements. A typical SAF approach uses an array of piezoelectric transducers that can act as both transmitters and receivers of ultrasonic waves. The image is constructed by extracting features from the received ultrasonic waveforms that are backpropagated in time to appropriately account for delay due to the relative spatial position of the transmitter, receiver, and focus point. This approach of temporal back propagation, commonly known as Delay-and-Sum (DAS) algorithm, can highlight the coherent wave components due to reflectors and suppress the random noises.

Figure 36:
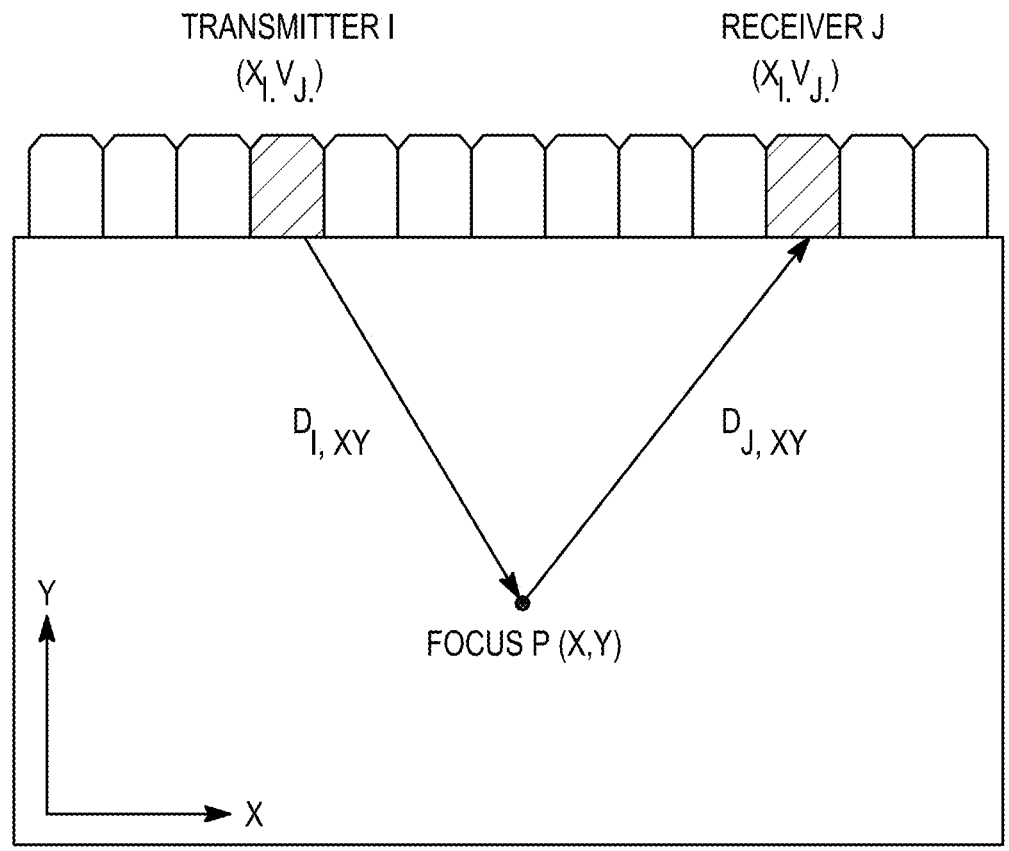
FIG. 36 is a schematic diagram showing the basic concept of synthetic aperture focus.
Figure 37A:
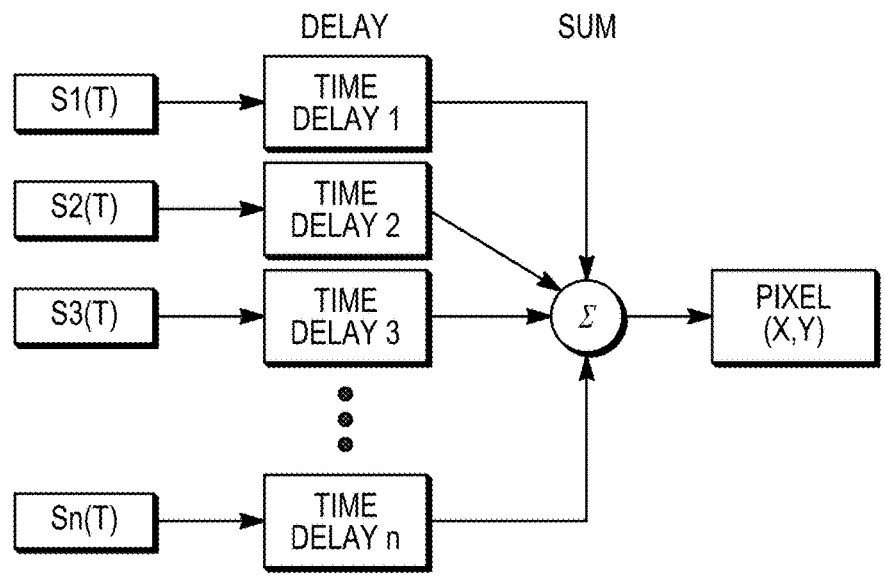
FIGS. 37A and 37B are block diagrams for DAS and DMAS, respectively.

Consider an ultrasonic transducer array with M transmitters and N receivers, as shown in FIG. 36, let the spatial coordinates of each transmitter i=1, M be $(x_i, y_i)$ and the spatial coordinates of each receiver j=1, . . . , N also be $(x_j, y_j)$. A standard DAS algorithm constructs an image I(x,y) by summing at each pixel P(x,y), the amplitudes of the received signals, $A_{ij}$, appropriately backpropagated, for each combination of transmitter i and receiver j. In the time domain, the backpropagated DAS algorithm is written as:

$$I^{DS}(x,y) = \Sigma_{i=1}^{M} \Sigma_{j=1}^{N} w_{ij}(x,y) A_{ij}(\tau_{ij,xy}) \qquad (7)$$

where $w_{ij}$ are apodization weights, and the backpropagation time, $\tau_{ij,xy}$, corresponds to the travel time of the wave from the transmitter i, to the focus point P(x,y), and back to the receiver j:

$$\tau_{ij,xy} = \frac{\sqrt{(x_i - x)^2 + (y_i - y)^2} + \sqrt{(x_j - x)^2 + (y_j - y)^2}}{v} \qquad (8)$$

where the denominator is the wave speed v in the solid. The DAS algorithm with uniform unity apodization weights is schematically illustrated as a block diagram in FIG. 37A.

Figure 37B:
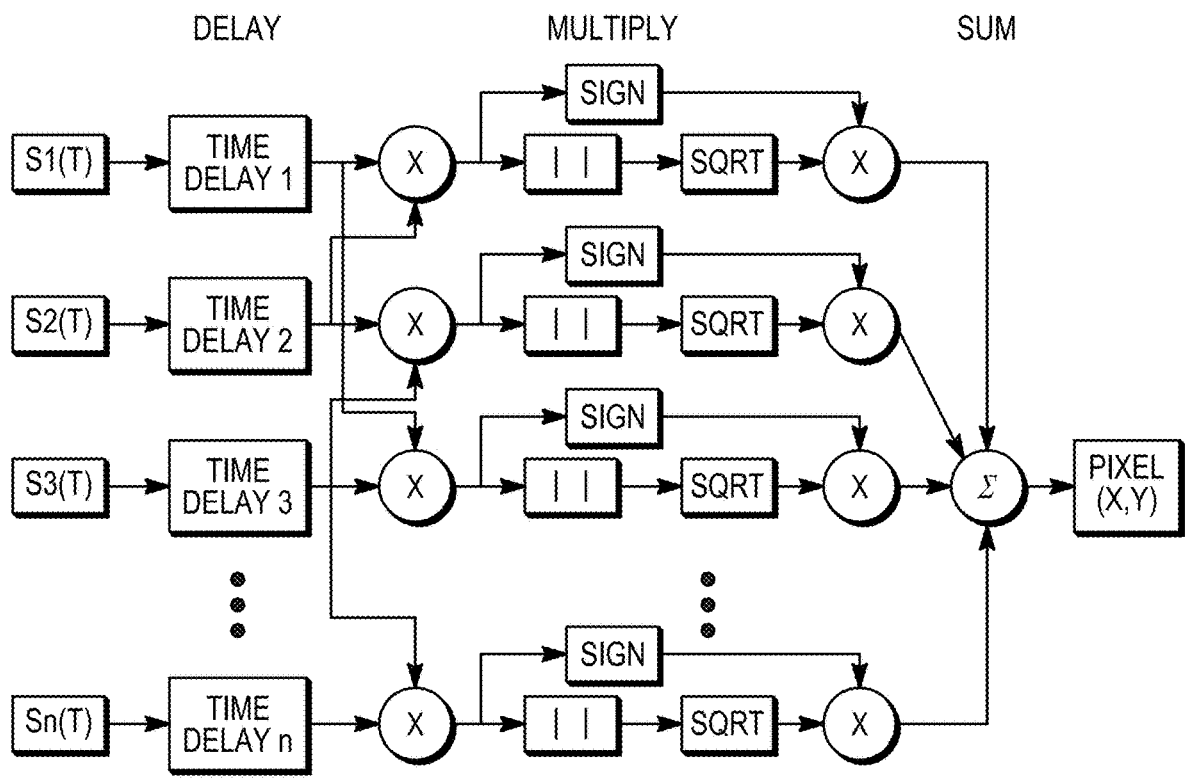

An improved SAF technique based on Delay-Multiply-and-Sum (DMAS) algorithm is schematically illustrated as a block diagram in FIG. 37B. To reconstruct an image I(x,y) at each pixel P(x,y) with DMAS, considering a linear array of 1×M elements, if the element that transmits does not serve as receiver, with each transmission, M−1 ultrasound signals are recorded, so the total number of signals received is M·(M−1). The amplitudes of the received signals, A, are appropriately backpropagated (realigned as in DAS) for each combination of transmitter and receiver. Once all the signals are in phase with regard to pixel P(x,y), they are combinatorially coupled and multiplied: if the number of received signals is N, then the number of multiplications to be performed is given by all the possible signal pair combinations $$\binom{N}{2} = \frac{N^2 - N}{2}.$$

The DMAS beamformed signal is obtained as:

$$I^{DMAS}(x,y) = \Sigma_{i=1}^{N-1} \Sigma_{j=i+1}^{N} A_i(\tau_{i,xy}) A_j(\tau_{j,xy}) \qquad (9)$$

where $A_i$ and $A_j$ are the signals received by the $i^{th}$ and $j^{th}$ transmitter-receiver pairs, respectively, and $\tau_{i,xy}$ and $\tau_{j,xy}$ are the backpropagation times corresponding to the travel times of the wave from the $i^{th}$ and $j^{th}$ transmitter-receiver pairs, respectively, through the focus point P(x,y). To keep the correct scale and same dimensionality without losing its sign, the 'signed' square root of the absolute value of each couple of multiplied signals is placed inside the summation, and the DMAS algorithm can be expressed as (53):

$$I^{DMAS}(x,y) = \Sigma_{i=1}^{N-1} \Sigma_{j=i+1}^{N} \frac{\text{sign}[A_i(\tau_{i,xy}) A_j(\tau_{j,xy})]}{\sqrt{|A_i(\tau_{i,xy}) A_j(\tau_{j,xy})|}} \qquad (10)$$

This process can be interpreted as the auto-correlation function of the receiver aperture and is expected to outperform the conventional DAS framework in terms of improved image lateral resolution and noise rejection, due to the artificially enhanced aperture and coherent component extraction.

Figure 28A:
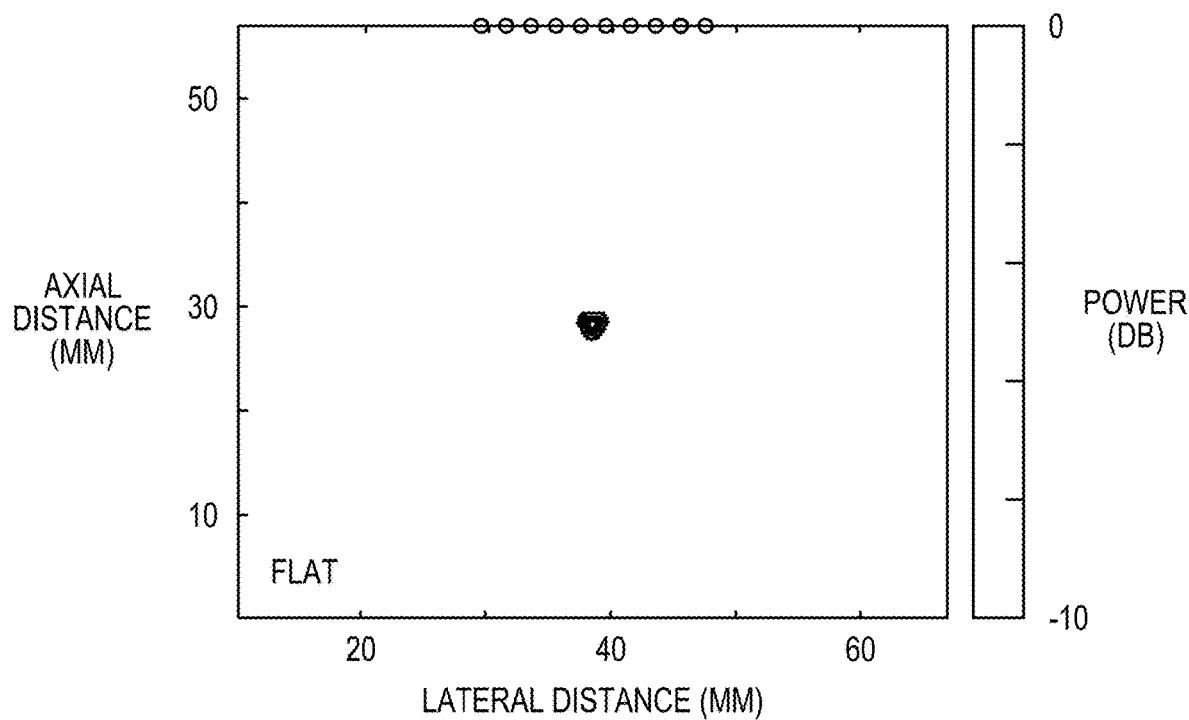
FIGS. 28A-28C show reconstructed images based on simulation under flat, concave, and convex surfaces.
Figure 28B:
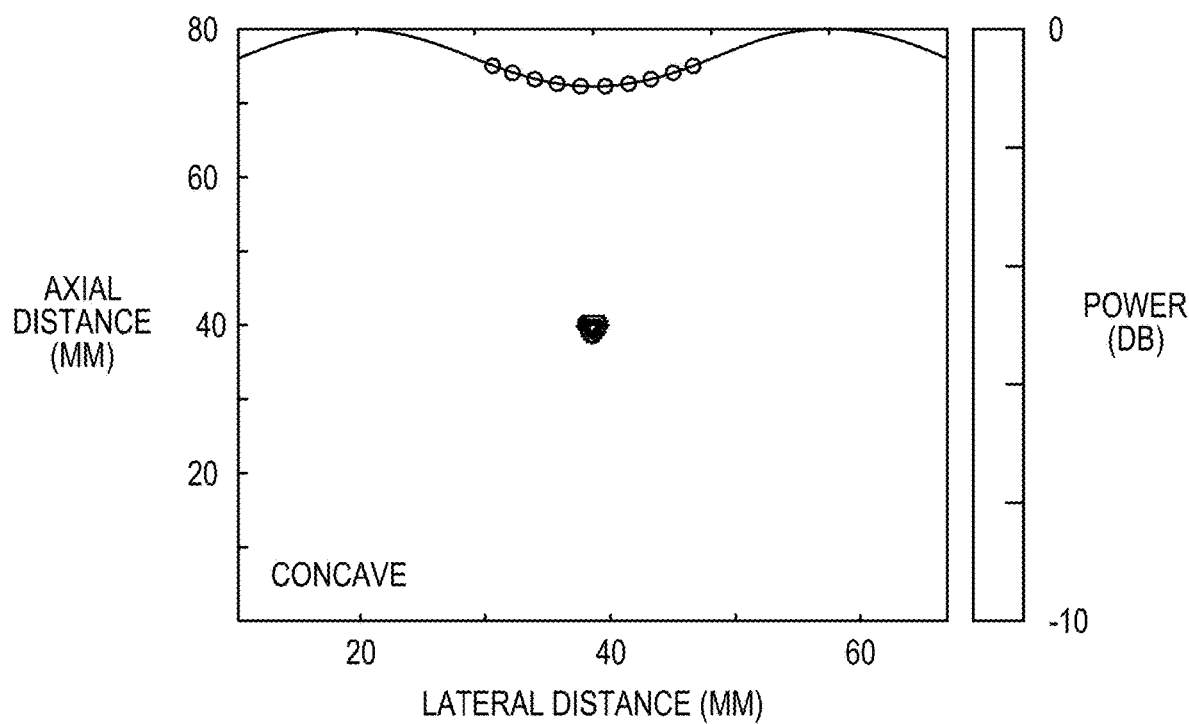
Figure 28C:
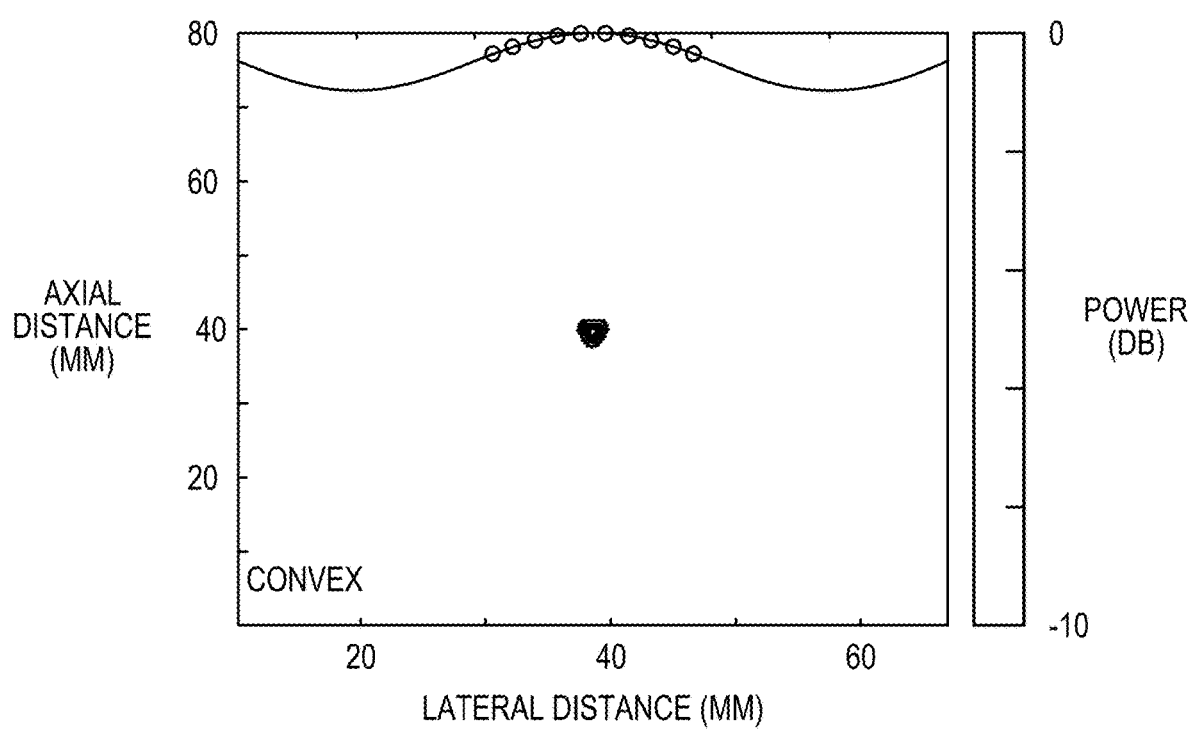
Figure 29A:
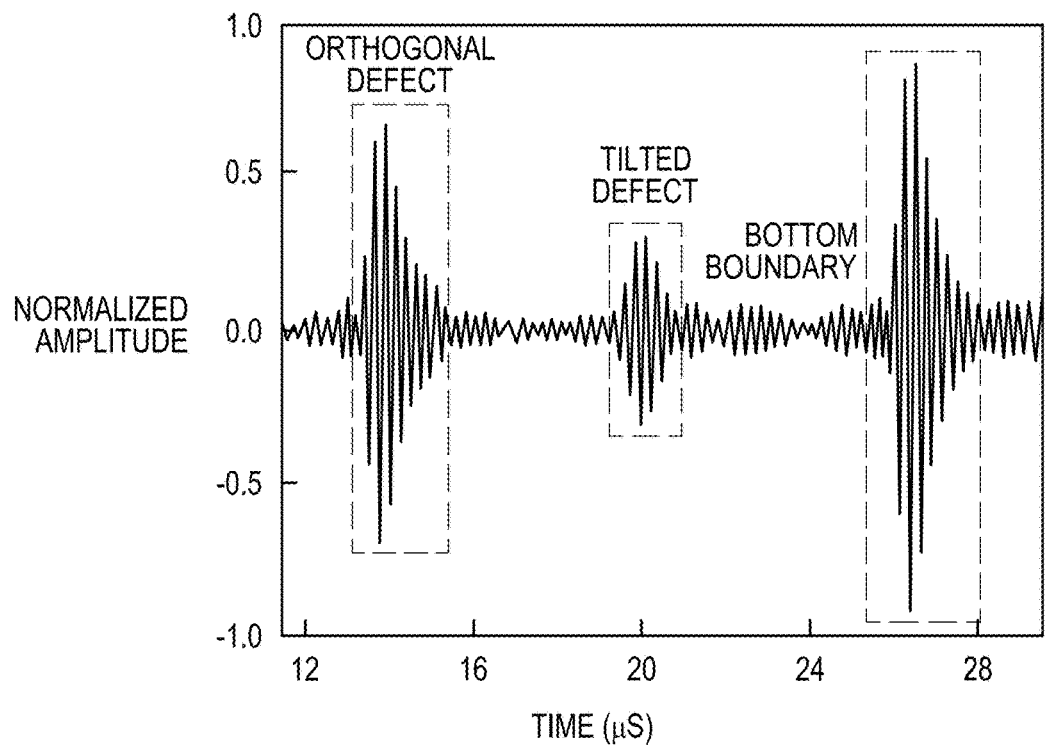
FIG. 29A shows the pulse-echo signal and FIG. 29B shows the reconstructed 2D image of two defects with different depths and orientations.
Figure 29B:
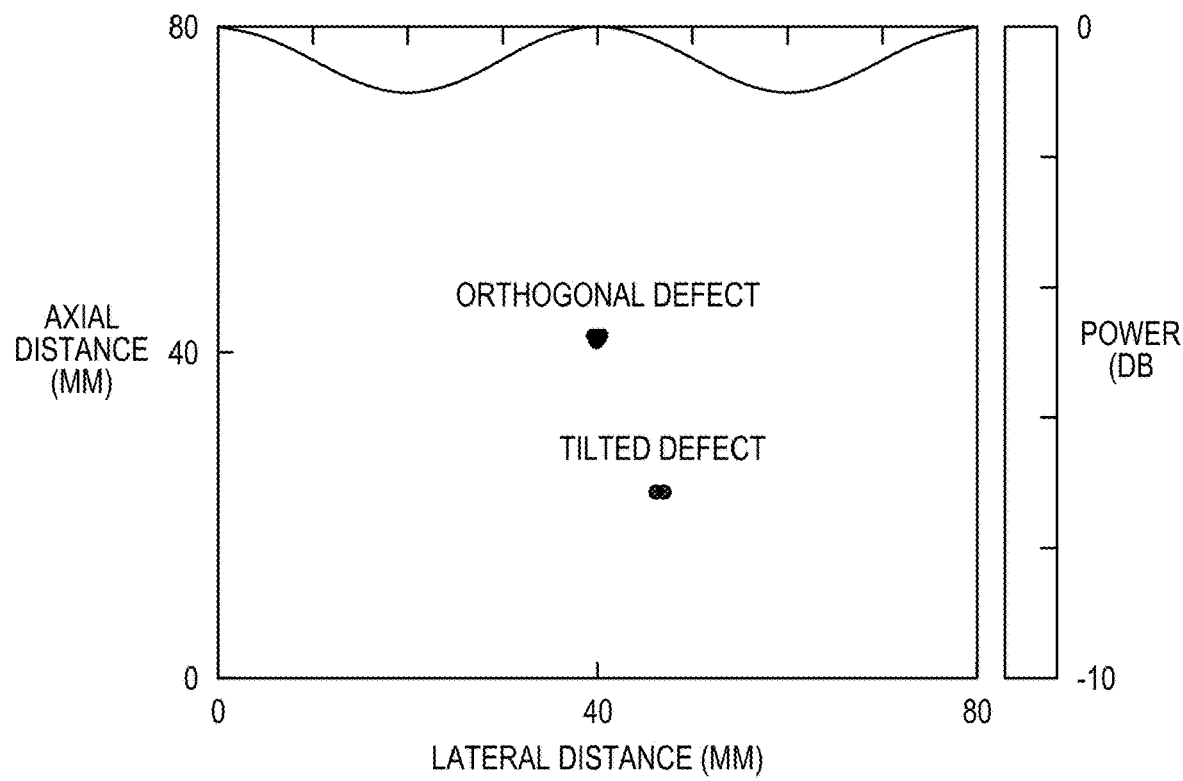

The SAF method allows a sparse transmitter-receiver scheme that bypasses the need for simultaneous excitations, minimizing the number of simultaneously active elements while preserving the image quality. As indicated by the wave field simulation results, the main lobes of the transducer are parallel, divergent, and focused for the planar, concave, and convex surfaces, respectively (FIGS. 4A to 4C, second column). Considering that the central defect acts as a secondary wave source and the transducer is primarily sensitive to out-of-plane motion (direction normal to transducer's sensing surface), the target surface curvature can greatly influence the captured signal strength. Specifically, for the convex surface, the majority of the reflected longitudinal wave motion from the defect aligns with the direction perpendicular to the sensing surface; for the concave surface, the reflected wave motion aligns with the in-plane motion (direction parallel to the sensing surface); for the planar surface, which is an intermediate case, the sensitivity of the transducer mainly depends on the component of the reflected wave vector normal to the sensing surface. To acquire the defect signals, for each case, 90 sets of data are obtained. Longitudinal-wave reflection signals from the defects and the bottom boundaries, with more than 18 dB SNR, can be collected with predicted times of arrival (FIGS. 4A to 4C, third column). The obtained full-field images of the defects are shown in the fourth column of FIGS. 4A to 4C, which have no artifacts and match extremely well with the simulation results shown in FIGS. 28A-28C. These results suggest that the stretchable ultrasound probe is capable of accurately imaging defects in media of complex surface geometries.

Figure 5A:
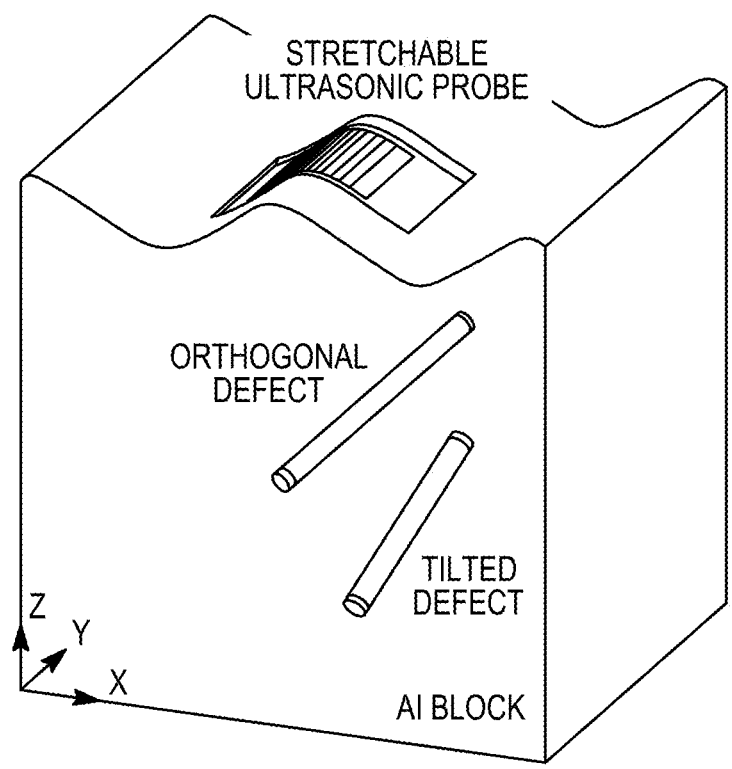
FIG. 5A schematically shows the experimental setup used for 3D image reconstruction of intricate defects under a convex surface, illustrating the spatial location and relative orientation of the two defects in the test subject.
Figure 5B:
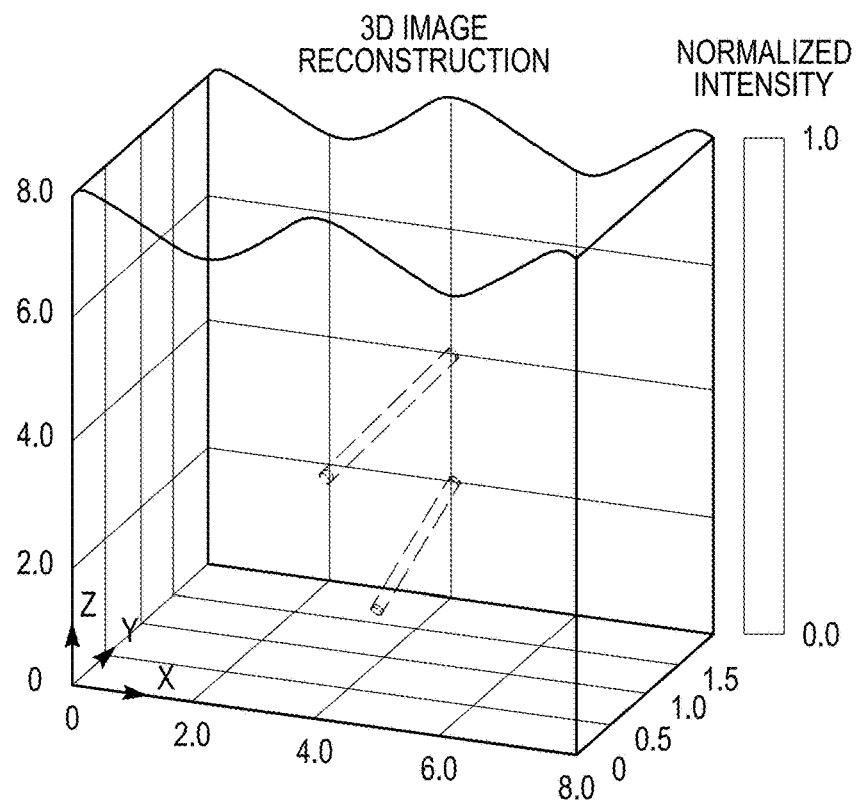
FIG. 5B shows the reconstructed 3D image, showing complete geometries of the two defects.
Figure 5C:
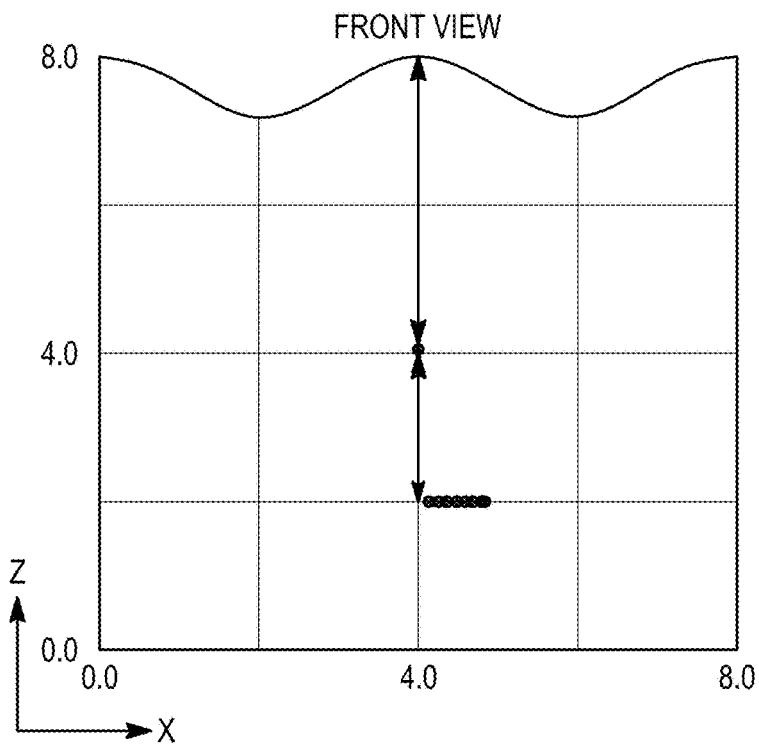
FIGS. 5C-5E show the 3D image from different view angles, illustrating the relative positions and orientations of the two defects to the top surface.
Figure 5D:
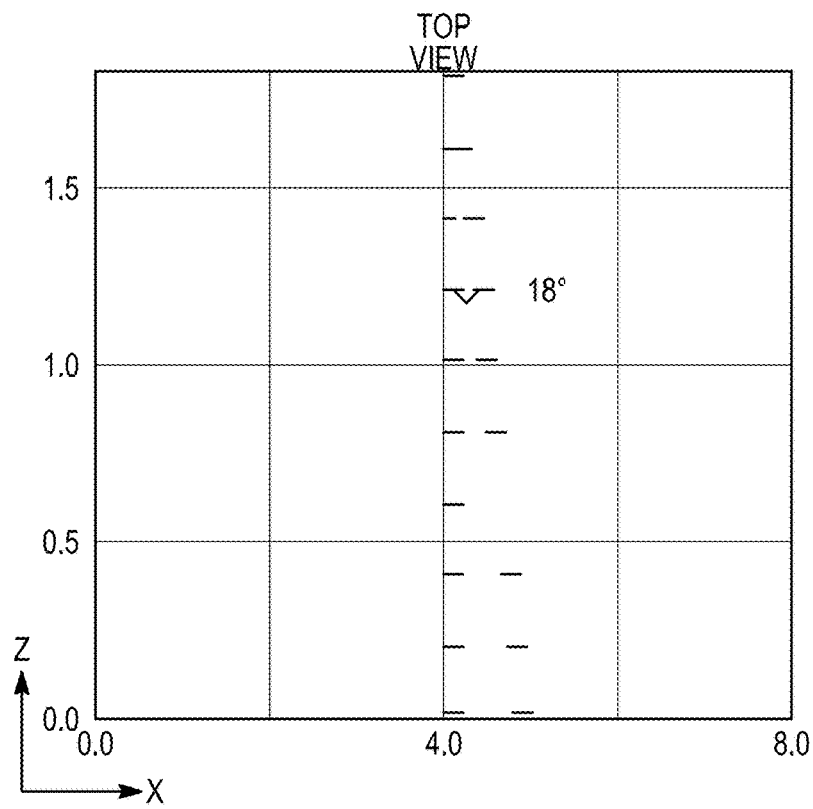
Figure 5E:
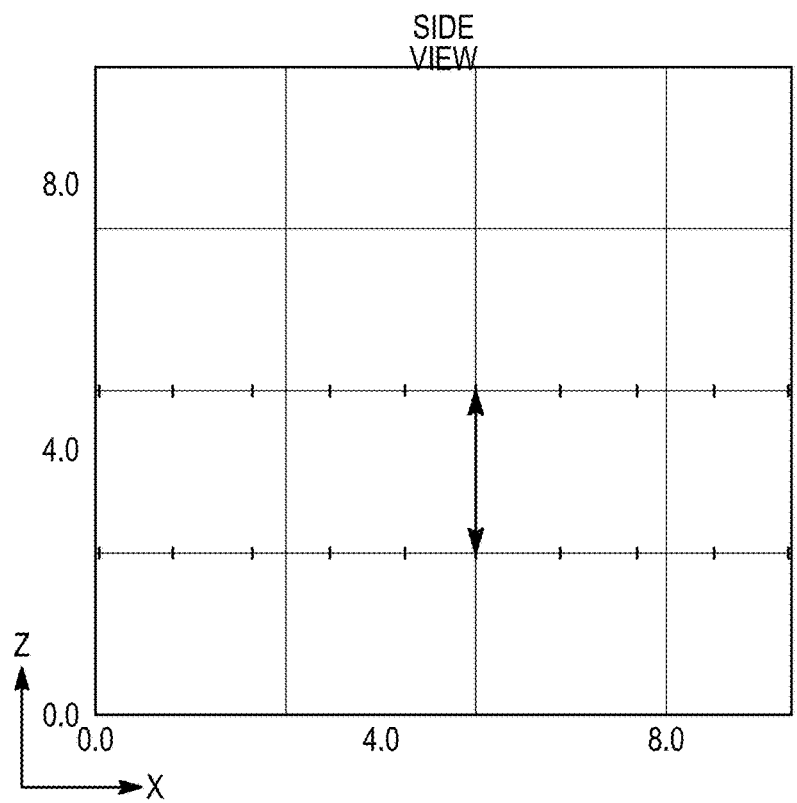
Figure 6A:
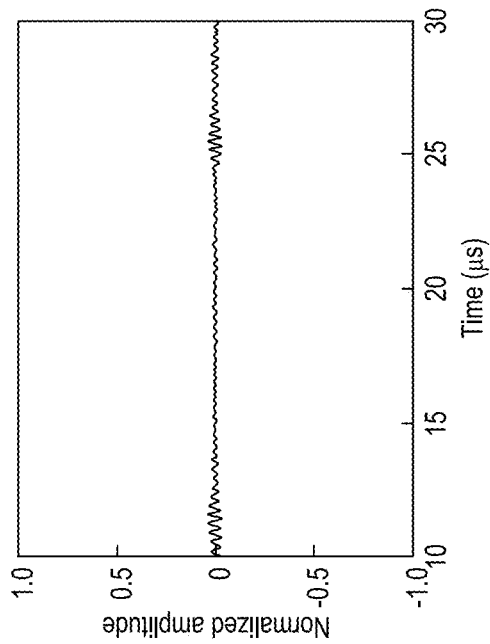
FIGS. 6A and 6B show the performance of a commercial rigid probe on a concave and convex surface, respectively.
Figure 6A:
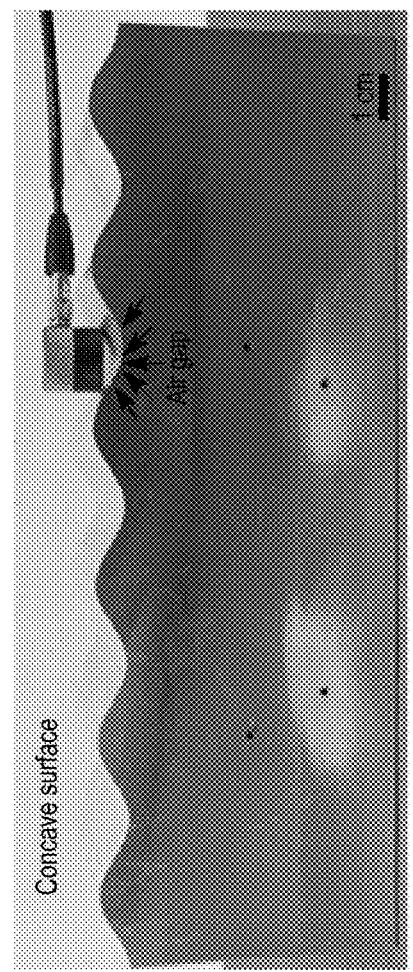
Figure 6B:
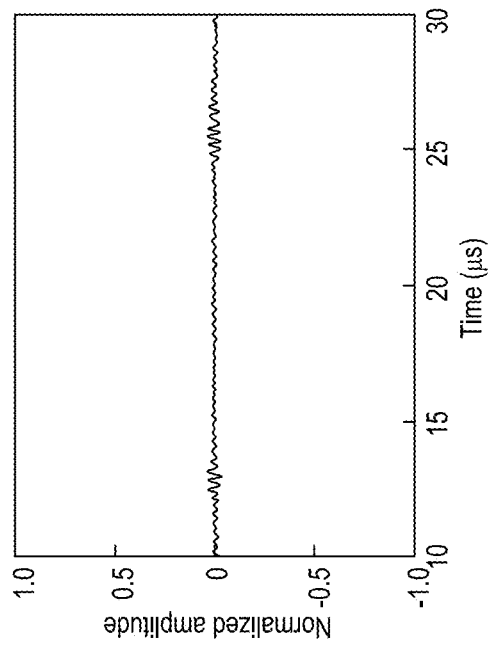
Figure 6B:
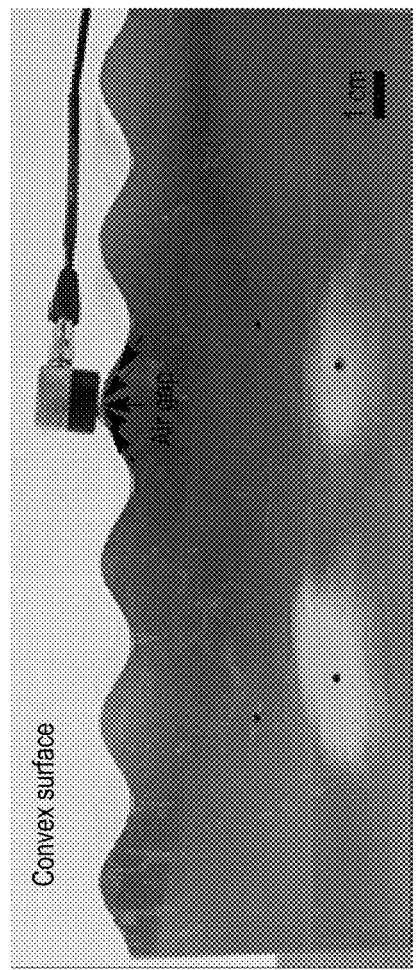
Figure 7A:
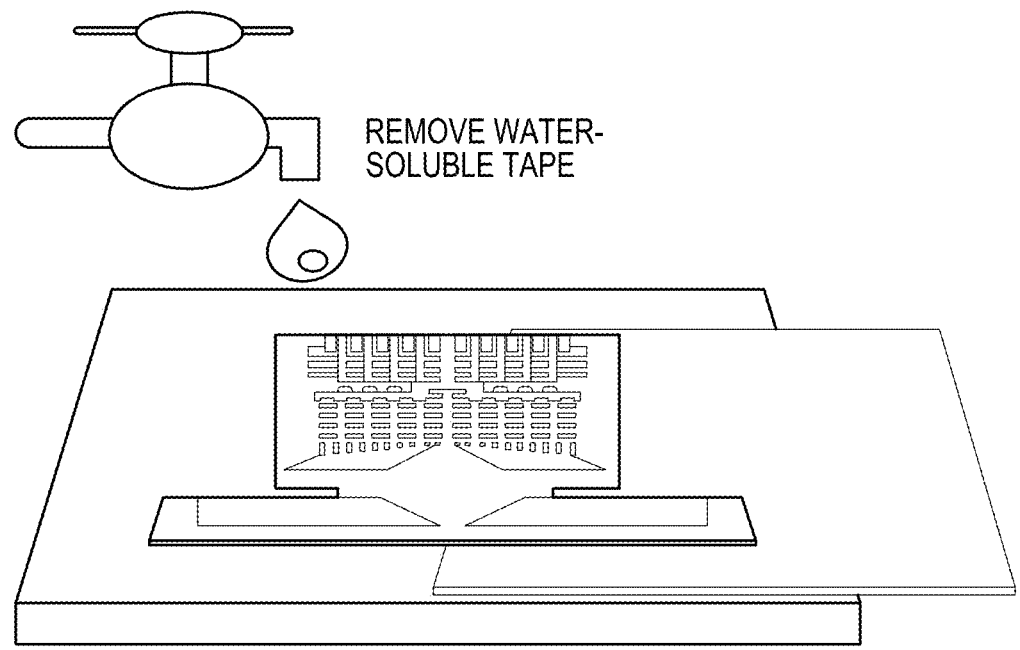
FIGS. 7A-7F is a schematic illustration of the device fabrication process.
Figure 7B:
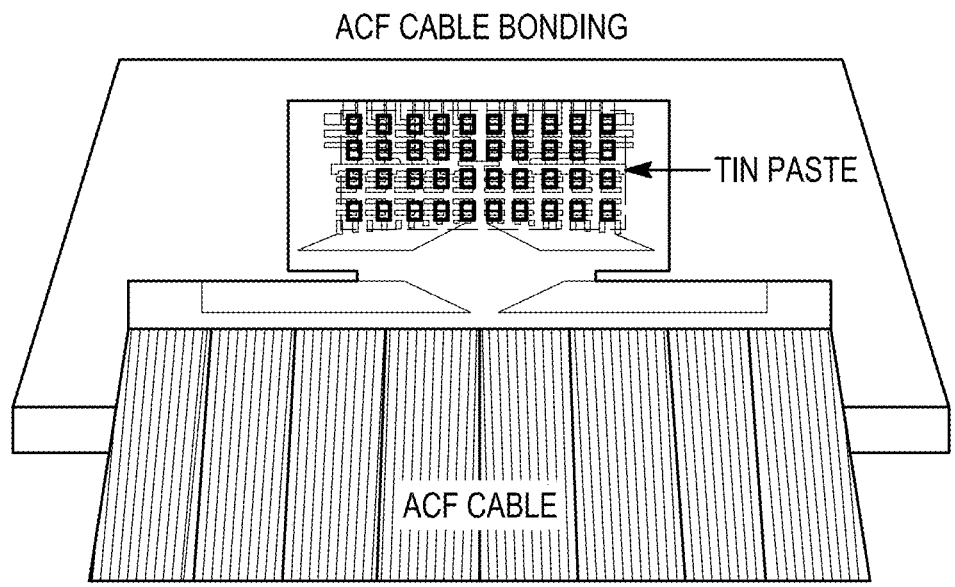
Figure 7C:
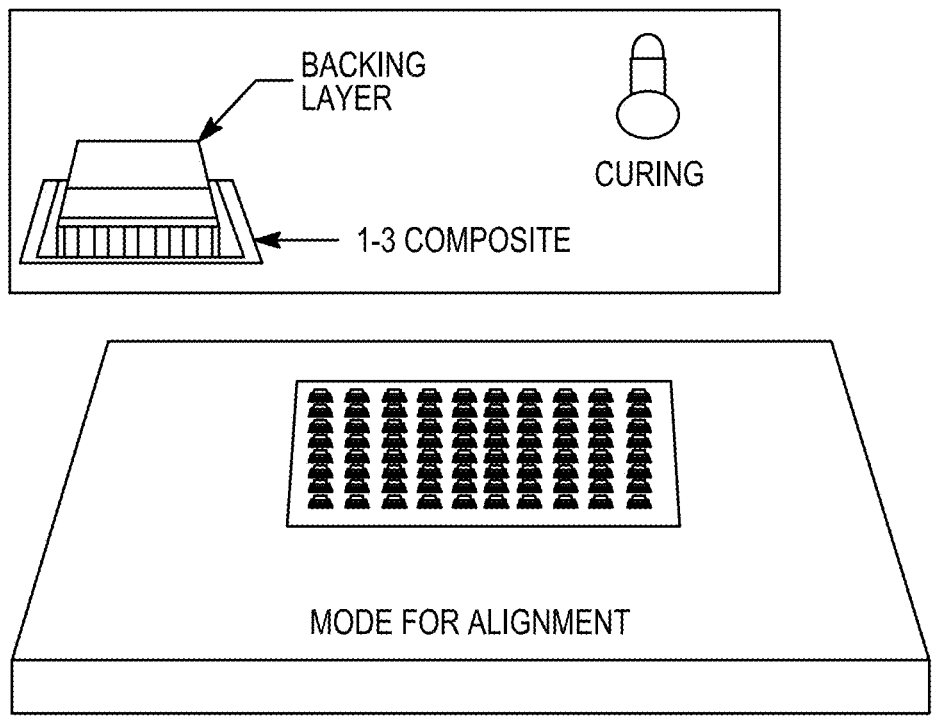
Figure 7D:
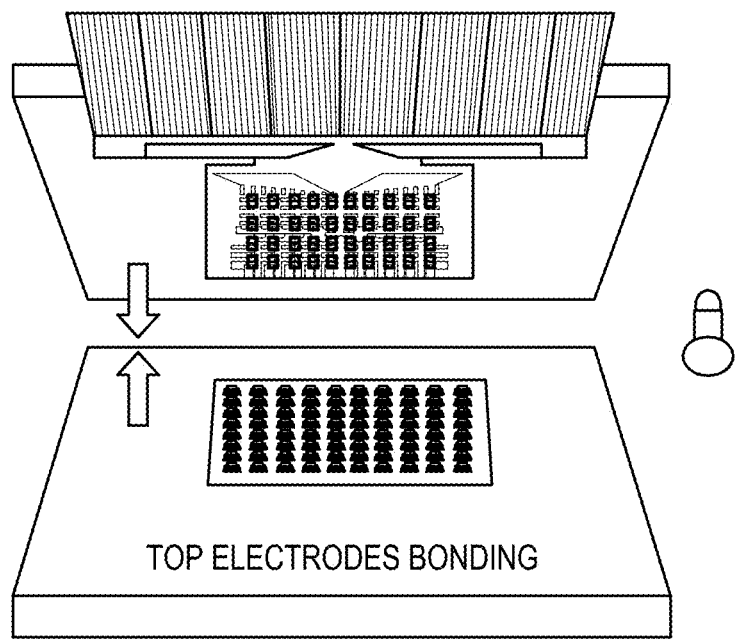
Figure 7E:
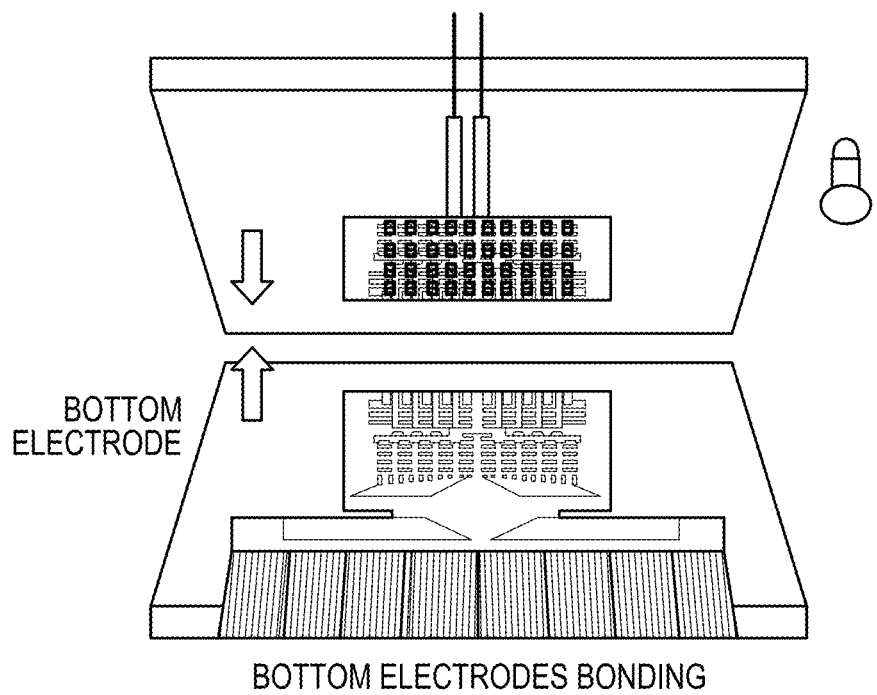
Figure 7F:
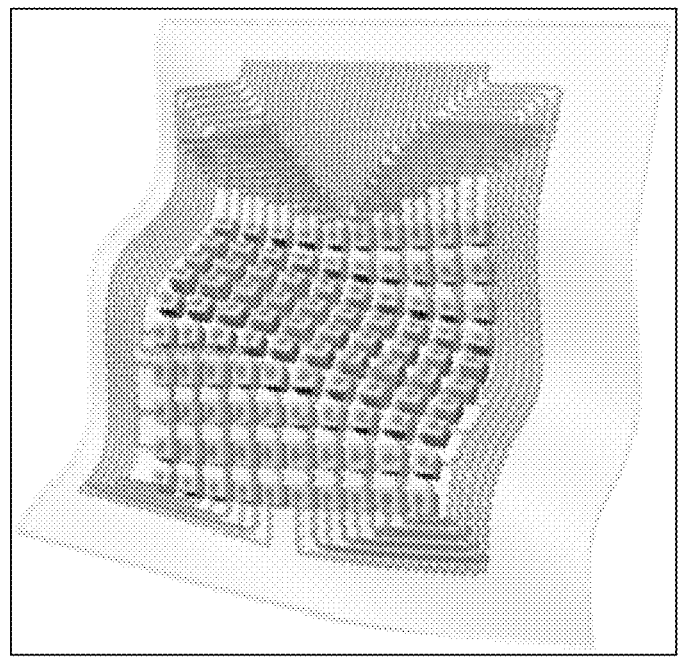

For practical engineering inspections, the detection of multiple defects is of particular interest, e.g. welding inspection of a pipeline and rail track detection under shelling. The stretchable ultrasonic device is used for 3D internal structure visualization by imaging two defects with different depths and orientations under a sinusoidal curved surface. A schematic of the experimental setup is shown in FIG. 5A, with one defect orthogonal to the x-z plane at a depth of 4.0 cm below the top surface, and the other defect 18° tilted away from the x axis at a depth of 6.0 cm below the top surface. Each 1×10 linear array in the x-z plane generates a 2D cross-sectional image of the two defects using the DMAS algorithm (Figs. S29A and S29B), similar to FIG. 4. The upper defect reflects part of the wave and reduces the wave energy reaching the lower defect. Thus, it produces a shadowing effect, which is exacerbated by the tilted configuration of the lower defect as the array scans from the y=0 to the y=1.8 plane. The 3D image can be reconstructed by integrating the 10 slices with a 2-mm pitch along the y-axis, as shown in FIG. 5B. The shadowing effect is removed by normalizing against the peak intensity of each defect. The corresponding front, top, and side views are shown in FIGS. 5C to 5E, which accurately match the design in FIG. 5A, thereby demonstrating a capability of volumetric imaging using the stretchable ultrasonic probe. Similar protocols of testing and imaging reconstruction can be applied to general and more sophisticated surfaces.

Discussion

The hybridized material integration, electrode design strategies, and imaging algorithm development introduced here provide a foundational basis for stretchable ultrasound imaging arrays that allow non-destructive 3D volumetric inspections under general complex surfaces. The high performance anisotropic 1-3 piezoelectric composites suppress shear vibrations, reduce cross-talk among the transducer, enhance longitudinal vibrations, and thus improve the overall sensitivity and signal-to-noise ratio. Five-layered serpentine electrodes enable a high level of integration and large stretchability of over 50%. The stretchable ultrasound probe, consisting of a 10×10 array of individually addressable transducer elements, can focus at different depths, with comparable spatial resolutions with existing rigid probes. The unique device design, combined with the advanced DMAS imaging algorithms, enables accurate, artifact-free, full-field, and non-destructive examinations underneath general complex surfaces.

Materials and Methods

The process of fabricating the five-layered electrodes began with a coating of PI (2 μm thick) on Cu sheets (20 μm thick). PI [poly(pyromellitic dianhydride-co-4,40-oxydianiline) amic acid solution, PI2545 precursor, HD MicroSystems] was first spin-coated on the Cu sheets (Oak-Mitsui, Inc.) at 4000 r.p.m. for 60 s (MicroNano Tools). Then PI/Cu was baked on a hotplate at 110° C. for 3 min and 150° C. for 1 min sequentially, then fully cured in nitrogen oven at 300° C. for 1 h. A glass slide coated with a layer of PDMS (Sylgard 184 silicone elastomer, 20:1) served as a substrate for laminating the PI/Cu sheet. The PI and PDMS were activated for bonding by ultraviolet light (PSD series Digital UV Ozone System, Novascan) for 1.5 min. Five separate pieces of Cu sheets were then patterned in "island-bridge" structured geometries (designed by AutoCAD software) by pulsed laser ablation (Laser Mark's). The laser parameters (1059 nm-1065 nm central wavelength, 0.228 mJ power, 35 kHz frequency, 300 mm/s speed, and 500 ns pulse width) were optimized to process Cu with the highest yield. Thin silicone superstrates/substrates of devices (15 μm each, Ecoflex-0030, Smooth-On) were prepared by mixing two precursor components together in a 1:1 ratio, spin-coating at 4000 r.p.m. for 60 s, and curing at room temperature for 2 h. In this study, PDMS was used as a temporary substrate where the PI/Cu sheet was laminated for laser ablation. Compared with the PDMS, Ecoflex has lower Young's modulus (Young's moduli of Ecoflex-0030 1:1 and PDMS 20:1 are ~60 kPa and ~1 MPa, respectively.). Thus, we chose Ecoflex as the substrate, superstrate, and filler in our device to ensure the low modulus of the device that allows intimately conforming to the highly curved surfaces.

For the first layer, water-soluble tape (3M) was used to transfer print the patterned Cu electrode to the Ecoflex superstrate after 3 min UV activation (78). A separate piece of water-soluble tape was used to selectively mask the connect pads at the center and top of the electrode that will be exposed to bond the transducer array and ACF cables (Elform). Next, a 35 μm thick Ecoflex film was spin-coated at 3000 r.p.m. for 60 s, and cured at 80° C. for 20 min, forming an insulating layer while the Ecoflex on top of the water-soluble tape mask was removed by dissolving the water-soluble tape. Subsequent layers of electrodes were laminated, with alignment to the previous layer of electrodes, in a similar manner. The integrated four-layer top electrodes are shown in the FIG. 13. The bottom electrode was fabricated and transfer printed to a separate Ecoflex substrate (FIG. 12). Finally, ACF cables were hot pressed onto the electrodes, to serve as the connection access for data communication and power supply (FIG. 8).

Assembling of Transducer Arrays and their Integration with Electrodes

As shown in the schematic illustration of the device fabrication process of FIGS. 7A-7F, the process began with the fabrication of the backing layer and 1-3 composite (Smart Material Corp.). The conductive backing layer was prepared by mixing Ag-epoxy composite with hardener (E-Solder 3022, Von Roll) in a 12.5:1 ratio, and then curing at 60° C. for 8 h. The backing layer thickness was fixed at 580 μm by mounting between two pieces of glass slides. The backing layer was then diced into pieces of 1.2 mm×1.2 mm by a dicing saw (DAD3220, DISCO). The 1-3 composites were fabricated from PZT ceramics and epoxy using the dice-and-fill technique. The size of each PZT pillar is 100 μm×100 μm with a spacing of 55 μm (FIG. 1E). Each one of the 1-3 composite elements was diced to 1.2 mm×1.2 mm, and bonded with the backing layer via Ag-epoxy (EPO-TEK H20E, Epoxy Technology) under 150° C. for 5 min. The single layer bottom electrode was bonded with the 10×10 arrayed 1-3 composite, using a customized scaffold, by solder pastes ($Sn_{42}Bi_{57.6}Ag_{0.4}$, melting point 138° C., Chip Quik Inc.) cured in the oven at 150° C. for 6 min. The same approach was used to bond the four-layer top electrode with the backing layer. The gap between the sandwiched device was then filled by Ecoflex and cured at room temperature for 2 h. Afterwards, the glass slides were removed, yielding a free-standing stretchable ultrasound transducer array.

Electromechanical and Mechanical Testing of the Device

Figure 30A:
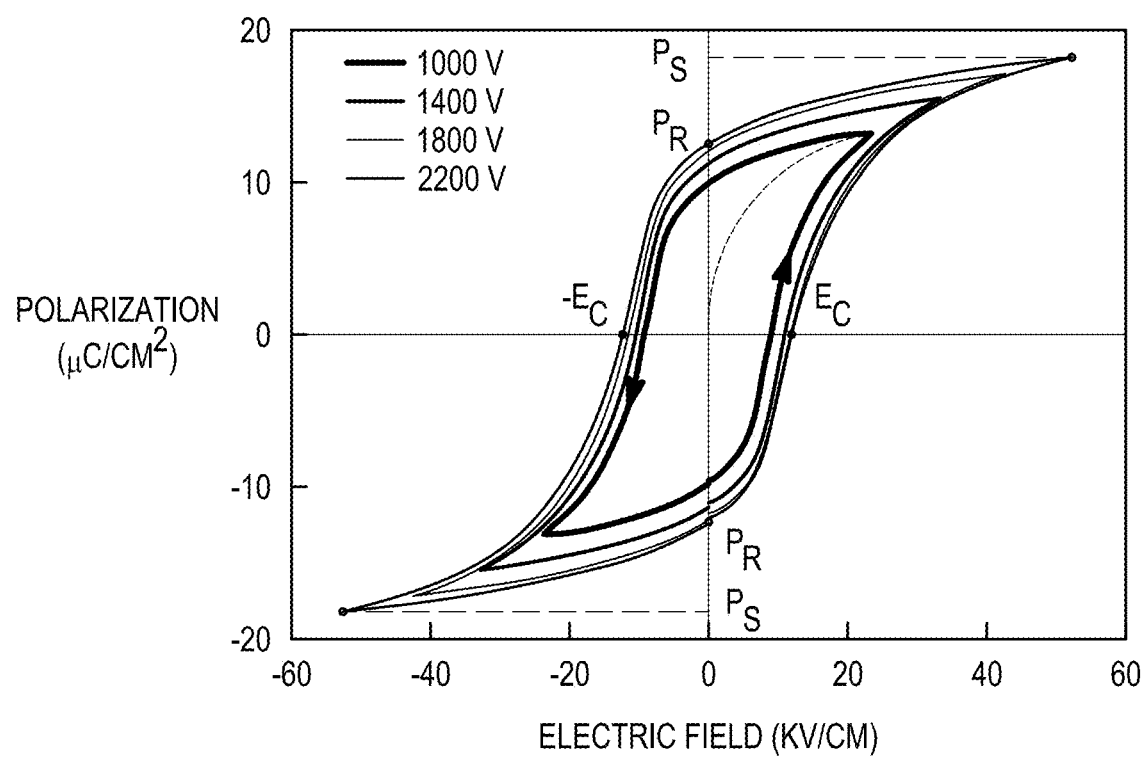
FIG. 30A shows the polarization hysteresis loop to determine the minimal voltage needed to fully polarize the 1-3 composite in the silicone medium without electrical breakdown and FIGS. 30B and 30C shows a cross-section of a transducer element after normal polarization at 52.38 kV/cm in a silicone medium and after breakdown above 52.38 kV/cm, respectively.
Figure 30B:
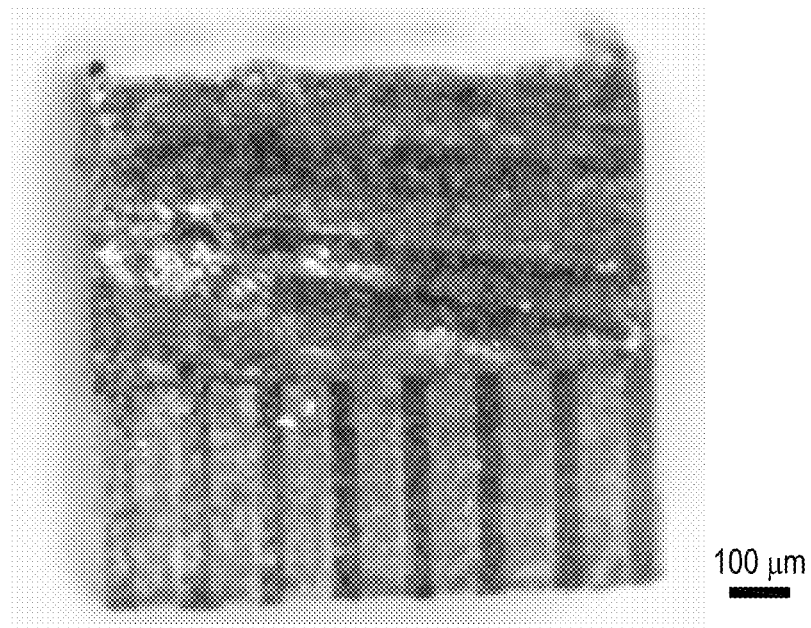
Figure 30C:
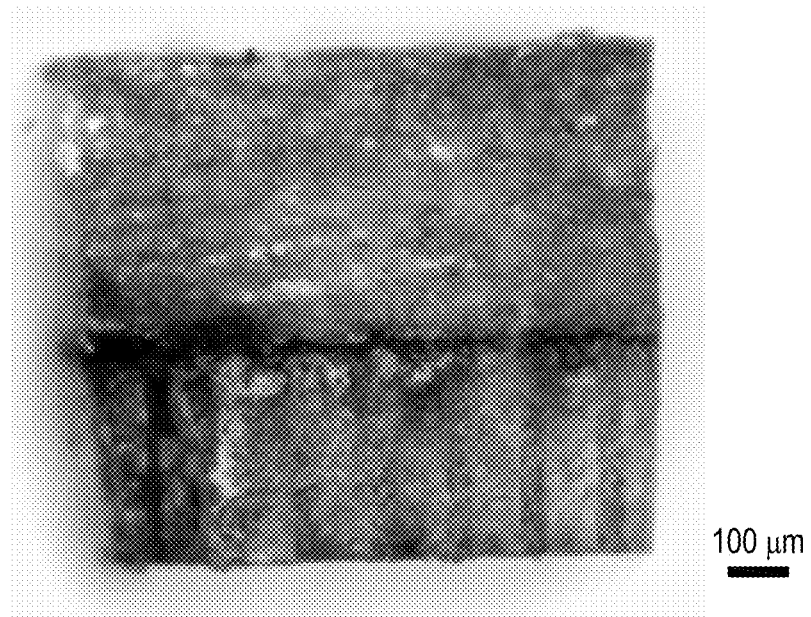

A high voltage power supply (Model 355, Bertan), with a 52.38 kV/cm direct voltage output, provides a platform to polarize the device for 15 min. The polarization hysteresis loop (FIG. 30A) was measured to determine the minimal voltage needed to fully polarize the 1-3 composite in the silicone medium without electrical breakdown. FIGS. 30B and 30C shows a cross-section of a transducer element after normal polarization at 52.38 kV/cm in a silicone medium and after breakdown above 52.38 kV/cm, respectively. A network analyzer (Agilent Technologies) with a scanning range of 2 MHz to 6 MHz under Smith mode gave the impedance and phase angles of the transducer. Electromechanical efficiency is a parameter that characterizes the degree of energy coupling efficiency between electrical and mechanical forms. Electromechanical coupling coefficient, k, is the factor that quantitatively evaluates the electromechanical efficiency. The electromechanical coupling coefficients of 1-3 composite and transducer, $k_t$ and $k_{eff}$, were derived from the equation (1) and (2), respectively:

$$k_t = \sqrt{\frac{\pi}{2}\frac{f_r}{f_a}\tan\left(\frac{\pi}{2}\frac{f_a - f_r}{f_a}\right)} \quad (1)$$

$$k_{eff} = \sqrt{1 - \frac{f_r^2}{f_a^2}} \quad (2)$$

Where the resonant frequency $f_r$ and anti-resonant frequency $f_a$ were extracted from the impedance and phase angle spectra. An experimental system, including the pulse receiver (model Panametric 5077PR, Olympus), oscilloscope (LeCroy WaveJet 314), and a 300 μm diameter copper wire in the phantom, was used to obtain the pulse-echo signal and frequency spectra. The frequency bandwidth (BW) of the signal at −6 dB was determined by the equation (3):

$$BW = \frac{f_u - f_l}{f_c} \times 100\% \quad (3)$$

where $f_u$ is the upper frequency, $f_l$ is the lower frequency, and $f_c$ is the central frequency (60). A function generator (AFG 3251, Tektronix) and oscilloscope (LC534, LeCroy Corp.) were used to assess the cross-talk. The sinusoid burst mode with 5 V peak-to-peak voltage was used to excite the elements in the array. The frequency was scanned between 2 MHz to 6 MHz with a step size of 0.2 MHz. The cross-talk level was then defined by counting the ratio of the peak voltages to the reference voltage (the voltage under a 1 MΩ coupling on the oscilloscope). The capacitance and dielectric loss of array elements were measured by a LCR digital bridge machine (Quadtech).

Mechanical testing of a 2×2 transducer array was performed with a customized biaxial stretcher. To accurately evaluate the biaxial stretchability, the strain was quantified based on the distance between the two electrodes. Images of the device under different strain levels were collected with a charge-coupled device (OMAX) on an optical microscope (Amscope). The electric impedance of the transducer under stretching and bending states, and the relative resistance change of the Cu serpentines at various tensile strain levels were tested by a network analyzer and a source meter (Keysight Technologies), respectively.

Finite Element Analysis Simulations

The commercial software package ABAQUS allowed for simulating the mechanical response of transducer arrays. The composite layer (Ecoflex, Cu, and PI) consisted of hybrid hexahedral elements (C3D8H). The simulations used values of the elastic modulus of Ecoflex, PI, and Cu of 0.06, 2300, and 41500 MPa, respectively. In order to get the yield strength value of the Cu, four pieces of Cu slides with high aspect ratio (width: 4.18 mm, thickness: 0.02 mm, length: 18.78 mm) were measured the tensile testing. The testing rate was 0.01 mm/mm/min and the load cell was 1 kN (Instron 5965). The stress-strain curves were obtained where the yield strength value of Cu slides (187 Ma) was extracted and used in simulations.

Non-Invasive Inspection of the Internal Defects

Figure 26:
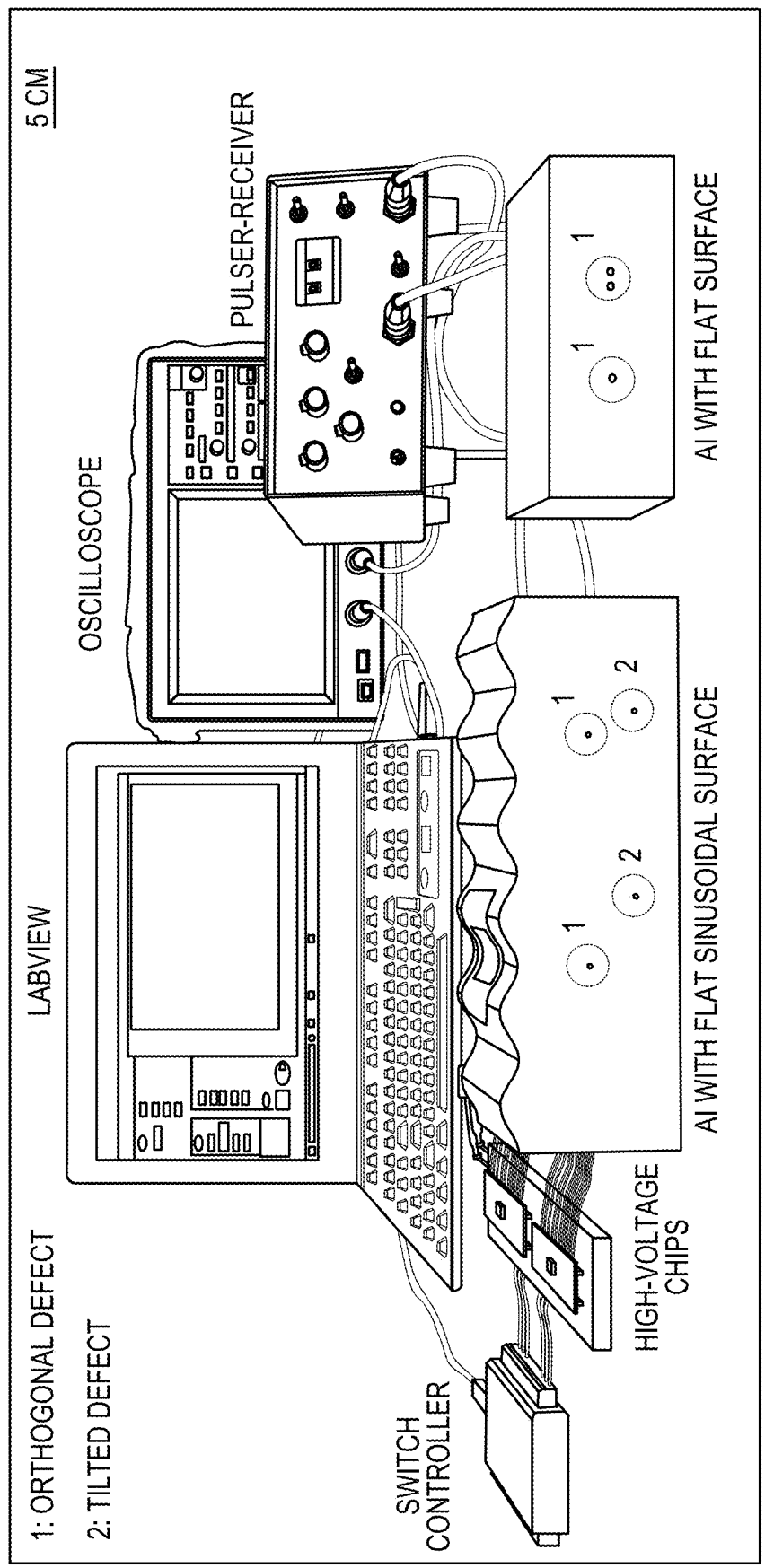
FIG. 26 shows the instruments used for NDE testing.
Figure 27:
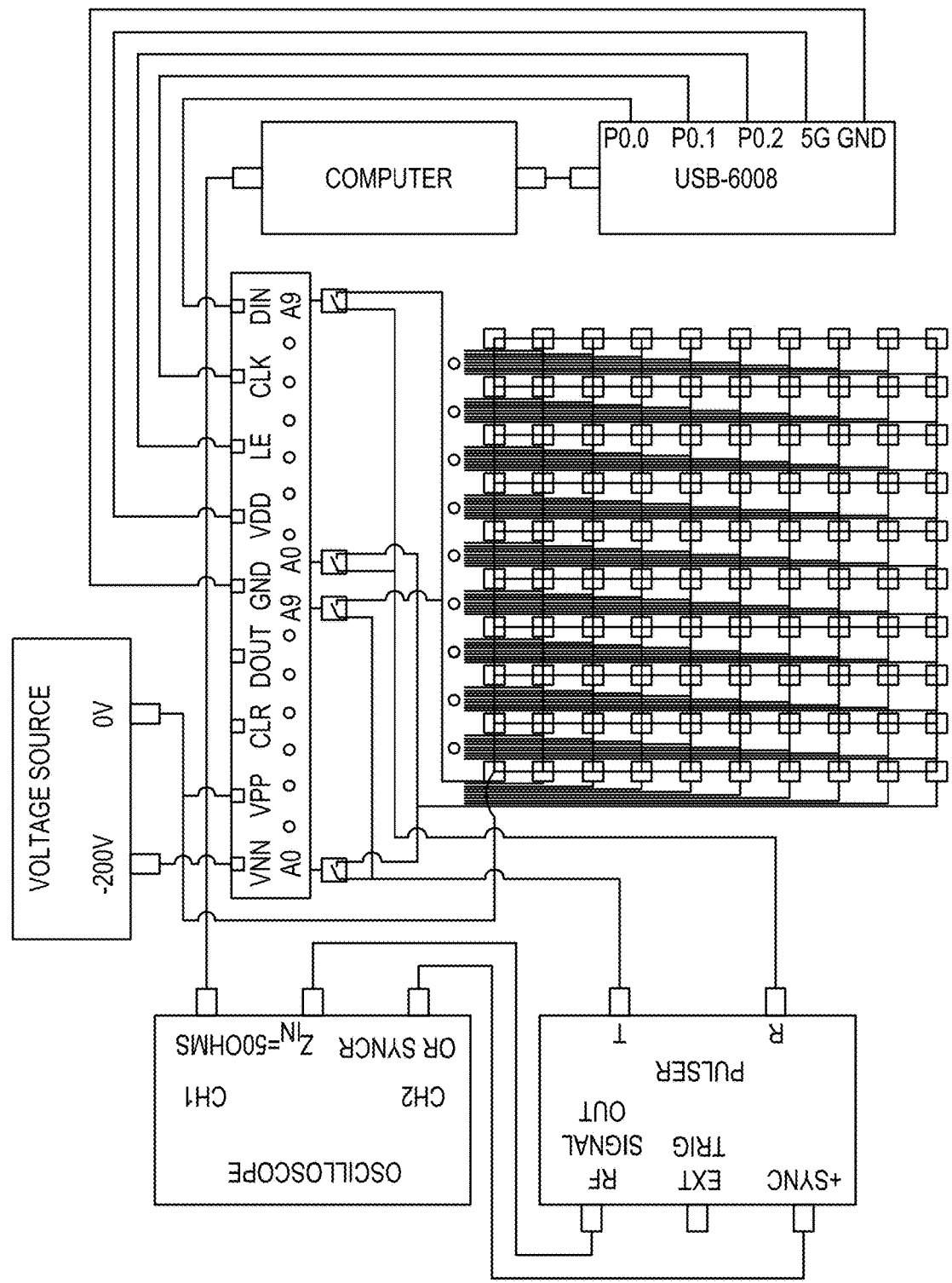
FIG. 27 shows the switch circuit of the entire testing system, which allows the device to automatically transmit and receive ultrasound signals.
Figure 31A:
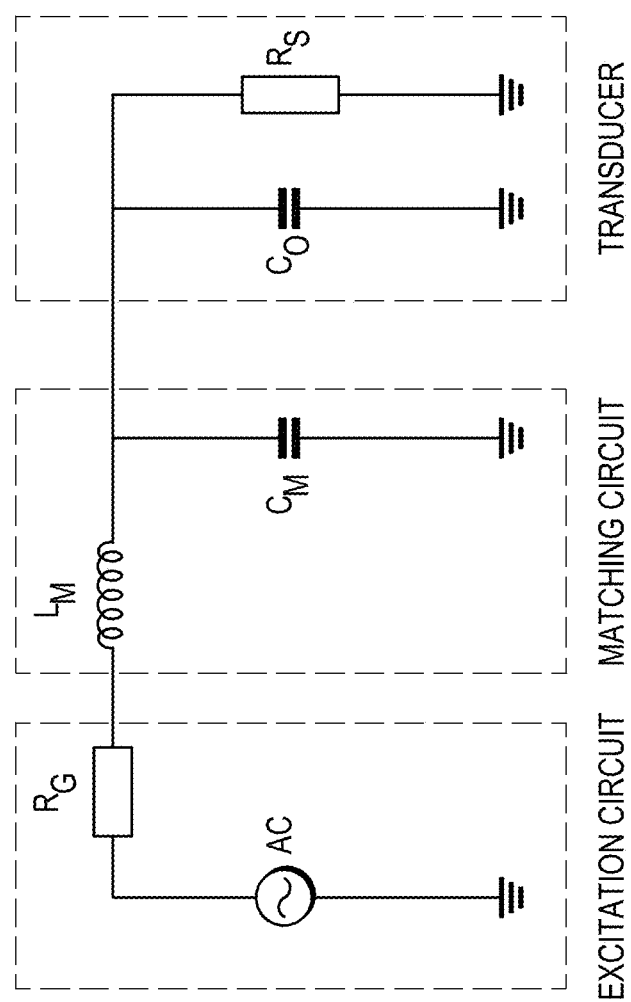
FIG. 31A shows the matching circuit of the ultrasound testing system and FIG. 31B shows the ultrasound echo signal before and after implementing the matching circuit in the testing system.
Figure 31B:
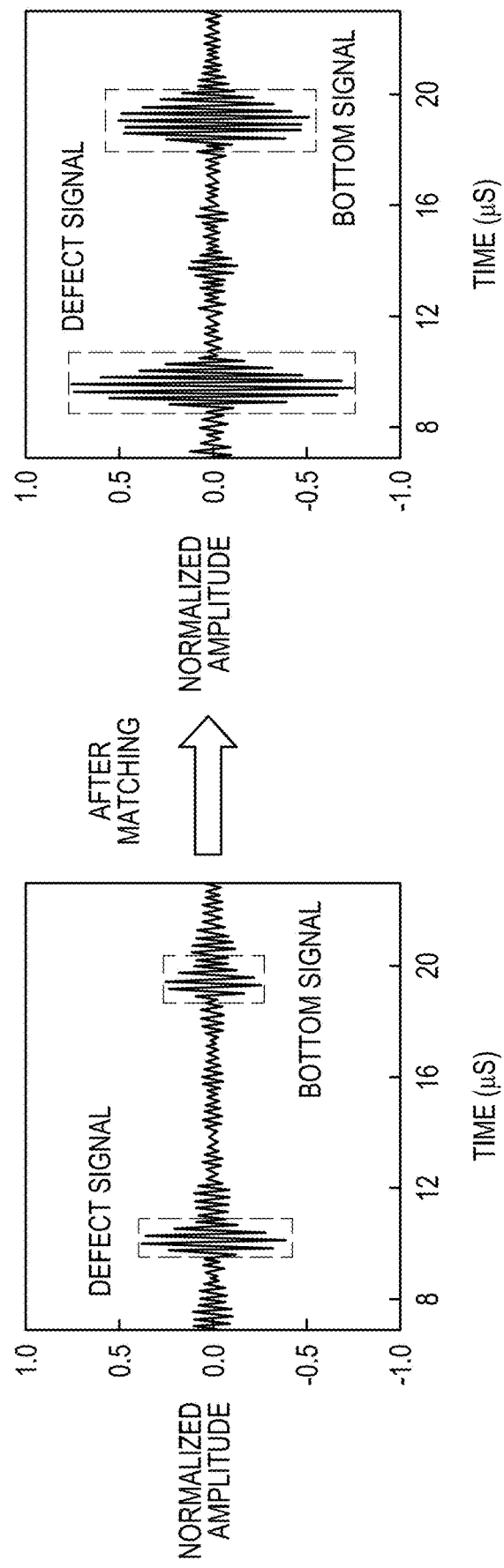
Figure 32A:
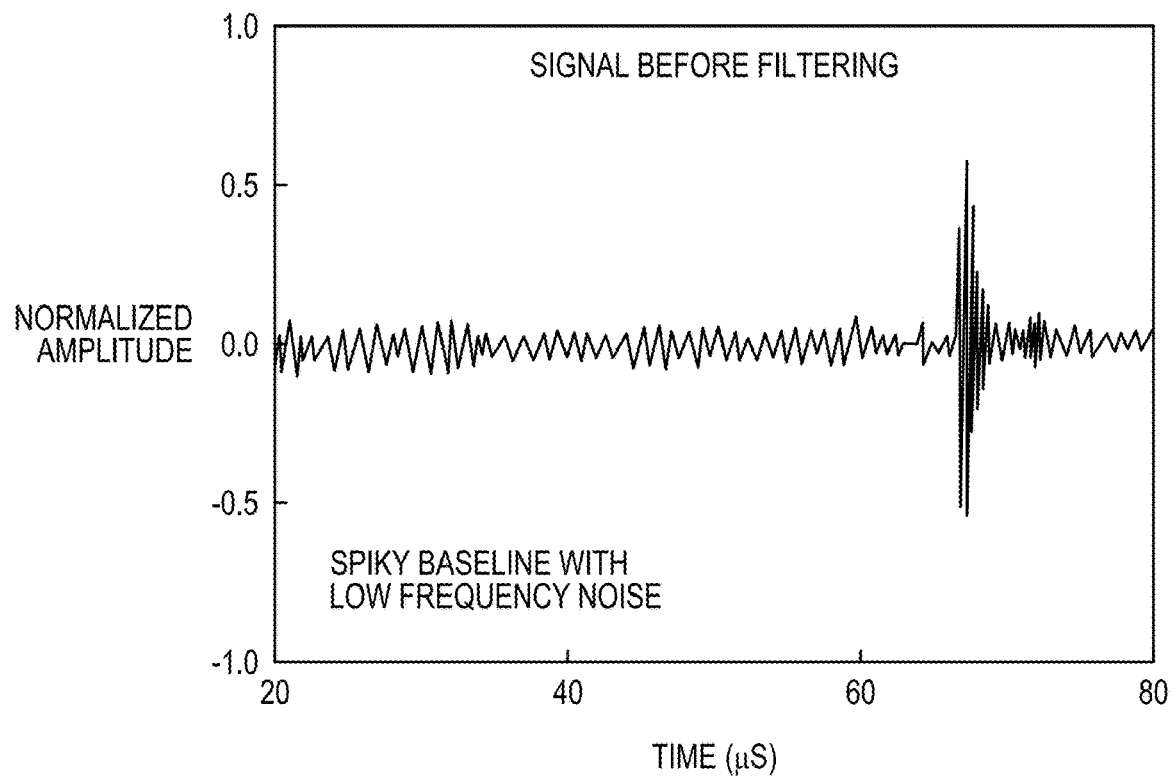
FIGS. 32A and 32B shows a comparison of the ultrasonic performance before and (B) after signal filtering, respectively.
Figure 32B:
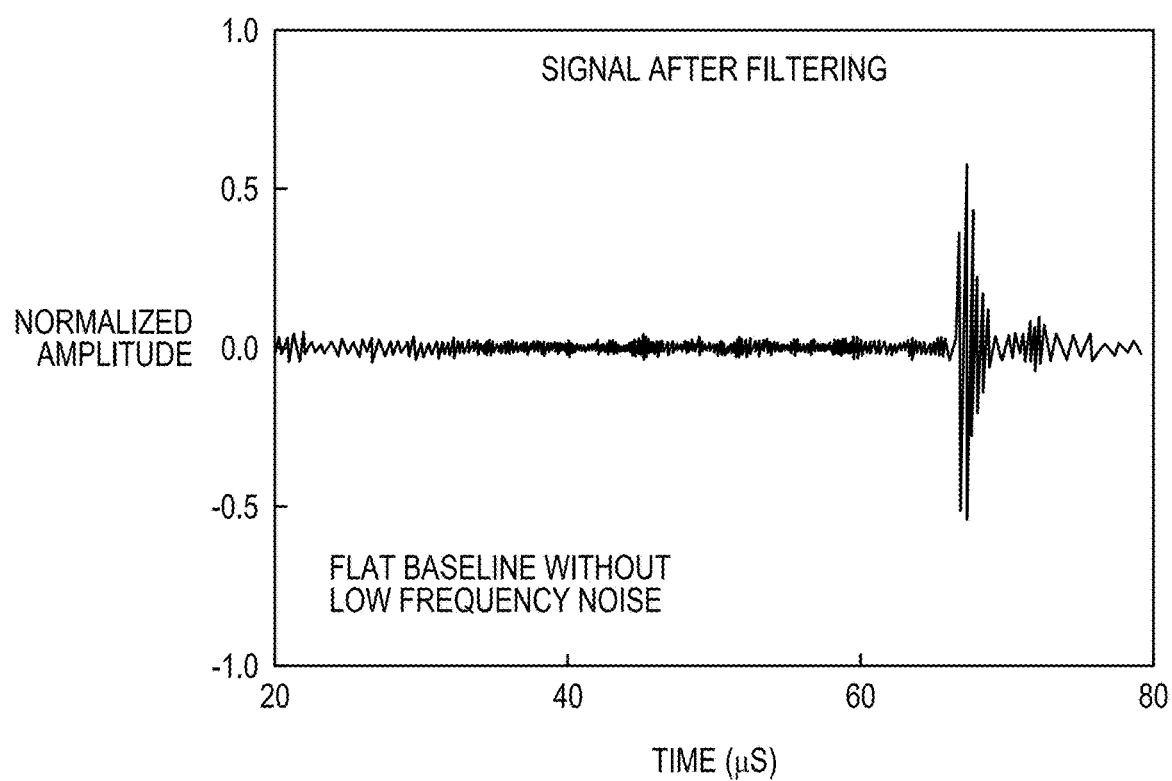

For testing on specimens with planar, concave, and convex surfaces, the coordinate location of each transducer element in the array was determined by aligning the device with a known marker position on the surface. For more complex surfaces, a 3D scanner can be used to locate the exact coordinates of each element. For the specimens whose surfaces are sinusoidal, the amplitude is 4 mm peak-to-peak and the wavelength is 40 mm. A data acquisition system, composed of a pulser-receiver, an oscilloscope, switch controller (NI USB-6008) and high-voltage chips (HV2601), was developed using LabVIEW (National Instrument), as shown in FIGS. 26 and 27. We used Labview to program the switch controller so that it could turn on and off the high voltage chip. This system allows the device to automatically transmit and receive ultrasound signals. An electrical impedance matching system (FIG. 31A) between the transducer and the pulser-receiver (50Ω) was used to minimize power reflection when exciting the transducer. The enhanced power transmission efficiency improved the SNR (FIG. 31B). A step pulse excitation (−100 V) was applied on the selected element, and the responses from the other elements were collected. By iterating this procedure over a 1×10 linear array, 90 sets of waveform data could be acquired. The received raw signals were first filtered with a bandpass filter based on Continuous Wavelet Transform to remove the unwanted frequency components and minimize the filter-induced phase shift. FIGS. 32A and 32B show the ultrasonic performance before and after filtering, respectively. Each filtered waveform was decomposed into its in-phase and phase-quadrature components through the Hilbert transform, and an improved Synthetic Aperture Focus (SAF) algorithm would then be applied to each of the Hilbert transformed components separately. Finally, pixel intensity of the final images was reconstructed by computing the modulus of the two components from the Hilbert Transform and converting it to decibel dynamic range. The image resolution of 20 pixels per mm, which well suffices the half wavelength spatial sampling of longitudinal waves in the phantom at 3.5 MHz (Nyquist-Shannon sampling theorem), is applied here to completely preserve the information in signals.

In this study, the SAF technique based on Delay-Multiply-and-Sum (DMAS) was implemented for image reconstruction (62-64). To reconstruct an image I(x,y) at each pixel P(x,y) with DMAS, considering a linear array of 1×M elements, M−1 ultrasound signals were recorded each time when one element was activated as the transmitter and the remaining M−1 elements were the receivers. Thus, a total of M·(M−1) signals were obtained. The amplitudes of the received signals, A, were appropriately backpropagated for each combination of transmitter and receiver. Once all the signals were in phase with regard to pixel P(x,y), they were combinatorially coupled and multiplied. If the number of received signals was N, then the number of multiplications to be performed was given by all the possible signal pair combinations $$\binom{N}{2} = \frac{N^2 - N}{2}.$$

The backpropagated DMAS algorithm can be written as (64):

$$P^{DMAS}(x,y) = \sum_{i=1}^{N-1} \sum_{j=i+1}^{N} \text{sign}[A_i(\tau_{i,xy})A_j(\tau_{j,xy})] * \sqrt{|A_i(\tau_{i,xy})A_j(\tau_{j,xy})|} \quad (4)$$

where $A_i$ and $A_j$ are the signals received by the $i^{th}$ and $j^{th}$ transmitter-receiver pairs, respectively, and $\tau_{i,xy}$ and $\tau_{j,xy}$ are the backpropagation time corresponding to the travel time of the wave from the $i^{th}$ and $j^{th}$ transmitter-receiver pairs, respectively, through the focus point P(x,y). DMAS suppresses the level of noise floor to −40 dB. Thus, the energy ratio of noise to reflector is 0.01% which can be calculated by:

$$-40 = 10 * lg\left(\frac{P_1}{P_0}\right) \quad (5)$$

where $P_1$ and $P_0$ are the energies of noise and reflector, respectively.

Application to Central Blood Pressure Monitoring

The conformal ultrasonic device described herein may be employed in a wide variety of different applications. By way of example one application, the use and fabrication of such a device for monitoring central blood pressure (CBP) will be described in detail.

The monitoring of blood pressure waveforms from arterial and venous vessels is of great significance due to its predictive nature to cardiovascular diseases prior to their disruptive outbreak. For example, the arterial blood pressure waveform is directly related to the left heart activity; the venous blood pressure to the right heart activity. Existing technologies for blood pressure waveform monitoring, including photoplethysmography and applanation tonometry, are limited to only peripheral artery sites, due to the limited penetration depth of light (~8 mm) or reduced propagation distance of pulse waves that can only be deployed on superficial arteries supported by a bony structure. While monitoring the blood pulse waves at peripheral sites is valuable for certain symptoms, emerging evidence suggests that the central arterial and venous blood pressure waveforms possess more relevance to cardiovascular events than the PBP. Firstly, major organs, including the heart, kidneys, lungs, and the brain, are directly exposed to the central arteries. Therefore the distending pressure in the large elastic-type arteries (such as aorta and carotid) is a key determinant of the degenerative changes that characterize accelerated aging and hypertension. Secondly, amplification and reflection effect caused by the complexities of peripheral vascular resistance along the conduit artery, namely the stiffness mismatch between the peripheral and central vessels, is extremely hard to evaluate. This often creates irregular and unpredictable influence on the PBP waveform. Thirdly, although the CBP waveform can sometimes be derived from the PBP waveform, demographic results indicate that clinical treatment, such as using blood pressure lowering drugs, can exert a divergent effect on peripheral blood pressure (PBP) and CBP waveforms, causing inaccurate estimations. Such inaccuracy can cause errors in the assessment of myocardial oxygen requirements and ventricular load and hypertrophy, as well as disparities in the actions of different vasodilator agents. Therefore, treatment decisions for cardiovascular disease diagnosis should be based on CBP rather than PBP waveforms.

The gold standard for recording the CBP waveforms in the carotid artery and jugular venous sites, cardiac catheterization (also known as cannulation), involves implanting a fiber-based pressure sensor into the relevant vasculature. It causes patient suffering and increases the risk of infection and is thus too invasive for routine inspections. Wearable devices with mechanical properties similar to the skin offer the capability of non-invasive, continuous monitoring of a variety of vital signals, such as local field potentials, temperature, sweat content, and skin hydration. Their applications have typically been limited to recording signals on the skin or shallow tissue underneath the epidermis. With deep tissue penetrating capabilities, ultrasound can be a powerful tool for continuous CBP waveform monitoring of deeply embedded vessels. However, existing medical ultrasonic probes are rigid and bulky, typically with a thickness >3 cm, which does not allow conformal contact with the human skin without being manually held to the desired location. This will introduce squeezing and a varying incident angle to the target blood vessel, leading to fluctuating or inaccurate results.

Described herein is an approach for continuous CBP monitoring with soft ultrasonic devices that allow self-adherent conformal contact with the skin. This approach marries the performance advantage of rigid piezoelectric materials with the mechanical stretchability of soft polymers to create an anisotropic 1-3 piezoelectric composite array in a silicone elastomer matrix. The anisotropic 1-3 composite possesses better acoustic coupling with soft biological tissue than isotropic piezoelectric materials. The fabricated device can emit ultrasonic waves to deep tissues and carry critical information back from the central vasculatures non-invasively. Specifically, the device can continuously detect the pulsating blood vessel diameter change, which can be translated into CBP waveforms. Due to its similar mechanical properties to the skin, it ensures conformal intimate contact with the curvilinear and time-dynamic skin surface, which overcomes the operational difficulties and instabilities associated with the rigid and bulky ultrasonic probes. As a result, accurate and clinically relevant CBP data on the central arterial and venous sites can be acquired in a gel-free manner. This capability of non-invasive, continuous, and accurate monitoring of deep biological tissues/organs opens up opportunities for diagnosing and predicting a broad range of cardiovascular diseases in a wearable format.

Device Design and Fabrication of Device for Monitoring CBP

Figure 38A:
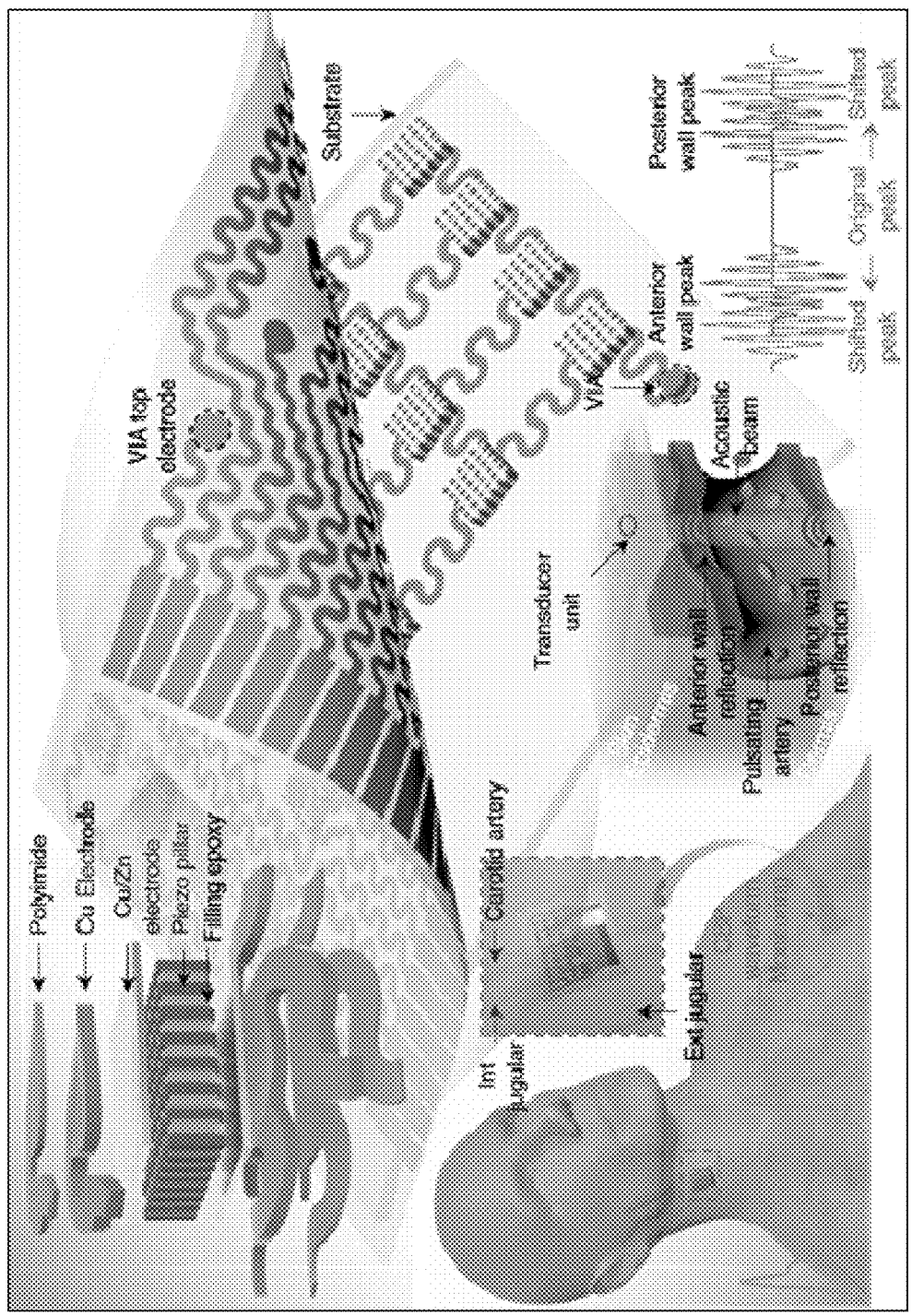
FIGS. 38A and 38B illustrate the design and working principle of the stretchable ultrasonic device.

As described above, and as further described below, the soft ultrasonic device hybridizes high performance rigid functional materials with soft structural components. FIG. 38a shows a schematic diagram of an embodiment of the soft ultrasonic device that is suitable for monitoring CBP. The high-performance piezoelectric material (1-3 piezocomposite) with periodic piezoelectric rods embedded in an epoxy matrix suppresses shear vibration modes and enhances longitudinal ultrasonic penetration into the skin. Vertical interconnect access (VIA) are employed as the top and bottom electrical connection, allowing the co-planar ACF bonding of the top and bottom electrodes to enhance the robustness of the device. When mounted on the human neck, the device allows monitoring of CBP via capturing the pulsating vessel diameter changes by locating the dynamic anterior and posterior walls of the blood vessel using the pulse-echo method.

Figure 43A:
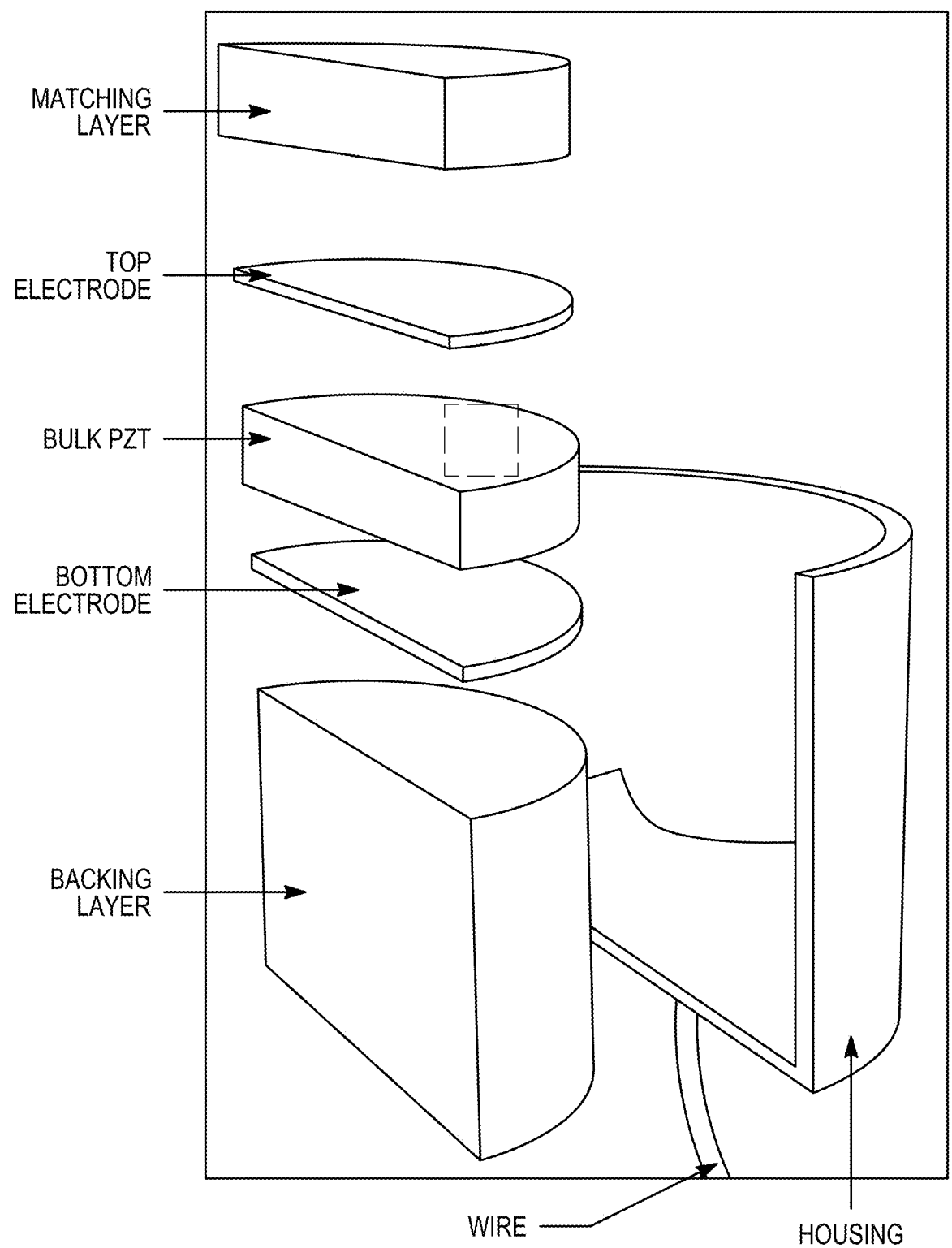
FIGS. 43A-43D compares rigid and stretchable ultrasonic devices.
Figure 43B:
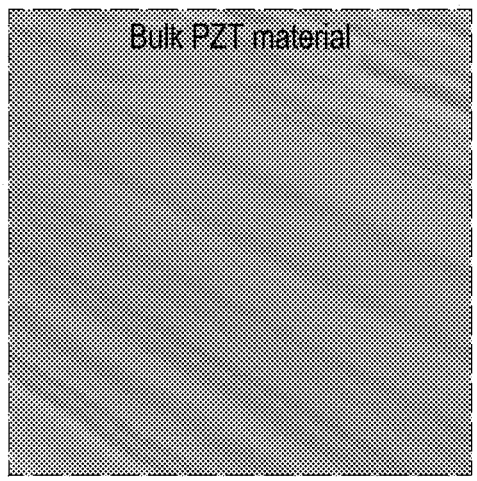
Figure 43C:
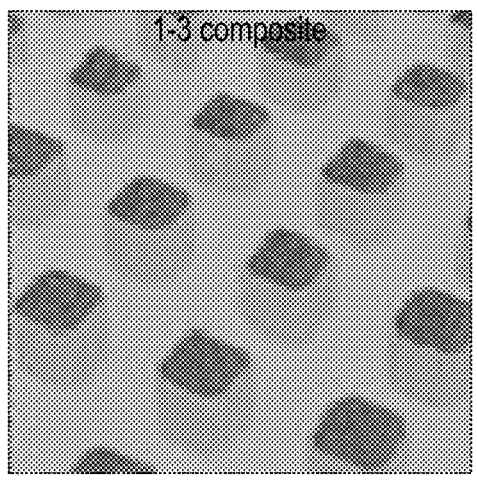
Figure 43D:
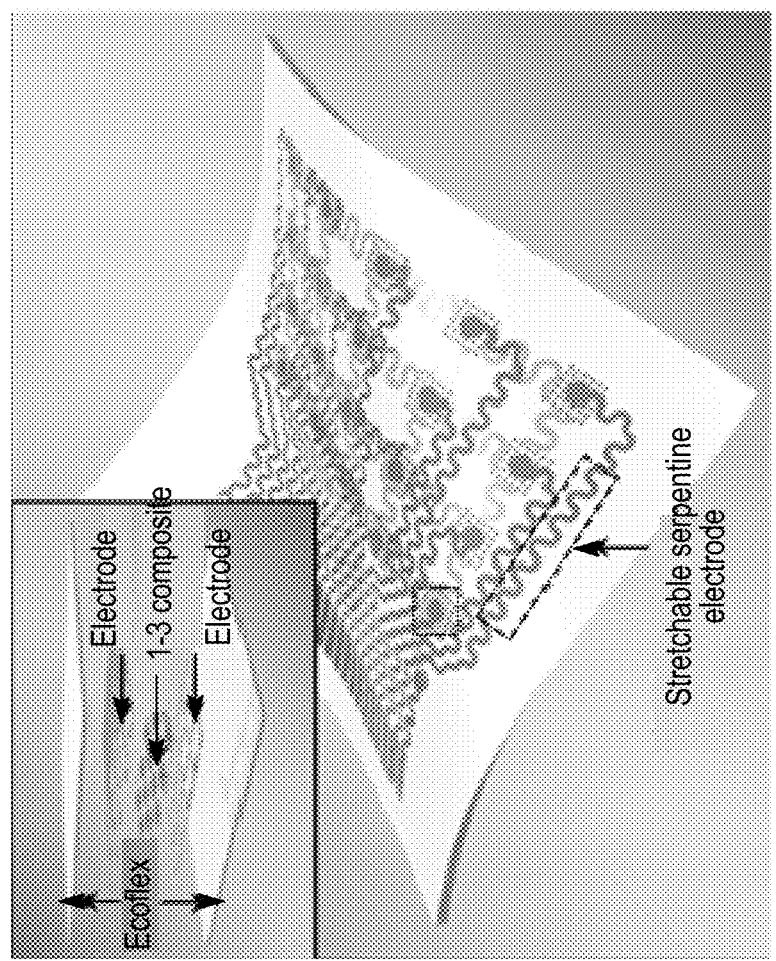

FIGS. 43A and 43B compares rigid and stretchable ultrasonic devices. In particular, FIG. 43A shows the structural design of a traditional ultrasonic transducer, which contains a matching layer, top and bottom electrodes, bulk PZT materials, backing layer, housing, and connection wires. FIGS. 43B and 43C compare the isotropic bulk PZT material and the anisotropic 1-3 composite. FIG. 43D shows an exploded view of an ultrathin and stretchable ultrasonic device. The comparison between FIG. 43A and FIG. 43D shows the simplifications and re-engineering strategies that are employed, which reduce device thickness and substitute rigid materials with soft materials where necessary. The 1-3 composite can provide better acoustic matching with the tissue than isotropic PZT, thus eliminating the necessity of the matching layer. Silicone elastomer encapsulation acts as a good dielectric and protective layer for the housing. The bottom Ecoflex layer acts as an acoustic damping layer, thus removing the backing layer.

Figure 44A:
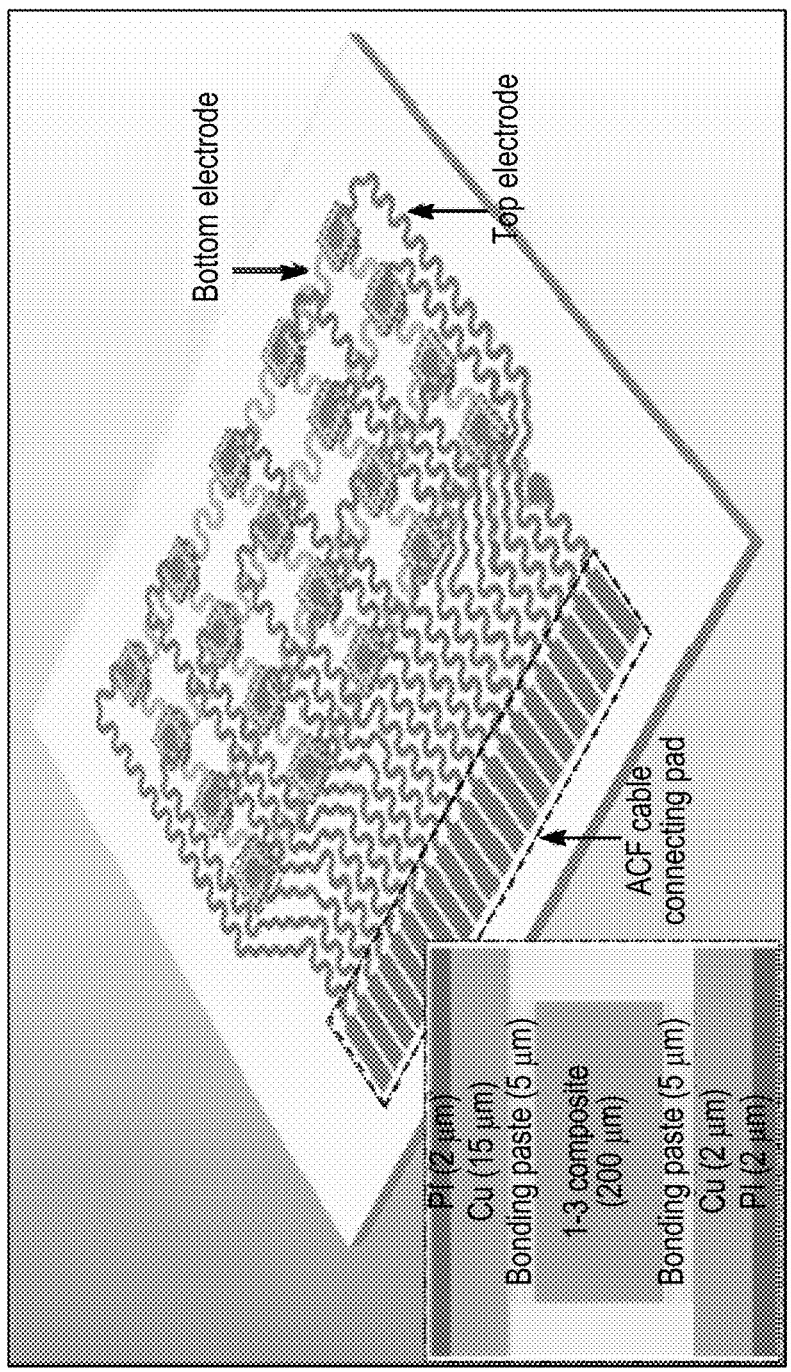
FIGS. 44A-44C show the overall device schematics and the device layout.
Figure 44B:
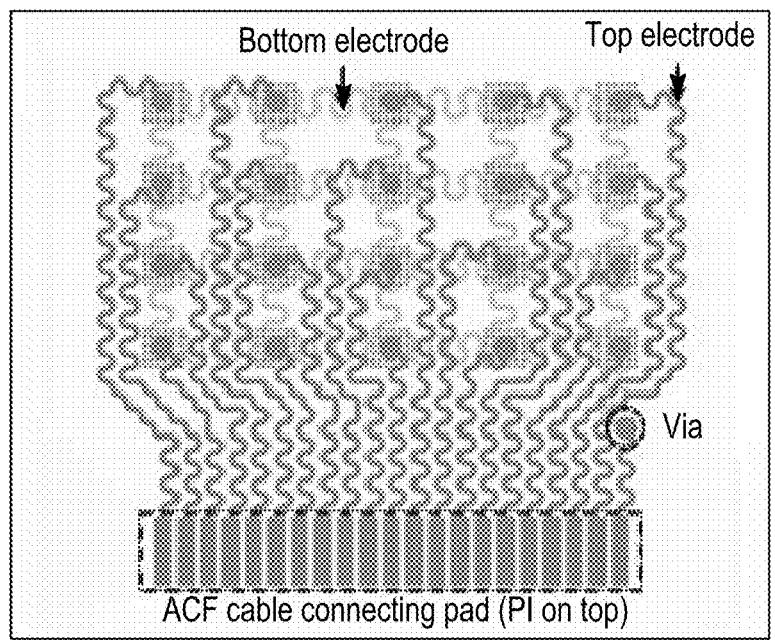
Figure 44C:
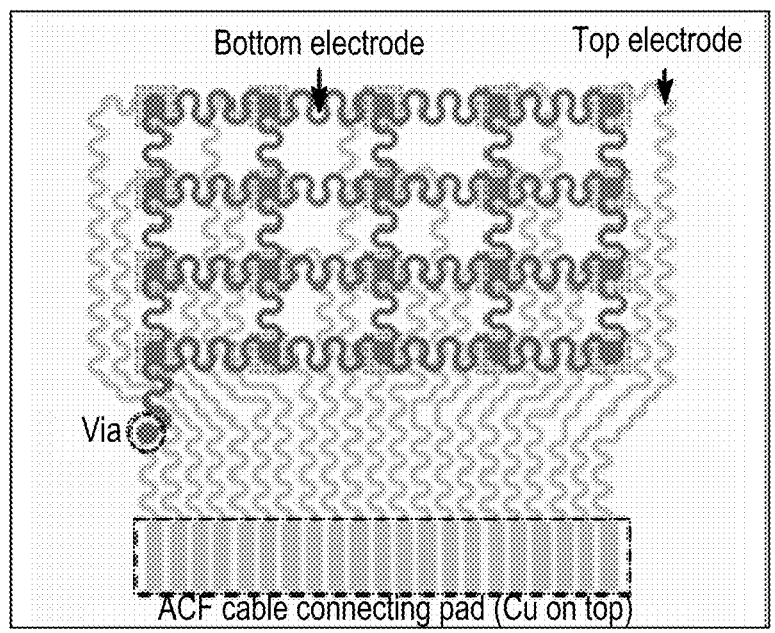

FIGS. 44A-44C show the overall device schematics and the device layout. In particular, FIG. 44A shows the device in its flat state in a perspective view. The inset image shows the cross-sectional structure and layer thickness. FIG. 44B show a top view of the device and FIG. 44C shows a bottom view of the device.

Figure 45A:
FIGS. 45A-45E show photographs of the uniaxial tensile test.
Figure 45B:
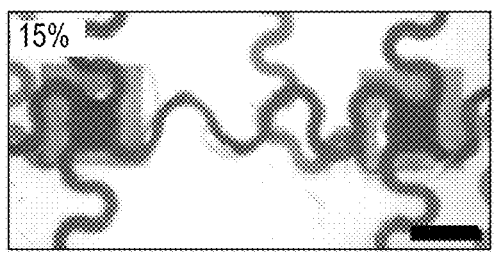
Figure 45B:
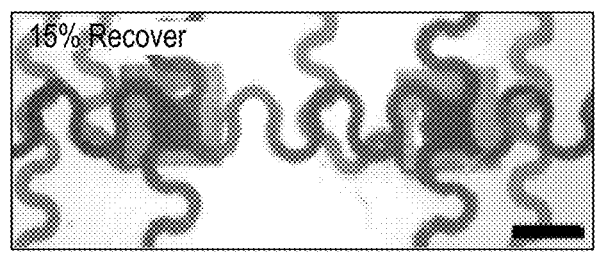
Figure 45C:
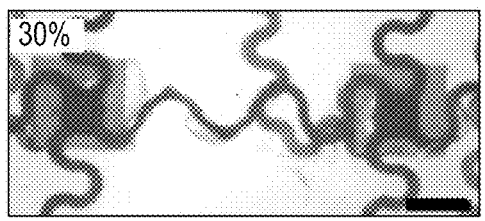
Figure 45C:
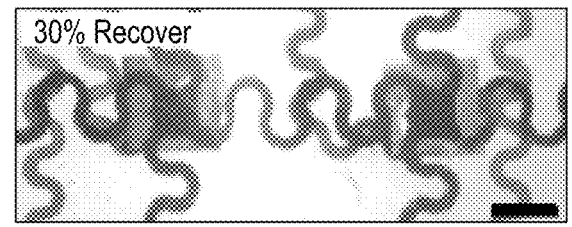
Figure 45D:
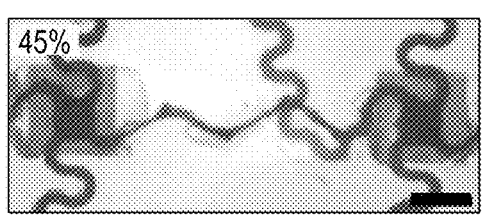
Figure 45D:
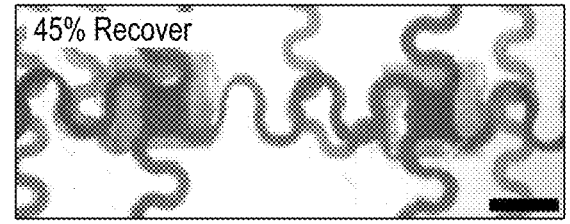
Figure 45E:
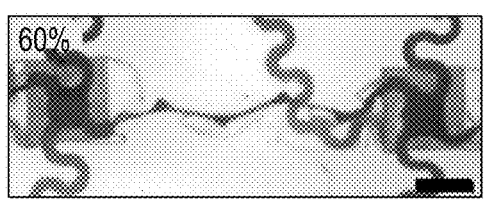
Figure 45E:
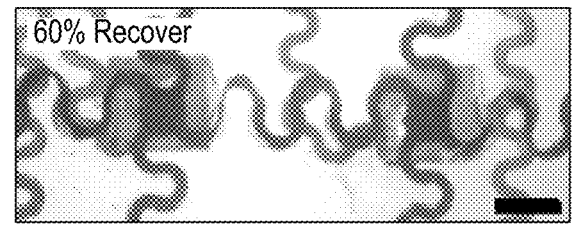
Figure 46A:
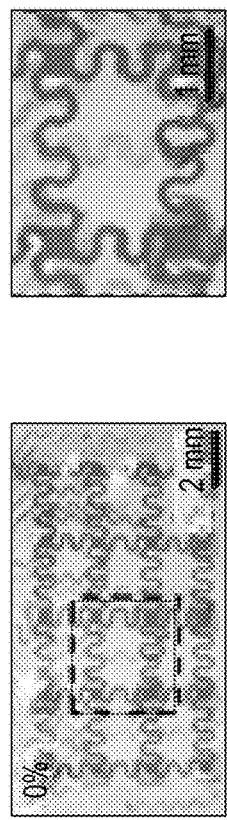
FIGS. 46A-46C show photographs of the bi-axial tensile test.
Figure 46B:
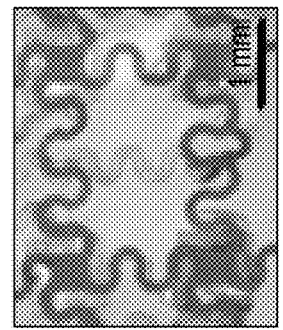
Figure 46B:
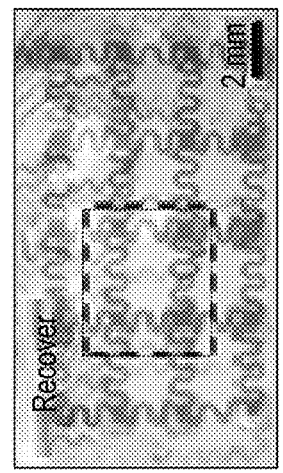
Figure 46B:
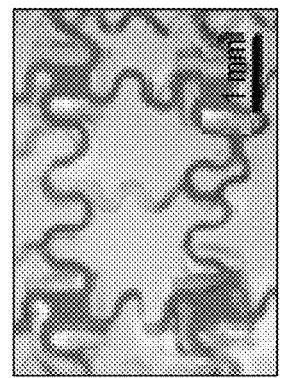
Figure 46B:
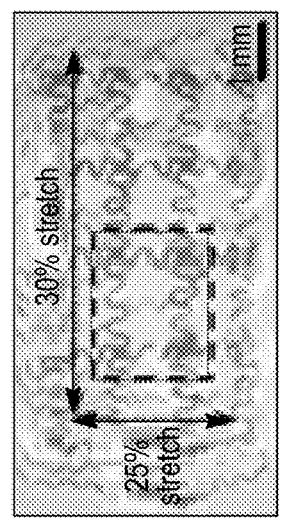
Figure 46C:
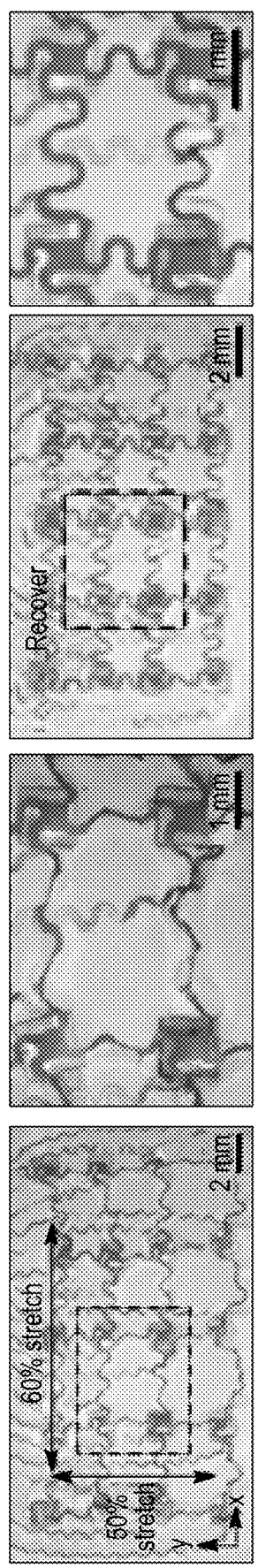

By balancing geometrical and electrical designs, the ultrasonic device shown above can, in some embodiments, reach an ultrathin thickness (240 μm, two orders of magnitude thinner than existing medical ultrasonic probes). The elastic and failure strain levels may be up to 30% and 60%, respectively. FIG. 45 shows photographs of the uniaxial tensile test, where FIG. 45A shows 0% original state; FIG. 45B shows 15% tensile state and its recovery; FIG. 45C show 30% tensile state and its recovery; FIG. 45D shows 45% tensile state and its recovery and FIG. 45E shows 60% tensile state and its recovery. In FIG. 45 the scale bars are all 0.8 mm. FIGS. 46A-46C shows photographs of the bi-axial tensile test, where FIG. 46A shows 0% original state of the device; FIG. 46B shows 30% stretch in x-direction and 25% in y-direction and the recovered status; and FIG. 46C shows 60% stretch in x-direction and 50% stretch in y-direction and the recovered status.

Figure 47A:
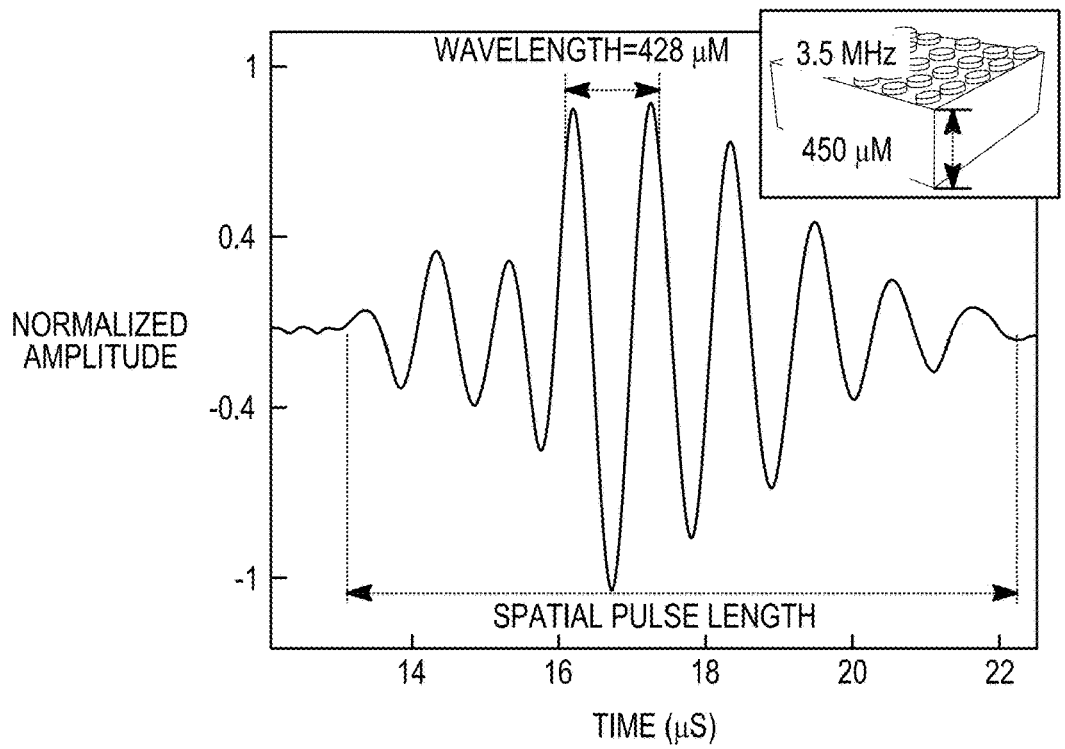
FIGS. 47A and 47B show the reflected signal spatial pulse length comparison between 1-3 composites with working frequencies of 3.5 MHz (FIG. 47A) and 7.5 MHz (FIG. 47B).
Figure 47B:
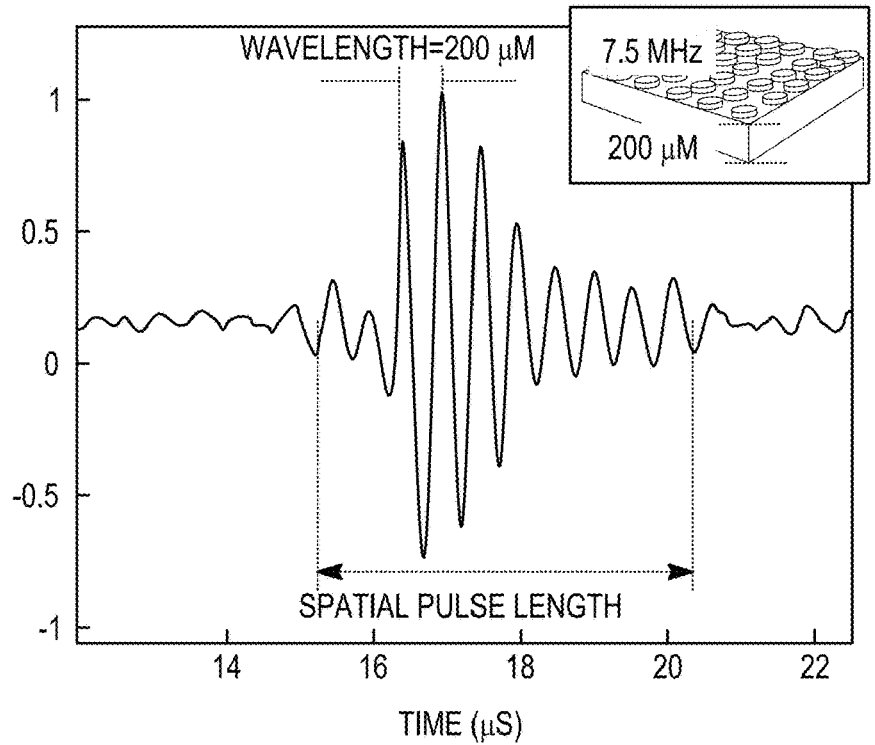
Figure 48A:
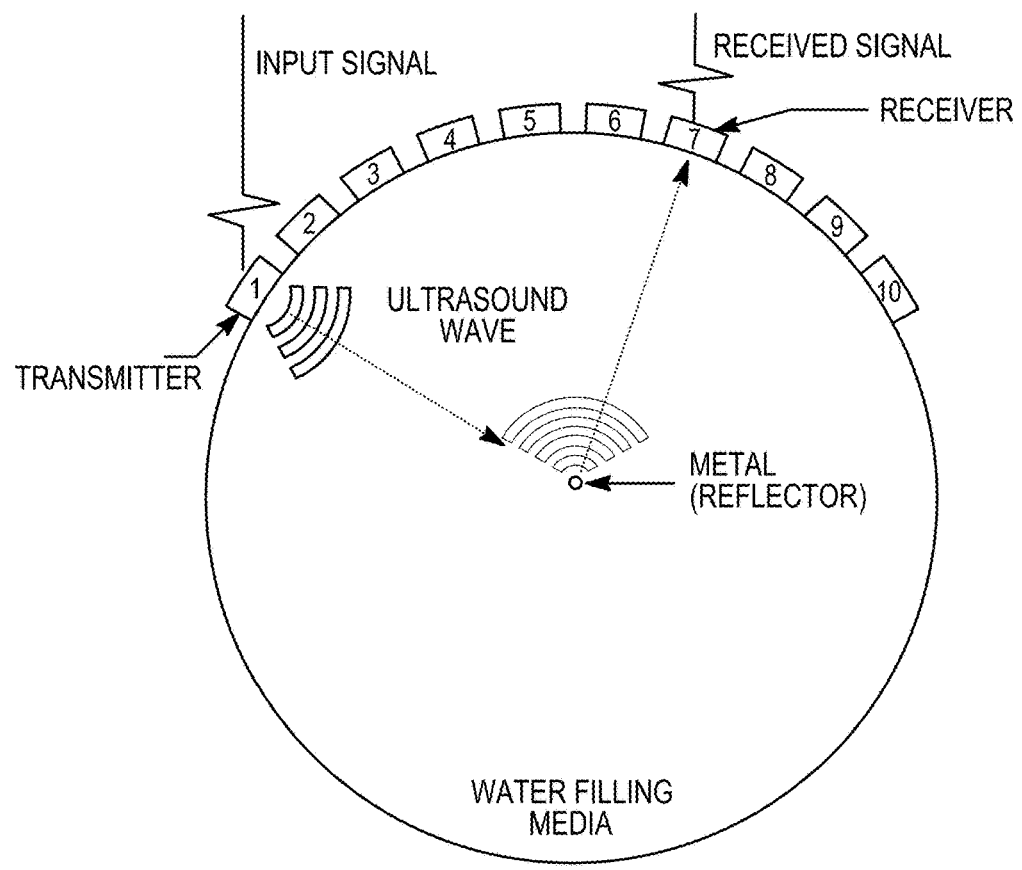
FIGS. 48A, 48B, 48C and 48D show the axial resolution characterization of the stretchable ultrasonic device.
Figure 48B:
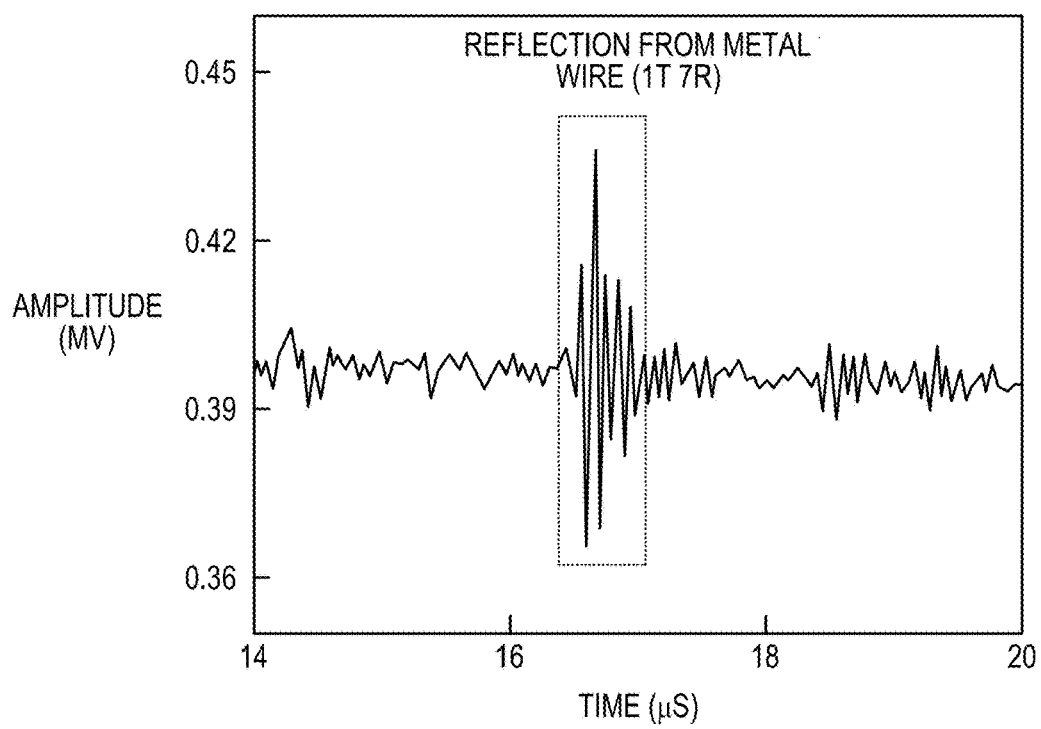
Figure 48C:
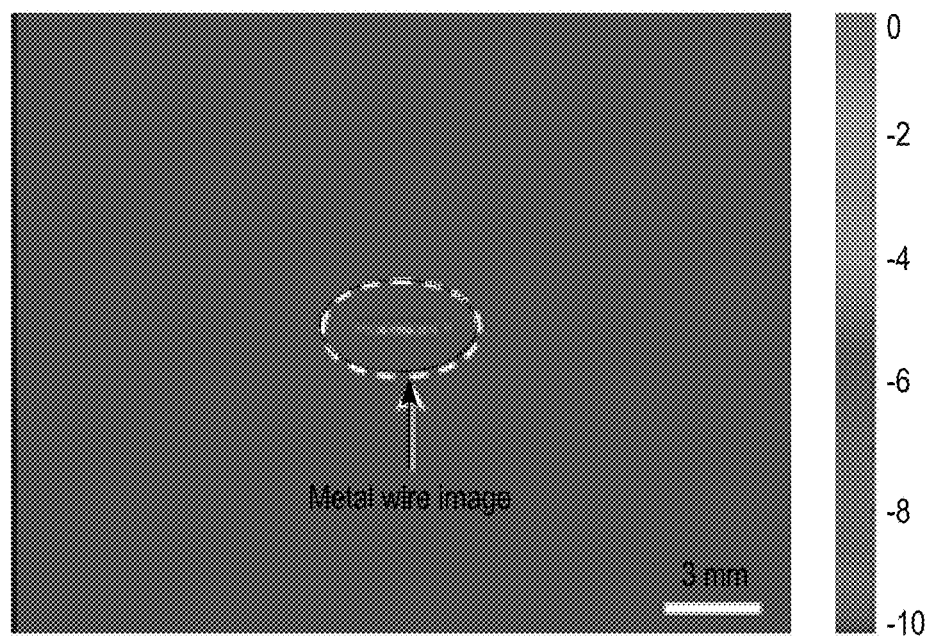
Figure 48D:
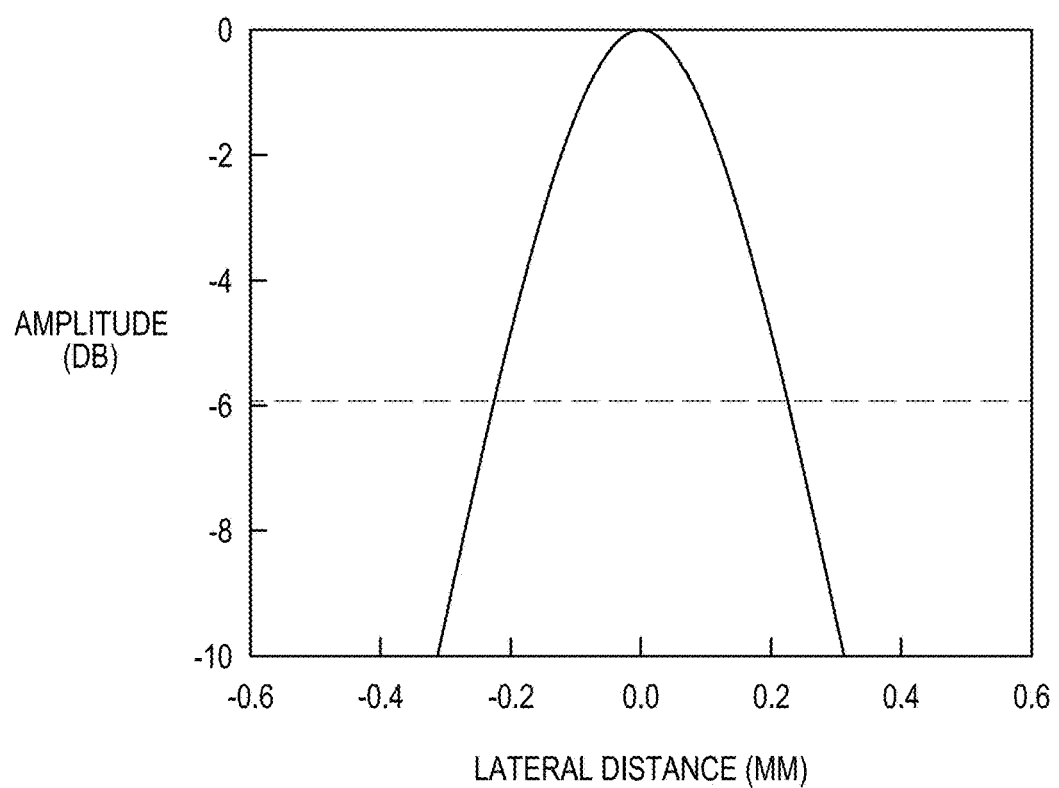

In one embodiment, the functional material that is employed is a 1-3 piezoelectric composite with a thickness of 200 μm, has a working frequency of 7.5 MHz, which enables a 400 μm axial resolution that is comparable with available medical ultrasonic probes at the same working frequency. FIG. 47 shows the reflected signal spatial pulse length comparison between 1-3 composites with working frequencies of 3.5 MHz (FIG. 47A) and 7.5 MHz (FIG. 47B), showing that the higher frequency has better-defined peaks than low frequency due to the smaller wavelength of the ultrasound wave. FIG. 48 shows the axial resolution characterization of the stretchable ultrasonic device. In particular, FIG. 48A shows the testing setup and representative 1T7R acoustic wave emitting and receiving. FIG. 48B shows the signal of 1T7R. FIG. 48C shows the image reconstruction of the metal wire. The image is shown using the dB scale with 0 dB set to be the maximum and −10 dB the minimum grey scale of the image. FIG. 48D shows the axial resolution curve calculated from the reconstructed image, illustrating that the axial resolution can reach down to ~0.4 mm.

Figure 38B:
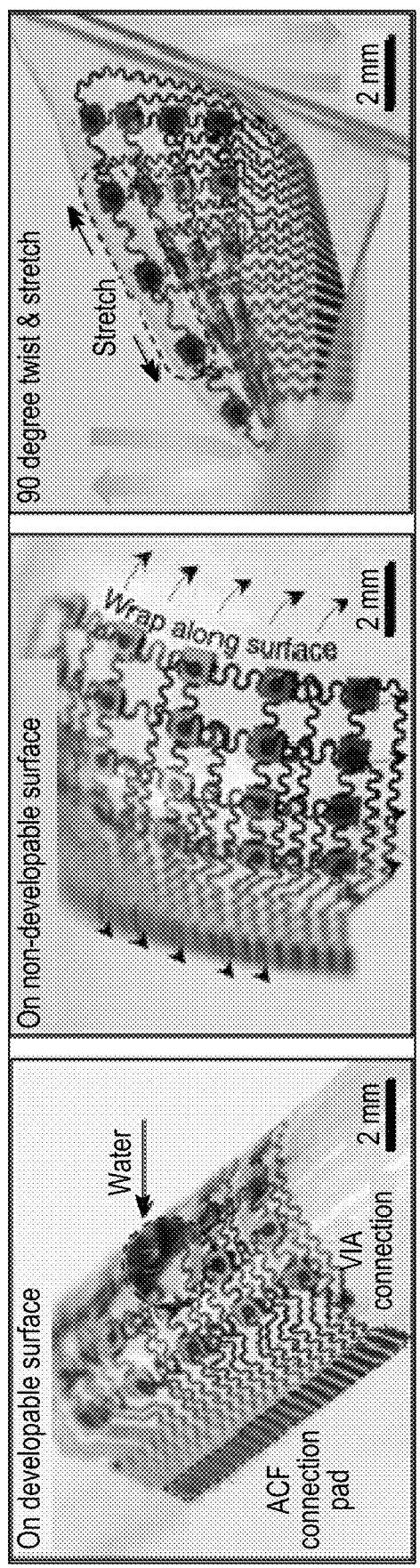
Figure 49:
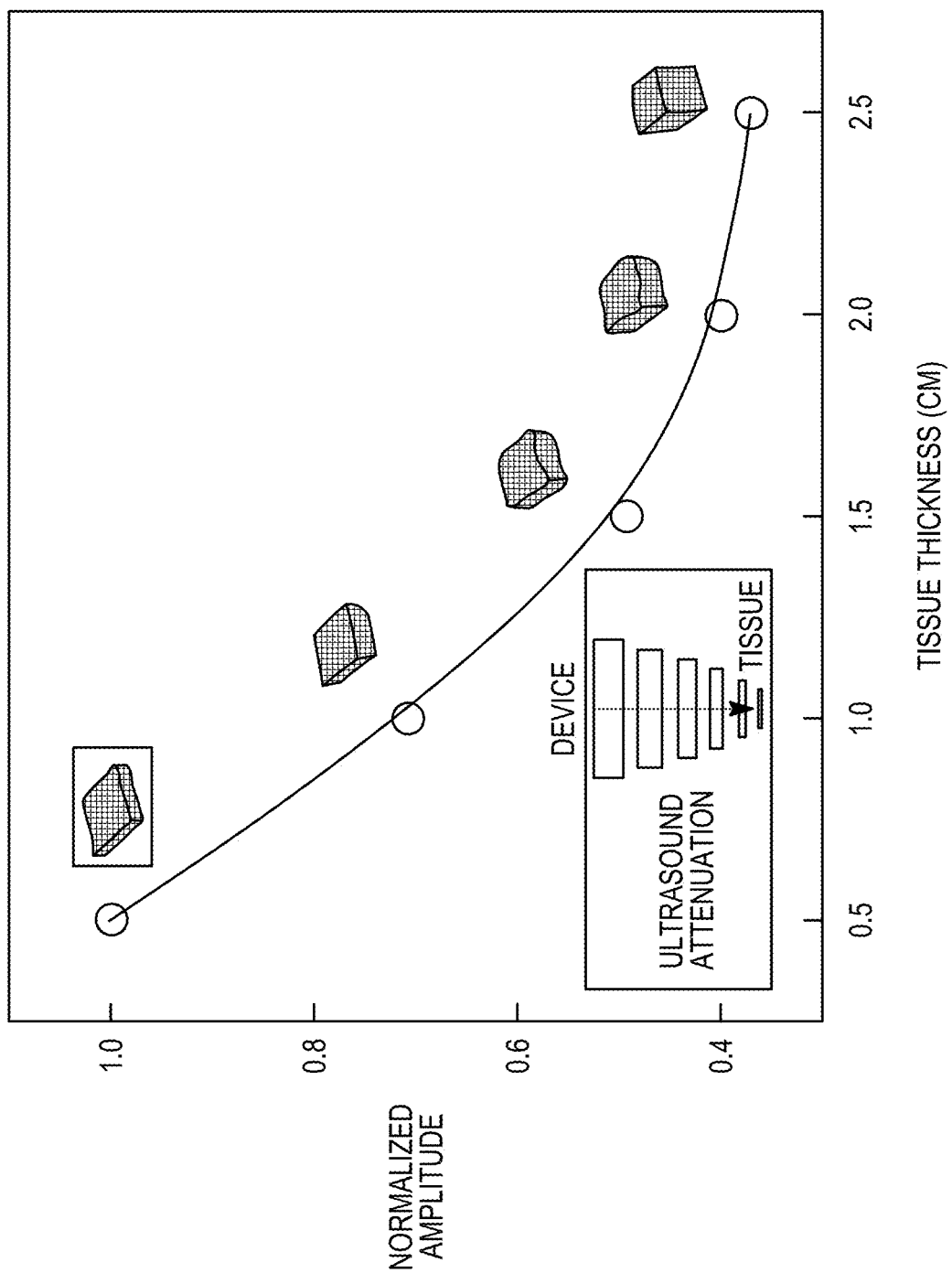
FIG. 49 shows the ultrasound attenuation in tissues with different thicknesses using a 0.9*0.9 mm$^2$ 1-3 composite.

The 1-3 composite has piezoelectric micro-rods embedded, in a periodic configuration in a passive epoxy matrix, which substantially increases the longitudinal coupling coefficient $k_{33}$ by suppressing the shear vibrating modes. In one embodiment, the rigid piezoelectric transducer element is designed to have a 0.9*0.9 mm in footprint to allow sufficient penetration depth into the tissue, maintain moderate damping at the bottom substrate, and also has minimal mechanical loading to the entire device, which is illustrated FIG. 38b by showing the device conforming to developable and non-developable surfaces and under mixed modes of stretching and twisting. FIG. 49 shows the ultrasound attenuation in tissues with different thicknesses using a 0.9*0.9 mm$^2$ 1-3 composite, illustrating the exponential decay of ultrasonic energy in deep tissue measurements.

Bilayer stacking of PI (4 μm)/Cu (20 μm) (FIG. 1a top left) is utilized to fabricate the stretchable electrodes that interconnect a 4×5 array of transducers in the device. Each of transducer is individually addressable by 20 stimulating electrodes on the top and a common ground at the bottom. The array design aims to locate the vessel's position, thus enabling actuating and sensing using the exact transducer overlaying above the targeted vessel without tedious manual positioning.

The alignment of the vessel can be done by the following procedures: Firstly, we activate and receive every transducer individually, 20 in total, and then collect the echo signals. Then, comparison was made to check the correspondence of peak position with accurate measurement on the same artery region. The best corresponding transducer is the accurate localization of the artery. In later monitoring, this transducer will be utilized to monitor the diameter waveform of the targeted artery.

The top simulating electrodes and the bottom ground are routed to the same plane by a vertical-interconnect-access (VIA) (FIG. 1a), which is designed for electrical connection that goes through the plane of one or more adjacent layers in an electronic circuit. With the VIA, optimized mechanical robustness and ease of electrical bonding can be achieved.

Figure 50A:
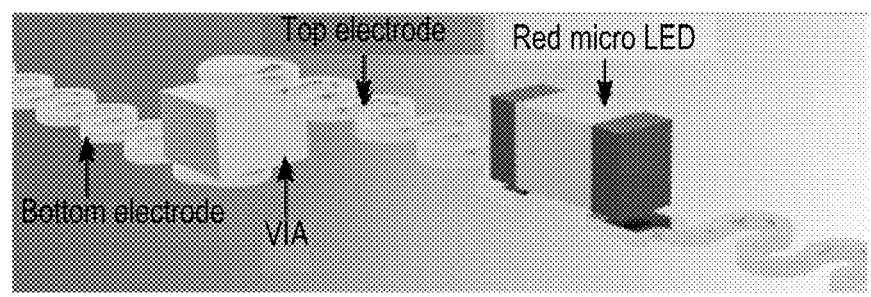
FIGS. 50A-50D show a double-layered electrode with a vertical interconnect access (VIA) under tensile test.
Figure 50B:
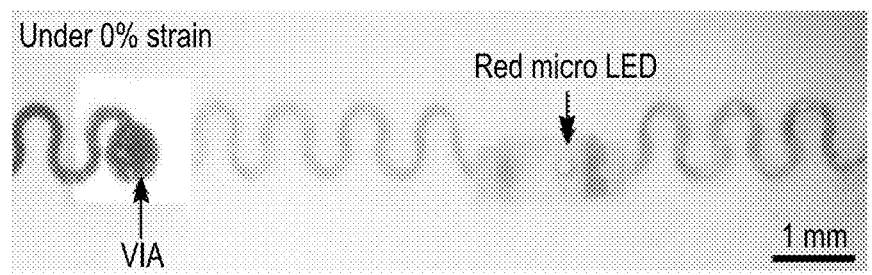
Figure 50C:
Figure 50D:

To optimize the circuitry design and minimize the electrical bonding difficulties, a vertical interconnect access (VIA) structure is designed (FIG. 1a) to route the bottom common ground to a unified region for ACF cable bonding. With this VIA, the ground line can be incorporated into the plane of the top electrode. The VIA consists of the top electrode, the bottom electrode, and a jumper made of silver epoxy. This structure can guarantee that the device has good connectivity and stretchability. FIG. 50 shows a double-layered electrode with a vertical interconnect access (VIA) under tensile test. In particular, FIG. 50A shows an illustration of the circuit structure, FIG. 50B shows an image of the circuit when the LED is off, FIG. 50C shows an image of the circuit when the LED is turned on, and FIG. 50D shows an image of the circuit when the LED is under 15% tensile strain, showing the mechanical integrity of the VIA.

The entire device is encapsulated by silicone (Ecoflex 0030, Smooth-On, 15 μm thick) whose modulus is equivalent to that of the human skin. The hydrophobic nature of silicone elastomer provides a barrier for moisture, which protects the device from sweat corrosion (FIG. 1b).

Figure 51A:
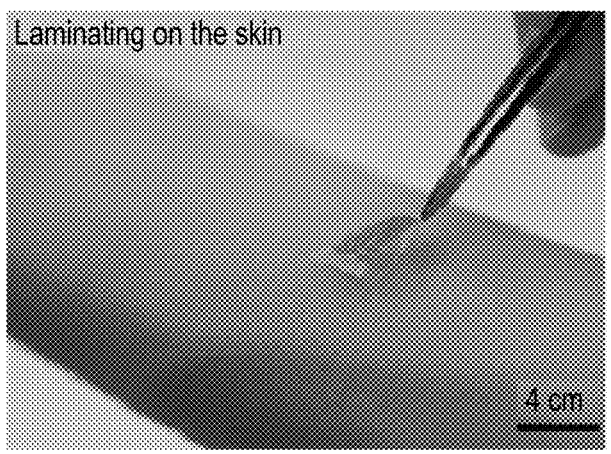
FIG. 51A shows the process of mounting the device on the skin and FIG. 51B shows the device on the skin.
Figure 51B:
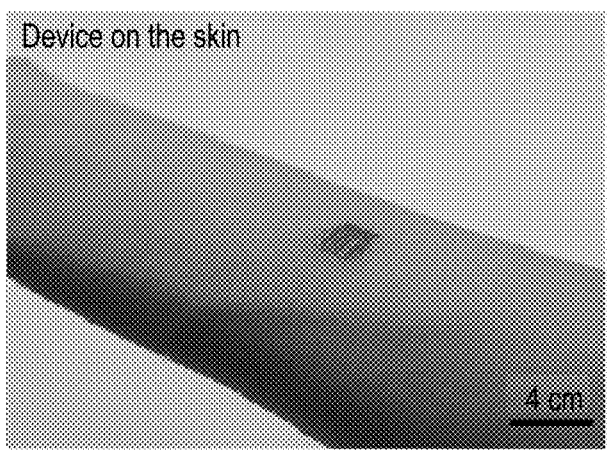
Figure 51C:
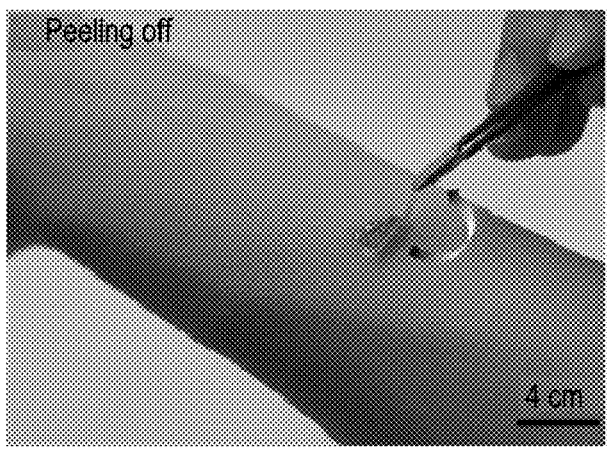
FIG. 51C shows the device being peeled off.
Figure 52A:
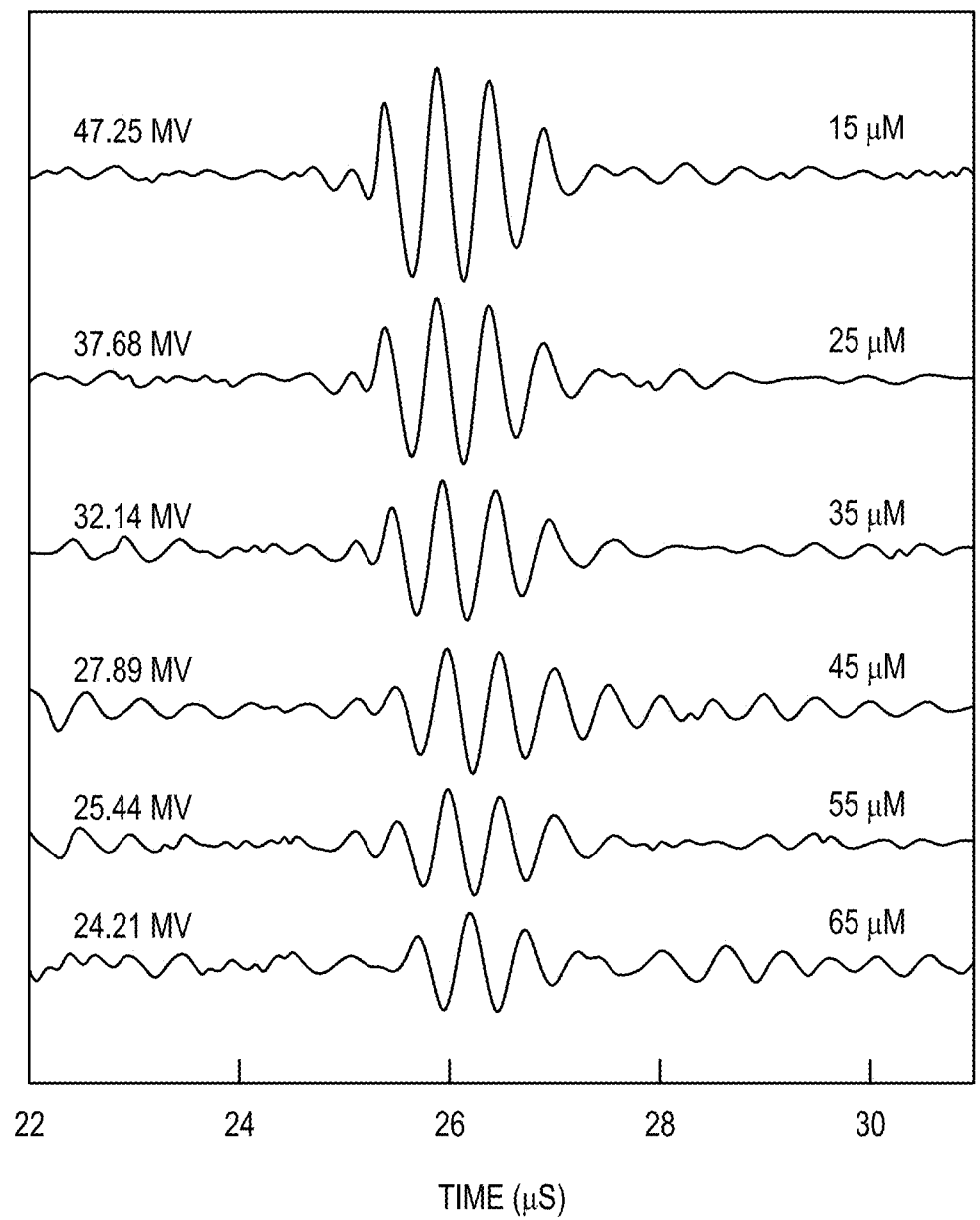
FIG. 52A show the device acoustic emission performance under different thicknesses of Exco-flex encapsulation at the bottom.
Figure 52B:
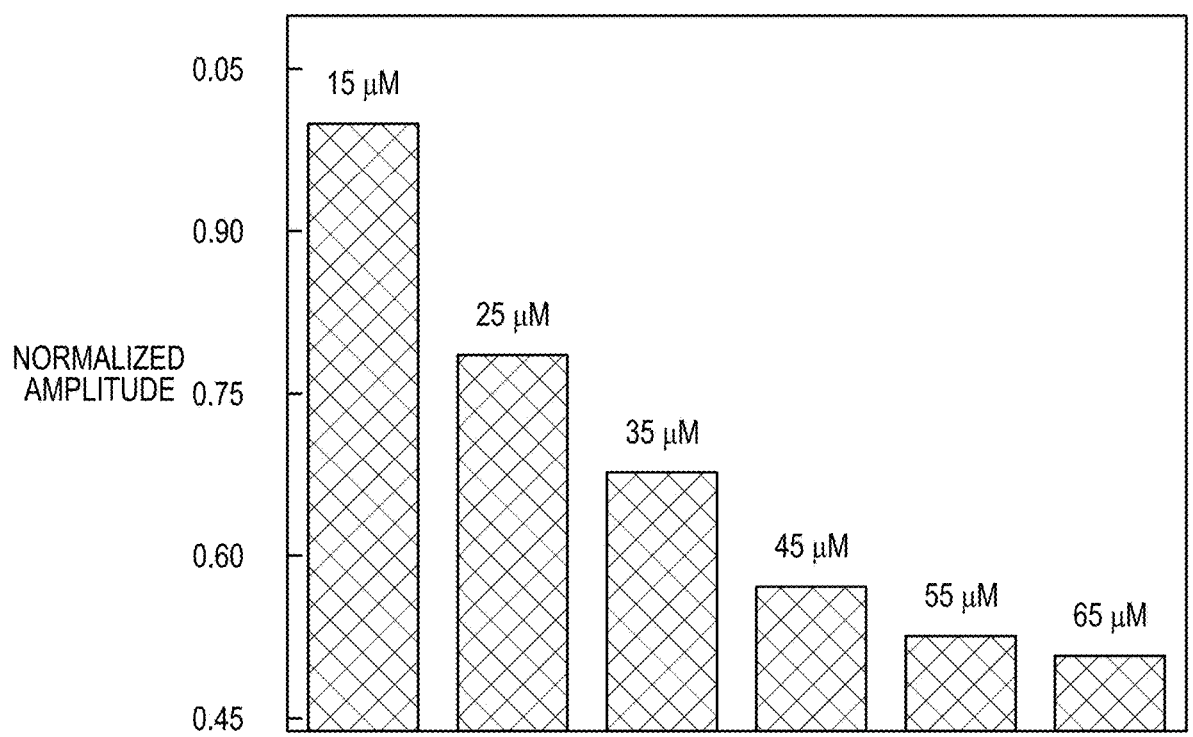
FIG. 52B shows the statistics of FIG. 52A.

The working principle is illustrated in FIG. 1a bottom. When the device is softly laminated on the skin, each transducer can be individually activated and controlled with a power consumption of 23.6 mW. FIG. 51A shows the process of mounting the device on the skin and FIG. 51B shows the device on the skin, and FIG. 51C shows the device being peeled off. After activation, the ultrasonic transducer can launch ultrasonic waves that propagate through the tissues. When the ultrasonic wave reaches interfaces, both transmission and reflection will occur. The transmission wave with reduced intensity allows penetrating into deeper layers of tissues. The reflection wave that carries critical information of the interface can be sensed by the same or another transducer. At high pulse repetitive frequency (2000 Hz), locations of the pulsating anterior and posterior walls can be accurately recorded by the time of flight (TOF) of the acquired signals, which will appear as separate and shifting peaks in amplitude mode (FIG. 1a right bottom). In this way, the device can capture the pulsating blood vessel diameter dynamically, which is correlated with the blood pressure waveform with high spatial (axial resolution 400 µm) and temporal resolution (500 µs). We use a 15 µm thick layer of Ecoflex as encapsulation to provide enough mechanical support for the device and allow sufficient acoustic emission performance and excellent coupling into the tissue. FIG. 52A shows the device acoustic emission performance under different thicknesses of Exco-flex encapsulation at the bottom and FIG. 52B shows the statistics of FIG. 52A.

In one embodiment, the manner in which the device dynamically correlates the pulsating blood vessel diameter with the blood pressure waveform is as follows. The realization of arterial wall positioning is by picking the highest positive peak in the anterior wall and posterior wall echoes. Then the vessel diameter is extracted by subtracting the position of the posterior wall from that of the anterior wall. Therefore, the diameter waveform d(t) can be captured. A(t) is the function of cross-section area and can be calculated in equation (1) based on the assumption that the artery is rotationally symmetrical.

$$A(t) = \frac{\pi \times d^2(t)}{4} \quad (1)$$

The relationship between vessel cross-section area waveform A(t) and blood pressure waveform p(t) appears as follows:

$$p(t) = p_d \cdot e^{\alpha\left(\frac{A(t)}{A_d} - 1\right)} \quad (2)$$

Where $p_d$ is diastolic pressure, $A_d$ is the diastolic arterial cross-section, and $\alpha$ is the rigidity coefficient. The relationship of diameter waveform and blood pressure waveform in equation (1) is validated over a large pressure range. The measurement assumes the $p_d$ and $\alpha$ do not change significantly throughout the arterial tree.

We assume the human blood vessel is elastic with negligible viscoelasticity. That is to say, the pressure-diameter curve has a moderate hysteresis, below 0.2%. This is suitable for subjects with normal local vascular conditions or with slight local atherosclerosis. In this situation, the diameter of vessel won't lag behind the pressure waveforms. And the aforementioned equation (2) can be used to reconstruct the accurate blood pressure waveforms from the vessel diameter waveforms. The largest hysteresis caused by vessel atherosclerosis is within 5.2%.

$\alpha$ can be calculated by equation (3):

$$\alpha = \frac{A_d \ln(p_s / p_d)}{A_s - A_d} \quad (3)$$

Wherein $A_s$ is the systolic arterial cross-section, $p_s$ is the systolic pressure which can be measured by commercial blood pressure cuff. Using the aforementioned equation and a brief calibration for $\alpha$ and $p_d$, the accurate pressure waveform p(t) can be achieved. It is worth noting that the diameter measurement is critical from the equation above. The method adopted here is to calibrate the systolic diameter with that captured by the clinical ultrasonic machine at the same vascular location. By this comparison, we can know the exact position of peak extraction to guarantee the exact diameter waveform measurement.

Figure 53A:
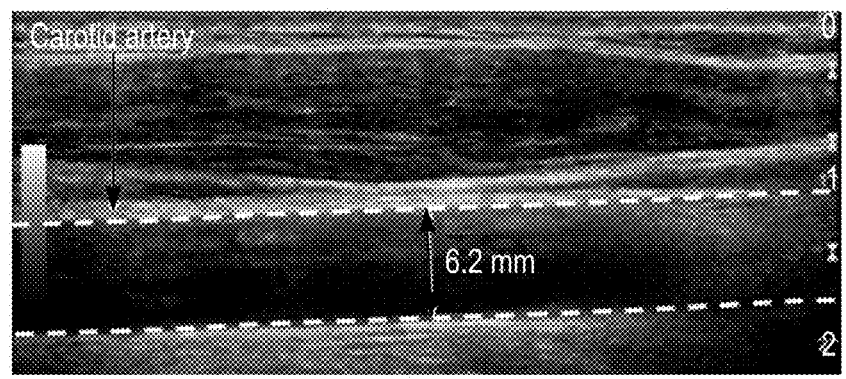
FIGS. 53A-53C show images of blood vessels from central to peripheral under gray scale measured by Doppler ultrasound.
Figure 53B:
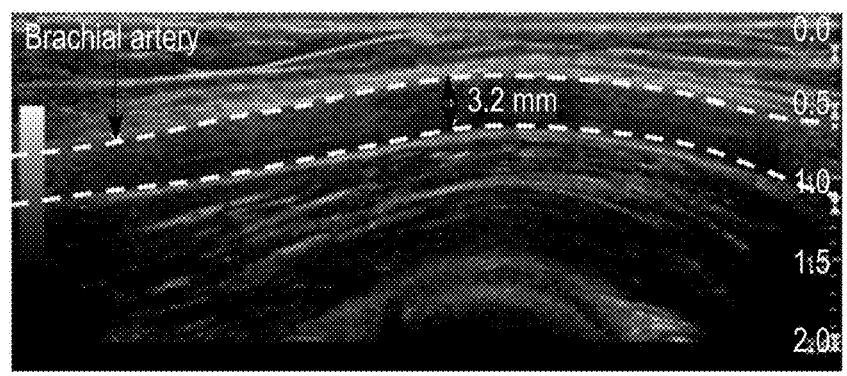
Figure 53C:
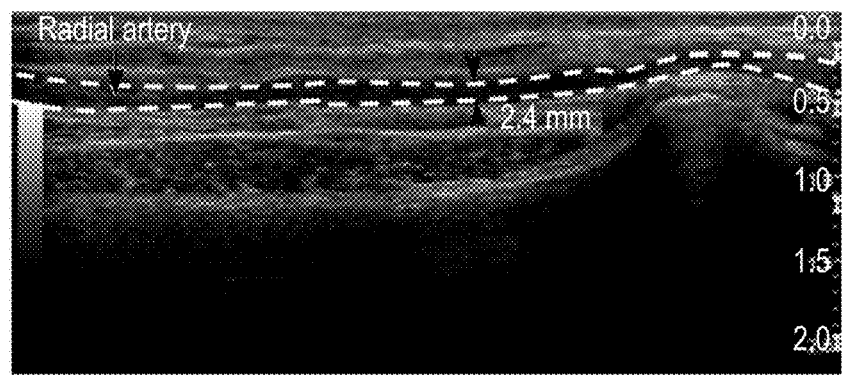

FIG. 53A show images of blood vessels from central to peripheral under gray scale measured by Doppler ultrasound. The results show the gradual shrinkage of the vessel diameter. FIG. 53A shows the carotid artery with a diameter of 6.2 mm, FIG. 53B shows the brachial artery with a diameter of 3.2 mm, and FIG. 53C shows the radial artery with a diameter of 2.4 mm, which will introduce progressive vascular resistance.

Device Characterization

Figure 39A:
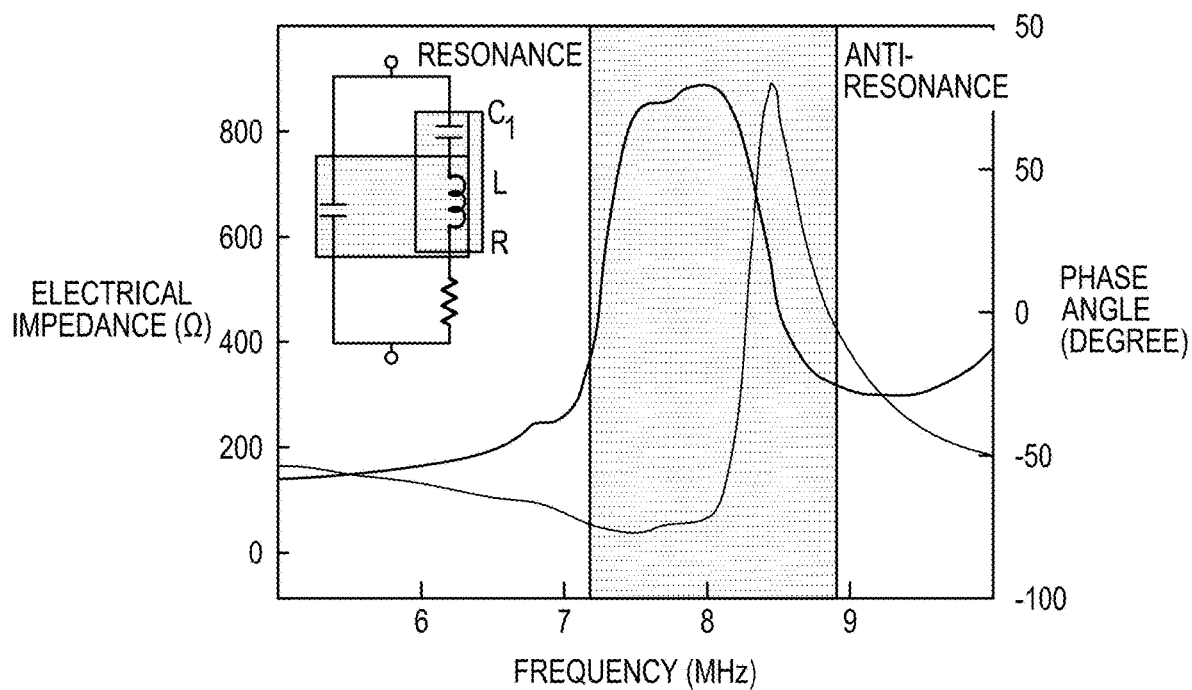
FIGS. 39A-39F illustrate the electrical, mechanical and biocompatibility characteristics of the stretchable ultrasonic device.
Figure 39B:
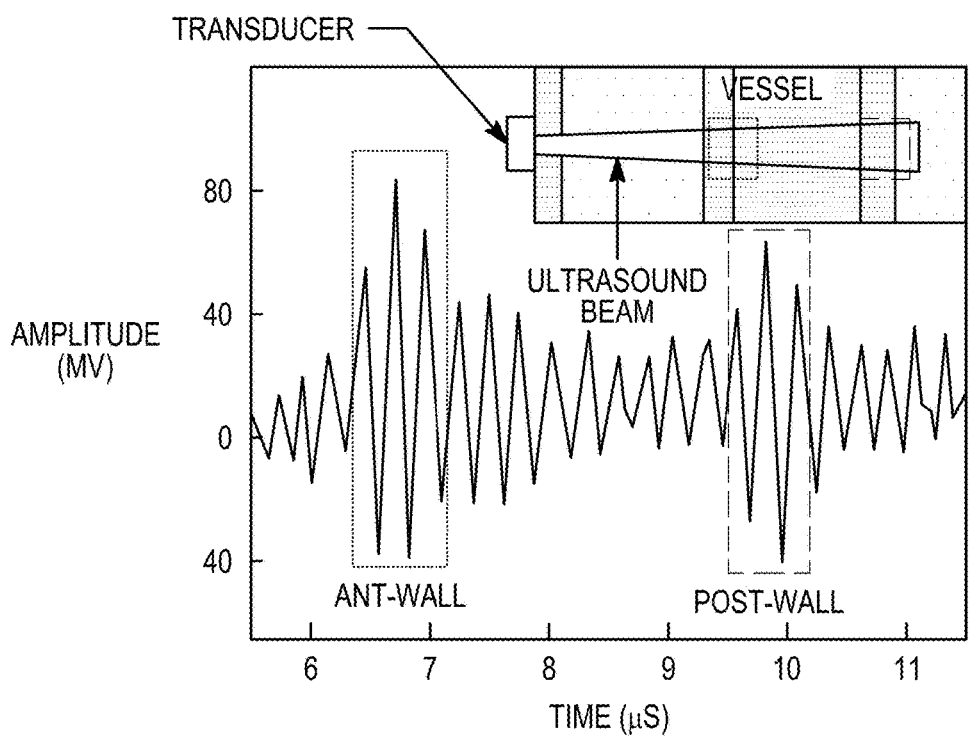
Figure 39C:
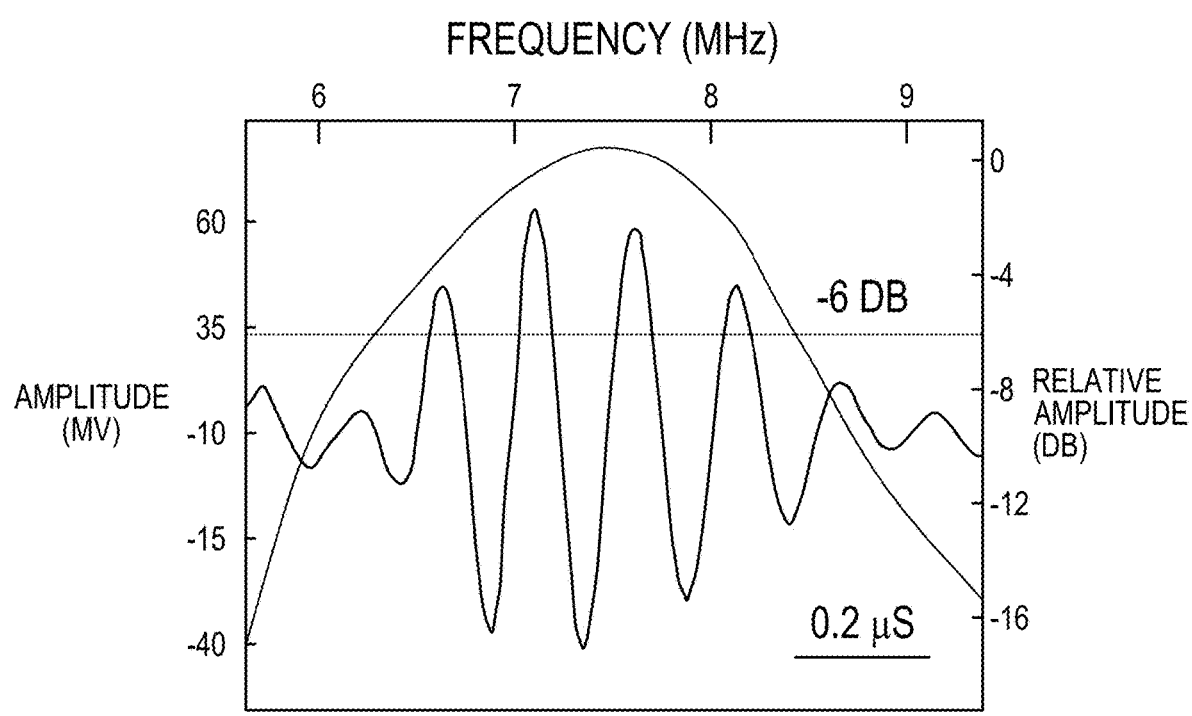
Figure 39D:
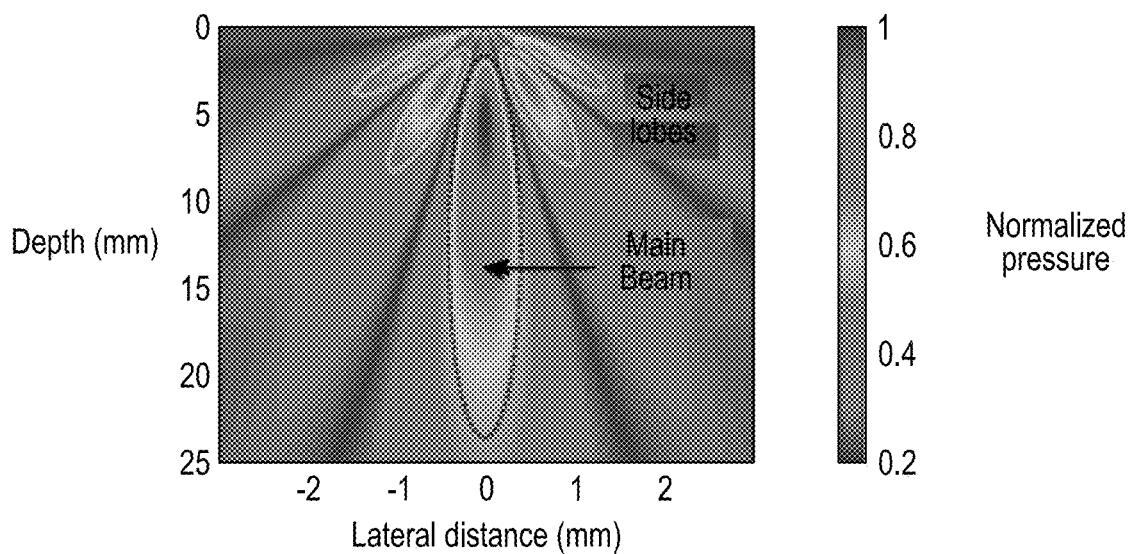
Figure 54A:
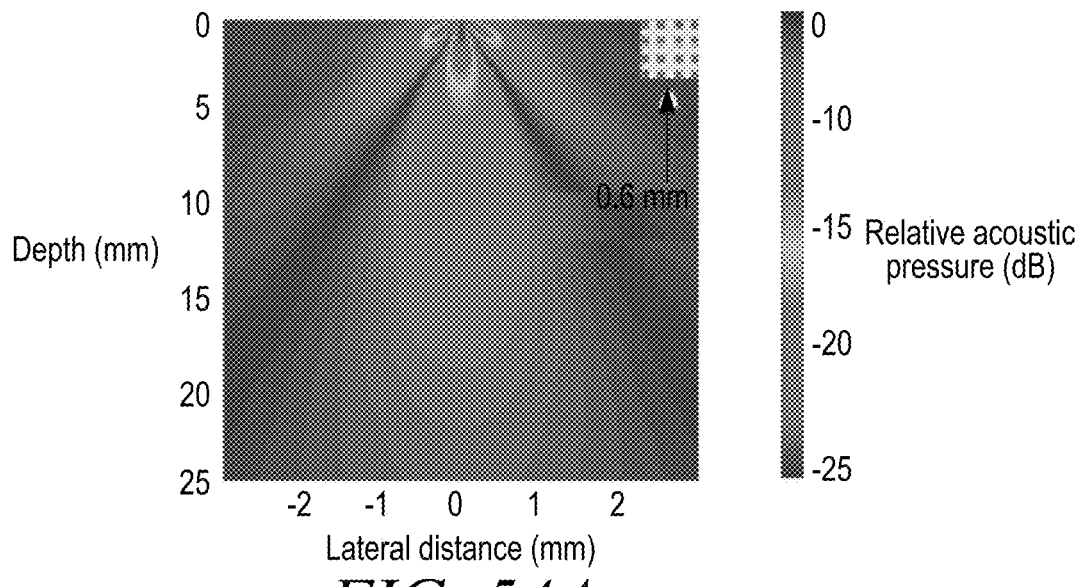
FIGS. 54A-54C show the acoustic field simulation for 1-3 piezoelectric composites with different sizes.
Figure 54B:
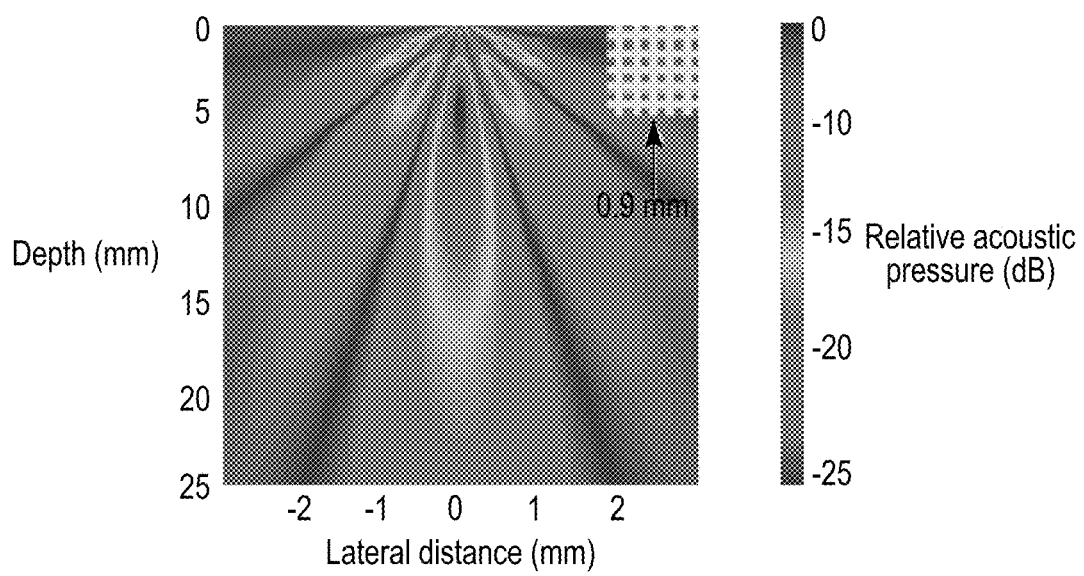
Figure 54C:
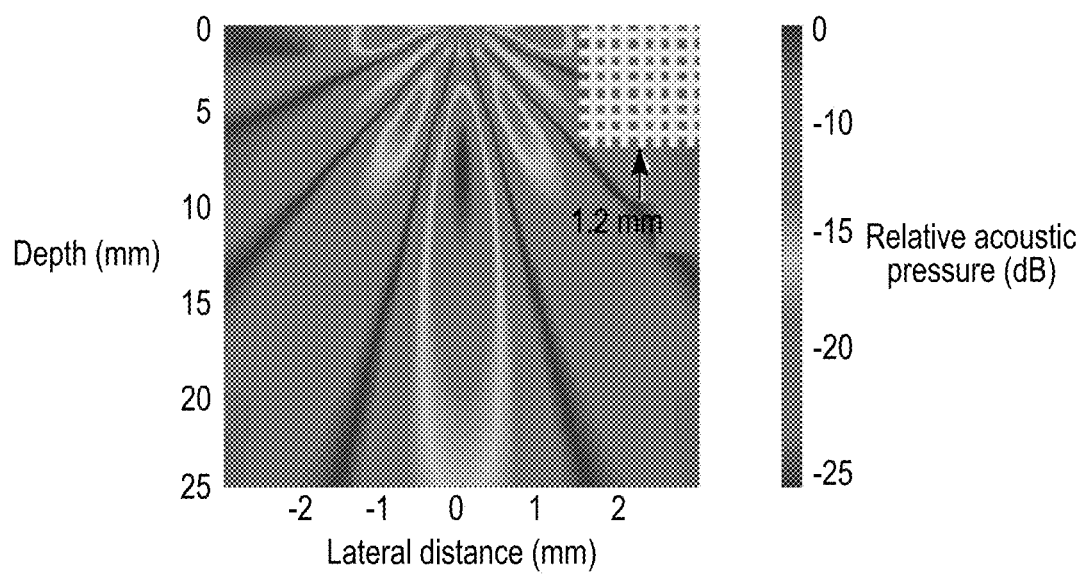

The piezoelectric transducer converts electrical potential between the top and bottom electrodes to mechanical vibrations, and vice versa. The measured impedance and phase angle spectra, shown in FIG. 39A), exhibit excellent piezoelectricity whose $k_{33}$ was measured to be 0.81 which is much higher than bulk PZT (~0.58) due to its anisotropic high aspect ratio rod configuration compared with the isotropic bulk PZT. The transducer performance is tested on the wrist ulnar artery of a healthy male. The echo is shown in FIG. 39B, in which the TOF of the two peaks corresponds to the positions of the anterior and posterior walls of the ulnar artery, respectively. Signal analysis in the time and frequency domains of posterior wall is illustrated in FIG. 39C, demonstrating that the material has a central frequency of 7.5 MHz and possesses good sensitivity of 32% at −6 dB bandwidth and a peak to peak voltage of 100 mV. Prediction of the beam pattern (Matlab R2016b, TAC GUI toolbox) of our stretchable ultrasonic device appears in FIG. 39D. The results show that in the longitudinal direction, our device has excellent beam directivity and sufficient penetration for deep tissue detection, reaching a penetration depth of up to 25 mm (with the piezoelectric material size of 0.9*0.9 mm). The larger the piezoelectric material size, the deeper the ultrasonic wave penetrates. FIG. 54 shows the acoustic field simulation for 1-3 piezoelectric composites with different sizes: FIG. 54A has a size of 0.6 mm*0.6 mm, FIG. 54B has a size of 0.9 mm*0.9 mm, and FIG. 54C has a size of 1.2 mm*1.2 mm. All images are shown using the dB scale with 0 dB set to be the maximum and −25 dB the minimum.

Figures 55A, 55B:
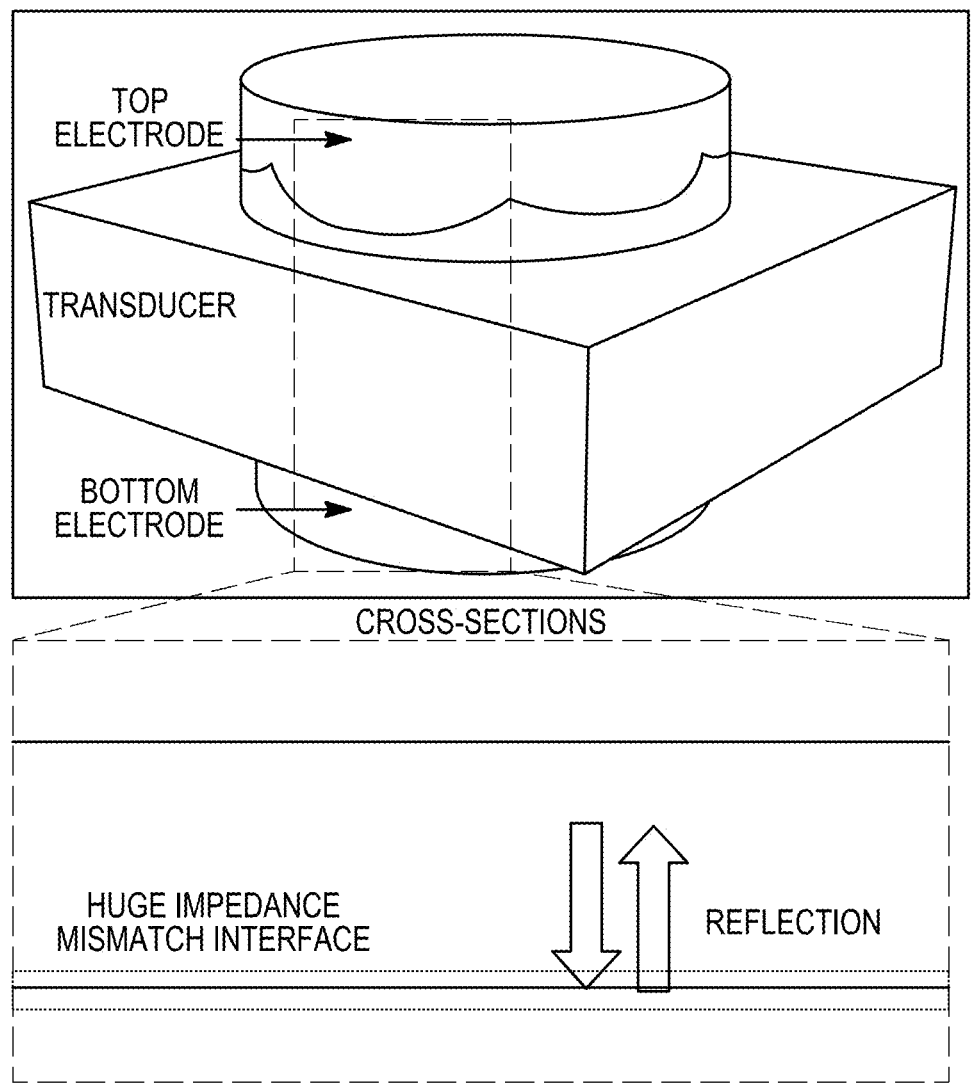
FIGS. 55A-55C compare the acoustic emission performance of devices with different diameters of the circular bottom electrode.
Figure 55C:
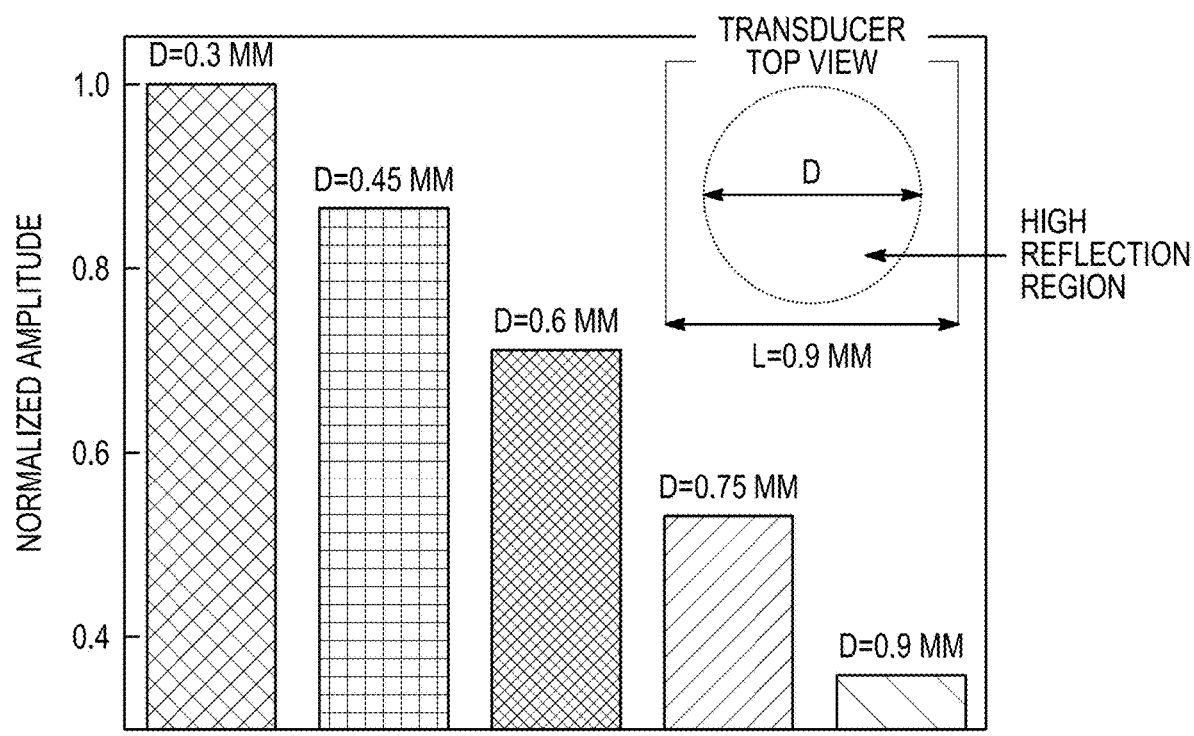

The 1-3 composite has a low acoustic impedance (17 MRayl), which provides excellent acoustic coupling with the human skin. Additionally, the bottom circular electrode diameter is designed to be 0.6 mm to balance the practical bonding robustness and impedance matching. FIG. 55 compares the acoustic emission performance of devices with different diameters of the circular bottom electrode, showing different portions of ultrasonic energy reflected by the bottom electrode. FIG. 55A shows the layered structure of the device. FIG. 55B shows a cross sectional view of the device, showing the interfacial reflection caused by impedance mismatch between the Cu electrode and the 1-3 composite. FIG. 55C shows the experimental results of the acoustic emission performance of the device with different bottom electrode diameters. The signal amplitudes are normalized.

Figure 39E:
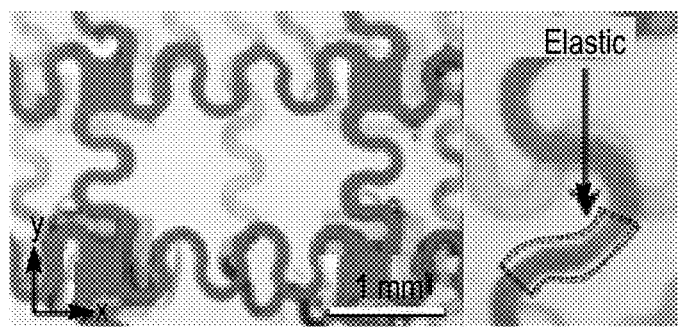
Figure 39E:
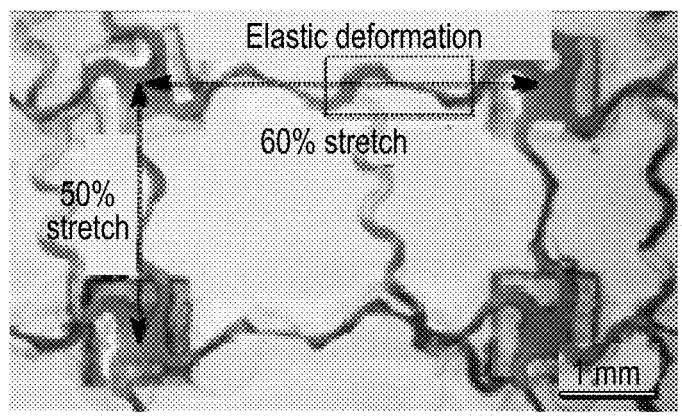
Figure 39F:
Figure 39F:
Figure 56A:
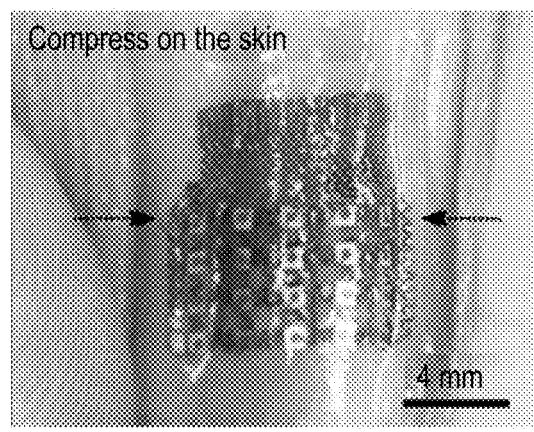
FIG. 56A-56C shows photographs of the skin integration behavior of the device.
Figure 56B:
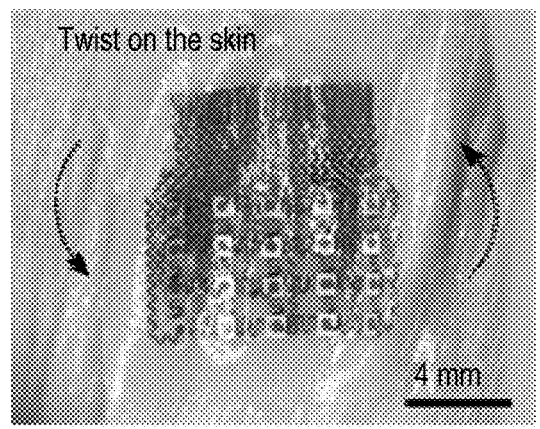
Figure 56C:
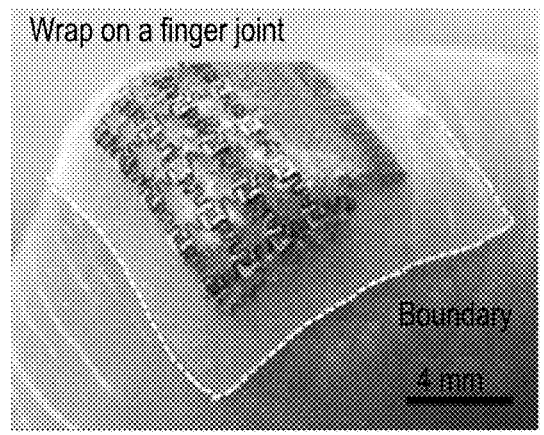

The elastomeric matrix with iterative stretchable circuit designs and ultrathin encapsulation assemblies provides exceptionally conformal contacts to the human skin under various deformation modes. FIG. 56A-56C shows photographs of the skin integration behavior of the device, illustrating the mechanical compliance of the device. As shown in FIG. 39E, the stretchability can reach up to 60% in the x-direction and 50% in the y-direction. The device has a good recovery with an elastic deformation strain of 30% in x-direction and 25% in y-direction. The plastic deformation after more than 30% strain appears in the top right panel of FIG. 39E. Most importantly, as indicated by FIG. 57, the device's electrical performance can remain stable under stretching and moist environment.

Figure 57:
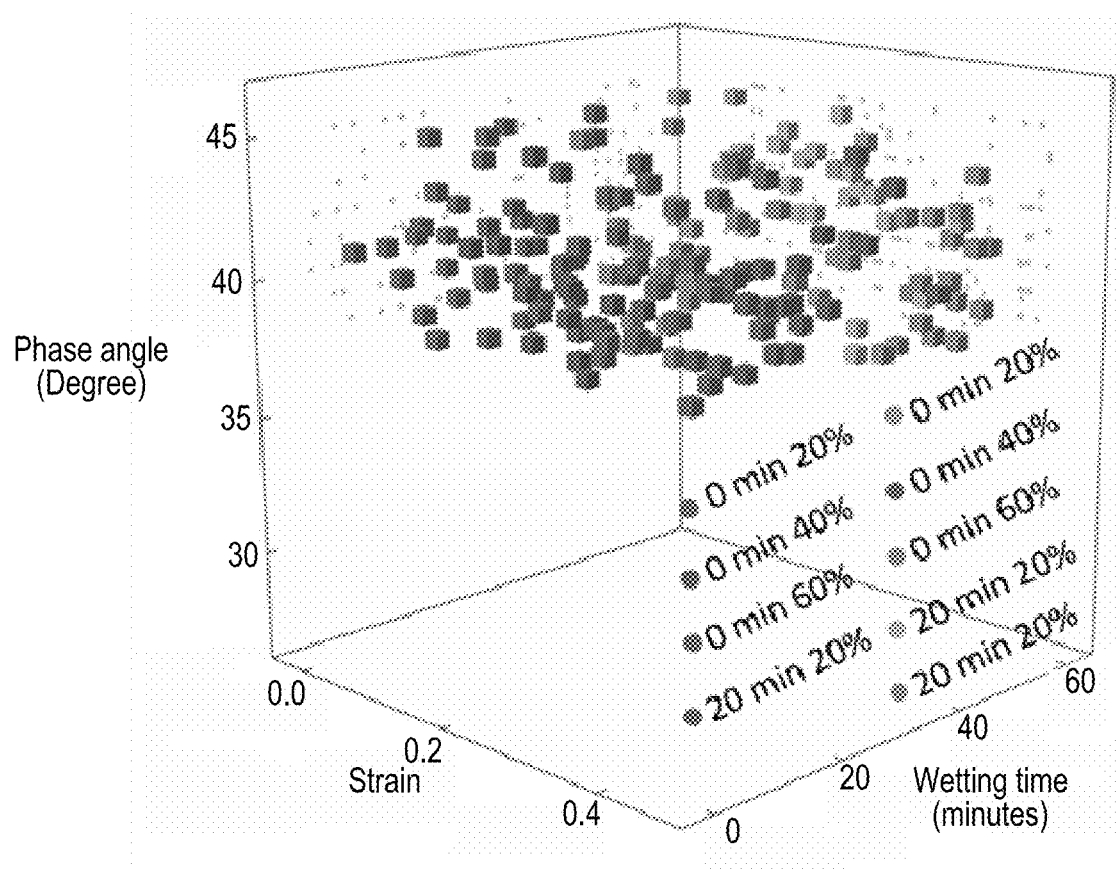
FIG. 57 shows the electrical performance of the device under various levels of tensile strain and moisture conditions at room temperature.

FIG. 57 shows the electrical performance of the device under various levels of tensile strain and moisture conditions at room temperature. The strain levels are 20%, 40%, and 60%. The device is dipped in water for 0, 20, and 40 min in the aforementioned three tensile strain levels. After that, the phase angles of 20 transducers were measured under each condition. The results show the stable electric performance of the device under harsh environments.

Figure 58A:
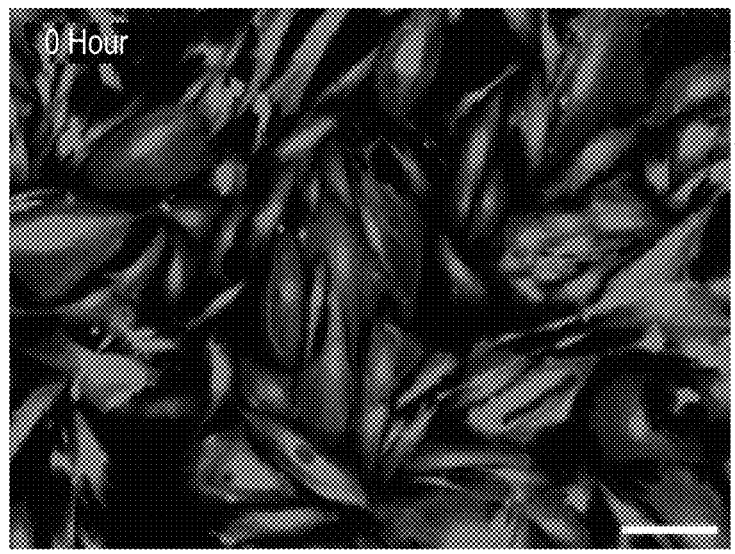
FIGS. 58A-58E shows fluorescent images of HFF-1 cells.
Figure 58B:
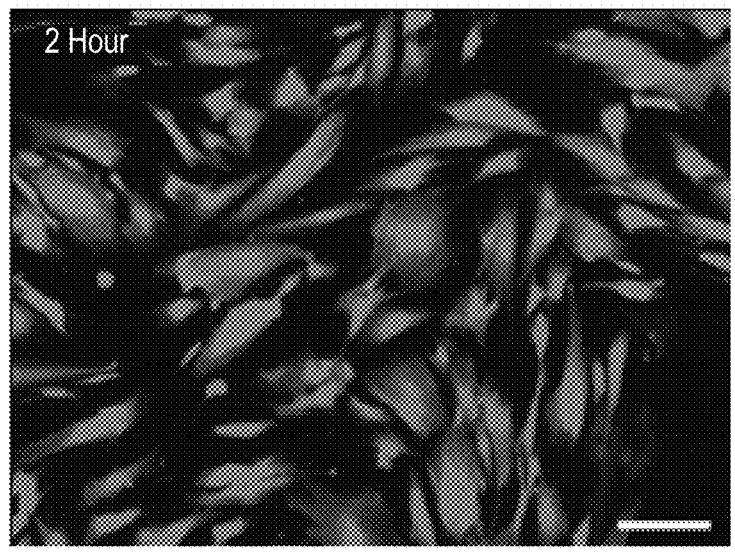
Figure 58C:
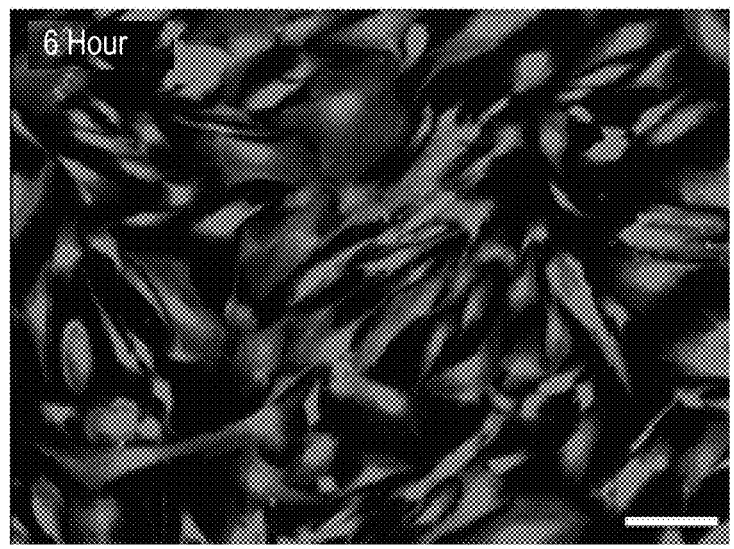
Figure 58D:
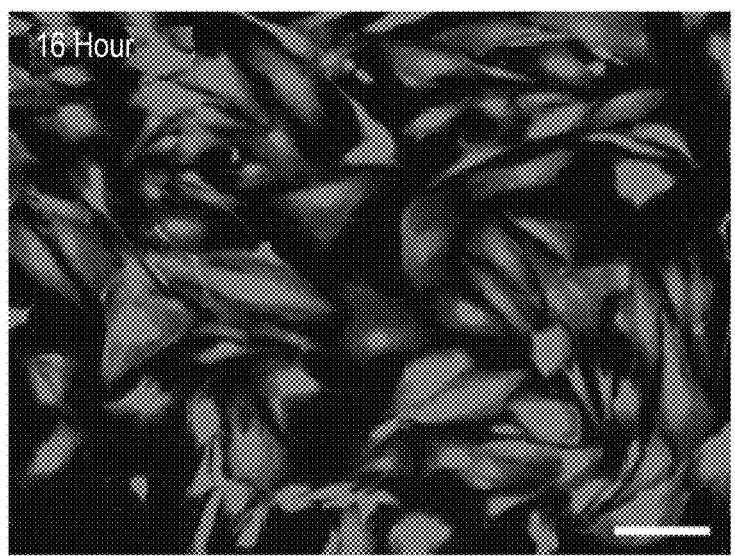
Figure 58E:
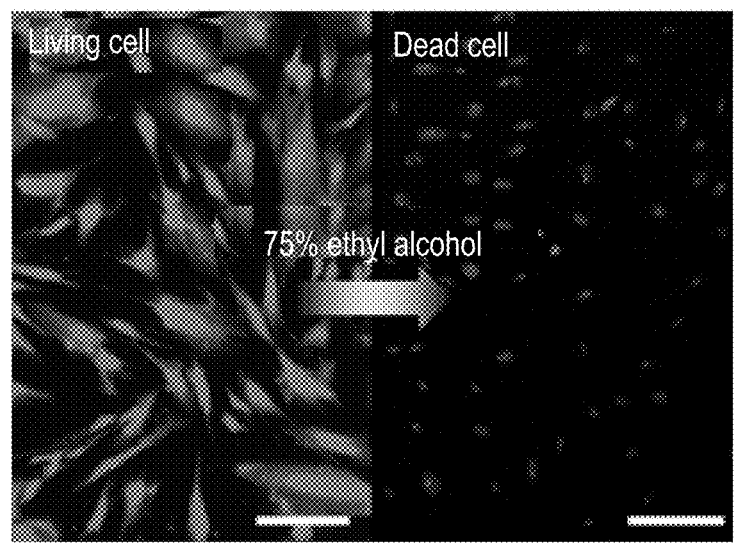
Figure 58F:
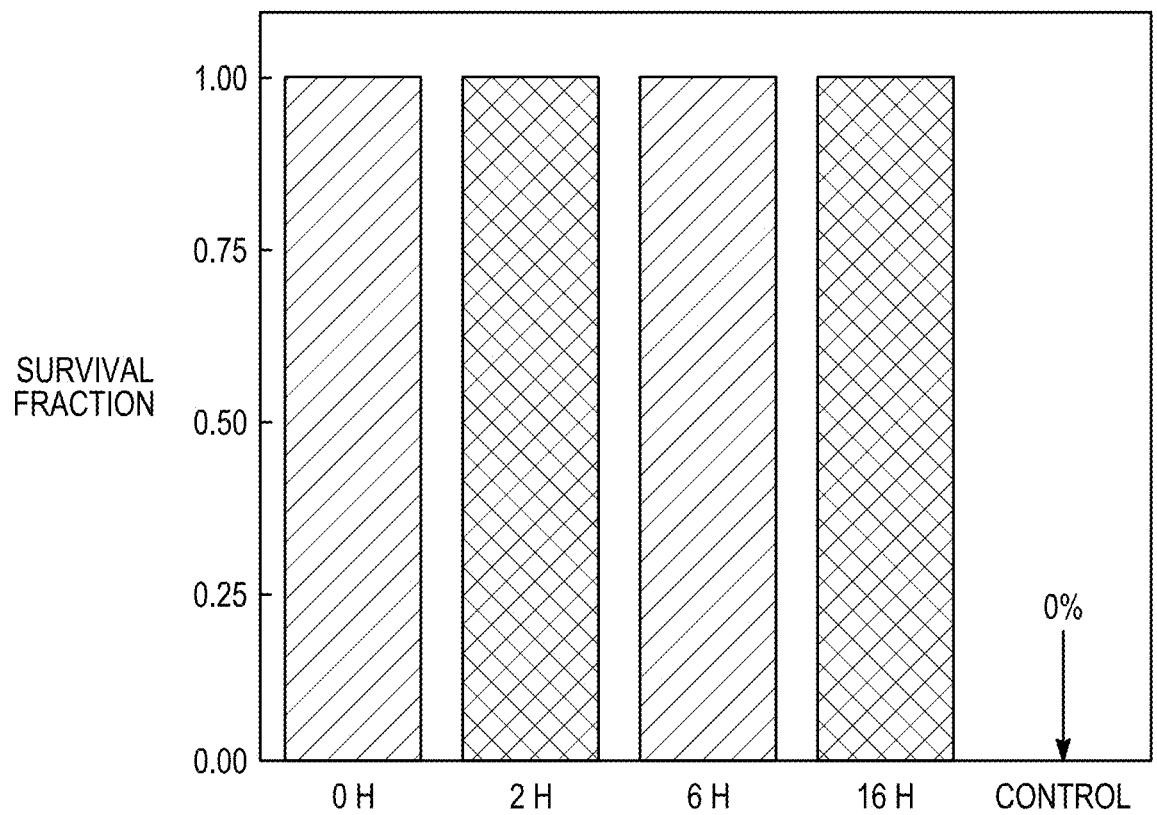
FIG. 58F shows statistics of the survival fraction of epidermal cells.

As shown in the fluorescent images in FIG. 39F FIGS. 58A-58E, fibroblast cells are cultured under the ultrasonic wave emission of our device with a 100% survival rate after 16 hours of continuous exposure, showing excellent biocompatibility. FIG. 58A-58E shows fluorescent images of HFF-1 cells cultured under exposure of the stretchable ultrasound device for a continuous period of time. FIG. 58A shows healthy HFF-1 cells. FIGS. 58B, 58C and 58D show HFF-1 cells under a continuous ultrasound exposure for 2 hours, 6 hours, and 16 hours, respectively, showing good cell viability and survival under the acoustic pressure of the device. FIG. 58E illustrates a positive control experiment demonstrating the robustness of the testing and observing method. FIG. 58F show statistics of the survival fraction of HFF-1 cells. The results are averaged from five different observations. The scale bars are all 20

Dynamic Blood Vessel Distention Recording

Figure 40A:
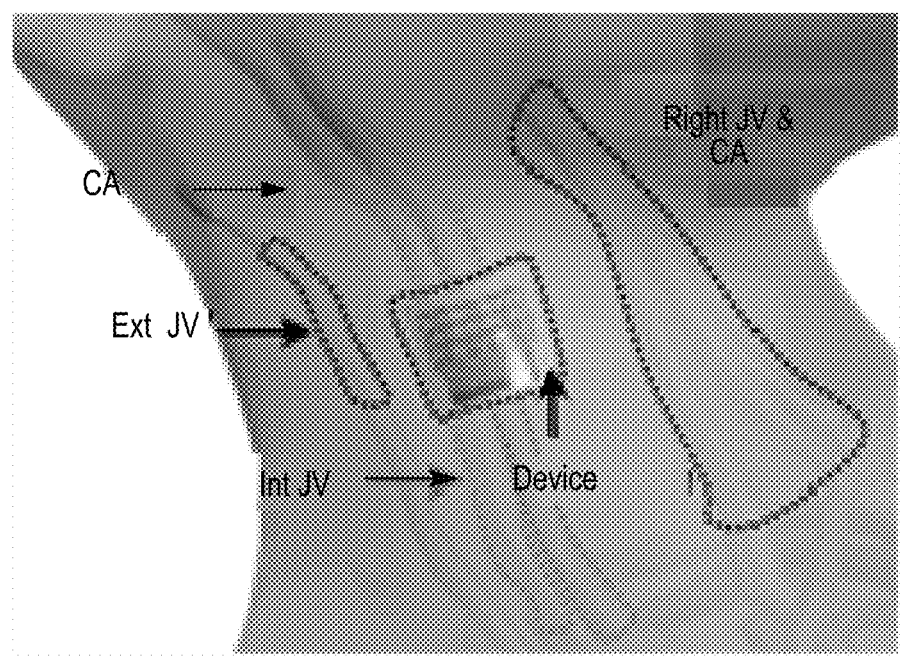
FIGS. 40A-40F show central arterial and venous pulse measurements.
Figure 40B:
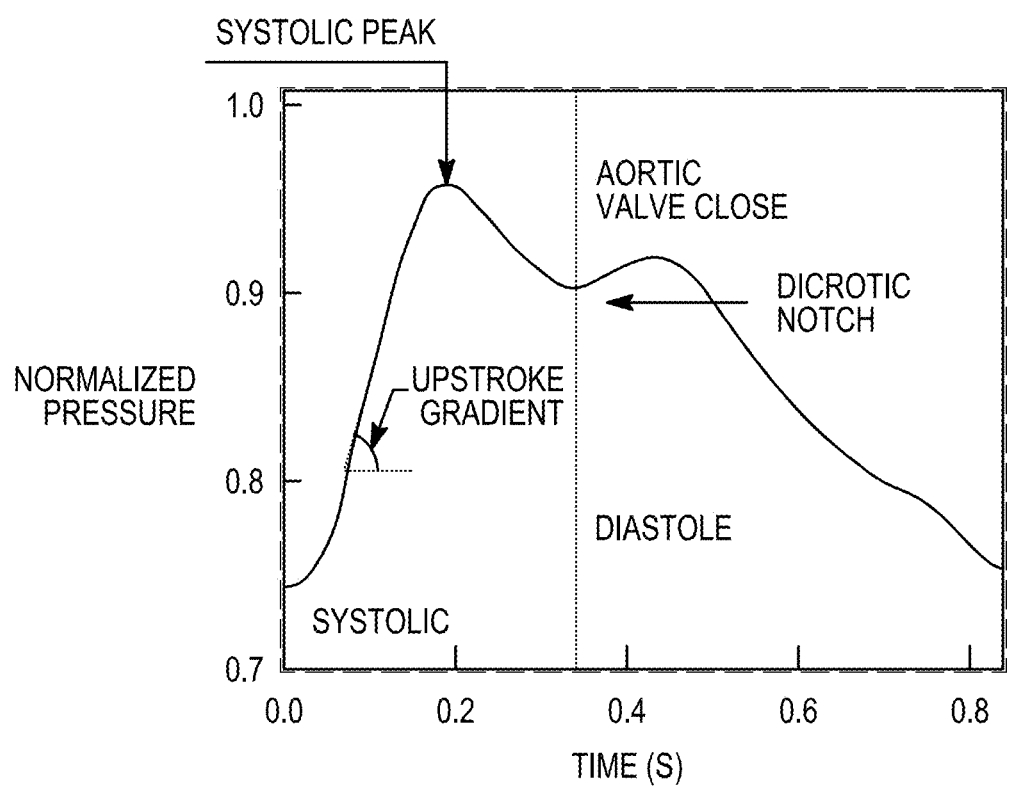
Figure 59:
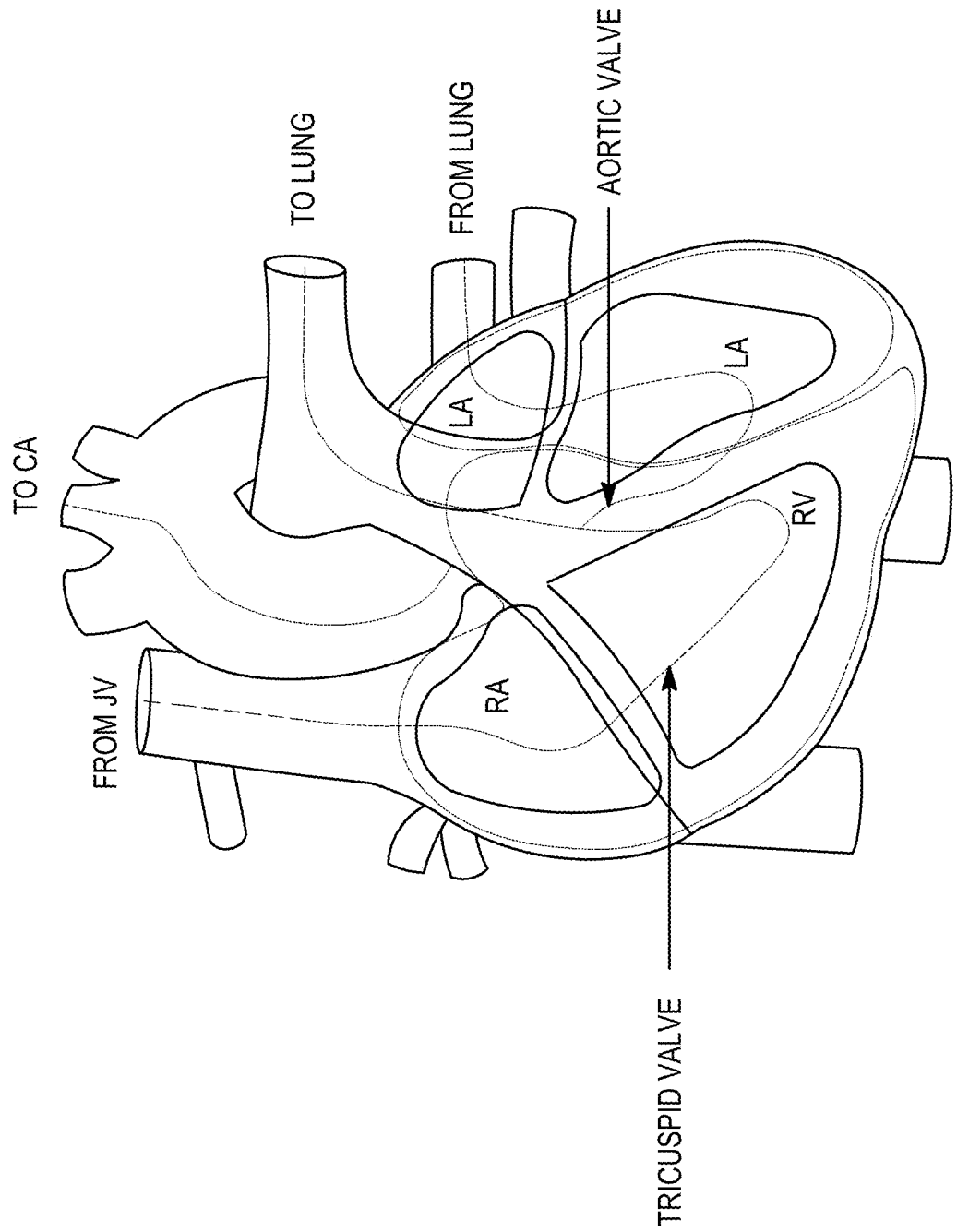
FIG. 59 shows the blood flow sequence in the central cardiovascular system and the direct relationship between central vessels and the heart.

From the pathophysiological perspective, the CBP waveform is a key predictor for main cardiovascular events. For example, cardiac status can be predicted by jugular vein distention (JVD), which can be seen as a vessel bulging on the neck, often caused by the right-side heart failure. We demonstrate for the first time highly accurate measurement of central vasculatures, including carotid artery, internal and external jugular veins. A schematic illustration of a sensor on a subject's neck is shown in FIG. 40A. The carotid artery (CA, ~25 mm underneath the skin with slight individual variation, in close proximity to the central aorta) carries a large amount of blood from the left ventricle (LV) and left atrium (LA) to the rest of the body. A typical period of the carotid artery blood pressure waveform measured by our device shows a clear systolic peak and dicrotic notch (FIG. 40B). The former indicates the ventricular systole and the latter indicates the closure of the aortic valve. FIG. 59 shows the blood flow sequence in the central cardiovascular system and the direct relationship between central vessels and the heart.

Figure 40C:
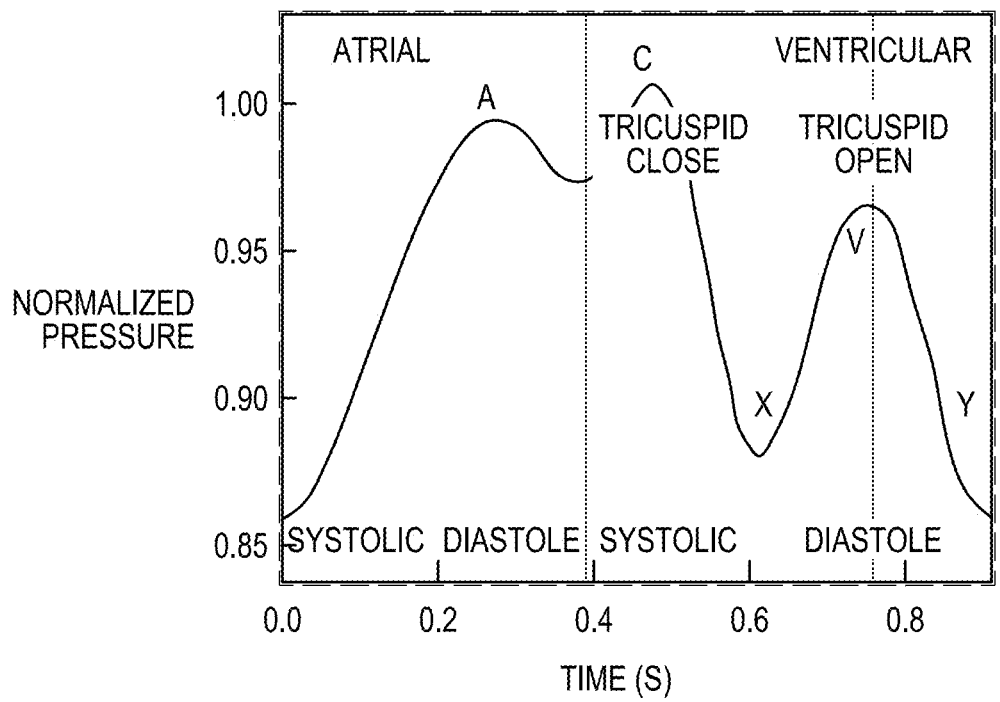
Figure 60:
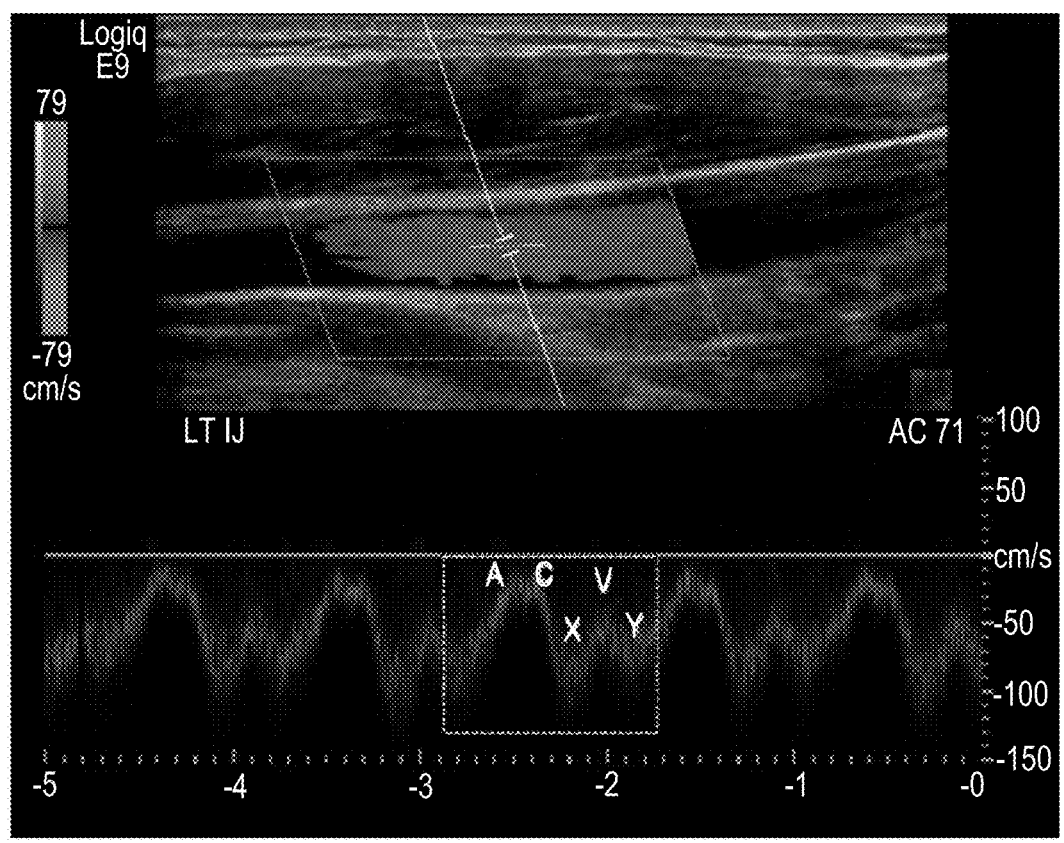
FIG. 60 shows the jugular venous waveform measured by a color Doppler imaging machine on the same testing subject.
Figure 61A:
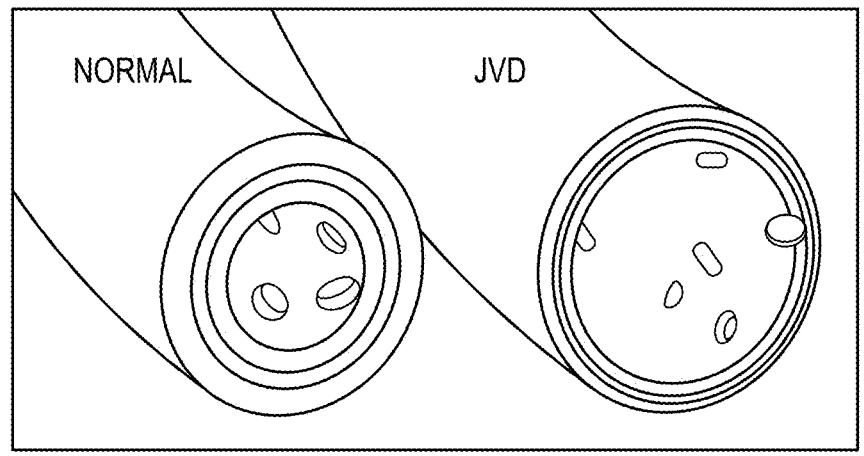
FIG. 61A shows schematics for external JVD caused by dramatic increases in thoracic pressure.
Figure 61B:
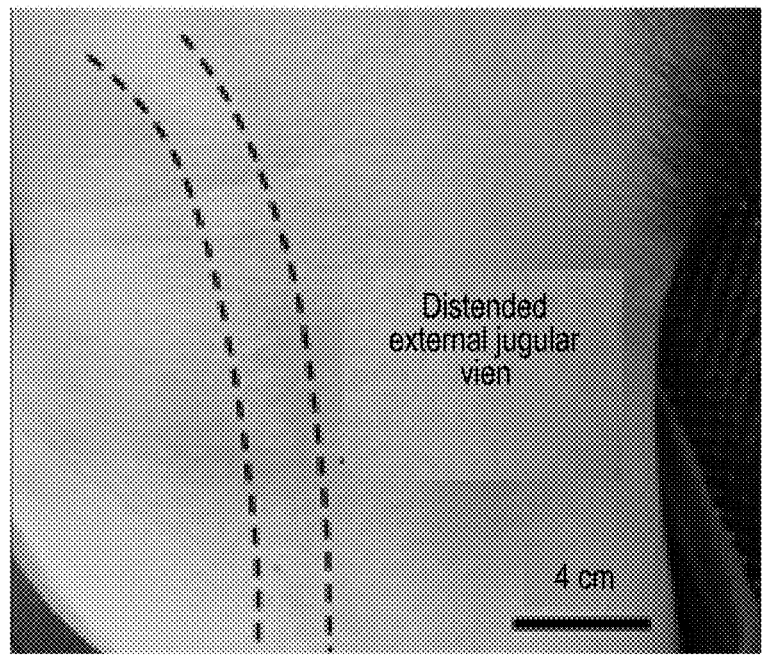
FIG. 61B shows a photograph of the human neck with a JVD created by deep exhalation.
Figure 61C:
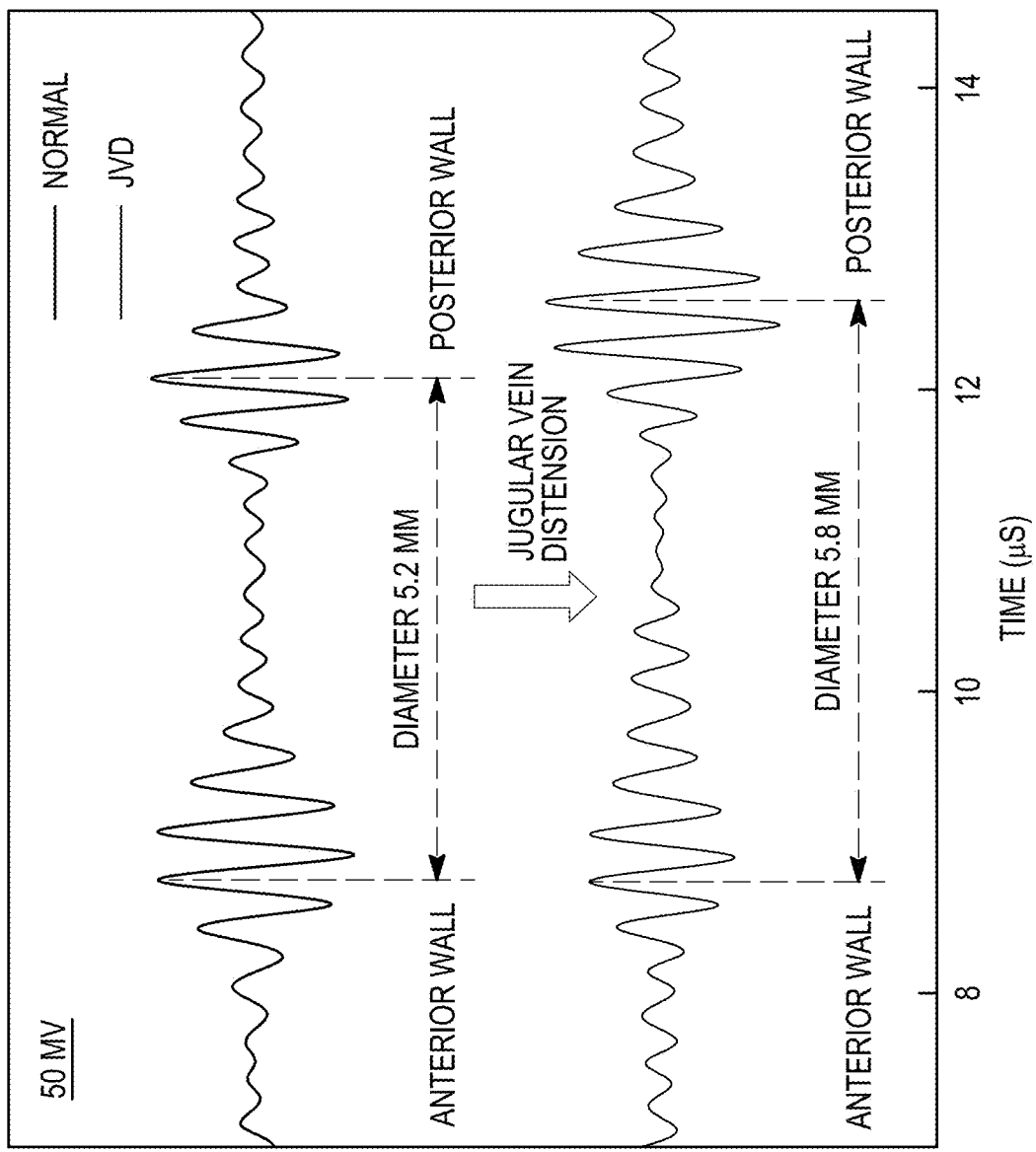
FIG. 61C shows the vessel wall measurement before and after JVD.

The internal jugular vein, carrying the venous blood to the right atrium (RA) and right ventricle (RV) and finally to the lung, reflects the right heart activities. A typical jugular venous pressure waveform measured by our device is shown in FIG. 40C, which shows three peaks: A (Atrial contraction), C (Tricuspid bulging, ventricular contraction), and V (Systolic filling of the atrium); and two descents: X (Atrial relaxation) and Y (Early ventricular filling). Those components correspond to various events during each cardiac cycle. The jugular venous waveform measured by color Doppler imaging machine (Mindray DC 7) on the same testing subject is shown FIG. 60, which shows the corresponding A, C, X peaks and V, Y descents. The jugular venous distension (JVD) is observed by measuring the diameter increase of the external jugular vein, created by deep exhalation of the subject. This is shown in FIG. 61, where FIG. 61A shows schematics for external JVD caused by dramatic increases in thoracic pressure; FIG. 61B shows a photograph of the human neck with a JVD created by deep exhalation; and FIG. 61C shows the vessel wall measurement before and after JVD, showing evident diameter distension after deep exhalation. The reason of the simulated JVD caused by exhalation is that the breathing creates suction in the chest, reducing pressure and allowing greater venous return—forcing the jugular to increase pressure, thus inflating the external jugular vein.

Exercise Hemodynamics Monitoring

Figure 40D:
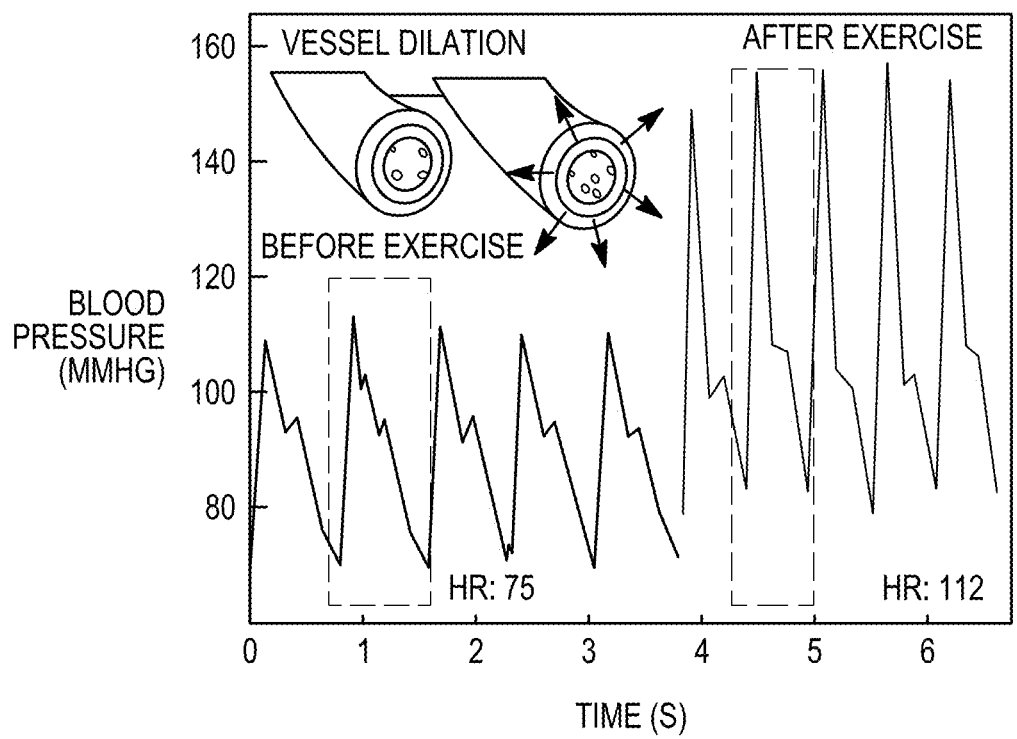
Figure 40E:
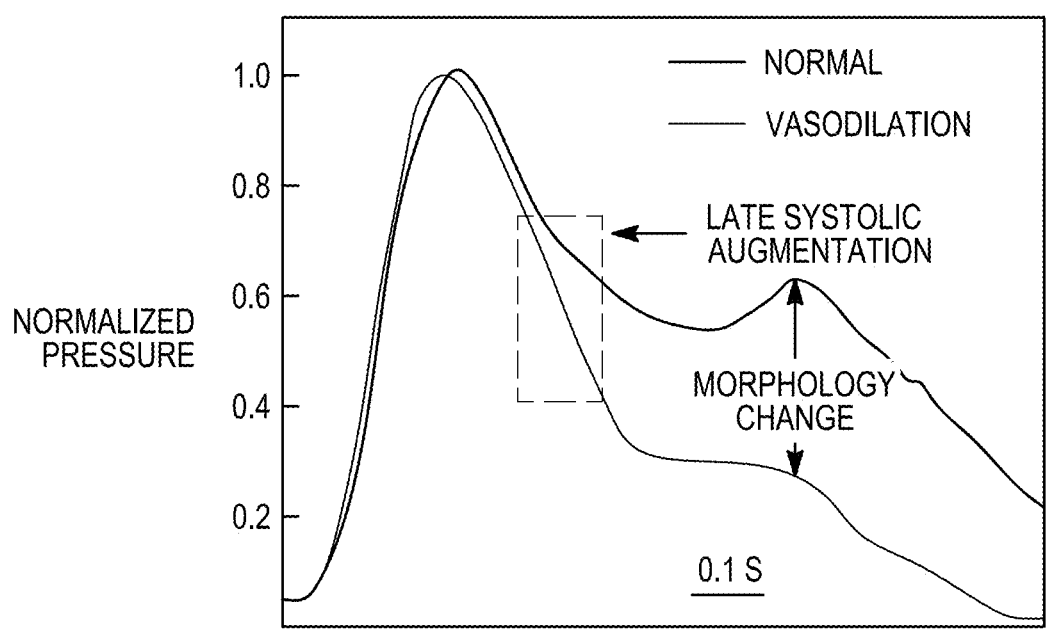
Figure 62A:
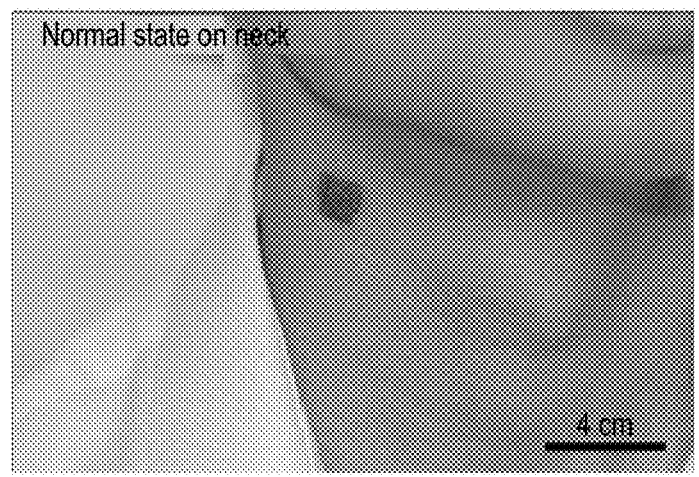
FIGS. 62A-62C shows the device conformability and self-adhesion on the neck under different postures.
Figure 62B:
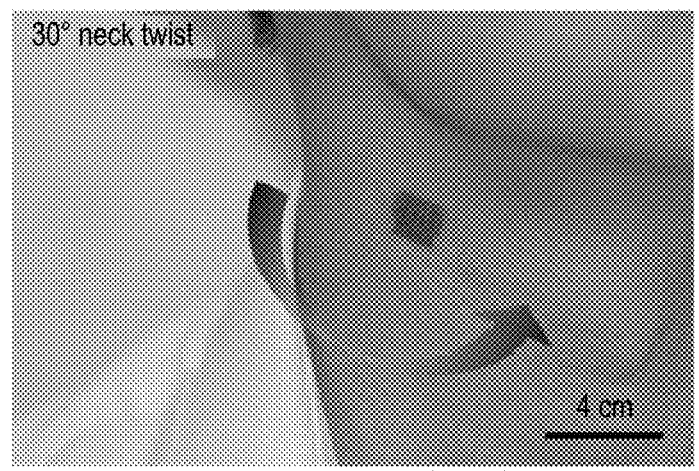
Figure 62C:
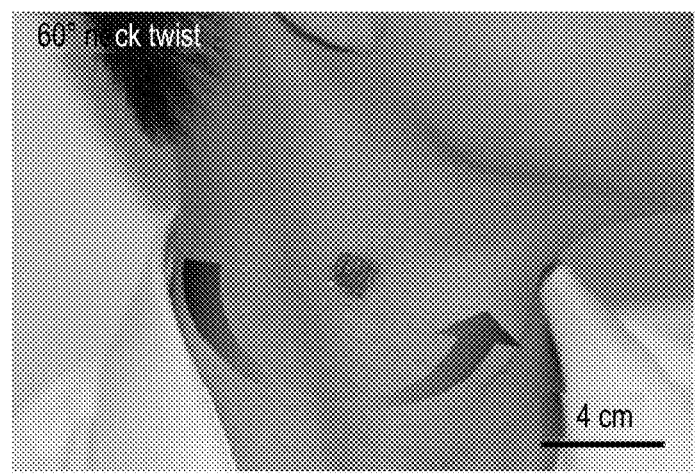

Due to its excellent mechanical compliance and light-weight (0.15 g), the device described herein can maintain intimate and stable contact with the human skin both mechanically and acoustically in different body postures with pure van der Waals force. The device conformability and self-adhesion on the neck under different postures is illustrated in FIG. 62, where FIG. 62A shows a normal state; FIG. 62B show a posture with a 30° twist; and FIG. 62C shows a posture with 60° twist. During exercise, the muscles need more blood carrying nutrients and oxygen, and the cardiac output increases to meet the need. On the one hand, human vessel goes into a vessel dilation situation (FIG. 40D, inset) to enlarge the vessel diameter to increase the blood flow for sufficient nutrient and oxygen supply. The vascular resistance and reflection are therefore reduced. On the other hand, the heart rate and systolic strength increase to boost up the cardiac output. The measured heart rate on radial artery during resting (~75/min) and immediately after exercise (~112/min) is shown in FIG. 40D. The blood pressure waveform has a higher systolic peak due to the stronger ventricular systole (FIG. 40E) to get larger cardiac output. The average waveform morphology change before and after intense exercise appears in FIG. 40E (Normalized to same systolic pressure and diastolic pressure), showing a steep drop of the systolic peak after exercise due to the vasodilation induced vascular resistance decrease.

Device Performance Robustness Testing

Figure 25:
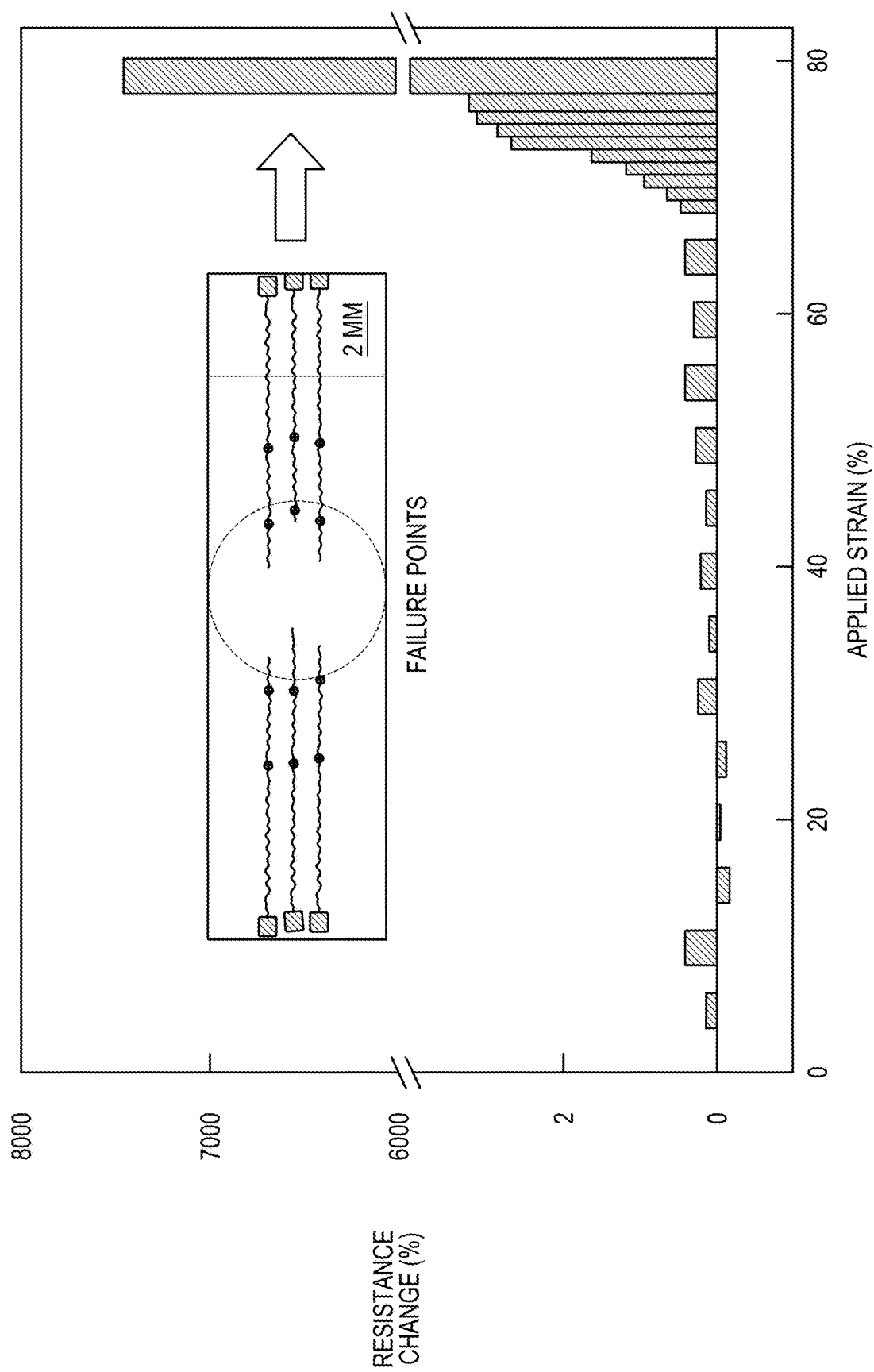
FIG. 25 shows the relative resistance changes of the Cu serpentine interconnect under stretching.
Figure 40F:
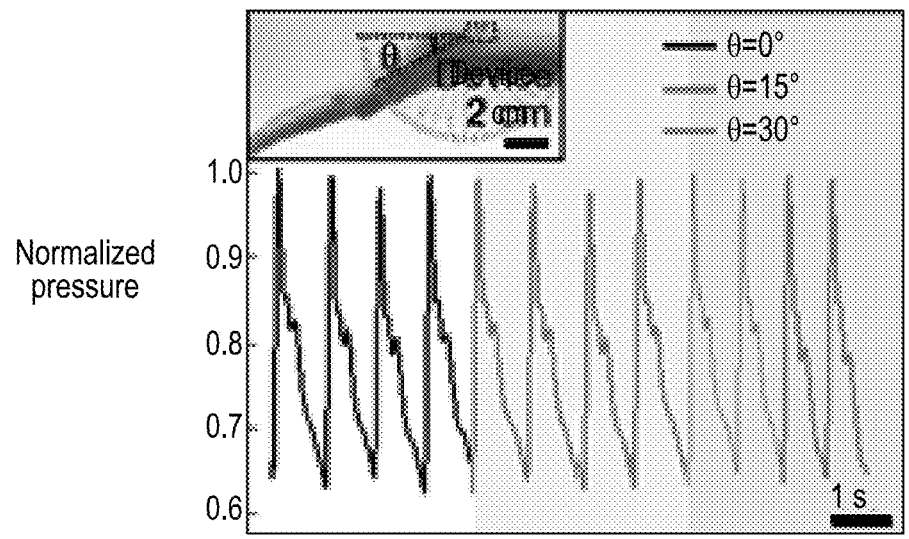
Figure 41A:
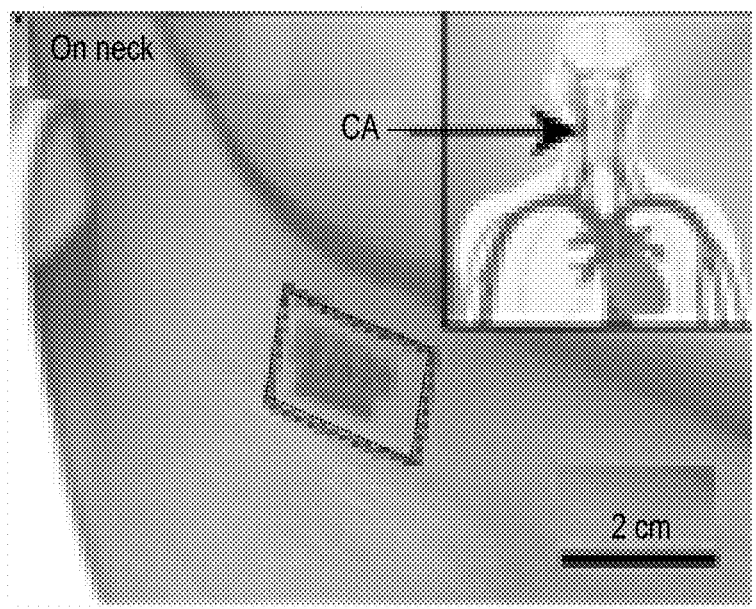
FIGS. 41A-41D show measurement positions from the central to peripheral arteries.
Figure 41B:
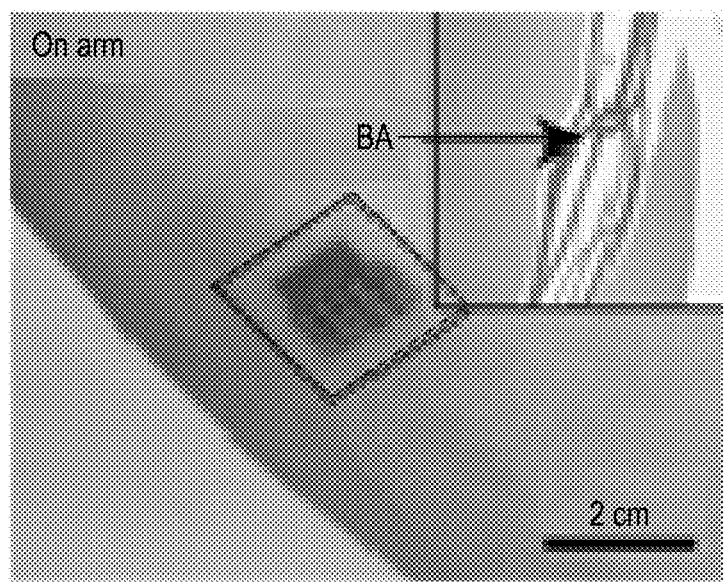
Figure 41C:
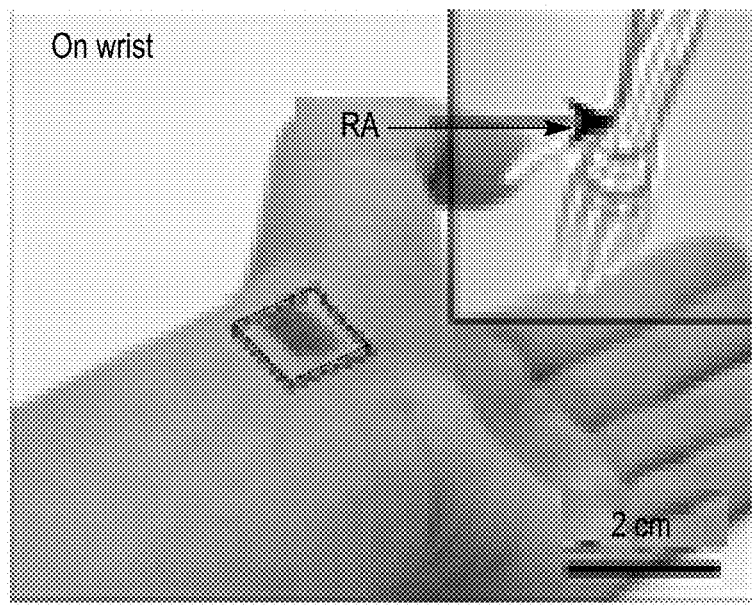
Figure 41D:
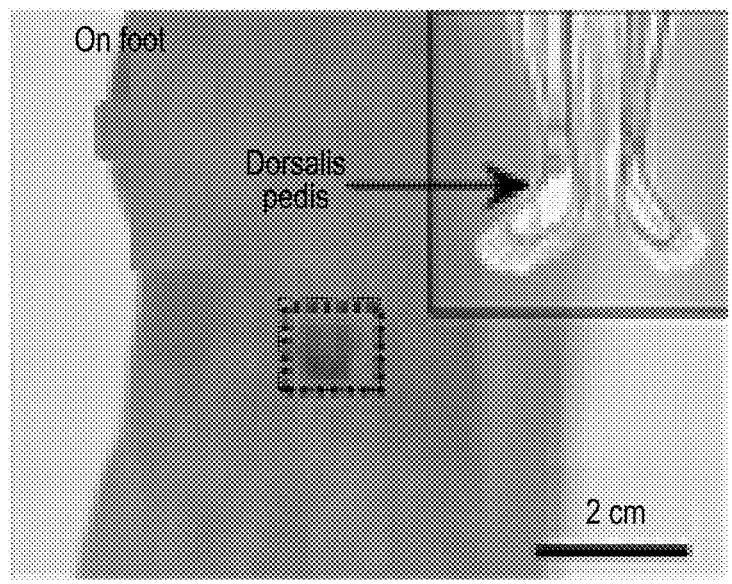
Figure 41E:
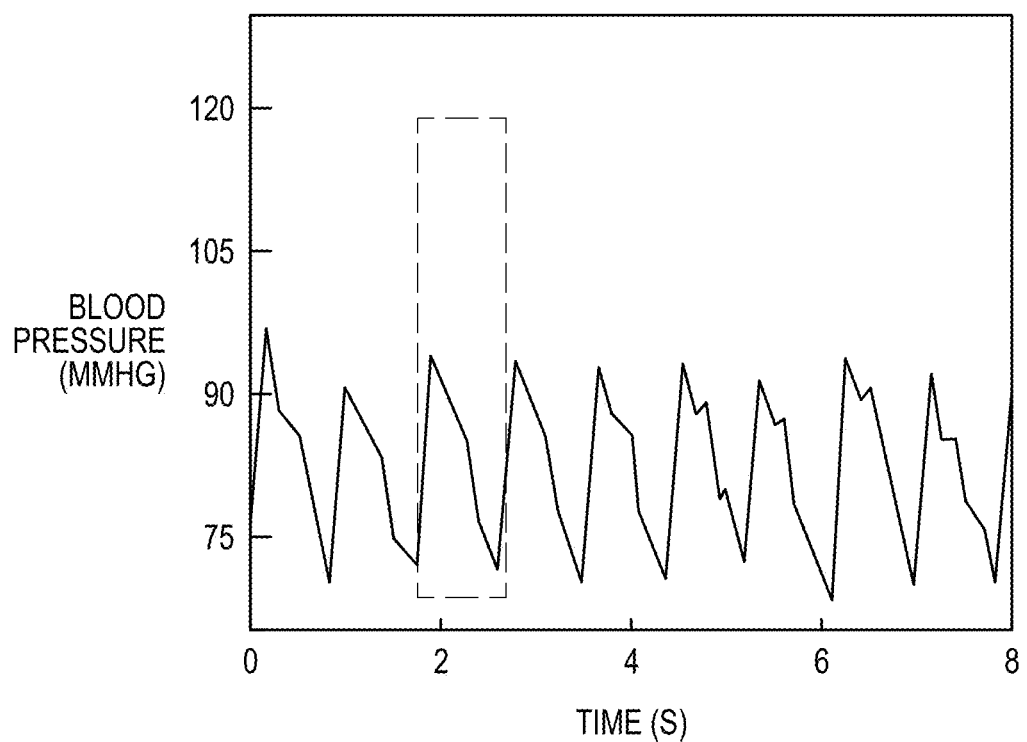
FIGS. 41E-41L show blood pressure measurements from the central to peripheral arteries.
Figure 41F:
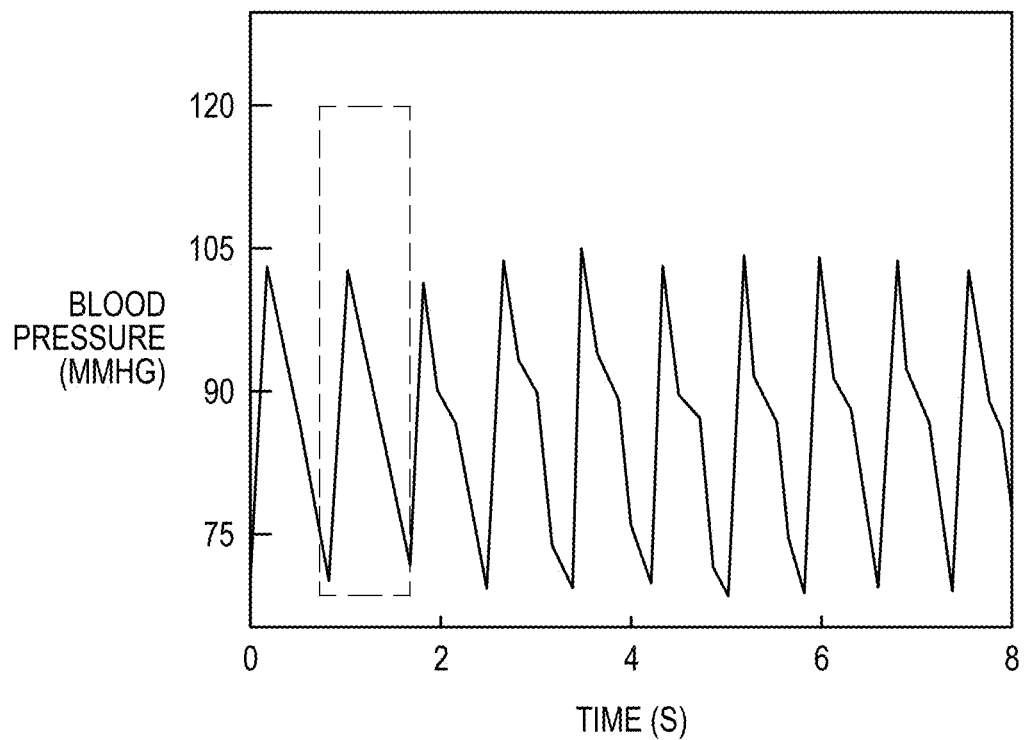
Figure 41G:
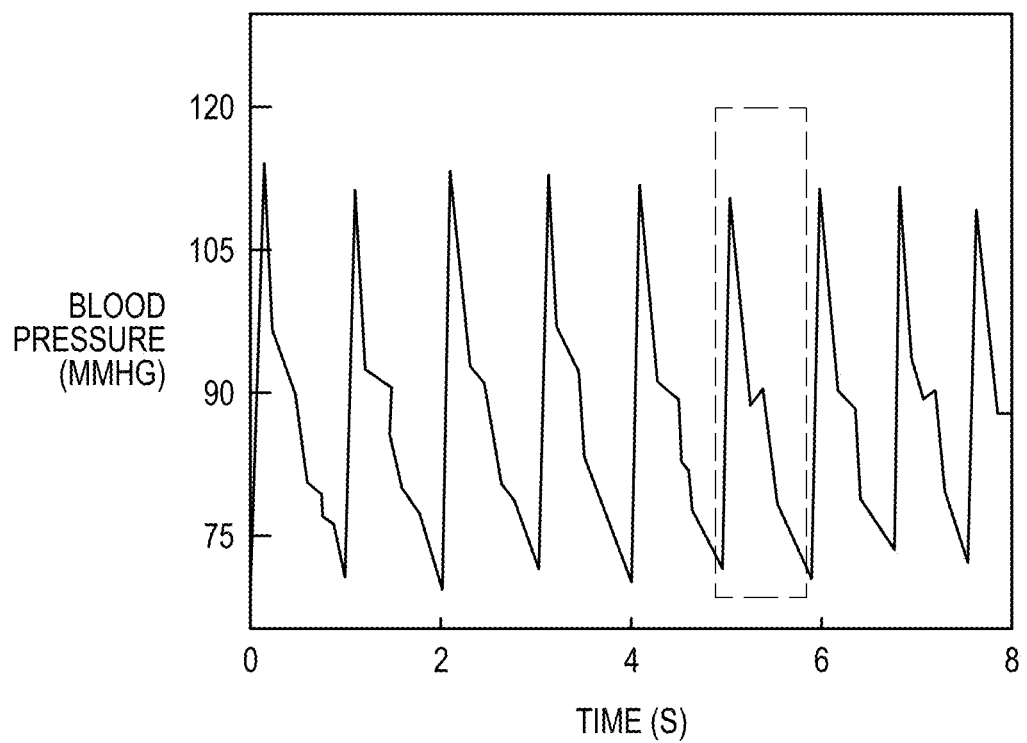
Figure 41H:
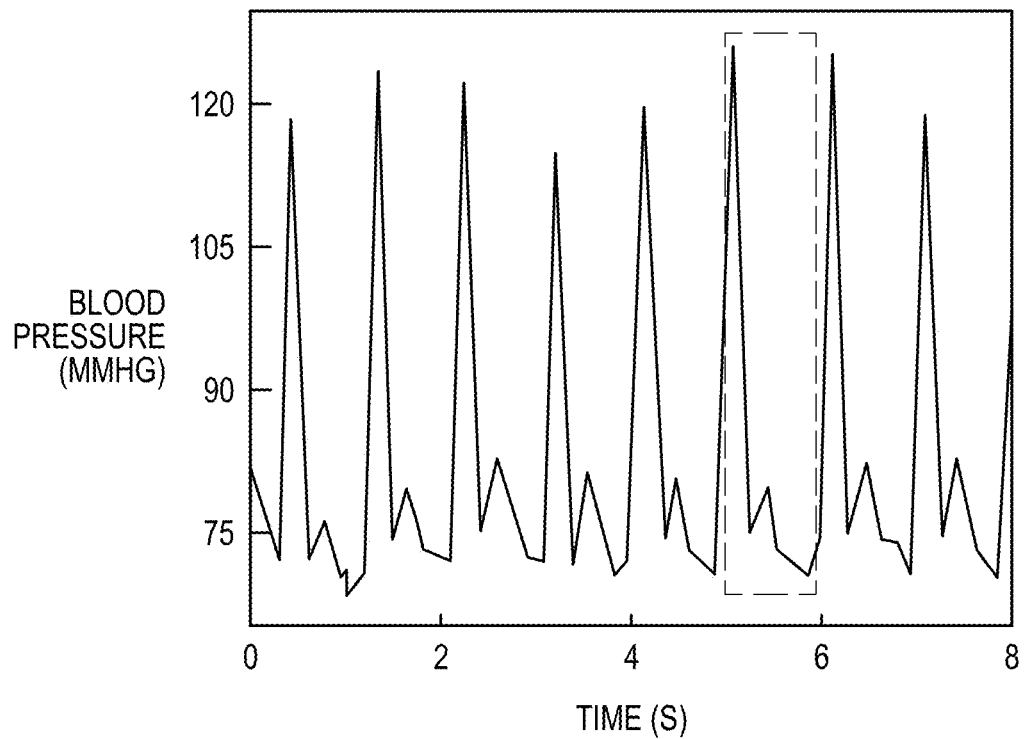
Figure 41I:
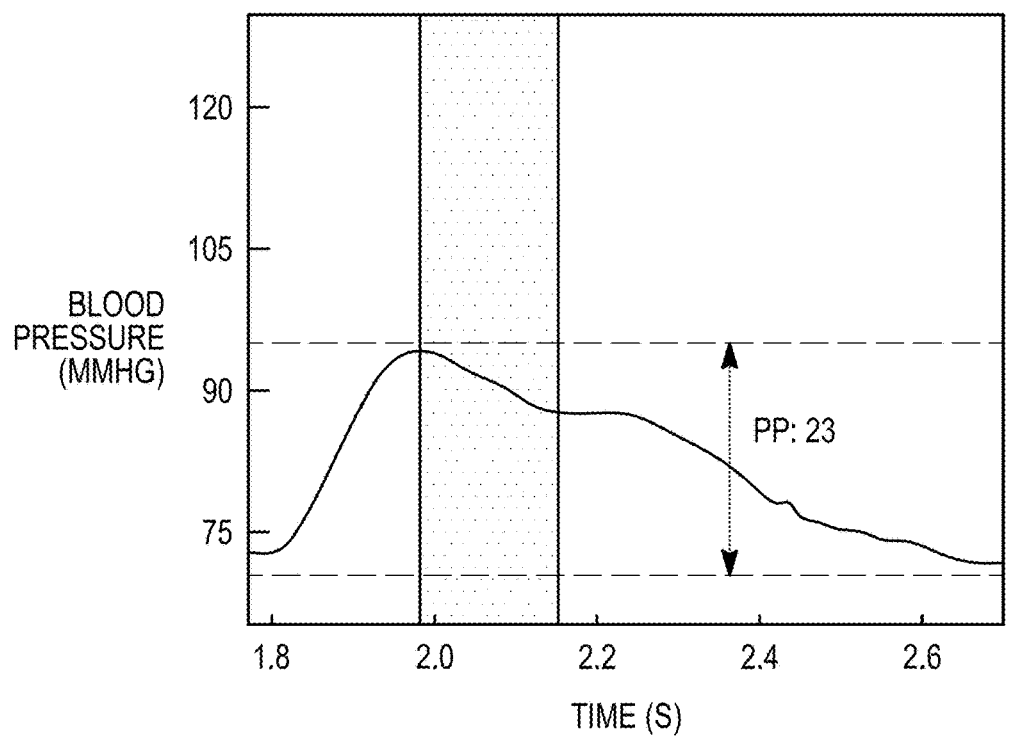
Figure 41J:
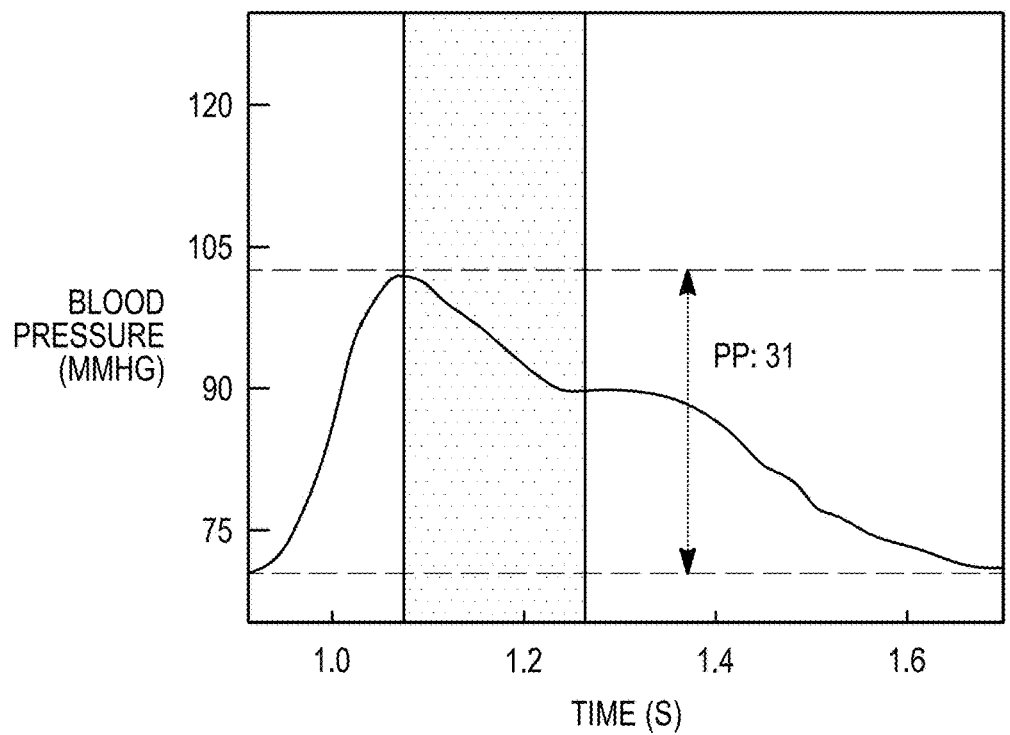
Figure 41K:
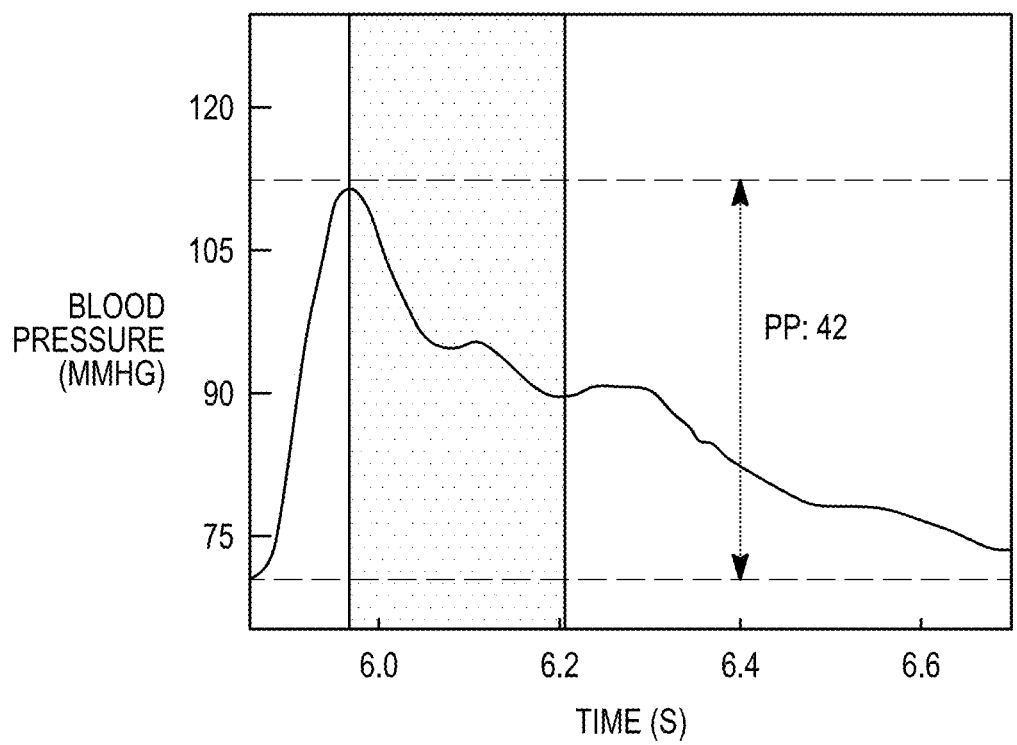
Figure 41L:
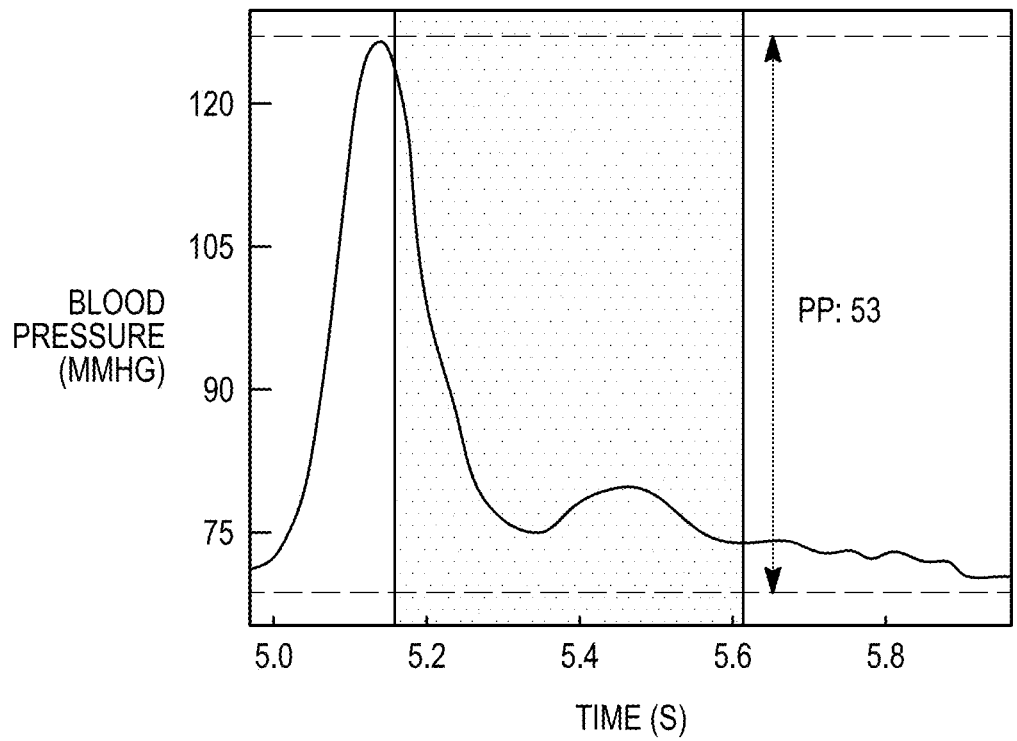
Figure 63:
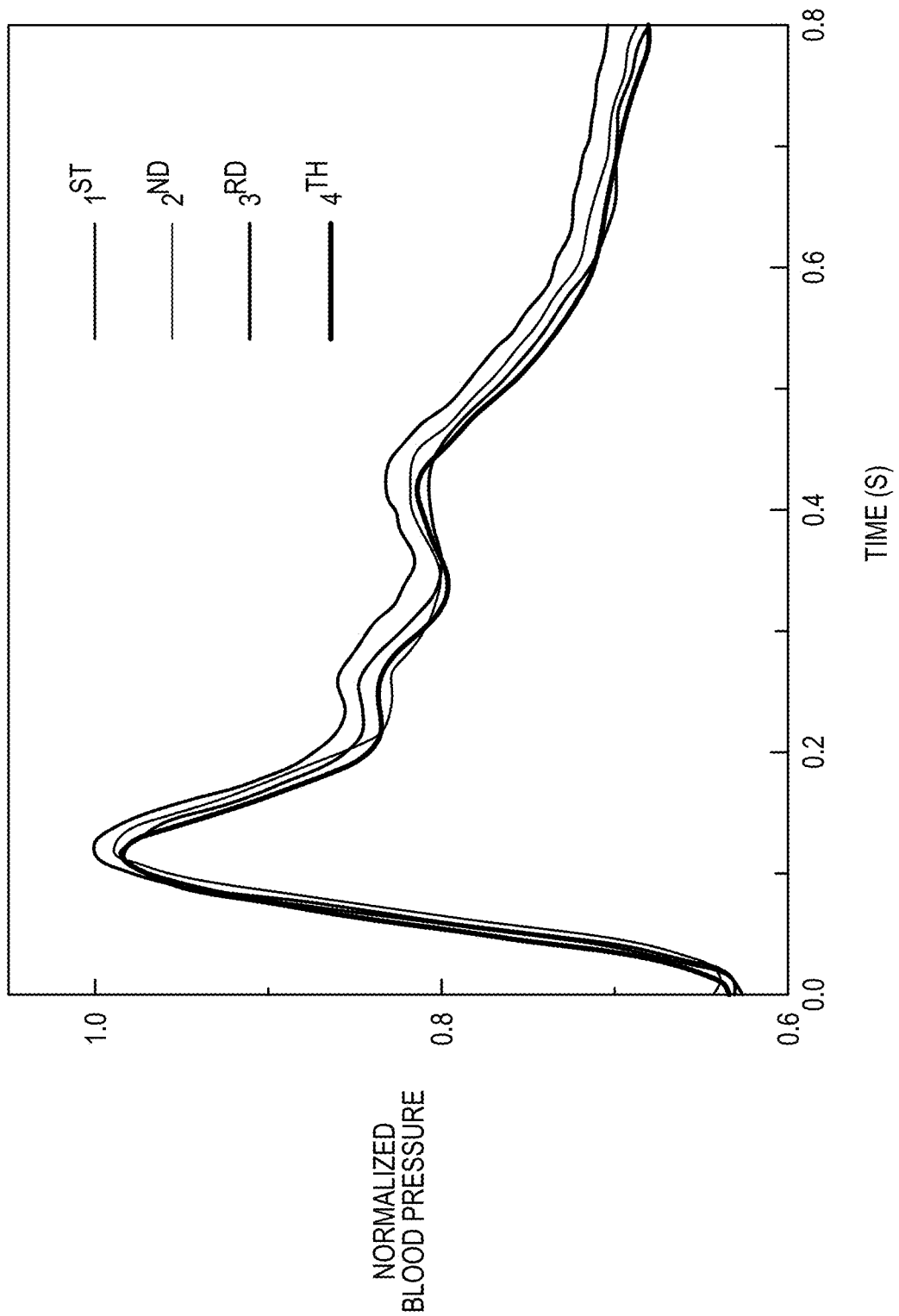
FIG. 63 shows a reusability test of the device during 1$^{st}$ (the first day), 2$^{nd}$ (after two days), 3$^{rd}$ (after one week), and 4$^{th}$ (after two weeks) measurements.

The conformal and intimate contact between the device and the human skin leads to robust device performance. Measurement results of the radial artery waveform under different wrist bending modes (0°, 15°, and 30°) remains stable without any manual adjustment (FIG. 40F), Additionally, the results of a device durability test shown in FIG. 25 illustrate the highly reproducible results by the same device within two weeks. In particular, FIG. 63 shows a reusability test of the device during $1^{st}$ (the first day), $2^{nd}$ (after two days), $3^{rd}$ (after one week), and $4^{th}$ (after two weeks) measurements. The measurements are carried out on the same subject under the same conditions. The four measurements are normalized to the same pressure value (same diastolic and systolic pressure).

Figure 64A:
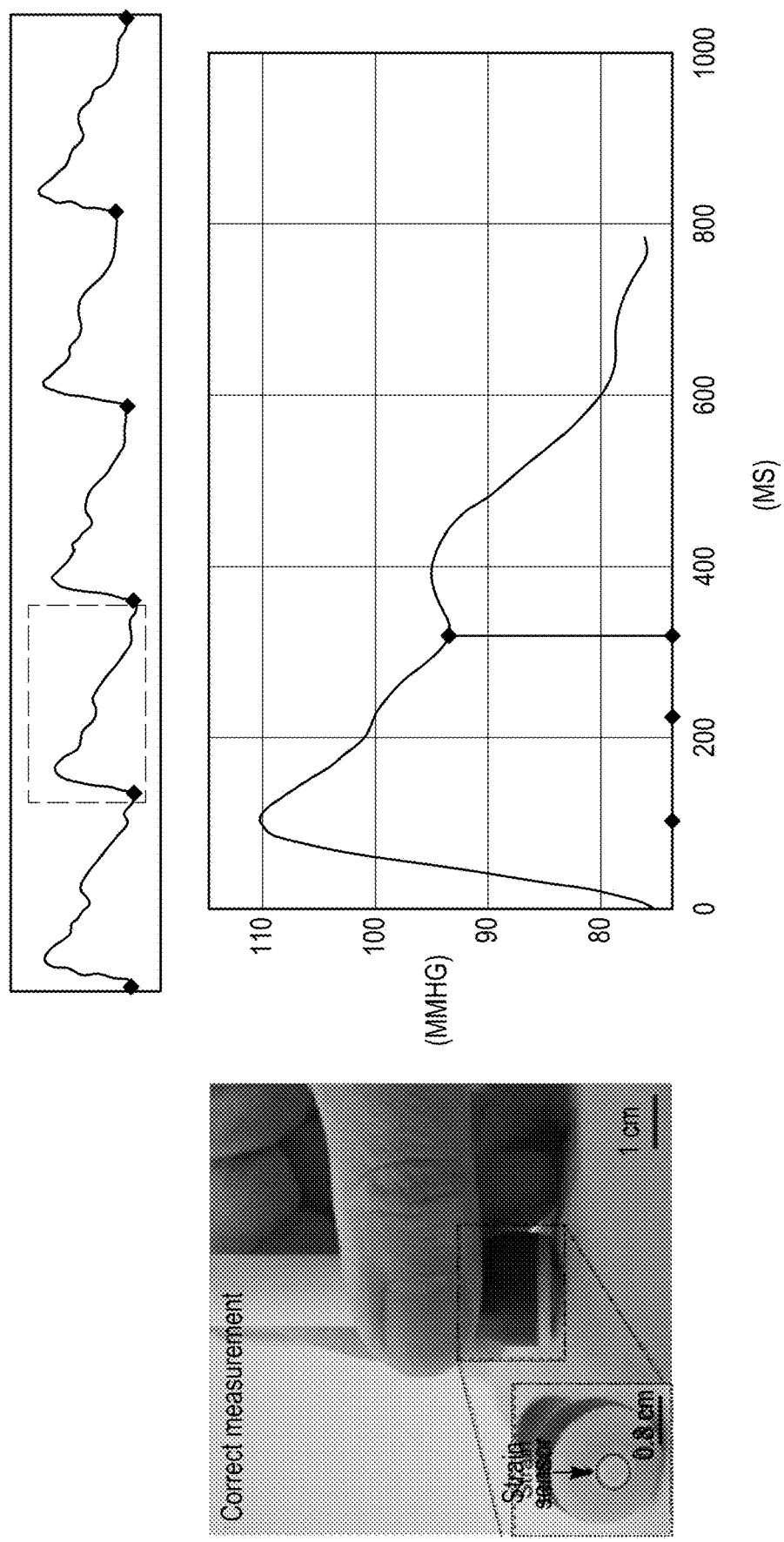
FIG. 64A shows the correct operator measurement condition for using a commercial applanation tonometry system and the corresponding waveform that results.
Figure 64B:
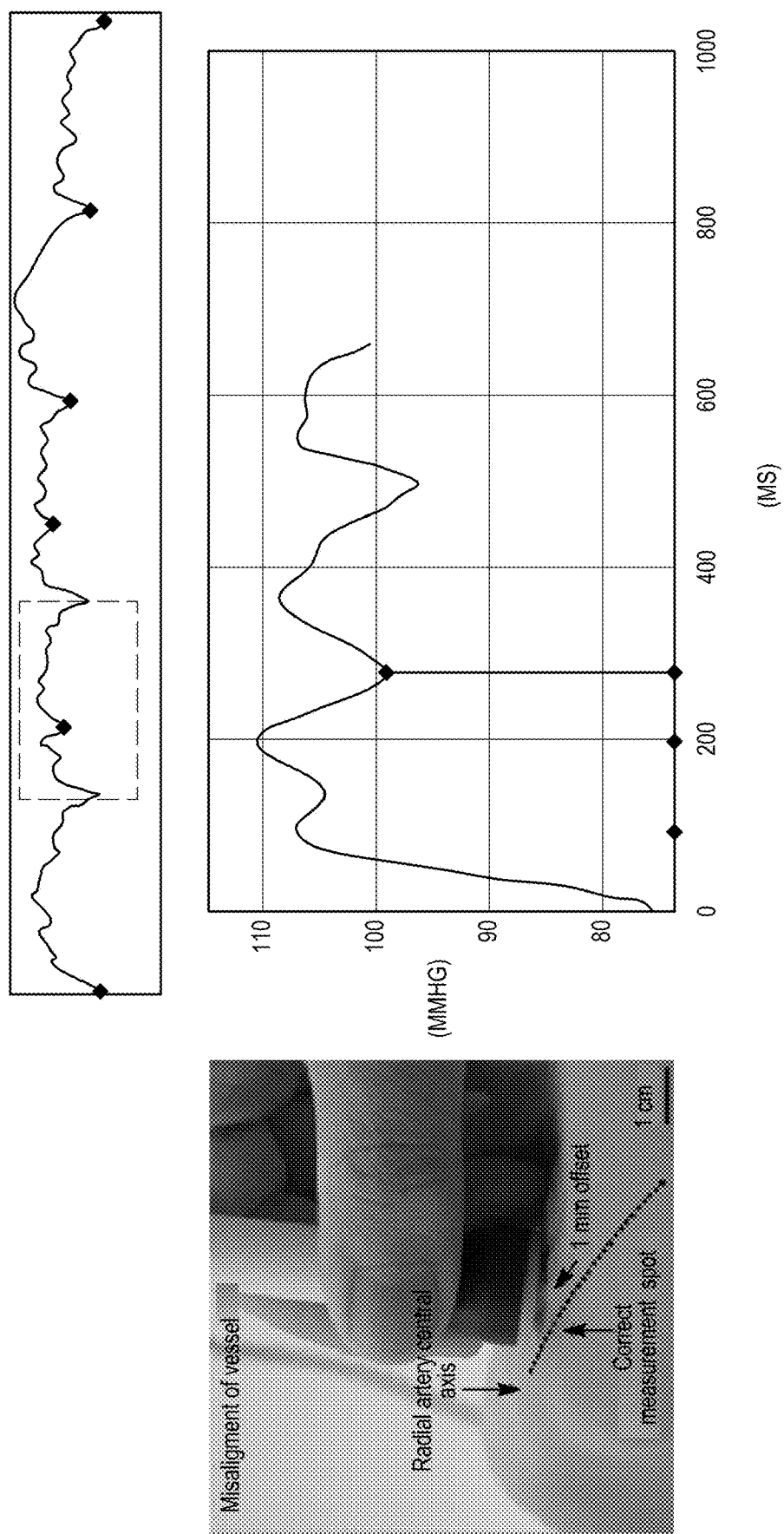
FIG. 64B shows incorrect vessel positioning and the erroneous recording that results.
Figure 64C:
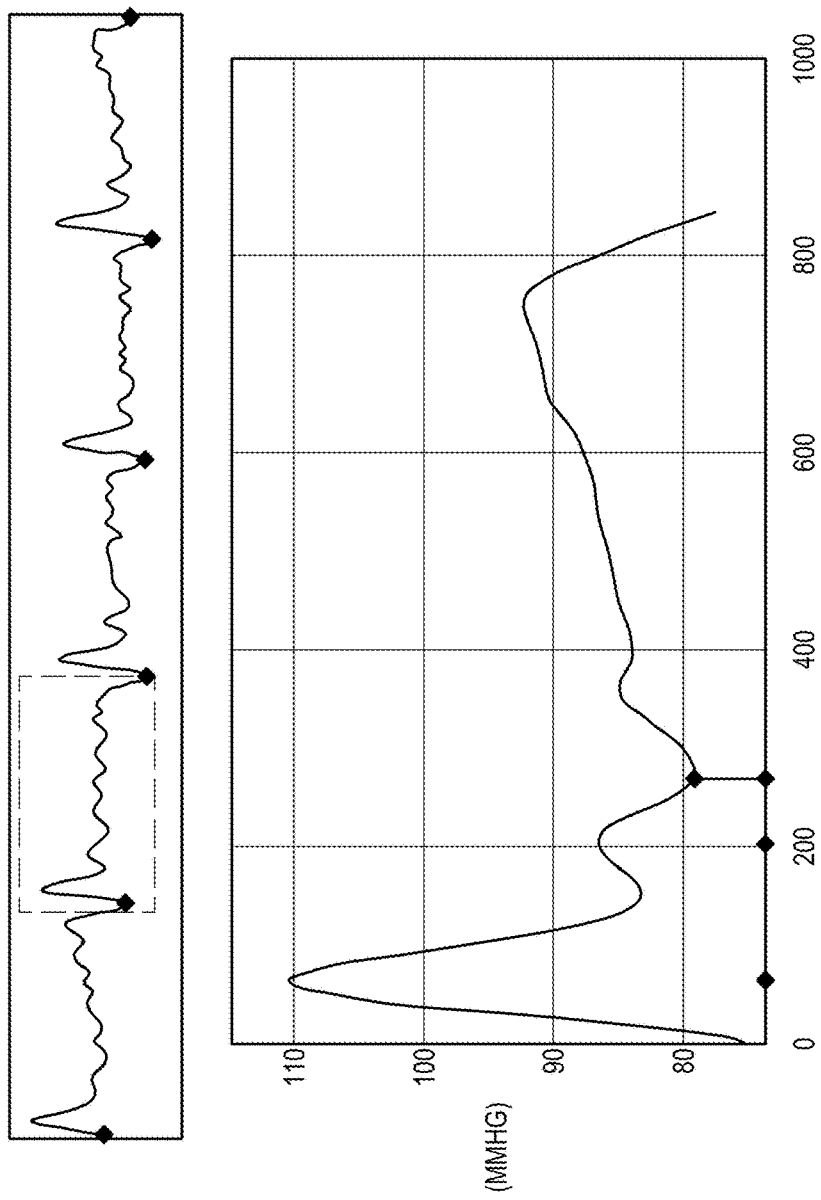
FIG. 64C shows that a moderately excessive holding pressure induces squeezing the vessel, leading to waveform morphology distortion.
Figure 64C:
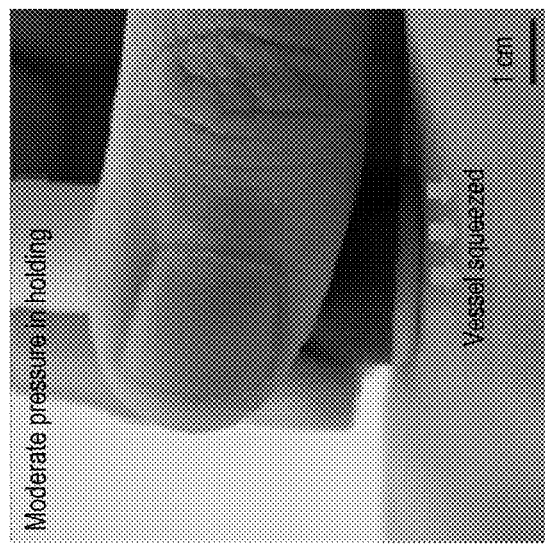

These features represent a huge advantage over the applanation tonometry, the noninvasive gold standard for blood pressure waveform measurement. The tonometry is highly operator-dependent, which is reflected by the fact that either tiny offset from the central arterial axis or moderate holding forces of the tonometry probe will introduce a large recording error of the BP waveform. The operator dependency of commercial applanation tonometry system is shown in FIG. 64. Specifically, FIG. 64A shows the correct measurement condition and the corresponding waveform; FIG. 64B shows incorrect vessel positioning and the erroneous recording that results; and FIG. 64C shows that a moderately excessive holding pressure induces squeezing the vessel, leading to waveform morphology distortion.

Figure 65A:
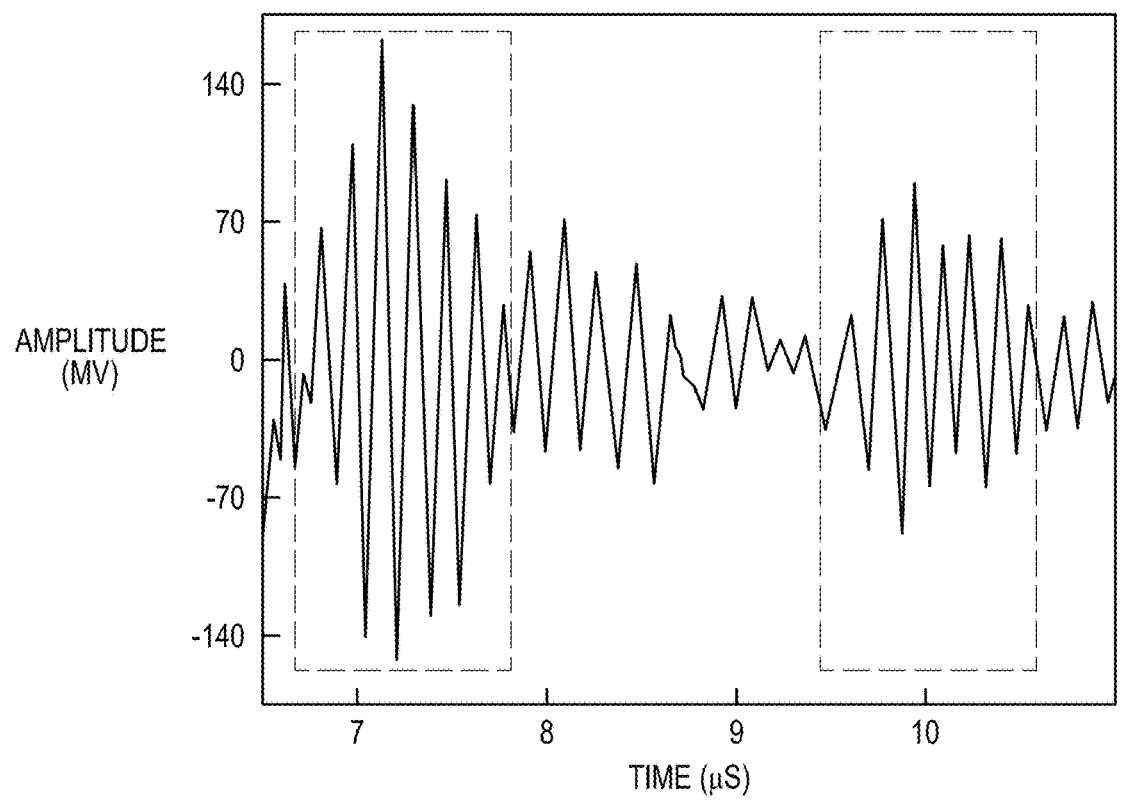
FIGS. 65A-65D show a comparison of the device acoustic emission performance with and without ultrasonic gel.
Figure 65B:
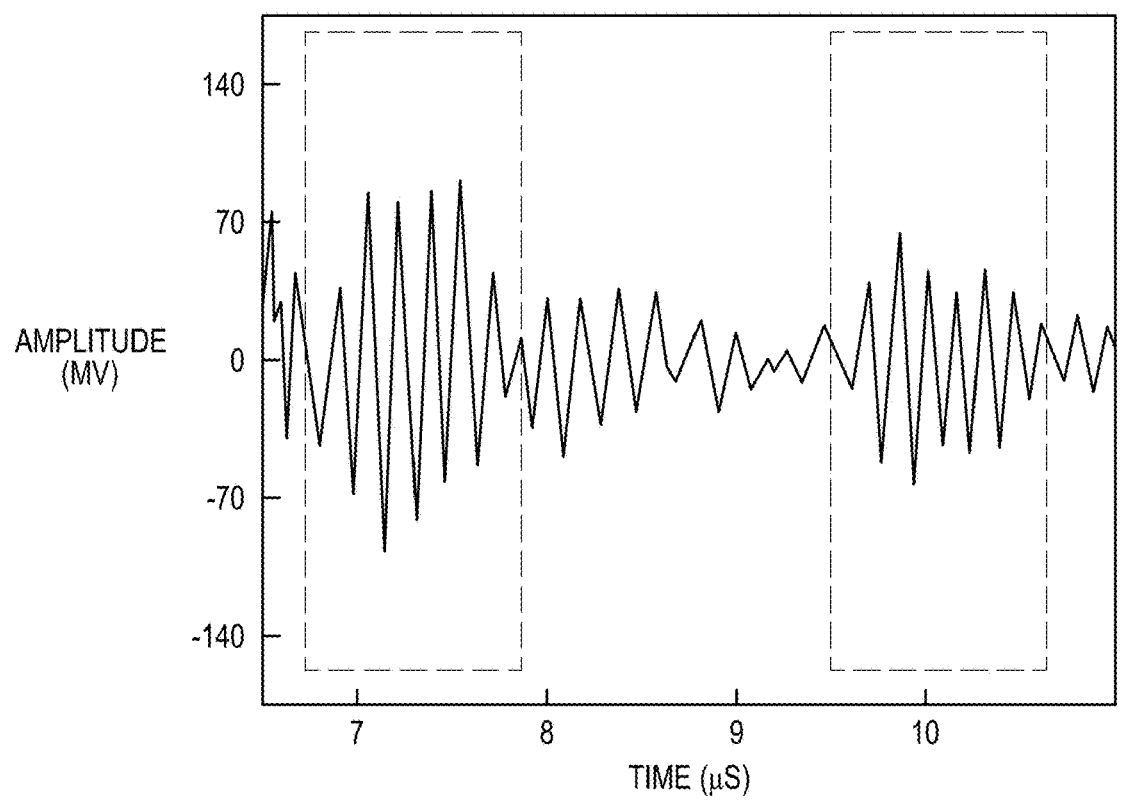
Figure 65C:
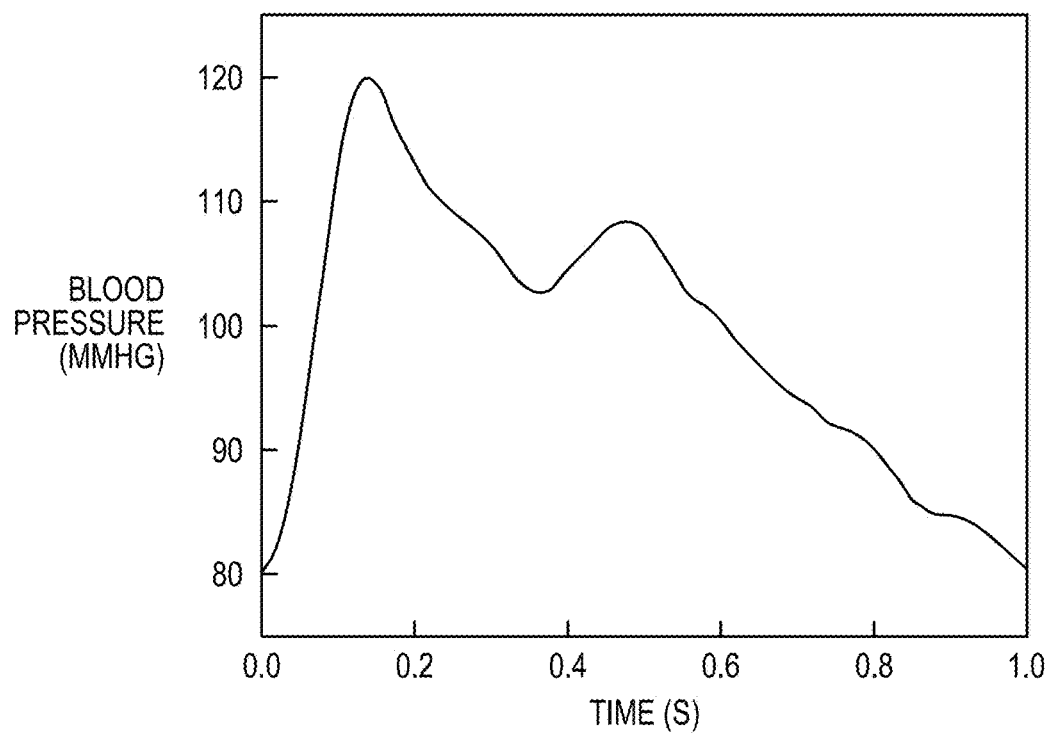
Figure 65D:
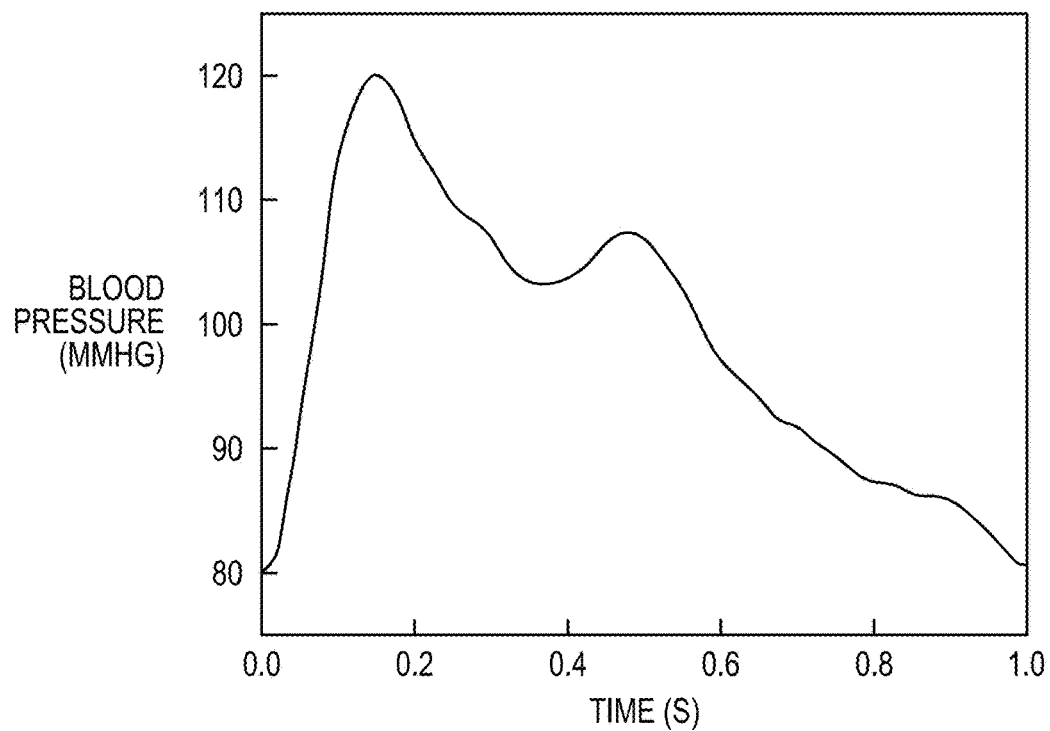

It is worth mentioning that traditional ultrasonic transducers rely on ultrasound gel to eliminate the interfacial air gap between the probe and the skin for good acoustic coupling. The gel is unpleasantly cold and needs to be frequently reapplied to prevent it from drying out. In the device described herein, we add a 15 μm thick layer of silicone, Silbione °, as acoustic coupling layer. Silbione has a Young's modulus of 200 Pa, lower than the human skin. Silbione is sticky to ensure intimate contact on the skin. In this way, we can achieve excellent acoustic coupling at the device/skin interface without applying any gel and maintain comparable signal and waveform measurement quality to those acquired with gel. FIG. 65 shows a comparison of the device acoustic emission performance with and without ultrasonic gel. In particular, FIG. 65A shows the echo received with and FIG. 65B shows the echo received without the ultrasonic gel. The measured waveform from the radial artery after decoding is shown in FIG. 65C with and in FIG. 65D without the ultrasonic gel. The results show comparable signal quality.

Continuous Blood Pressure Waveform Monitoring, from Central to Peripheral

Due to the vasculature amplification effect, namely the progressive vascular resistance, stiffness, and impedance mismatch between central and peripheral vessels, the arterial pressure waveform varies from central to peripheral. Although the diastolic and mean arterial pressures are relatively constant, systolic pressure can be up to 40 mmHg higher in the peripheral than the central artery. As the pressure wave travels from the large and highly elastic central arteries (i.e., the carotid) to the small and stiff peripheral artery (e.g., the radial and dorsalis pedis) (FIGS. 41A-41D show the measurement positions), the systolic pressure becomes higher and the systolic peak becomes narrower (FIGS. 41E-41H show the collected arterial pressure waveforms). FIG. 53 shows images of blood vessels from central to peripheral under gray scale measured by Doppler ultrasound. The results show the gradual shrinkage of the vessel diameter. In particular, FIG. 53A shows the carotid artery with a diameter of 6.2 mm, FIG. 56B shows the brachial artery with a diameter of 3.2 mm, and FIG. 56C shows the radial artery with a diameter of 2.4 mm, which will introduce progressive vascular resistance.

Figure 66:
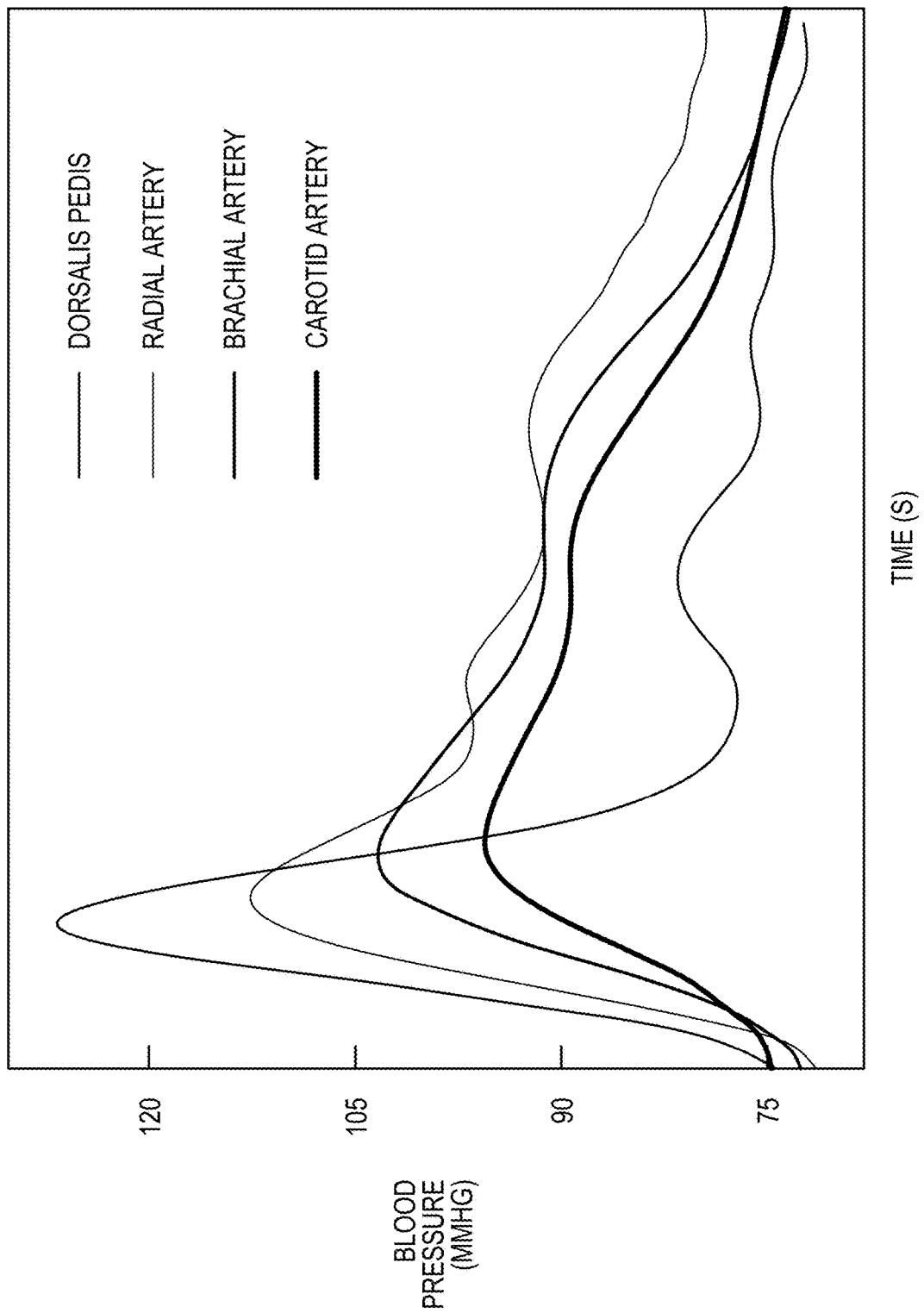
FIG. 66 shows a comparison of the upstroke gradient from the central to peripheral arteries.
Figure 67:
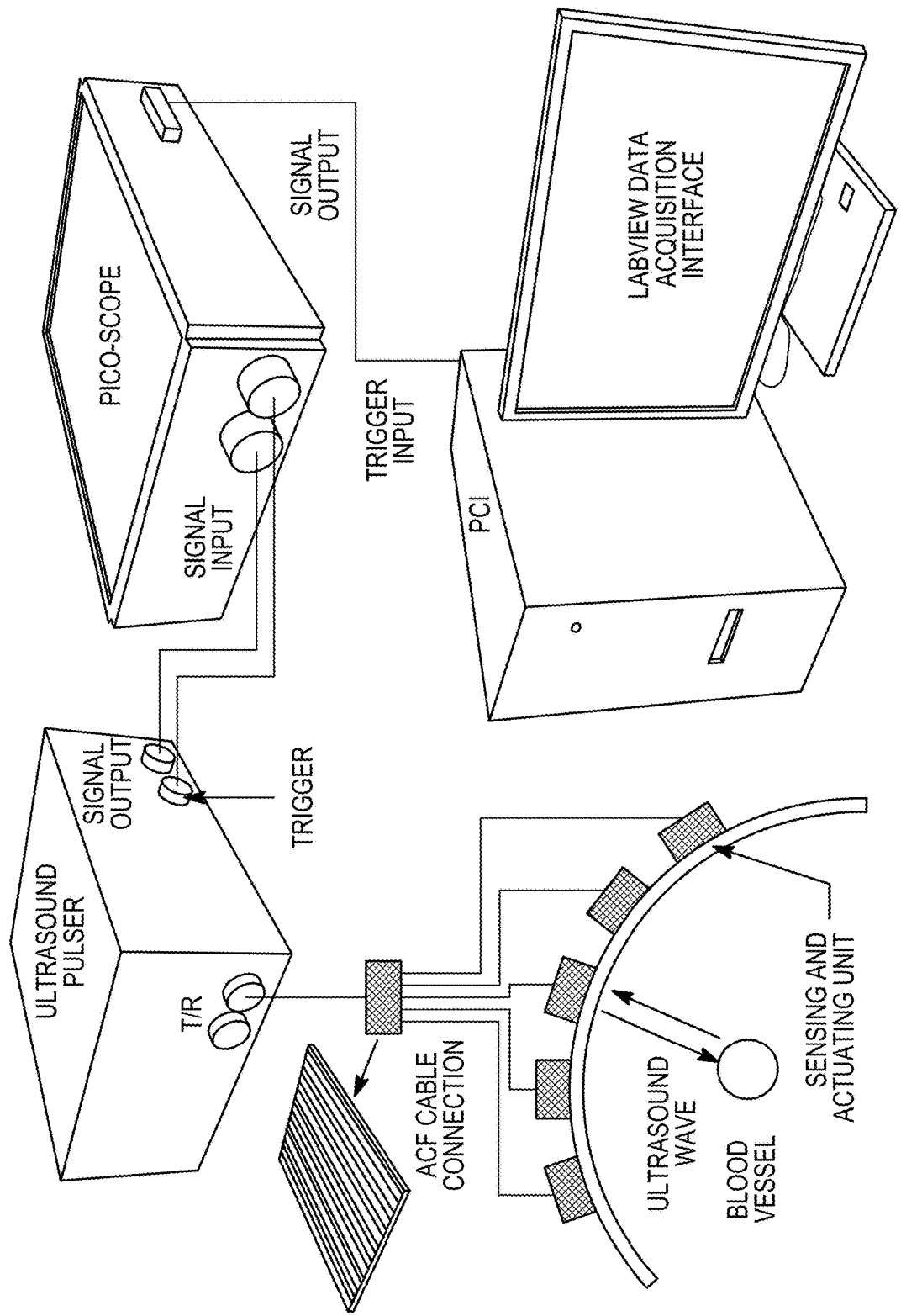
FIG. 67 shows the measurement setup for the blood pressure measurements shown in FIG. 62.

The upstroke gradient increases as a result of the pressure amplification. FIG. 66 shows a comparison of the upstroke gradient from the central to peripheral arteries, illustrating that the systolic upstroke gets steeper as the artery goes away from the heart, due to the progressive arterial stiffness. The measurement setup is illustrated in FIG. 67, and the process is calibrated using measurements on the brachial artery with a commercial pressure cuff.

Another notable feature is the progressive time interval between the systolic peak and the dicrotic notch. When the pressure wave travels down from the central arteries, its magnitude increases due to impedance mismatches encountered on the way, which creates a reflected wave that travels backward to the heart during late systole and early diastole. This reflected wave takes a longer time to travel from a location that is more distant from the heart, thus contributing to an increase in the time interval between the systolic peak and the dicrotic notch, which is indicated by the gray areas in the waveforms (FIGS. 41I-41L show one period of the waveforms). The capability of capturing those subtle variations demonstrates the device's potential for accurate clinically relevant diagnosis.

ECG Correlation for Arterial Stiffness Calculation

Propagation of the arterial pulse is a physiological phenomenon, and its characteristics possess a strong relationship with vascular stiffness, which is one of the key determinants of cardiovascular risks. Among all vascular parameters, pulse wave velocity (PWV), is the most accessible and reliable way to evaluate the arterial stiffness and can be calculated as follows, $$PWV = \frac{D}{PTT} \quad (1)$$

Wherein D is the distance between the ECG sensor and the ultrasonic sensor.

Physiologically, the pulse wave velocity of the blood vessel can be expressed in the following format.

$$PWV = \frac{E \times h}{2r \times \rho} \quad (4)$$

Wherein r is the internal radius of the blood vessel, h is the wall thickness, ρ is the blood density, and E is the artery modulus. In those parameters, the artery radius plays a dominating role, much more than the other three. The central artery has a larger diameter, and thus has the lower arterial stiffness, resulting in a smaller pulse pressure. Likewise, arteries in the extremities have higher stiffness and thus more significant pulse pressure than central arteries.

Another significance for PWV is its capability for absolute blood pressure calculation with a simple calibration by a conventional blood pressure cuff. That is, the variation of PWV can be utilized to correlate the absolute blood pressure change, which is highly dependent on the arterial stiffness. The calculation of PWV requires simultaneous measurements of ECG and pulse pressure at predefined locations. The pulse transit time (PTT) is defined by the time delay between ECG R peak and the starting point of the systolic upstroke. After the PTT is measured, the PWV can be calculated using the known distance divided by the PTT.

Figure 42A:
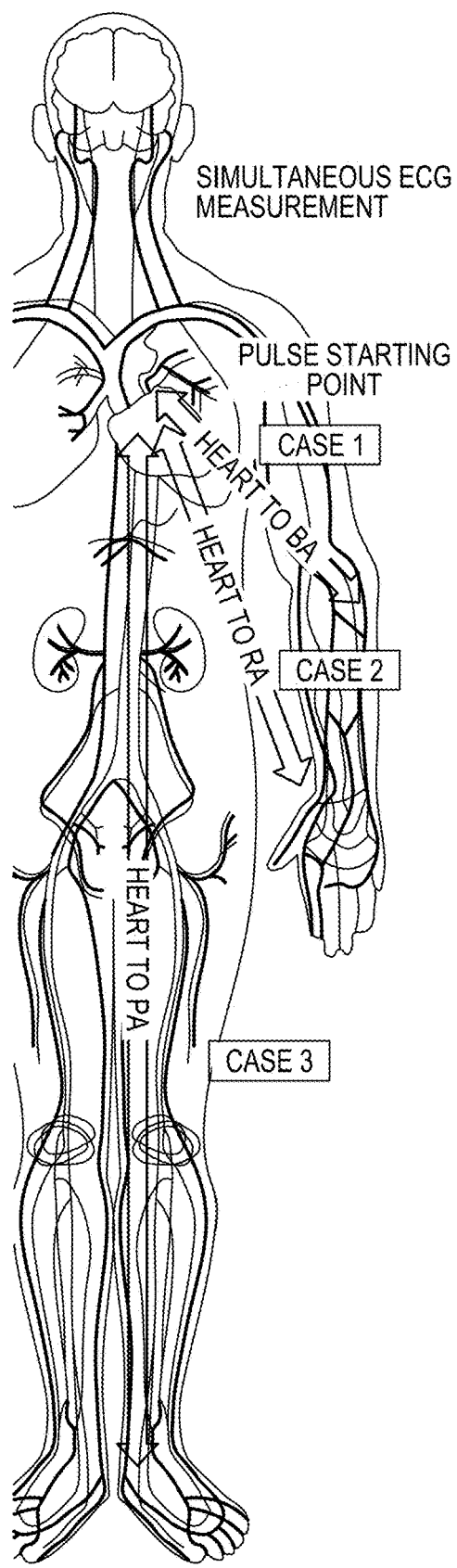
FIGS. 42A-42D shows ECG correlation based PWV calculation to evaluate the arterial stiffness.
Figure 42B:
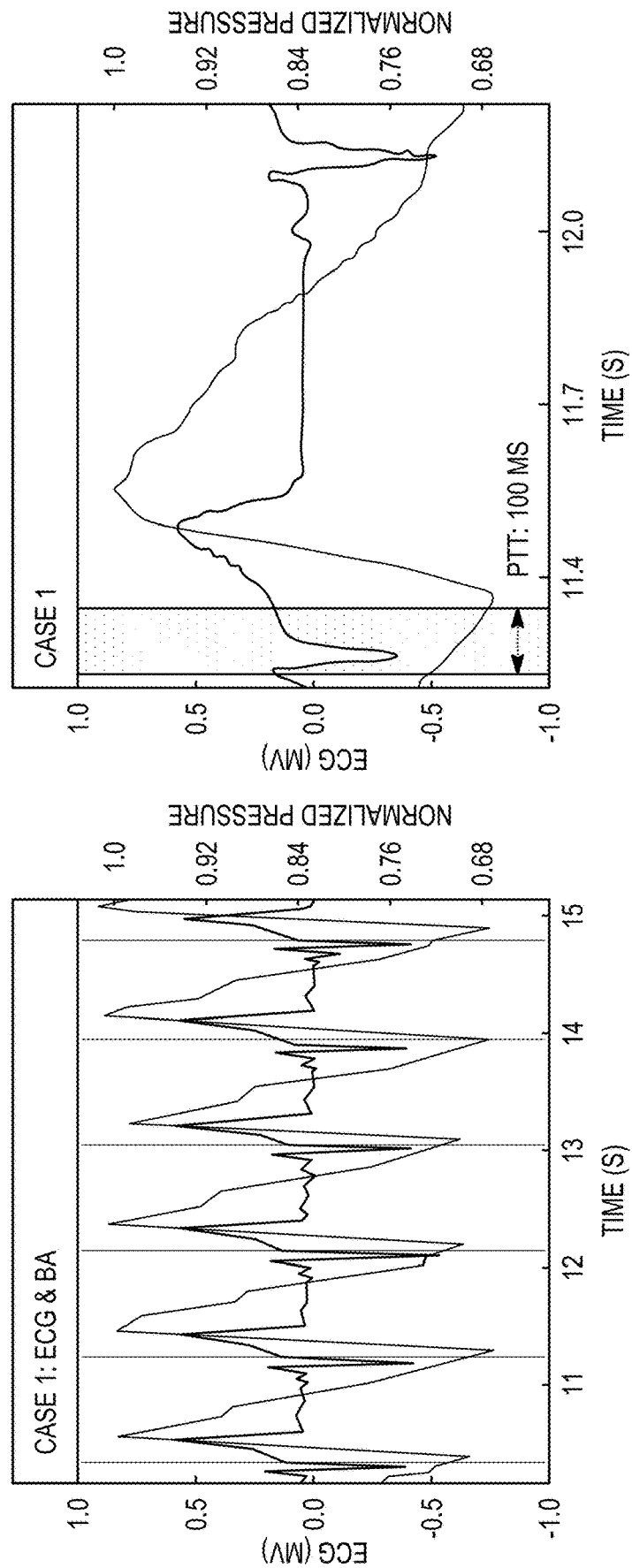
Figure 42C:
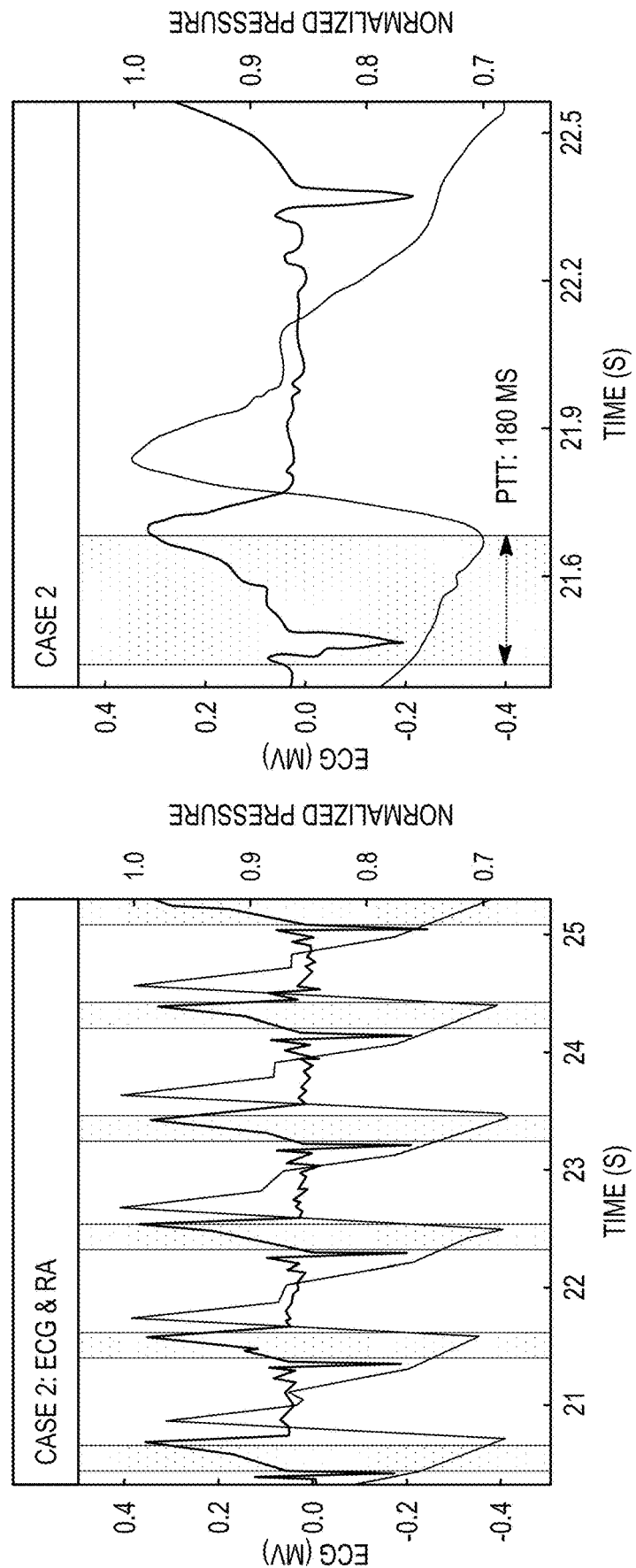
Figure 42D:
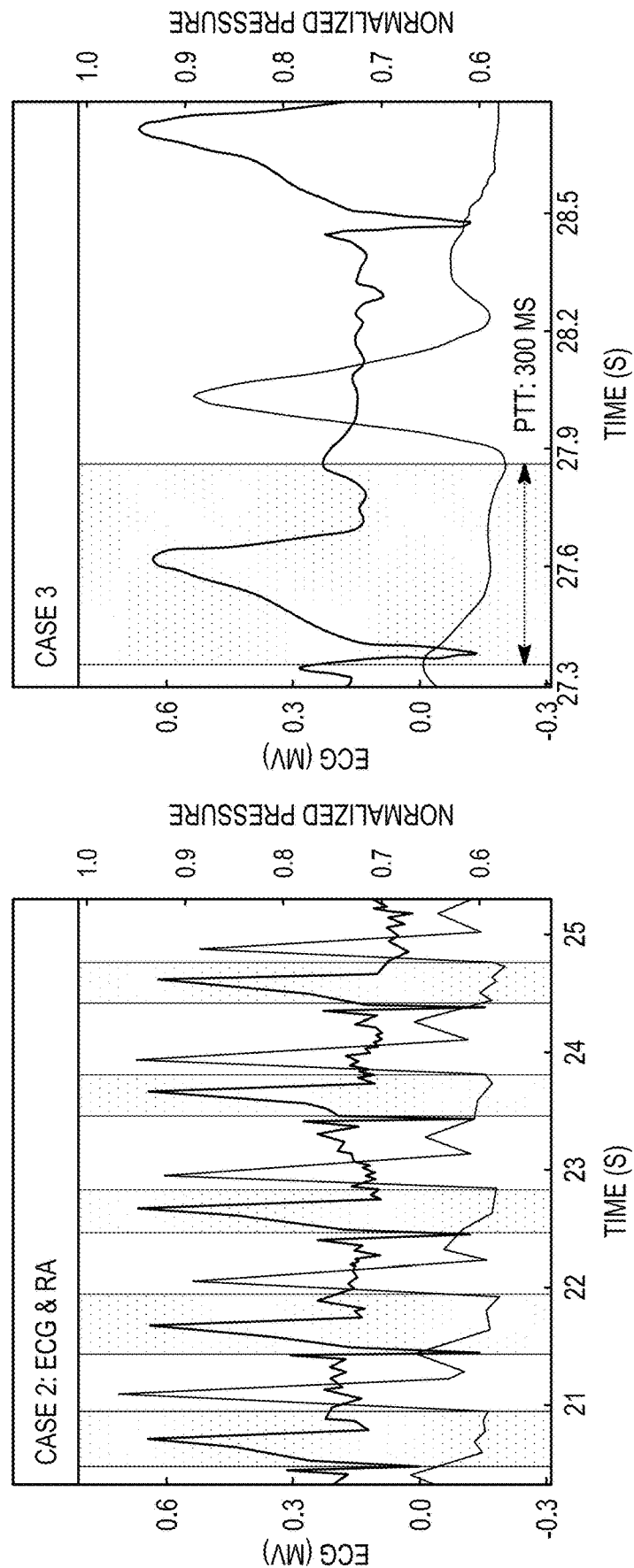
Figure 68A:
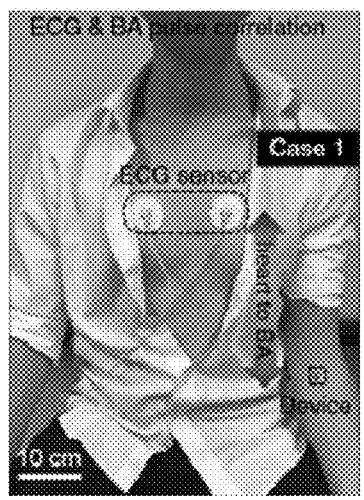
FIGS. 68A-68C show the testing conditions of Case 1, 2, and 3 for ECG correlation to brachial artery (FIG. 68A), radial artery (FIG. 68B), and pedal artery (FIG. 68C).
Figure 68B:
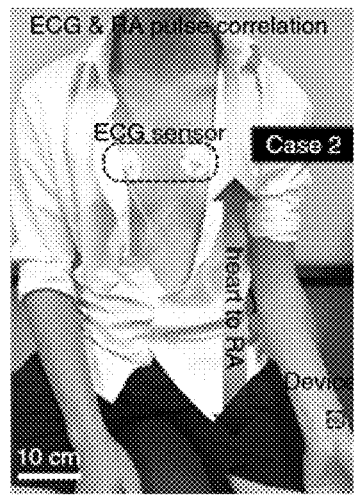
Figure 68C:
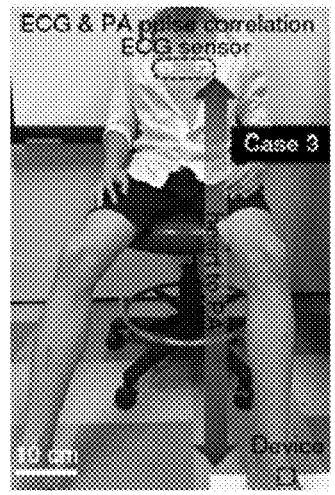
Figure 69A:
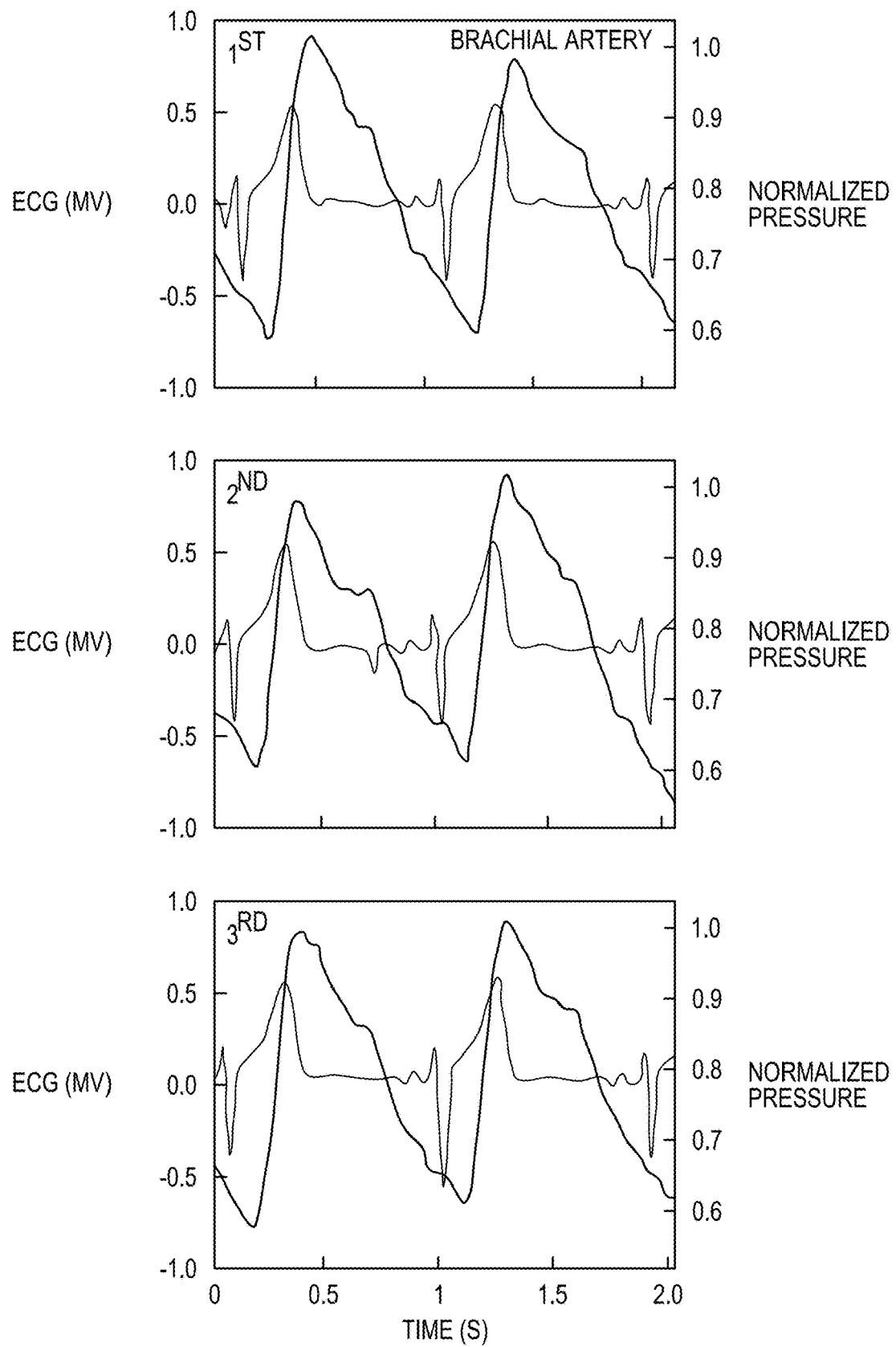
FIGS. 69A-69D show a robustness test on the ECG correlation (pressure waveforms are normalized) with measurements made on the brachial (FIG. 69A), radial (FIG. 69B), and pedal arteries (FIG. 69C)
Figure 69B:
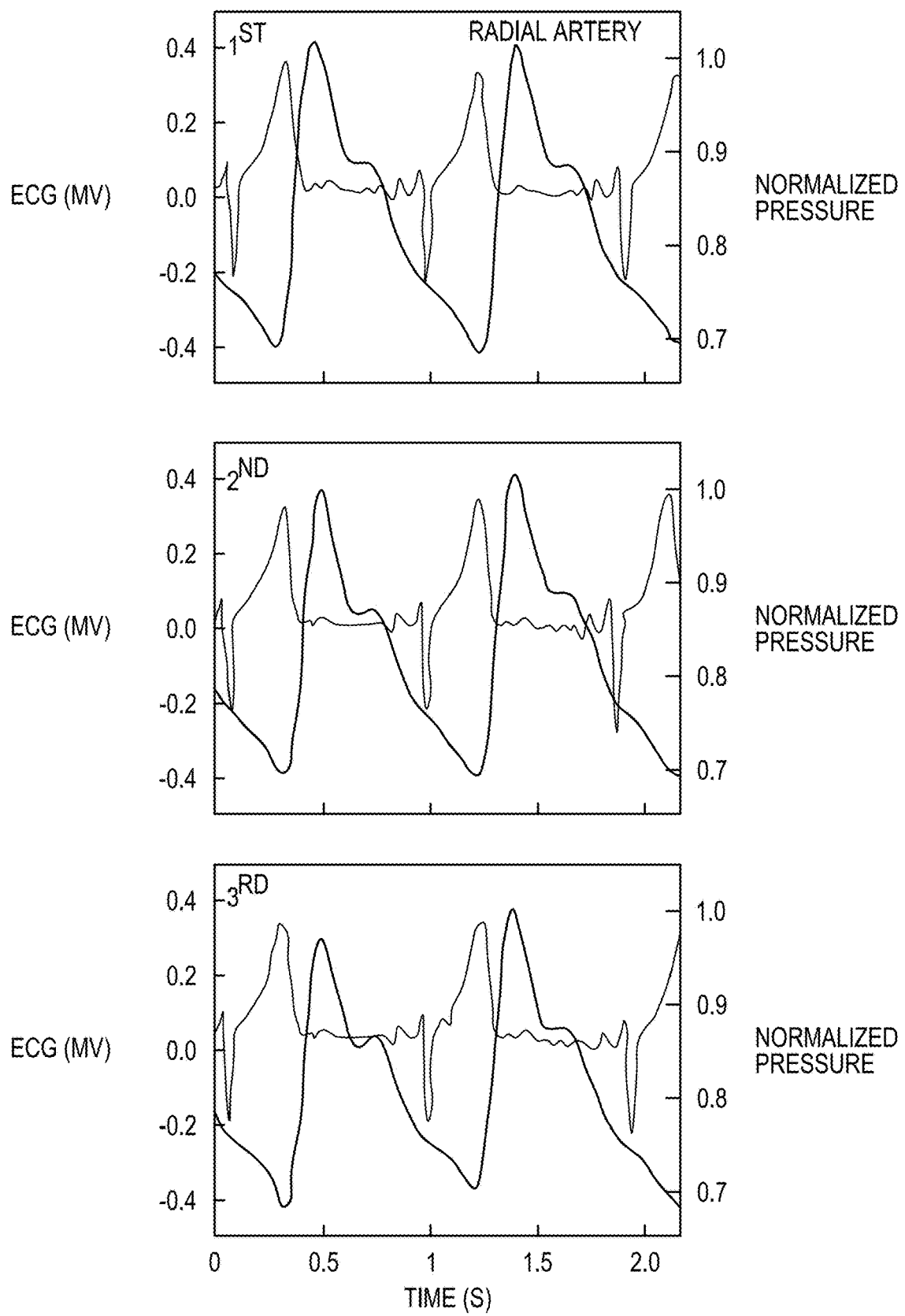
Figure 69C:
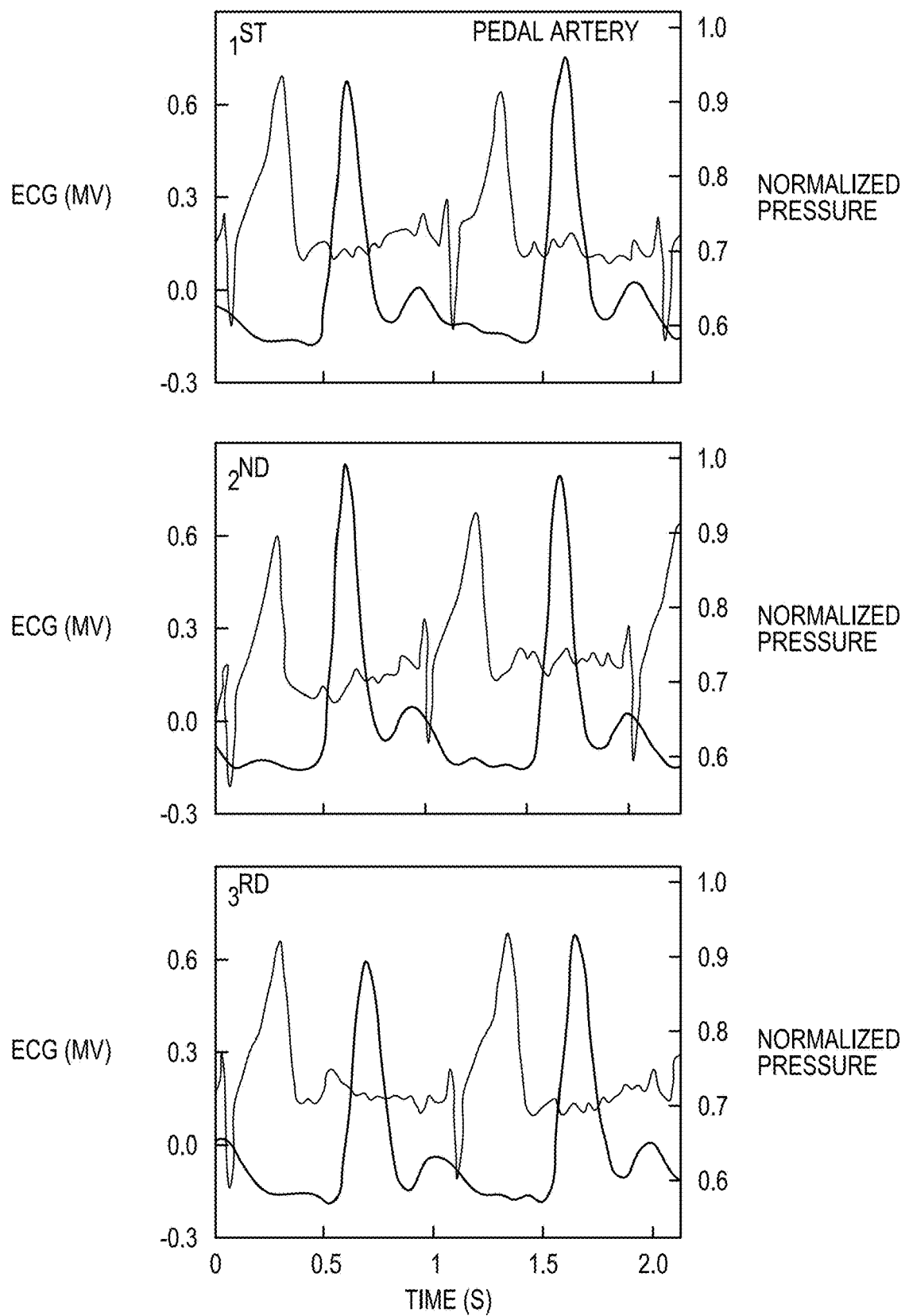
Figure 69D:
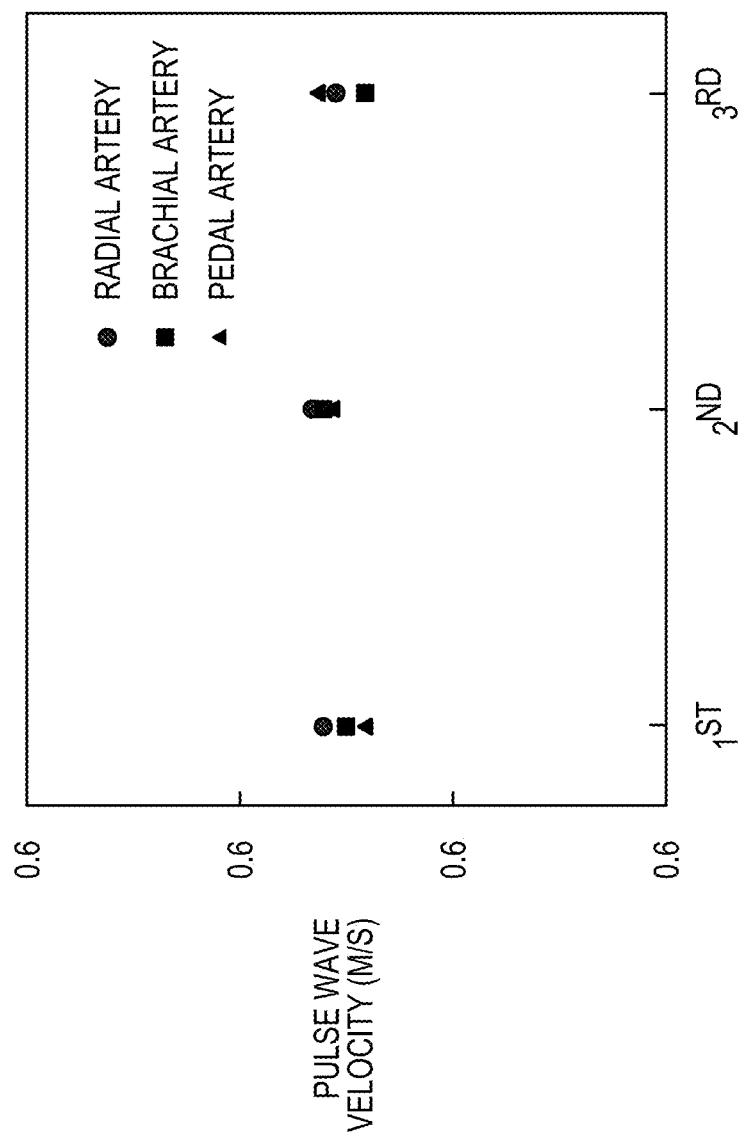

The measurement schematics are shown in FIG. 42A, with the simultaneous measurement of ECG and pulse measurements at three different sites including brachial, radial, and dorsalis pedis. FIGS. 42B-42D present the ECG correlation results of three cases: Case 1, brachial artery; Case 2, radial artery; and Case 3, dorsalis pedis artery, where ECG is measured on the chest for all three cases. FIG. 68 shows the testing conditions of Case 1, 2, and 3 for ECG correlation to brachial artery (FIG. 68A), radial artery (FIG. 68B), and pedal artery (FIG. 68C). As seen in FIGS. 42B-42D, PWV in Case 1 is 5.4 m/s, where D is 54 cm and time difference is 100 ms; PWV in Case 2 is 5.8 m/s, where D is 104 cm and time difference is 180 ms; and PWV in Case 3 is 5.3 m/s, where the D is 159 cm and the time difference is 300 ms. The PWV measurements are reproducible. FIG. 69 shows a robustness test on the ECG correlation (pressure waveforms are normalized). Three measurements were made on the same subject with the same and stable physiological status on brachial (FIG. 69A), radial (FIG. 69B), and pedal arteries (FIG. 69C), showing consistent results of Pulse Wave Velocity (PWV). FIG. 69D provide statistics of the PWV in these measurements.

Discussion

The results demonstrated here show a new class of conformal and stretchable ultrasonic device that offers non-invasive, accurate, and continuous monitoring of vital signs from well below the human skin, adding a new dimension to the sensing modality of conventional stretchable electronics. This device exploits the anisotropic piezoelectric material as the functional building block, and advanced mechanical design for encapsulation, to achieve physical and acoustical intimate coupling with the human skin. With the adoption of biocompatible encapsulating material and robust structural design, this device can be used to capture a series of key features in the central blood vessels with excellent and stable performance. For future work, improvements in the device performance and functionality are possible by the following explorations. The measurement of diastolic pressure using PTT is feasible by ECG correlation. In this way, this device can give exact blood pressure values without the calibration using commercial pressure cuff before each measurement. Additionally, integrating the post-end functions such as electric control, signal processing, waveform pattern recognition, wireless communications, and power sources in a stretchable and light-weight format would significantly enhance the device wearability, empowering a diverse range of clinically relevant prognosis and diagnosis.

Fabrication of the Stretchable Ultrasonic Device

Figure 70:
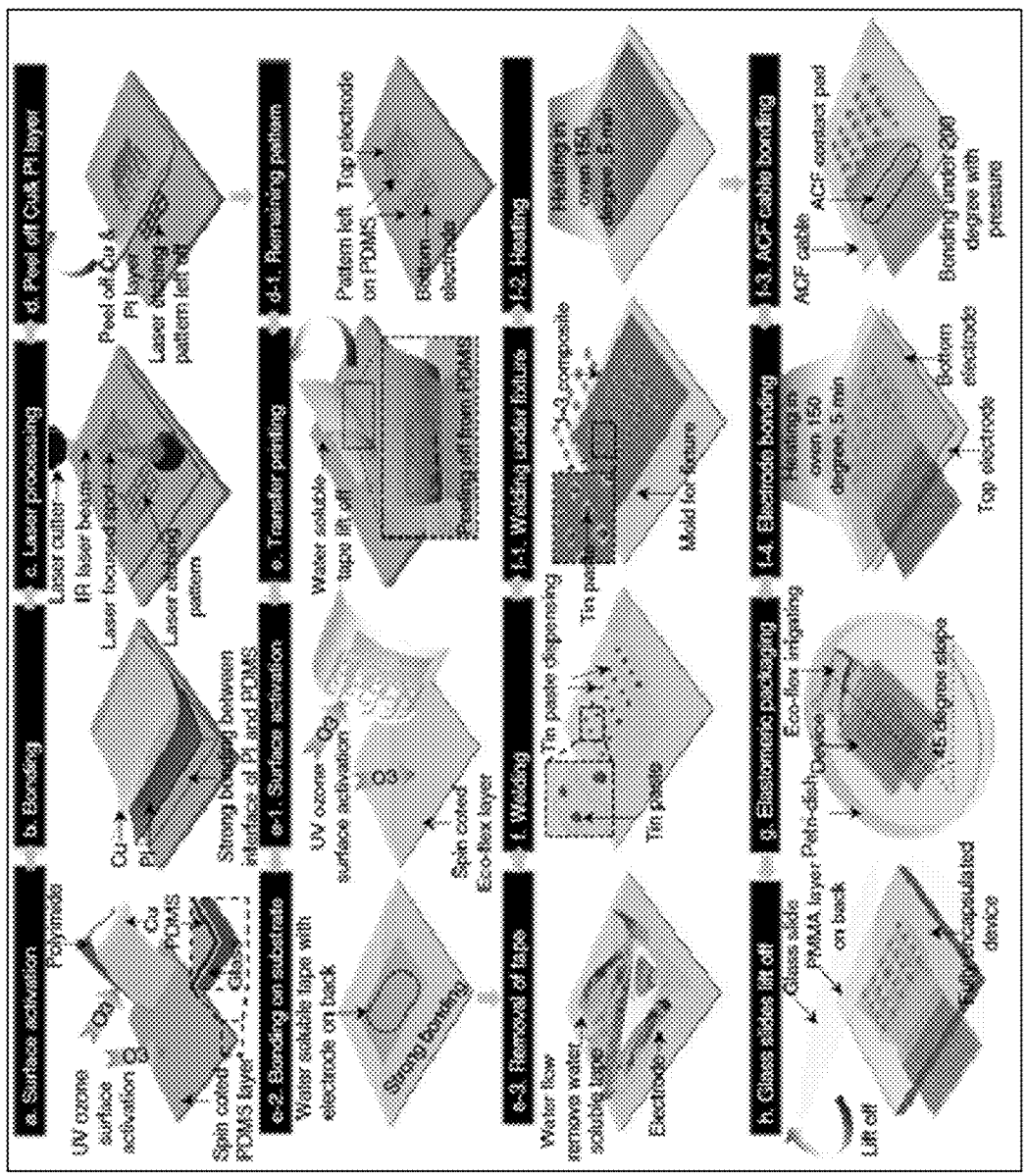
FIG. 70 shows one example of a fabrication process that may be used to produce the conformable transducer array.
Figure 72:
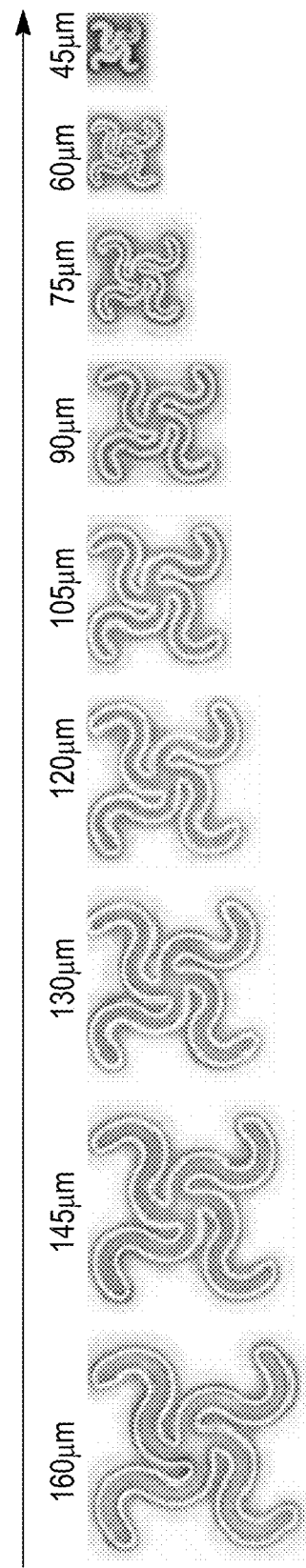
FIG. 72 shows photographs of the Cu serpentine patterns with different widths.

The fabrication can be summarized into three parts: (1) stretchable circuit patterning; (2) transfer printing; and (3) soft elastomeric packaging. These steps are described in more details in FIG. 70. Specifically, the circuit patterning exploited a commercial bilayer of Cu foil, with 20 µm on one side and 3 µm on the other side (MicroThin, Oak-Mitsui Inc.). First, a Cu foil (20 µm thick) was coated with PI from poly(pyromellitic dianhydride-co-4, 40-oxydianiline) amic acid solution, at 4000 rpm for 60 s, soft baked on a hotplate at 110° C. for 3 minutes and 150° C. for 1 min, and then cured in a nitrogen oven at 300° C. for 1 h. A glass slide coated with a layer of polydimethylsiloxane (PDMS, Sylgard 184® silicone elastomer, 20:1) served as a substrate to laminate the Cu foil with the PI layer in contact with PDMS. UV ozone surface activation for 3 minutes was used to increased the bonding between PI and PDMS. After the Cu foil is was attached on the PDMS substrate, a laser ablation system with the (power of 0.342 mJ power, 900 kHz pulse repetition frequency, 300 mm/s laser cutting speed, and 241 ns pulse width, was utilized to create the circuit pattern with the highest resolution. FIG. 72 shows photographs of the Cu serpentine patterns with different widths. The resolution of the laser ablation machine for 20 µm thick Cu foil is determined to be 45 µm.

Figure 71:
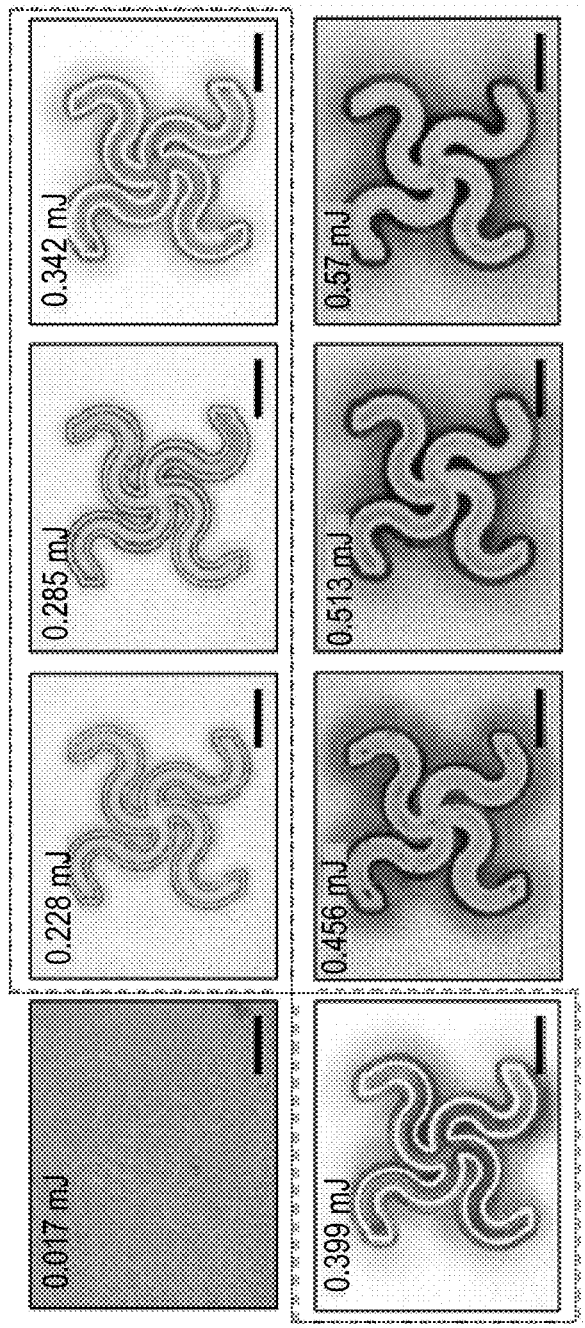
FIG. 71 shows photographs of Cu patterns processed under different laser power to illustrate how the laser power was selected.

FIG. 71 shows photographs of Cu patterns processed under different laser power to illustrate how the laser power was selected. When the laser power is low (e.g. below 0.228 mJ), Cu is not etched through. When the laser power is high (e.g. above 0.339 mJ), the thin Cu interconnects are ablated away. Therefore, an ideal range of laser power is 0.228 mJ-0.339 mJ. The other parameters including pulse repetitive frequency: 900 KHz, speed: 300 mm/s, and pulse width: 241 ns. The scale bars in FIG. 71 are 250 µm.

Figure 73:
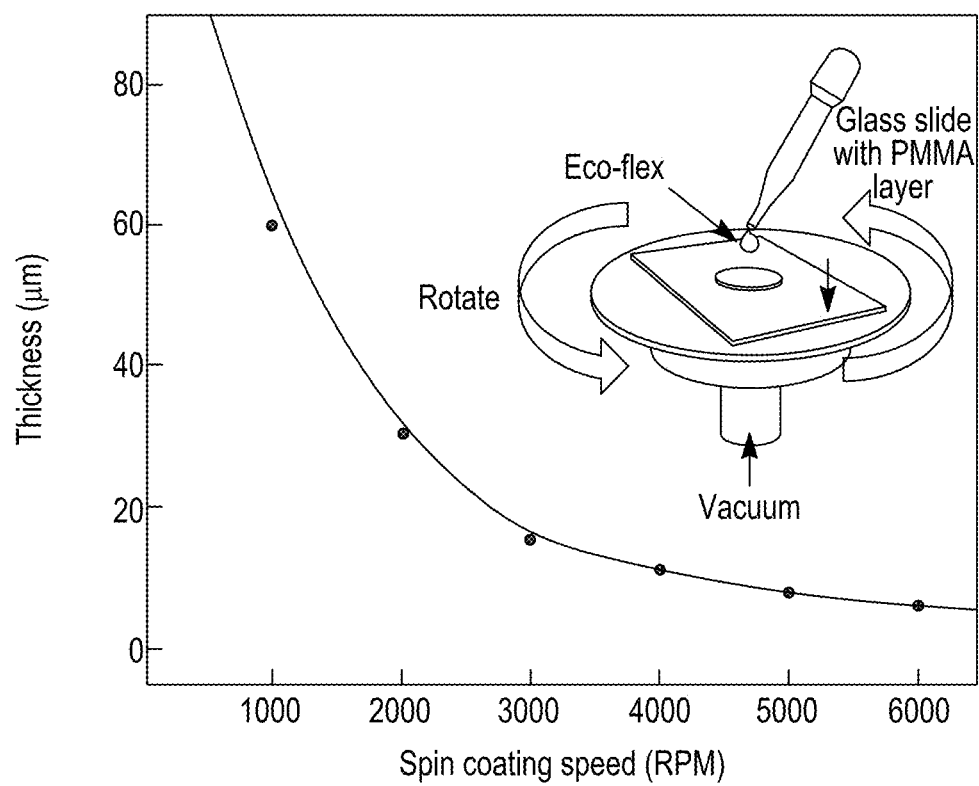
FIG. 73 shows the relationship between Ecoflex thickness and spin speed on a glass slide.

The other parameters used for laser etching are: 900 KHz PRF, 300 mm/s laser cutting speed, 241 ns pulse width. After the laser processing, transfer printing was implemented using water-soluble tape (Aquasol) to transfer the circuit was transferred using water-soluble tape (Aquasol) on a 15 µm thick Eco-flex substrate spin-coated on a glass slide. The relationship between Ecoflex thickness and spin speed on a glass slide is shown in FIG. 73. The experiment is carried out at room temperature, and all Ecoflex spin coating are performed with the same viscosity.

Figures 74A, 74B:
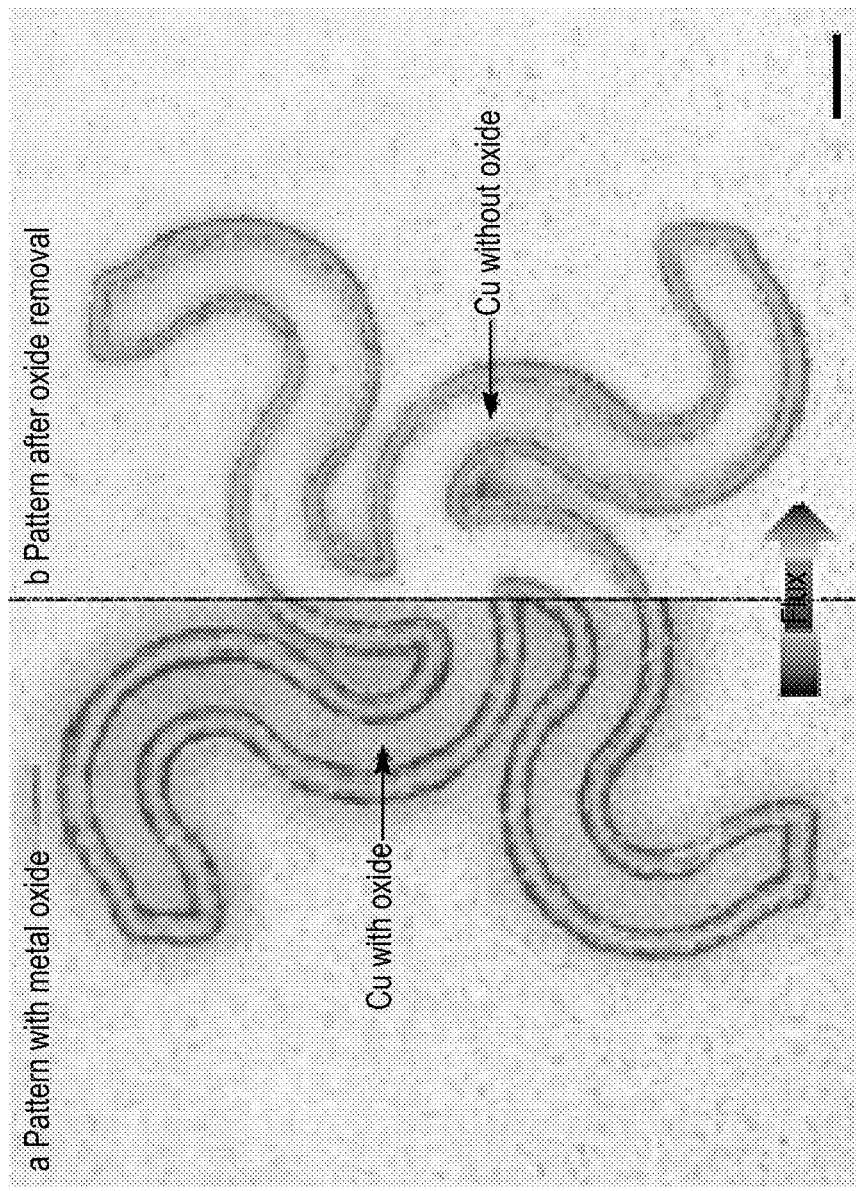
FIGS. 74A and 74B show photographs of the Cu pattern before (FIG. 74A) and after (FIG. 74B) surface oxide removal using flux.

Next, the circuit surface was cleaned using flux to remove the surface oxidation created by the laser ablation process to increase the welding strength. FIG. 74 shows photographs of the Cu pattern before (FIG. 74A) and after (FIG. 74B) surface oxide removal using flux. The existence of oxide will create a barrier for forming interface alloy of Cu and solder paste, leading to weak bonding. The scale bar in FIG. 74B is 150 µm.

The welding and bonding was achieved with the solder paste that was heated at 150° C. for 5 min for the top and bottom electrodes. After that, the device was encapsulated with Eco-flex. Curing was done at room temperature for 2 hours and then the glass slides were peeled off. Finally, spin-coating an additional 15 µm thick layer of silbione on the Ecoflex substrate facilitates removing the interfacial gap and thus the necessity of the gel during testing.

Poling of the 1-3 Composite

Figure 75:
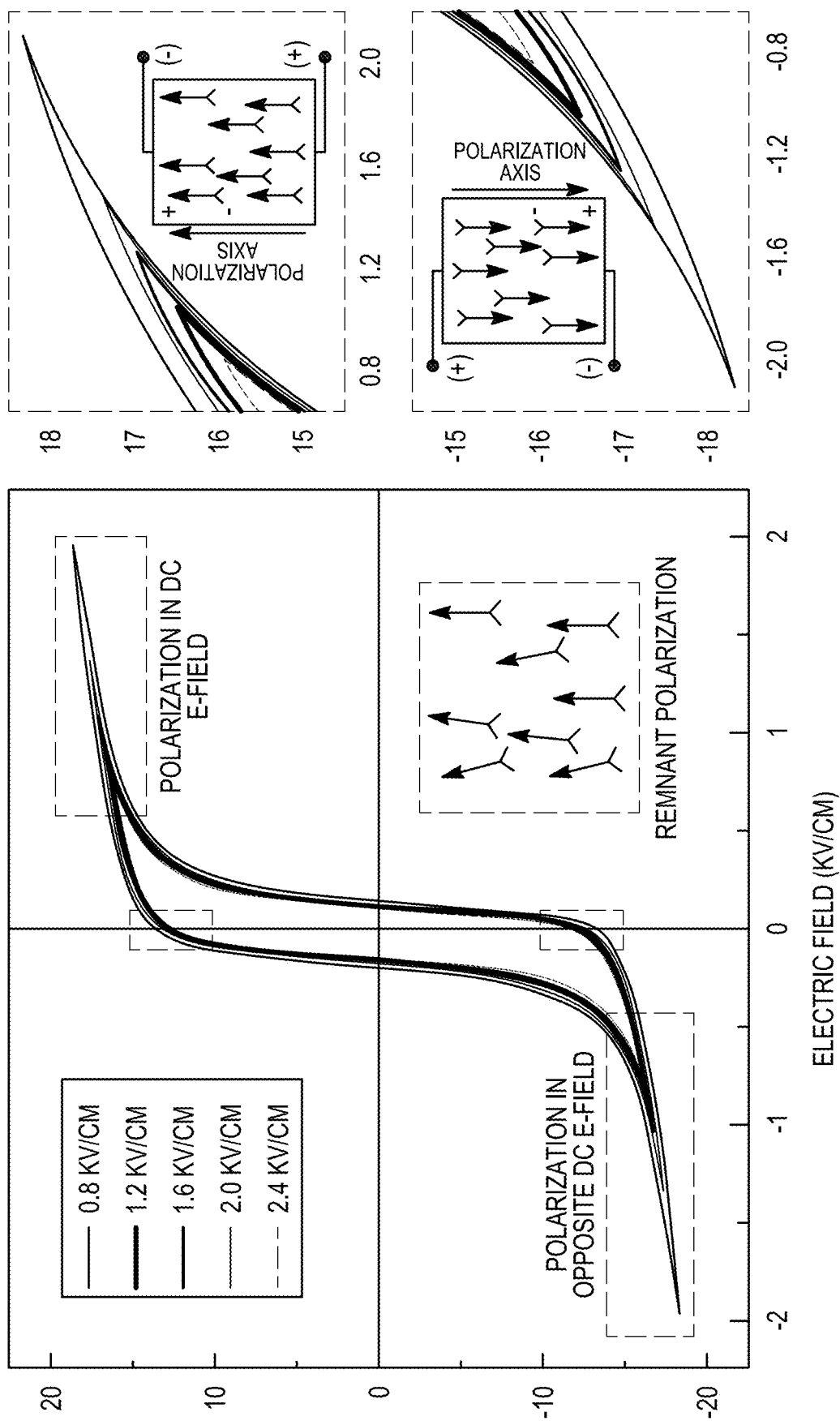
FIG. 75 shows the polarization hysteresis loop, illustrating the switchable dipole alignment of the piezoelectric materials under an electrical field.
Figure 76A:
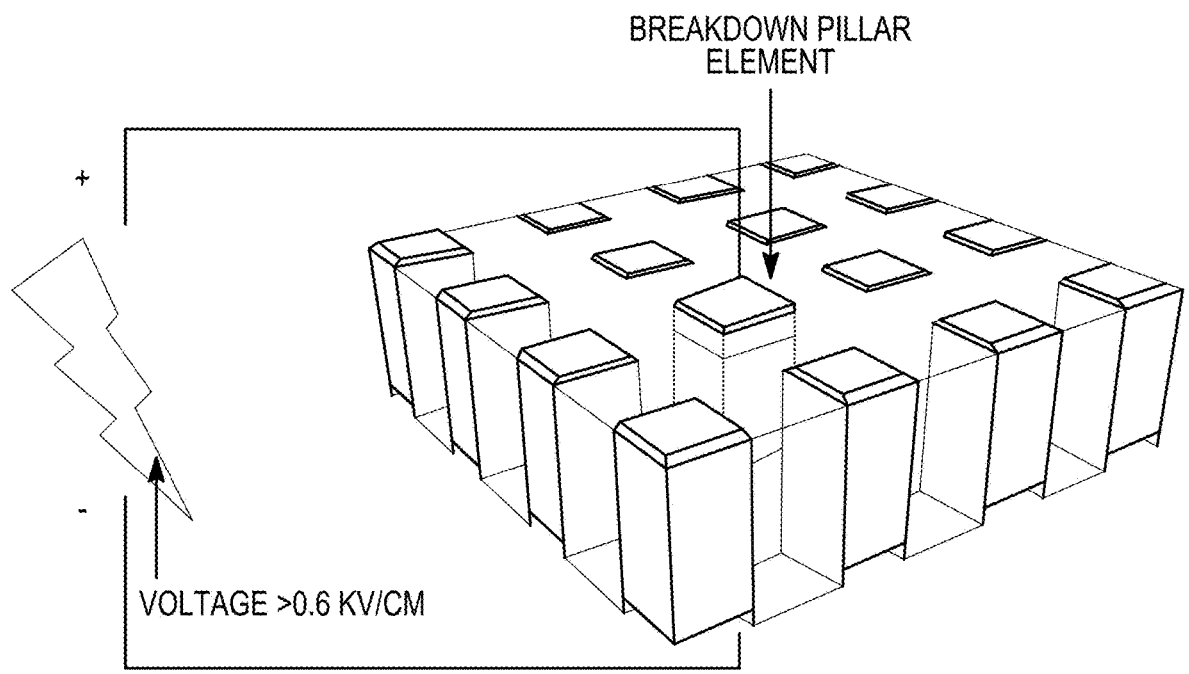
FIG. 76A shows the polarization setup used to obtain the acoustic emission performance between normal polarization and breakdown.
Figure 76B:
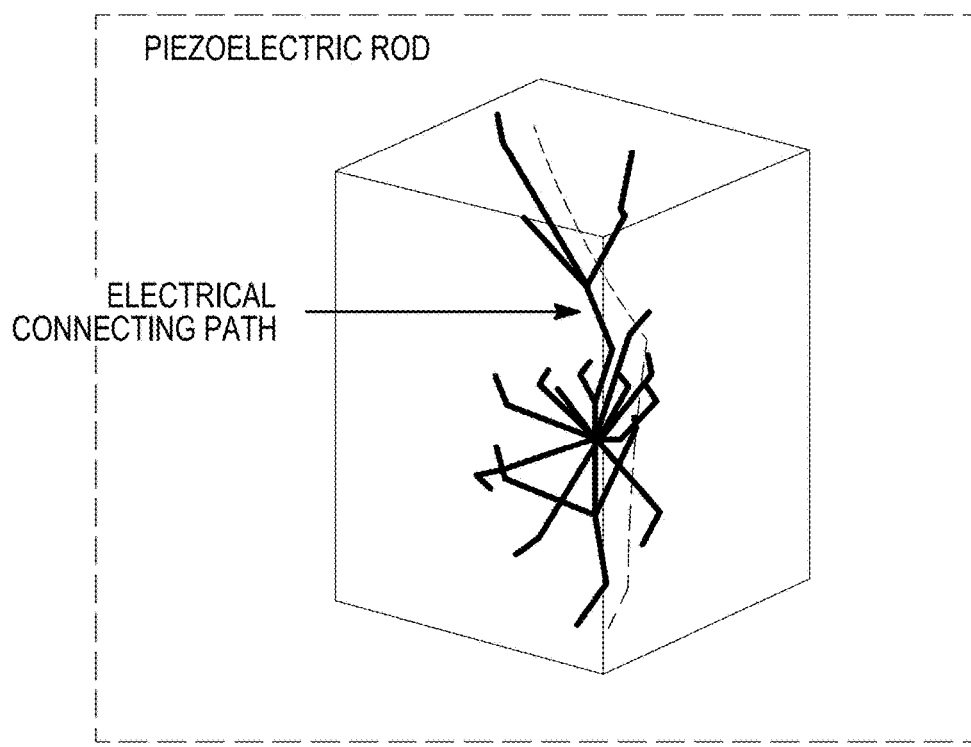
FIG. 76B schematically illustrates the existence of an electrical connecting path caused by poling above the threshold voltage.
Figure 76C:
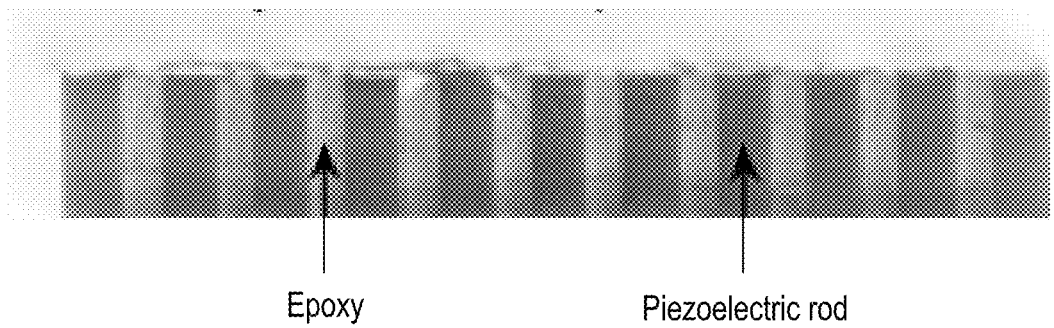
FIG. 76C is a cross-sectional view of an intact 1-3 composite under 800 V polarization.
Figure 76D:
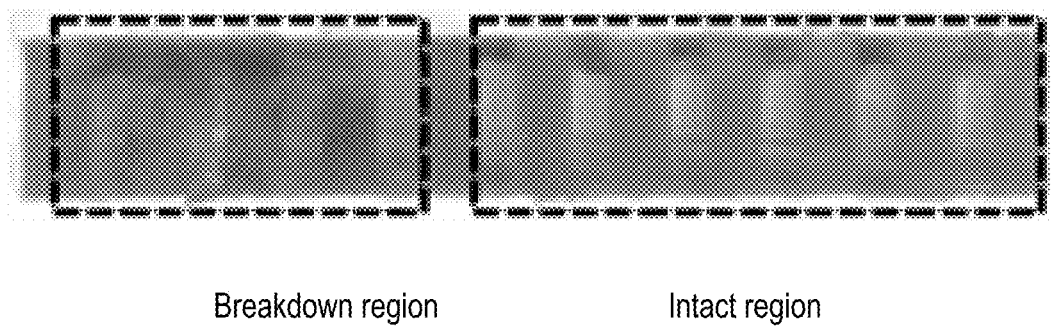
FIG. 76D is a cross-sectional view of a broken down 1-3 composite under 1200 V.
Figure 76E:
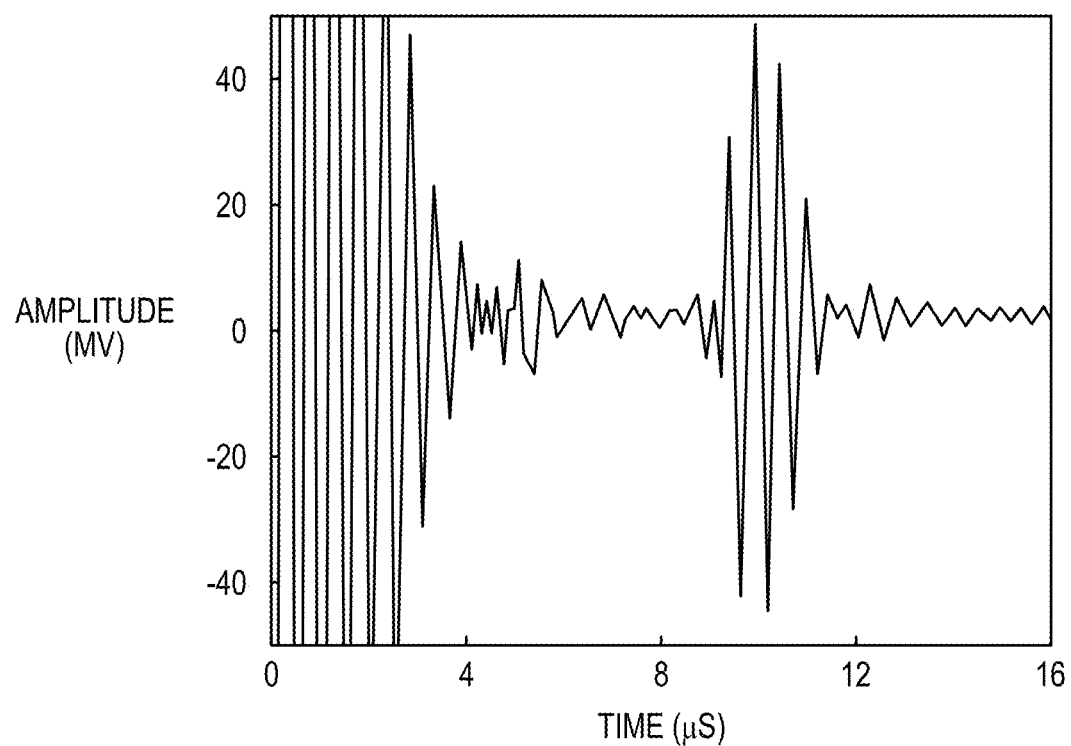
FIG. 76E shows reflected signals from devices made of an adequately polarized 1-3 composite.
Figure 76F:
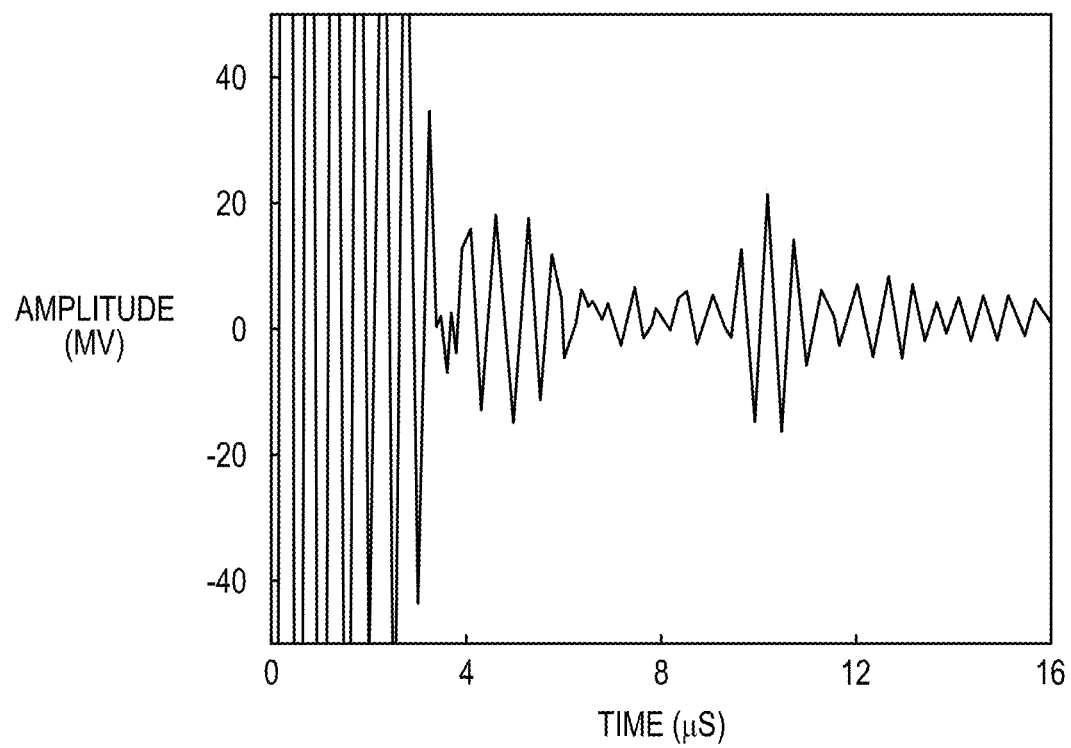
FIG. 76F shows reflected signals from devices made of a broken down 1-3 composite.

Poling the 1-3 composite (Smart Material Corp.) increased its piezoelectric coefficient and electromechanical coupling factor of the composite. The poling involved using an electric field from a DC power supply to align the dipoles of the piezoelectric materials, which enhances the piezo-electricity and performance of the device. The polarizing hysteresis loop was measured in silicone oil. FIG. 75 shows the polarization hysteresis loop, illustrating the switchable dipole alignment of the piezoelectric materials under electrical field. The dipoles are better aligned under the stronger electrical field. However, the piezoelectric material would breakdown if the electrical field goes over a threshold. The poling of the device was implemented at 1.2 kV/cm for 15 min. Excessive poling voltage caused breakdown of the piezoelectric materials, thus reducing the signal strength.

FIG. 76 illustrates the acoustic emission performance between normal polarization and breakdown. FIG. 76A shows the polarization setup. FIG. 76B schematically illustrates the existence of an electrical connecting path caused by poling above the threshold voltage. FIG. 76C is a cross-sectional view of an intact 1-3 composite under 800 V polarization. FIG. 76D is a cross-sectional view of a broken down 1-3 composite under 1200 V. FIG. 76E show reflected signals from devices made of an adequately polarized 1-3 composite and FIG. 76F show reflected signals from devices made of a broken down 1-3 composite, showing a smaller amplitude caused by the broken down region.

Blood Pressure Waveform Measurement and Data Analysis

The blood pressure waveform measurement was carried out on a healthy male of age 22, under the approval by the Institutional Review Board of the University of California, San Diego (IRB no. 170812). All measurements were carried out on the subject when sitting. The signal analysis was based on the Time of Flight (TOF) analysis, which was the gauge of the time interval between the signal peak and zero-point time. Then the TOF was used to calculate the propagation distance, by multiplying the speed of ultrasound in the specimen. The device was activated by an ultrasonic pulser (Olympus 5077 PR) at 100 V, using the transmit/receive mode. Pulse repetitive frequency was 2000 Hz. The echo signal was received by Picoscope (Picoscope 6404) with a temporal resolution of 2000/s, which allowed precise vessel wall tracking.

ECG Correlation

The ECG correlation to the blood pressure waveform at different locations was taken on the same subject, when sitting, consecutively with a 2-minute interval, so the subject had a relatively constant blood pressure value and arterial stiffness. The longest duration of skin integration on the same skin region was 2 hours. No allergic reactions, redness, or damage to the skin were observed in any of our studies. The diastolic pressure was calibrated using the commercial blood pressure cuff (Smart Logic Technology, 6016) before each monitoring period. Additionally, the testing subject maintained stable physiological and psychological status to guarantee stable levels of blood pressure and vasculature stiffness.

Bandwidth and Resolution Characterization

The bandwidth of transducer (32%) was calculated by using the frequency range (2.4 MHz) divided by central frequency (7.5 MHz). The resolution characterization exploited a thin metal wire suspended at the center of a beaker filled with water. A 1×10 linear array of transducers was fabricated and attached to the beaker wall parallel to the ground. All signals of the ten transducer elements were acquired and combined with each other according to the principle with one transducer as the transmitter and the other as the receiver (e.g. 1T2R, 1T3R . . . 1T10R; 2T1R, 2T3R . . . 2T10R; . . . ; 10T1R, 10T2R . . . 10T9R). The total 90 signals were used, by the delay-and-sum (DAS) reconstruction algorithm, to reconstruct the image. The obtained image with low-level side lobes was resulted from the reconstruction algorithm and the limited number of elements used for imaging.

Cell Viability Assay of Ultrasonic Exposure

The human skin fibroblast cells HFF-1 were first purchased from American Type Culture Collection (ATCC) and cultured in Dulbecco's Modified Eagle's Medium (DMEM, Gibco) supplemented with 10% fetal bovine serum (FBS, Gibco) and 1% penicillin/streptomycin (Gibco) under 37° C. within 5% $CO_2$. HFF-1 cells were subcultured and seeded into 24-well plate at the density of $1×10^4$/ml and incubated for another 24 hours. Then a beam of ultrasound at the frequency of 7.5 MHz was applied to the bottom of the culture plate. After 2, 6, and 16 hours' ultrasound exposure, the cells were stained with calcein AM (Invitrogen, 3M, excitation/emission=488 nm/525 nm) and propidium iodide (PI, Invitrogen, 3M, excitation/emission=530 nm/620 nm) for 15 minutes, and then were imaged under fluorescence microscopy (EVOS, Thermofisher Scientifics). For positive control group, the cells were treated with 75% ethanol for 10 minutes.

The invention claimed is:

1. A conformable piezoelectric transducer array, comprising:
    a silicone elastomer substrate and a silicone elastomer superstrate;
    a plurality of piezoelectric transducer elements disposed between the substrate substrates and the superstrate;
    a first electrical interconnect layer electrically interconnecting a first surface of each of the plurality of piezoelectric transducer elements-adjacent to the substrate; and
    a second electrical interconnect layer electrically interconnecting a second surface of each of the plurality of piezoelectric transducer elements adjacent to the superstrate, wherein the first and second electrical interconnect layers have a patterned island and bridge structure that includes a plurality of islands electrically interconnected by bridges, wherein one of the first or second electrical interconnect layers include a plurality of electrical interconnect layers electrically isolated from one another, each of the transducer elements being supported by one of the islands, a conductive solder paste bonding the first surface of each of the plurality of piezoelectric transducer elements to the first electrical interconnect layer and the second surface of each of the plurality of piezoelectric transducer elements to the second electrical interconnect layer; and
    wherein the plurality of transducer elements includes an array of transducer elements, the first and second interconnect layers being configured so that each of the transducer elements in the array is individually addressable.

2. The conformable piezoelectric transducer array of claim 1, wherein at least one of the transducer elements comprises a 1-3 composite material.

3. The conformable piezoelectric transducer array of claim 2, wherein each of the transducer elements comprises a 1-3 composite material.

4. The conformable piezoelectric transducer array of claim 1, wherein the bridges have a serpentine configuration.

5. The conformable piezoelectric transducer array of claim 1, wherein the first and second electrical interconnect layers includes a bilayer formed from a metal layer and a polyimide layer.

6. The conformable piezoelectric transducer array of claim 5, wherein the metal layer in at least one of the first and second electrical interconnect layers is a copper layer.

7. The conformable piezoelectric transducer array of claim 1, further comprising a conductive vibration damping element disposed between each of the transducer elements and the superstrate.

8. The conformable piezoelectric transducer array of claim 7, wherein the conductive vibration damping elements each include a conductive epoxy.

* * * * *